US012275959B2

(12) United States Patent
Chalberg, Jr. et al.

(10) Patent No.: US 12,275,959 B2
(45) Date of Patent: Apr. 15, 2025

(54) COMPOSITIONS AND METHODS FOR ENHANCED GENE EXPRESSION IN CONE CELLS

(71) Applicants: Adverum Biotechnologies, Inc., Redwood City, CA (US); University of Washington, Seattle, WA (US)

(72) Inventors: Thomas W. Chalberg, Jr., Redwood City, CA (US); Jay Neitz, Seattle, WA (US); Maureen Neitz, Seattle, WA (US)

(73) Assignee: Adverum Biotechnologies, Inc., Redwood City, CA (US)

( * ) Notice: Subject to any disclaimer, the term of this patent is extended or adjusted under 35 U.S.C. 154(b) by 360 days.

(21) Appl. No.: 17/556,847

(22) Filed: Dec. 20, 2021

(65) Prior Publication Data

US 2022/0259568 A1 Aug. 18, 2022

Related U.S. Application Data

(63) Continuation of application No. 15/984,085, filed on May 18, 2018, now Pat. No. 11,248,214, which is a continuation of application No. 14/660,657, filed on Mar. 17, 2015, now Pat. No. 10,000,741.

(60) Provisional application No. 62/127,185, filed on Mar. 2, 2015, provisional application No. 61/954,330, filed on Mar. 17, 2014.

(51) Int. Cl.

| | |
|---|---|
| ***C12N 7/00*** | (2006.01) |
| ***A61K 35/761*** | (2015.01) |
| ***A61K 48/00*** | (2006.01) |
| ***C12N 15/86*** | (2006.01) |
| *A61K 38/00* | (2006.01) |

(52) U.S. Cl.

CPC .............. *C12N 7/00* (2013.01); *A61K 35/761* (2013.01); *C12N 15/86* (2013.01); *A61K 38/00* (2013.01); *A61K 48/00* (2013.01); *C12N 2750/14143* (2013.01); *C12N 2800/24* (2013.01); *C12N 2830/008* (2013.01); *C12N 2830/30* (2013.01); *C12N 2830/42* (2013.01)

(58) Field of Classification Search

None

See application file for complete search history.

(56) References Cited

U.S. PATENT DOCUMENTS

| | | | |
|---|---|---|---|
| 4,522,811 | A | 6/1985 | Eppstein et al. |
| 4,874,237 | A | 10/1989 | Cringle |
| 5,219,401 | A | 6/1993 | Cathignol et al. |
| 5,383,917 | A | 1/1995 | Desai et al. |
| 5,436,146 | A | 7/1995 | Shenk et al. |
| 5,527,533 | A | 6/1996 | Tso et al. |
| 5,641,749 | A | 6/1997 | Yan et al. |
| 5,712,380 | A | 1/1998 | Kendall et al. |
| 5,753,500 | A | 5/1998 | Shenk et al. |
| 5,773,700 | A | 6/1998 | Van Grinsven et al. |
| 5,792,845 | A | 8/1998 | O'Reilly et al. |
| 5,814,618 | A | 9/1998 | Bujard et al. |
| 5,861,484 | A | 1/1999 | Kendall et al. |
| 5,994,136 | A | 11/1999 | Naldini et al. |
| 6,013,516 | A | 1/2000 | Verma et al. |
| 6,040,183 | A | 3/2000 | Ferrari et al. |
| 6,054,485 | A | 4/2000 | Schwartz et al. |
| 6,093,570 | A | 7/2000 | Ferrari et al. |
| 6,096,548 | A | 8/2000 | Stemmer |
| 6,132,732 | A | 10/2000 | Young et al. |
| 6,153,436 | A | 11/2000 | Hermonat et al. |
| 6,287,815 | B1 | 9/2001 | Brown |
| 6,329,181 | B1 | 12/2001 | Xiao et al. |
| 6,387,670 | B1 | 5/2002 | Leblois-Prehaud et al. |
| 6,458,157 | B1 | 10/2002 | Suaning |
| 6,482,634 | B1 | 11/2002 | Wilson et al. |
| 6,491,907 | B1 | 12/2002 | Rabinowitz et al. |
| 6,548,286 | B1 | 4/2003 | Samulski et al. |
| 6,596,539 | B1 | 7/2003 | Stemmer et al. |
| 6,703,237 | B2 | 3/2004 | Samulski et al. |
| 6,710,036 | B2 | 3/2004 | Kurtzman et al. |
| 6,723,551 | B2 | 4/2004 | Kotin et al. |
| 6,733,757 | B2 | 5/2004 | Patel et al. |
| 6,855,314 | B1 | 2/2005 | Chiorini et al. |
| 6,943,153 | B1 | 9/2005 | Manning, Jr. et al. |
| 6,962,815 | B2 | 11/2005 | Bartlett |
| 7,070,959 | B1 | 7/2006 | Papadopoulos et al. |
| 7,071,159 | B2 | 7/2006 | Kendall et al. |
| 7,172,893 | B2 | 2/2007 | Rabinowitz et al. |
| 7,220,577 | B2 | 5/2007 | Zolotukhin |
| 7,252,997 | B1 | 8/2007 | Hallek et al. |
| 7,254,489 | B2 | 8/2007 | Mossel |
| 7,285,381 | B1 | 10/2007 | Hallek et al. |
| 7,314,912 | B1 | 1/2008 | Hallek et al. |
| 7,368,428 | B2 | 5/2008 | Serrero |
| 7,427,396 | B2 | 9/2008 | Arbetman et al. |
| 7,556,965 | B2 | 7/2009 | Hallek et al. |
| 7,585,676 | B2 | 9/2009 | Mitrophanous et al. |
| 7,629,322 | B2 | 12/2009 | Kleinschmidt et al. |

(Continued)

FOREIGN PATENT DOCUMENTS

| | | | |
|---|---|---|---|
| CA | 2379220 | A1 | 1/2001 |
| CN | 1325451 | A | 12/2001 |

(Continued)

OTHER PUBLICATIONS

Sulak, et al. (2024) "The concept of gene therapy for glaucoma: the dream that has not come true yet", Neural Regeneration Research, 19(1): 92-99.*

(Continued)

*Primary Examiner* — Robert M Kelly

(74) *Attorney, Agent, or Firm* — FisherBroyles, LLP; Adam K. Whiting; Adelaide K. Leitzel

(57) ABSTRACT

The present disclosure provides polynucleotide cassettes, expression vectors and methods for the expression of a gene in cone cells.

16 Claims, 20 Drawing Sheets

Specification includes a Sequence Listing.

(56) References Cited

U.S. PATENT DOCUMENTS

| | | | |
|---|---|---|---|
| 7,635,474 | B2 | 12/2009 | Daly et al. |
| 7,666,405 | B2 | 2/2010 | Amalfitano et al. |
| 7,749,492 | B2 | 7/2010 | Bartlett et al. |
| 7,858,367 | B2 | 12/2010 | Amalfitano et al. |
| 7,968,340 | B2 | 6/2011 | Hallek et al. |
| 7,972,278 | B2 | 7/2011 | Graham et al. |
| 8,075,137 | B2 | 12/2011 | Klistorner et al. |
| 8,118,752 | B2 | 2/2012 | Hetling et al. |
| 8,137,274 | B2 | 3/2012 | Weng et al. |
| 8,163,543 | B2 | 4/2012 | Urabe et al. |
| 8,343,067 | B2 | 1/2013 | Jones et al. |
| 8,524,446 | B2 | 9/2013 | Gao et al. |
| 8,574,583 | B2 | 11/2013 | Kay et al. |
| 8,632,764 | B2 | 1/2014 | Xiao et al. |
| 8,663,624 | B2 | 3/2014 | Schaffer et al. |
| 8,900,858 | B2 | 12/2014 | Trono et al. |
| 9,193,956 | B2 | 11/2015 | Schaffer et al. |
| 9,198,595 | B2 | 12/2015 | Neitz et al. |
| 9,233,131 | B2 | 1/2016 | Schaffer et al. |
| 9,441,244 | B2 | 9/2016 | Schaffer et al. |
| 9,457,103 | B2 | 10/2016 | Schaffer et al. |
| 9,458,517 | B2 | 10/2016 | Schaffer et al. |
| 9,587,282 | B2 | 3/2017 | Schaffer et al. |
| 9,856,539 | B2 | 1/2018 | Schaffer et al. |
| 9,943,573 | B2 | 4/2018 | Constable et al. |
| 10,000,741 | B2 | 6/2018 | Chalberg et al. |
| 10,004,788 | B2 | 6/2018 | Constable et al. |
| 10,046,016 | B2 | 8/2018 | Schaffer et al. |
| 10,202,657 | B2 | 2/2019 | Schaffer et al. |
| 10,214,566 | B2 | 2/2019 | Schaffer et al. |
| 10,214,785 | B2 | 2/2019 | Schaffer et al. |
| 11,021,519 | B2 | 6/2021 | Chalberg et al. |
| 11,160,488 | B2 | 11/2021 | Neitz et al. |
| 11,236,402 | B2 | 2/2022 | Schaffer et al. |
| 11,248,214 | B2 | 2/2022 | Chalberg et al. |
| 2002/0136710 | A1 | 9/2002 | Samulski et al. |
| 2002/0155610 | A1 | 10/2002 | Colosi |
| 2002/0168342 | A1 | 11/2002 | Wang et al. |
| 2002/0192823 | A1 | 12/2002 | Bartlett |
| 2002/0194630 | A1 | 12/2002 | Manning, Jr. et al. |
| 2003/0087889 | A1 | 5/2003 | Strong et al. |
| 2003/0143732 | A1 | 7/2003 | Fosnaugh et al. |
| 2003/0171254 | A1 | 9/2003 | Sasaki et al. |
| 2004/0102765 | A1 | 5/2004 | Koenig |
| 2004/0180440 | A1 | 9/2004 | Zolotukhin |
| 2004/0234505 | A1 | 11/2004 | Naylor et al. |
| 2005/0053922 | A1 | 3/2005 | Schaffer et al. |
| 2005/0089973 | A1 | 4/2005 | Yocum et al. |
| 2005/0106558 | A1 | 5/2005 | Perabo et al. |
| 2005/0148069 | A1 | 7/2005 | Gage et al. |
| 2005/0220766 | A1 | 10/2005 | Amalfitano et al. |
| 2005/0260203 | A1 | 11/2005 | Wiegand et al. |
| 2005/0287122 | A1 | 12/2005 | Bartlett et al. |
| 2006/0051333 | A1 | 3/2006 | Arbetman et al. |
| 2006/0128020 | A1 | 6/2006 | Calos |
| 2006/0166363 | A1 | 7/2006 | Zolotukhin et al. |
| 2006/0193830 | A1 | 8/2006 | Hauswirth et al. |
| 2006/0234347 | A1 | 10/2006 | Harding et al. |
| 2006/0292117 | A1 | 12/2006 | Loiler et al. |
| 2007/0020624 | A1 | 1/2007 | Rubenfield et al. |
| 2007/0036760 | A1 | 2/2007 | Wilson et al. |
| 2007/0172460 | A1 | 7/2007 | Kleinschmidt et al. |
| 2007/0188710 | A1 | 8/2007 | Hetling et al. |
| 2007/0190028 | A1 | 8/2007 | Qu et al. |
| 2007/0190058 | A1 | 8/2007 | Shams |
| 2007/0196338 | A1 | 8/2007 | Samulski et al. |
| 2008/0152654 | A1 | 6/2008 | Reich |
| 2008/0269149 | A1 | 10/2008 | Bowles et al. |
| 2009/0112201 | A1 | 4/2009 | Young |
| 2009/0128776 | A1 | 5/2009 | Keating et al. |
| 2009/0191588 | A1 | 7/2009 | Hermens et al. |
| 2009/0191597 | A1 | 7/2009 | Samulski et al. |
| 2009/0202490 | A1 | 8/2009 | Schaffer et al. |
| 2009/0203071 | A1 | 8/2009 | Chen |
| 2009/0285826 | A1 | 11/2009 | Bonnel et al. |
| 2010/0008170 | A1 | 1/2010 | Sato et al. |
| 2010/0081707 | A1 | 4/2010 | Ali et al. |
| 2010/0091242 | A1 | 4/2010 | Baglini et al. |
| 2010/0166729 | A9 | 7/2010 | Madison et al. |
| 2010/0172871 | A1 | 7/2010 | Flannery et al. |
| 2010/0272719 | A1 | 10/2010 | Yu |
| 2010/0297084 | A1 | 11/2010 | Bennett et al. |
| 2011/0001465 | A1 | 1/2011 | Liu et al. |
| 2011/0014655 | A1 | 1/2011 | Otte et al. |
| 2011/0052678 | A1 | 3/2011 | Shantha et al. |
| 2011/0104120 | A1 | 5/2011 | Xiao et al. |
| 2011/0116046 | A1 | 5/2011 | Haeri et al. |
| 2011/0136227 | A1 | 6/2011 | Bakker et al. |
| 2011/0171262 | A1 | 7/2011 | Bakker et al. |
| 2011/0200530 | A1 | 8/2011 | Allemann et al. |
| 2011/0236353 | A1 | 9/2011 | Wilson et al. |
| 2011/0270256 | A1 | 11/2011 | Nelson et al. |
| 2012/0093772 | A1 | 4/2012 | Horsager et al. |
| 2012/0100606 | A1 | 4/2012 | Zolotukhin et al. |
| 2012/0141422 | A1 | 6/2012 | Barkats |
| 2012/0164106 | A1 | 6/2012 | Schaffer et al. |
| 2012/0172419 | A1 | 7/2012 | Neitz et al. |
| 2012/0225930 | A1 | 9/2012 | Acland et al. |
| 2013/0023034 | A1 | 1/2013 | Noordman et al. |
| 2013/0031709 | A1 | 2/2013 | Chen |
| 2013/0317091 | A1 | 11/2013 | Ye et al. |
| 2013/0323302 | A1 | 12/2013 | Constable et al. |
| 2014/0080900 | A1 | 3/2014 | Neitz et al. |
| 2014/0242031 | A1 | 8/2014 | Schaffer et al. |
| 2014/0275231 | A1 | 9/2014 | Boye et al. |
| 2014/0294771 | A1 | 10/2014 | Schaffer et al. |
| 2014/0341977 | A1 | 11/2014 | Constable et al. |
| 2014/0364338 | A1 | 12/2014 | Schaffer et al. |
| 2014/0371438 | A1 | 12/2014 | Constable et al. |
| 2015/0004101 | A1 | 1/2015 | Constable et al. |
| 2015/0025939 | A1 | 1/2015 | Chatterjee et al. |
| 2015/0079038 | A1 | 3/2015 | Deverman et al. |
| 2015/0111275 | A1 | 4/2015 | Palanker et al. |
| 2015/0118201 | A1 | 4/2015 | Xiao et al. |
| 2015/0132262 | A1 | 5/2015 | Schaffer et al. |
| 2015/0152142 | A1 | 6/2015 | Asokan et al. |
| 2015/0225702 | A1 | 8/2015 | Schaffer et al. |
| 2015/0232953 | A1 | 8/2015 | Schaffer et al. |
| 2015/0259395 | A1 | 9/2015 | Chalberg et al. |
| 2015/0315610 | A1 | 11/2015 | Nishie et al. |
| 2016/0015288 | A1 | 1/2016 | Neitz et al. |
| 2016/0017295 | A1 | 1/2016 | Schaffer et al. |
| 2016/0102324 | A1 | 4/2016 | Duchateau et al. |
| 2016/0184394 | A1 | 6/2016 | Schaffer et al. |
| 2016/0340393 | A1 | 11/2016 | Schaffer et al. |
| 2016/0375151 | A1 | 12/2016 | Schaffer et al. |
| 2016/0376323 | A1 | 12/2016 | Schaffer et al. |
| 2017/0044504 | A1 | 2/2017 | Schaffer et al. |
| 2017/0096683 | A1 | 4/2017 | Scaria et al. |
| 2017/0183647 | A1 | 6/2017 | Chavez et al. |
| 2018/0066022 | A1 | 3/2018 | Chalberg et al. |
| 2018/0066285 | A1 | 3/2018 | Ojala et al. |
| 2018/0125948 | A1 | 5/2018 | Constable et al. |
| 2018/0127471 | A1 | 5/2018 | Keravala |
| 2018/0289757 | A1 | 10/2018 | Schaffer et al. |
| 2018/0311319 | A1 | 11/2018 | Constable et al. |
| 2018/0320145 | A1 | 11/2018 | Chalberg et al. |
| 2018/0344197 | A1 | 12/2018 | Neitz et al. |
| 2019/0142975 | A1 | 5/2019 | Keravala et al. |
| 2019/0154667 | A1 | 5/2019 | Keravala et al. |
| 2019/0169237 | A1 | 6/2019 | Schaffer et al. |
| 2019/0218627 | A1 | 7/2019 | Schaffer et al. |
| 2019/0255192 | A1 | 8/2019 | Kirn et al. |
| 2020/0010851 | A1 | 1/2020 | Keravala |
| 2020/0149033 | A1 | 5/2020 | Chavez et al. |
| 2020/0231942 | A1 | 7/2020 | Schaffer et al. |
| 2021/0040501 | A1 | 2/2021 | Keravala |
| 2021/0077552 | A1 | 3/2021 | Schaffer et al. |

(56) References Cited

U.S. PATENT DOCUMENTS

| | | | |
|---|---|---|---|
| 2021/0130413 | A1 | 5/2021 | Keravala |
| 2021/0388030 | A1 | 12/2021 | Chalberg, Jr. et al. |

FOREIGN PATENT DOCUMENTS

| | | | |
|---|---|---|---|
| CN | 1826414 | A | 8/2006 |
| CN | 1966082 | A | 5/2007 |
| CN | 101484005 | A | 7/2009 |
| CN | 101532024 | A | 9/2009 |
| CN | 103561774 | A | 2/2014 |
| CN | 106232618 | A | 12/2016 |
| EP | 0407122 | A1 | 1/1991 |
| EP | 2292781 | A1 | 3/2011 |
| EP | 2298925 | A2 | 3/2011 |
| GB | 2545763 | A | 6/2017 |
| JP | H11100327 | A | 4/1999 |
| JP | 2002539176 | A | 11/2002 |
| JP | 2002363107 | A | 12/2002 |
| JP | 2008523813 | A | 7/2008 |
| JP | 2014518614 | A | 8/2014 |
| WO | WO-9208796 | A1 | 5/1992 |
| WO | WO-9428143 | A1 | 12/1994 |
| WO | WO-9522618 | A1 | 8/1995 |
| WO | WO-9526409 | A1 | 10/1995 |
| WO | WO-9738723 | A1 | 10/1997 |
| WO | WO-9813071 | A1 | 4/1998 |
| WO | WO-9851323 | A1 | 11/1998 |
| WO | WO-9914354 | A1 | 3/1999 |
| WO | WO-9916889 | A1 | 4/1999 |
| WO | WO-9936511 | A2 | 7/1999 |
| WO | WO-9945952 | A2 | 9/1999 |
| WO | WO-9966959 | A2 | 12/1999 |
| WO | WO-9967393 | A2 | 12/1999 |
| WO | WO-0001815 | A2 | 1/2000 |
| WO | WO-0015822 | A1 | 3/2000 |
| WO | WO-0028004 | A1 | 5/2000 |
| WO | WO-0170276 | A2 | 9/2001 |
| WO | WO-0212525 | A2 | 2/2002 |
| WO | WO-02053703 | A2 | 7/2002 |
| WO | WO-02082904 | A2 | 10/2002 |
| WO | WO-03018820 | A2 | 3/2003 |
| WO | WO-03023032 | A2 | 3/2003 |
| WO | WO-03054197 | A2 | 7/2003 |
| WO | WO-03080648 | A2 | 10/2003 |
| WO | WO-03093436 | A2 | 11/2003 |
| WO | WO-2004079332 | A2 | 9/2004 |
| WO | WO-2004108922 | A2 | 12/2004 |
| WO | WO-2004112727 | A2 | 12/2004 |
| WO | WO-2005005610 | A2 | 1/2005 |
| WO | WO-2005033321 | A2 | 4/2005 |
| WO | WO-2006066066 | A2 | 6/2006 |
| WO | WO-2006110689 | A2 | 10/2006 |
| WO | WO-2007084773 | A2 | 7/2007 |
| WO | WO-2007120542 | A2 | 10/2007 |
| WO | WO-2007148971 | A2 | 12/2007 |
| WO | WO-2008131951 | A1 | 11/2008 |
| WO | WO-2008142124 | A1 | 11/2008 |
| WO | WO-2008150459 | A1 | 12/2008 |
| WO | WO-2009073551 | A2 | 6/2009 |
| WO | WO-2009104964 | A1 | 8/2009 |
| WO | WO-2009105669 | A2 | 8/2009 |
| WO | WO-2009137006 | A2 | 11/2009 |
| WO | WO-2009154452 | A1 | 12/2009 |
| WO | WO-2010093784 | A2 | 8/2010 |
| WO | WO-2010099960 | A2 | 9/2010 |
| WO | WO-2010138263 | A2 | 12/2010 |
| WO | WO-2011020710 | A2 | 2/2011 |
| WO | WO-2011034947 | A2 | 3/2011 |
| WO | WO-2011088081 | A1 | 7/2011 |
| WO | WO-2011112089 | A2 | 9/2011 |
| WO | WO-2011117258 | A2 | 9/2011 |
| WO | WO-2011122950 | A1 | 10/2011 |
| WO | WO-2011126808 | A2 | 10/2011 |
| WO | WO-2011137344 | A2 | 11/2011 |
| WO | WO-2012068317 | A2 | 5/2012 |
| WO | WO-2012145601 | A2 | 10/2012 |
| WO | WO-2013029030 | A1 | 2/2013 |
| WO | WO-2013170078 | A1 | 11/2013 |
| WO | WO-2013173129 | A2 | 11/2013 |
| WO | WO-2013173512 | A2 | 11/2013 |
| WO | WO-2013188316 | A1 | 12/2013 |
| WO | WO-2014186160 | A1 | 11/2014 |
| WO | WO-2014194132 | A1 | 12/2014 |
| WO | WO-2014207190 | A1 | 12/2014 |
| WO | WO-2015048534 | A1 | 4/2015 |
| WO | WO-2015054653 | A2 | 4/2015 |
| WO | WO-2015058048 | A1 | 4/2015 |
| WO | WO-2015134643 | A1 | 9/2015 |
| WO | WO-2015142941 | A1 | 9/2015 |
| WO | WO-2015168666 | A2 | 11/2015 |
| WO | WO-2015191693 | A2 | 12/2015 |
| WO | WO-2016141078 | A1 | 9/2016 |
| WO | WO-2016144892 | A1 | 9/2016 |
| WO | WO-2017023724 | A1 | 2/2017 |
| WO | WO-2017112868 | A1 | 6/2017 |
| WO | WO-2017190125 | A1 | 11/2017 |
| WO | WO-2017197355 | A2 | 11/2017 |
| WO | WO-2017218974 | A2 | 12/2017 |
| WO | WO-2017218981 | A2 | 12/2017 |
| WO | WO-2018075798 | A1 | 4/2018 |
| WO | WO-2018160686 | A1 | 9/2018 |
| WO | WO-2018170473 | A1 | 9/2018 |
| WO | WO-2019046069 | A1 | 3/2019 |

OTHER PUBLICATIONS

Guziewicz, et al. (2013) “Recombinant AAV-Mediated BEST1 Transfer to the Retinal Pigment Epithelium: Analysis of Serotype-Dependent Retinal Effects”, PLOS one, 8(10) article e75666, 11 pages long. (Year: 2013).*

Amato, et al. (2023) “Gene therapy in bestrophinopathies: Insights from preclinical studies in preparation for clinical trials”, Saudi Journal of Opthalmology, 37: 287-95. (Year: 2023).*

Acland, et al., “Long-term restoration of rod and cone vision by single dose rAAV mediated gene transfer to the retina in a canine model of childhood blindness.” Mol Ther. 2005; 12(6): 1072-1082.

Adachi, et al., “A New Recombinant Adeno-Associated Virus (AAV)-Based Random Peptide Display Library System: Infection-Defective AAV 1 .9-3 As A Novel Targeted Platform for Vector Evolution”; Gene Therapy and Regulation; vol. 5, No. 1, pp. 31-55 (Oct. 2010).

Adamis, et al., “Inhibition of vascular endothelial growth factor prevents retinal ischemia-associated iris neovascularization in a nonhuman primate.” Arch Ophthalmol. 1996; 114(1): 66-71.

Adhi, et al., “Optical coherence tomography current and future applications.” Curr Opin Ophthalmol. 2013; 24(3): 213-221.

Aflibercept FDA Entry and Label, 2015. 28 pages. downloaded fromhttp://www.accessdata.fda.gov/scripts/cder/drugsatfda/index.cfm?fuseaction=Search.Label_ApprovalHistory#apphist.

Aiello, et al., “Suppression of retinal neovascularization in vivo by inhibition of vascular endothelial growth factor (VEGF) using soluble VEGF-receptor chimeric proteins.” Proc Natl Acad Sci USA. 1995; 92(23):10457-10461.

Akimoto, et al., “Adenovirally expressed basic fibroblast growth factor rescues photoreceptor cells in RCS rats.” Invest Ophthalmol Vis Sci. 1999; 40(2): 273-279.

Akiyama, et al., “Intraocular Injection of an Aptamer that Binds PDGF-B: A Potential Treatment for Proliferative Retinopathies,” Journal of Cellular Physiology, vol. 207, pp. 407-412 (2006).

Albert, Henrik, et al. “Site specific integration of DNA into wildtype and mutant lox sites placed in the plant genome.” The Plant Journal (1995); 7.4: 649-659.

Alexander, John J., et al. “Restoration of cone vision in a mouse model of achromatopsia.” Nature Medicine (2007); 13.6: 685-687.

Ali, et al., “Gene therapy for inherited retinal degeneration.” Br J Ophthalmol. 1997; 81(9): 795-801.

Ali, et al., “Restoration of photoreceptor ultrastructure and function in retinal degeneration slow mice by gene therapy.” Nature Genetics; vol. 25, pp. 306-310 (Jul. 2000).

(56) References Cited

OTHER PUBLICATIONS

Allocca, et al., "Novel adeno-associated virus serotypes efficiently transduce murine photoreceptors", Journal of Virology (Oct. 2007), 81(20): 11372-11380.
Amado, et al., "Safety and efficacy of subretinal readministration of a viral vector in large animals to treat congenital blindness." Sci Transl Med. 2010; 2(21): 21ra16. doi: 10.1126/scitranslmed.3000659.
Anand, et al., "A deviant immune response to viral proteins and transgene product is generated on subretinal administration of adenovirus and adeno-associated virus." Mol Ther. 2002; 5(2): 125-132.
Arnold, et al., "Extracts from "clinical evidence": age related macular degeneration." BMJ. 2000; 321(7263):741-744.
Asokan, et al., "Reengineering a receptor footprint of adeno-associated virus enables selective and systemic gene transfer to muscle", Nat Biotechnol, (Jan. 2010); 28(1): 79-82.
Asuri, et al., "Directed evolution of adeno-associated virus for enhanced gene delivery and gene targeting in human pluripotent stem cells." Mol Ther. (Feb. 2012); 20(2): 329-338. Epub Nov. 22, 2011.
Auricchio, et al., "Exchange of surface proteins impacts on viral vector cellular specificity and transduction characteristics: the retina as a model." Hum Mol Genet. 2001; 10(26): 3075-3081.
Auricchio, et al., "Inhibition of retinal neovascularization by intraocular viral-mediated delivery of anti-angiogenic agents." Mol Ther. 2002; 6(4): 490-494.
[Author Unknown] Aflibercept, Drugs RD (2008); 9(4): 261-269.
Bailey, et al., "Exercise increases soluble vascular endothelial growth factor receptor-1 (sFlt-1) in circulation of healthy volunteers." Med Sci Monit. 2006; 12(2): CR45-50.
Bainbridge, et al., "Effect of gene therapy on visual function in Leber's congenital amaurosis." N Engl J Med. 2008; 358(21): 2231-2239.
Bainbridge, et al., "Inhibition of retinal neovascularisation by gene transfer of soluble VEGF receptor sFlt-1." Gene Ther. 2002; 9(5): 320-326.
Bainbridge, J. W., and Ali, R. R. "The eyes have it! Ocular gene therapy trials for LCA look promising." Gene Ther (2008); 15: 1191-1192.
Barleon, et al., "Mapping of the sites for ligand binding and receptor dimerization at the extracellular domain of the vascular endothelial growth factor receptor FLT-1." J Biol Chem. 1997; 272(16): 10382-10388.
Barleon, et al., "Soluble VEGFR-1 secreted by endothelial cells and monocytes is present in human serum and plasma from healthy donors." Angiogenesis. 2001; 4(2):143-154.
Belgore, et al., "Plasma levels of vascular endothelial growth factor (VEGF) and its receptor, Flt-1, in haematological cancers: a comparison with breast cancer." Am J Hematol. 2001; 66(1): 59-61.
Belteki, Gusztav, et al. "Site-specific cassette exchange and germline transmission with mouse ES cells expressing C31 integrase." Nature Biotechnology (2003); 21.3: 321-324.
Bennett, et al., "AAV2 gene therapy readministration in three adults with congenital blindness." Sci Transl Med. 2012; 4(120): 120ra15.
Bennett, et al., "Gene therapy for retinitis pigmentosa." Curr Opin Mol Ther. 2000; 2(4): 420-425.
Bennett, "Immune response following intraocular delivery of recombinant viral vectors." Gene Ther. 2003; 10(11): 977-982.
Bennicelli, et al., "Reversal of blindness in animal models of leber congenital amaurosis using optimized AAV2-mediated gene transfer." Mol Ther. 2008; 16(3): 458-465.
Berge, S. M. et al., "Pharmaceutical Salts," Journal of Pharmaceutical Sciences, Jan. 1977, vol. 66, No. 1, pp. 1-19.
Bethke, Bruce, and Sauer, Brian, "Segmental genomic replacement by Cre-mediated recombination: genotoxic stress activation of the p53 promoter in single-copy transformants." Nucleic Acids Research (1997); 25.14: 2828-2834.
Bhisitkul, "Vascular endothelial growth factor biology: clinical implications for ocular treatments." Br J Ophthalmol. 2006; 90(12): 1542-1547.
Bi, Yanzhen, et al. "Pseudo attP sites in favor of transgene integration and expression in cultured porcine cells identified by streptomyces phage phiC31 integrase." BMC Molecular Biology (2013); 14: 20, 12 pages.
Bichsel, et al., "Bacterial delivery of nuclear proteins into pluripotent and differentiated cells", PLoS One (Jan. 2011); 6(1): e16465, pp. 1-9.
Blacklow, et al., "A Seroepidemiologic Study of Adenovirus-Associated Virus Infection in Infants and Children." Am J Epidemiol.; vol. 94, No. 4, pp. 359-366 (Oct. 1971).
Boucas, et al., "Engineering adeno-associated virus serotype 2-based targeting vectors using a new insertion site-position 453-and single point mutations." J Gene Med., Dec. 2009, 11(12):1103-1113.
Brinkmann, et al., "Selective retina therapy (SRT): a review on methods, techniques, preclinical and first clinical results." Bull Soc Beige Ophtalmol. 2006; 302: 51-69.
Brinkmann, et al., "Origin of retinal pigment epithelium cell damage by pulsed laser irradiance in the nanosecond to microsecond time regimen." Laser Surg Med. 2000; 27: 451-464.
Brown, et al., "Ranibizumab versus verteporfin photodynamic therapy for neovascular age-related macular degeneration: Two-year results of the ANCHOR study." Ophthalmology. 2009; 116(1): 57-65.
Buch, et al., "In Contrast to AAC-Mediated Cntf Expression. AAV-Mediated Gdnf Expression Enhances Gene Replacement Therapy in Rodent Models of Retinal Degeneration"; Molecular Therapy; vol. 14, No. 5, pp. 700-709 (Nov. 2006).
Buning, et al., "Receptor targeting of adeno-associated virus vectors", Gene Therapy, 2003, vol. 10, pp. 1142-1511.
Buning, H. et al., "Recent Developments in Adeno-associated Virus Vector Technology", The Journal of Gene Medicine, (2008), vol. 10, No. 7, pp. 717-733.
Cai, Xue, et al. "Gene delivery to mitotic and postmitotic photoreceptors via compacted DNA nanoparticles results in improved phenotype in a mouse model of retinitis pigmentosa." The FASEB Journal (2010); 24.4: 1178-1191.
Calcedo, Roberto, et al. "Worldwide epidemiology of neutralizing antibodies to adeno-associated viruses." Journal of Infectious Diseases (2009); 199.3: 381-390.
Calos, Michele P. "The C31 Integrase System for Gene Therapy." Current Gene Therapy (2006); 6.6: 633-645.
Calvo, et al., "Upstream open reading frames cause widespread reduction of protein expression and are polymorphic among humans." PNAS (May 2009); 106 (18): 7507-7512. Epub Apr. 16, 2009.
Campochiaro, et al., "Adenoviral vector-delivered pigment epithelium-derived factor for neovascular age-related macular degeneration: results of a phase I clinical trial." Hum Gene Ther. 2006; 17(2): 167-176.
Campochiaro, et al., "Monitoring ocular drug therapy by analysis of aqueous samples." Ophthalmology. 2009; 116(11): 2158-2164.
Campochiaro, "Gene Transfer for Neovascular Age-Related Macular Degeneration." Human Gene Therapy (2011); 22(5): 523-529.
Campochiaro, "Molecular targets for retinal vascular diseases." J Cell Physiol. 2007; 210(3): 575-581.
Cao, et al., "A subretinal matrigel rat choroidal neovascularization (CNV) model and inhibition of CNV and associated inflammation and fibrosis by VEGF trap." Invest Ophthalmol Vis Sci. 2010; 51(11): 6009-6017.
Cayouette, et al., "Adenovirus-mediated gene transfer of ciliary neurotrophic factor can prevent photoreceptor degeneration in the retinal degeneration (rd) mouse." Hum Gene Ther. 1997; 8(4): 423-430.
Chadderton, et al., "Improved Retinal Function in a Mouse Model of Dominant Retinitis Pigmentosa Following AAV-delivered Gene Therapy", Molecular Therapy; vol. 17, No. 4, pp. 593-599 (Apr. 2009).
Chakrabarti, et al., "Normal T-cell turnover in sooty mangabeys harboring active simian immunodeficiency virus infection." J Virol. 2000; 74(3): 1209-1223.

(56) References Cited

OTHER PUBLICATIONS

Chalberg, et al., "Integration Specificity of Phage C31 Integrase in the Human Genome", J Mol Biol. (Mar. 17, 2006); 357(1): 28-48. Epub Dec. 22, 2005.
Chalberg, Thomas W., et al. "C31 integrase confers genomic integration and long-term transgene expression in rat retina." Investigative Ophthalmology & Visual Science (2005); 46.6: 2140-2146.
Chen, et al., "Use of nepafenac (Nevanac) in combination with intravitreal anti-VEGF agents in the treatment of recalcitrant exudative macular degeneration requiring monthly injections." Clin Ophthalmol. 2010; 4:1249-1252.
Chiu, M. I., and Nathans, J., "Blue cones and cone bipolar cells share transcriptional specificity as determined by expression of human blue visual pigment-derived transgenes." The Journal of Neuroscience (1994); 14.6: 3426-3436.
Choi, al., "AAV Hybrid Serotypes: Improved Vectors for Gene Delivery."; Current Gene Therapy; vol. 5, No. 3, pp. 299-310 (Jun. 2005).
Choi, et al., "Production of recombinant adeno-associated viral vectors." Curr Protoc Hum Genet. 2007; Chapter 12: Unit 12.9.doi: 10.1002/0471142905.hg1209s53.
Chung, et al., "Angiogenesis in myocardial infarction. An acute or chronic process?" Eur Heart J. 2002; 23(20): 1604-1608.
Cideciyan, Artur V., et al. "Human gene therapy for RPE65 isomerase deficiency activates the retinoid cycle of vision but with slow rod kinetics." Proceedings of the National Academy of Sciences (2008); 105.39: 15112-15117.
Cideciyan, et al., "Human RPE65 gene therapy for Leber congenital amaurosis: persistence of early visual improvements and safety at 1 year." Hum Gene Ther. 2009; 20(9): 999-1004.
Clark, et al., "Expression of clusterin/sulfated glycoprotein-2 under conditions of heat stress in rat Sertoli cells and a mouse Sertoli cell line." J Androl. 1997; 18(3): 257-63.
Clinical trial, A Phase I/II Controlled Dose-escalating Trial to Establish the Baseline Safety and Efficacy of a Single Subretinal Injection of rAAV.sFit-1 Into Eyes of Patients With Exudative Age-related Macular Degeneration (AMD). NCT01494805. Updated—Dec. 16, 2011, 4 pages.
Clinical Trial NCT01494805, "Safety and Efficacy Study of rAAV. sFlt-1 in Patients With Exudative Age-Related Macular Degeneration (AMD)." as published first posted on Dec. 19, 2011, 7 pages, Retrieved from: https://clinicaltrials.gov/ct2/show/NCT01494805.
Clinical Trial NCT01494805, History of Changes for "Safety and Efficacy Study of rAAV.sFIt-1 in Patients With Exudative Age-Related Macular Degeneration (AMD)", NCT01494805, Submitted Date: Dec. 15, 2011 (v1), ClinicalTrials.gov, https://clinicaltrials.gov/ct2/history/NCT01494805?V_1=View#StudyPage Top, 9 pages.
Clinical trial. Safety and Tolerability Study of AAV2-sFLT-1 in Patients With Neovascular Age-Related Macular Degeneration (AMD). NCT01024998. Last updated: Jan. 28, 2014.
Comparison of L-opsin promoter to SEQ ID No. 80. Printed Feb. 2, 2017, in U.S. Appl. No. 14/660,657, 4 pages.
Co-pending U.S. Appl. No. 14/444,347, inventor Schaffer; et al, filed on Jul. 28, 2014.
Co-pending U.S. Appl. No. 14/444,375, inventor Schaffer; et al, filed on Jul. 28, 2014.
Co-pending U.S. Appl. No. 14/606,543, inventor Schaffer; et al, filed on Jan. 27, 2015.
Co-pending U.S. Appl. No. 14/938,154, inventor Schaffer; et al, filed on Nov. 11, 2015.
Co-pending U.S. Appl. No. 15/229,699, inventor Schaffer; et al, filed on Aug. 5, 2016.
Co-pending U.S. Appl. No. 15/244,884, inventor Schaffer; et al, filed on Aug. 23, 2016.
Co-pending U.S. Appl. No. 15/244,892, inventor Schaffer; et al, filed on Aug. 23, 2016.
Co-pending U.S. Appl. No. 15/939,674, inventor Neitz, et al, filed on Mar. 29, 2018.
Costa, et al., "Intravitreal Bevacizumab for Choroidal Neovascularization Caused by AMD (IBeNA Study): Results of a Phase 1 Dose-Escalation Study." Investigative Ophthalmology & Visual Science (2006); 47 (10): 4569-4578.
Cronin, et al., "Efficient transduction and optogenetic stimulation of retinal bipolar cells by a synthetic adeno-associated virus capsid and promoter". EMBO Mol Med. (Sep. 2014); 6(9): 1175-1190.
Csermely, et al., "The 90-kDa molecular chaperone family: structure, function, and clinical applications." A comprehensive review. Pharmacol Ther. 1998; 79(2):129-168.
Curtis, et al., "Risks of mortality, myocardial infarction, bleeding, and stroke associated with therapies for age-related macular degeneration." Arch Ophthalmol. 2010; 128(10): 1273-1279.
Dalkara, Deniz, et al. "In vivo-directed evolution of a new adeno-associated virus for therapeutic outer retinal gene delivery from the vitreous." Science Translational Medicine (2013); 5 (189): 189ra76-189ra76.
Dalkara, et al., "Developing Photoreceptor Targeted AAV Variant by Directed Evolution." ARVO Annual Meeting Abstract Search and Program Planner; vol. 2011, pp. 4381 (May 2011).
Database Geneseq [Online] Oct. 16, 2008 (Oct. 16, 2008), "Modified Adeno-associated virus (hu.44) capsid protein, VP1, hu.44R2.", retrieved from EBI accession No. GSP:AEL63853, Database accession No. AEL63853, 1 page.
Database Geneseq [Online] Oct. 16, 2008 (Oct. 16, 2008), "Modified Adeno-associated virus (hu.44) capsid protein, VP1, hu.44R3.", retrieved from EBI accession No. Gsp: AEL63854, Database accession No. AEL63854.
Davidson, et al., "A model system for in vivo gene transfer into the central nervous system using an adenoviral vector." Nat Genet. 1993; 3(3): 219-223.
Davidson, et al., "Recombinant adeno-associated virus type 2, 4, and 5 vectors: transduction of variant types and regions in the mammalian central nervous system."; Proc Natl Acad Sci USA; vol. 97, No. 7, pp. 3428-3432 (Mar. 28, 2000).
Davis, et al., "Direct gene transfer into skeletal muscle in vivo: factors affecting efficiency of transfer and stability of expression." Hum Gene Ther. 1993; 4(2): 151-159.
Dawson, et al., "Pigment epithelium-derived factor: a potent inhibitor of angiogenesis." Science. 1999; 285(5425): 245-248.
Day, et al., "Advances in AAV vector development for gene therapy in the retina." Adv Exp Med Biol. (2014); 801: 687-693.
De Vries, et al., "The fms-like tyrosine kinase, a receptor for vascular endothelial growth factor." Science. 1992; 255(5047): 989-991.
Definition of "plasmid", Biology Dictionary, 2018, 1 page.
Dejneka, et al., "Gene therapy and animal models for retinal disease." Dev Ophthalmol. 2003; 37: 188-198.
Dejneka, et al., "Gene therapy and retinitis pigmentosa: advances and future challenges." Bioessays 2001; 23(7): 662-8.
Den Dunnen, et al., "Mutation nomenclature extensions and suggestions to describe complex mutations: a discussion."; Human Mutation; vol. 15, pp. 7-12 (2000).
Deonarain, "Ligand-targeted receptor-mediated vectors for gene delivery." Expert Opin. Ther. Pat. (1998); 8:53-69.
DeValois, R.L. and DeValois, K.K., "A multi-stage color model." Vision Research (1993); 33.8: 1053-1065.
Deyle and Russell, "Adeno-associated virus vector integration." Curr. Opin. Mol. Therapy (2009); 11 (4): 442-447.
Diab, et al., "Angiogenic factors for the prediction of pre-eclampsia in women with abnormal midtrimester uterine artery Doppler velocimetry." Int J Gynaecol Obstet. 2008; 102(2):146-151.
Diprimo, et al., "Surface loop dynamics in adeno-associated virus capsid assembly", Journal of Virology (2008); vol. 82, No. 11, pp. 5178-5189.
Dudus, et al., "Persistent trans gene product in retina, optic nerve and brain after intraocular injection of rAAV." Vision Res. 1999; 39(15): 2545-2553.
Dull et al., "A third-generation lentivirus vector with a conditional packaging system", Journal of Virology (1998), 72(11): 8463-8471.
Easton, et al., "The Hsp110 and Grp170 stress proteins: newly recognized relatives of the Hsp70s." Cell Stress Chaperones. 2000; 5(4): 276-290.

(56) References Cited

OTHER PUBLICATIONS

Edelstein et al., "Gene therapy clinical trials worldwide 1989-2004—an overview", Journal Gene Med. (2004); 6: 597-602.
Erles et al.; "Update on the prevalence of serum antibodies (IgG and IgM) to adeno-associated virus (AAV)." J Med Virol.; vol. 59, No. 3, pp. 406-411 (Nov. 1999).
European Patent Application No. 13791695.3, Extended European Search Report dated Dec. 21, 2015, 10 pages.
European Patent Application No. 15765668.7, Extended European Search Report dated Mar. 7, 2018, 18 pages.
European Patent Application No. 15765668.7, Partial Supplemental European Search Report dated Nov. 10, 2017, 8 pages.
European U.S. Appl. No. 16/759,427, Extended European Search Report dated Aug. 8, 2018, 9 pages.
European Patent Application No. EP 20189453.2, Extended European Search Report dated Feb. 25, 2021, 11 pages.
Excoffon et al., "Directed evolution of adeno-associated virus to an infectious respiratory virus," PNAS, Mar. 10, 2009, vol. 106, No. 10, pp. 3865-3870.
Ferrara, "Vascular endothelial growth factor: basic science and clinical progress." Endocr Rev. 2004; 25(4): 581-611.
Flotte, et al.; "Gene expression from adeno-associated virus vectors in airway epithelial cells." Am J Respir Cell Mol Biol.; vol. 7, No. 3, pp. 349-356 (Sep. 1992).
Fong, et al., "The use and development of retroviral vectors to deliver cytokine genes for cancer therapy." Crit Rev Ther Drug Carrier Syst. 2000; 17(1): 1-60.
Fotsis, et al., "The endogenous oestrogen metabolite 2-methoxyoestradiol inhibits angiogenesis and suppresses tumour growth." Nature. 1994; 368(6468): 237-239.
Framme, et al., "Selective targeting of the retinal pigment epithelium in rabbit eyes with a scanning laser beam." Investigative Ophthalmology & Visual Science (2007); 48(4): 1782-1792.
Funk, et al., "Neovascular age-related macular degeneration: intraocular cytokines and growth factors and the influence of therapy with ranibizumab." Ophthalmology. 2009; 116(12): 2393-2399.
Galan, et al., "Association of age-related macular degeneration with polymorphisms in vascular endothelial growth factor and its receptor." Ophthalmology. 2010; 117(9): 1769-1774.
Gardner, et al., "X-Linked Cone Dystrophy Caused by Mutation of the Red and Green Cone Opsins". Am J Hum Genet. (Jul. 9, 2010); 87(1): 26-39.
Geller, et al., "An HSV-1 vector expressing tyrosine hydroxylase causes production and release of L-dopa from cultured rat striatal cells." J Neurochem. 1995; 64(2):487-496.
Geller, et al., "Infection of cultured central nervous system neurons with a defective herpes simplex virus 1 vector results in stable expression of *Escherichia coli* beta-galactosidase." Proc Natl Acad Sci USA. 1990; 87(3): 1149-1153.
Geller, et al., "Long-term increases in neurotransmitter release from neuronal cells expressing a constitutively active adenylate cyclase from a herpes simplex virus type 1 vector." Proc Natl Acad Sci USA. 1993; 90(16): 7603-7607.
GenBank accession No. ABZ10812; AAV13 capsid protein sequence downloaded from NBCI; downloaded on Nov. 3, 2008.
GenBank accession No. AAZ79678; rat AAV1 VP3 capsid protein sequence downloaded from NCBI; downloaded on Nov. 3, 2008.
GenBank [online], Accession No. U47119.2, "Cloning vector pCI, mammalian expression vector." May 10, 2004—uploaded, [retrieved on Apr. 12, 2017], https://www.ncbi.nlm.nih.gov/nuccore/U47119, 2 pages.
Gerdes, et al., "Cell cycle analysis of a cell proliferation-associated human nuclear antigen defined by the monoclonal antibody Ki-67." J Immunol. 1984; 133(4):1710-1715.
Girod, et al., "Genetic capsid modifications allow efficient re-targeting of adeno-associated virus type 2." Nat. Med. (1999); vol. 5, No. 9, pp. 1052-1056.
Glushakova, Lyudmyla G., et al., "Human blue-opsin promoter preferentially targets reporter gene expression to rat s-cone photoreceptors." Investigative Ophthalmology & Visual Science (2006); 47.8: 3505-3513.
Goldman, et al., "Paracrine expression of a native soluble vascular endothelial growth factor receptor inhibits tumor growth, metastasis, and mortality rate." Proc Natl Acad Sci USA. 1998; 95(15): 8795-8800.
Goverdhana, et al., Regulatable gene expression systems for gene therapy applications: progress and future challenges. Molecular Therapy : The Journal of the American Society of Gene Therapy. 2005; 12(2): 189-211.
Gragoudas, et al., "Pegaptanib for neovascular age-related macular degeneration." N Engl J Med. 2004; 351(27): 2805-2816.
Graubert, et al., "Vascular repair after menstruation involves regulation of vascular endothelial growth factor-receptor phosphorylation by sFLT-1." Am J Pathol. 2001; 158(4): 1399-1410.
Gray and Zolotukhin, "Design and Construction of Functional AAV Vectors." Methods in Molecular Biology. 2011; 807: 25-46.
Gray, et al., "Directed Evolution of a Novel Adeno-associated Virus (AAV) Vector That Crosses the Seizure-compromised Blood-Brain Barrier (BBB)." Molecular Therapy; vol. 18, No. 3, pp. 570-578 (2010).
Gregory-Evans, et al., "Ex vivo Gene Therapy Using Intravitreal Injection of GDNF-secreting Mouse Embryonic Stem Cells in a Rat Model of Retinal Degeneration." Molecular Vision; vol. 15, pp. 962-973 (May 13, 2009).
Grieger, et al., "Separate Basic Region Motifs within the Adeno-Associated Virus Capsid Proteins Are Essential for Infectivity and Assembly." J. Virol. (2006), 80(11): 5199-5210.
Grifman, et al., "Incorporation of tumor-targeting peptides into recombinant adeno-associated virus capsids". Molecular Therapy (2001); vol. 3, No. 6, pp. 964-975.
Grimm, et al., "In Vitro and In Vivo Gene Therapy Vector Evolution via Multispecies Interbreeding and Retargeting of Adeno-Associated Viruses." Journal of Virology; vol. 82, No. 12, pp. 5887-5911 (Jun. 2008).
Groth, Amy C., et al., "A phage integrase directs efficient site-specific integration in human cells." Proc Natl Acad Sci U S A. (2000); 97.11: 5995-6000.
Gunther, Karen L., et al., "A novel mutation in the short-wavelength-sensitive cone pigment gene associated with a tritan color vision defect." Visual Neuroscience (2006); 23.3-4: 403-409.
Halbert, et al., "Repeat transduction in the mouse lung by using adeno-associated virus vectors with different serotypes." J. Virol.; vol. 74, No. 3, pp. 1524-1532 (Feb. 2000).
Hasumi, et al., "Soluble FLT-1 expression suppresses carcinomatous ascites in nude mice bearing ovarian cancer." Cancer Res. 2002; 62(7): 2019-2023.
Hauswirth, et al., "Treatment of leber congenital amaurosis due to RPE65 mutations by ocular subretinal injection of adeno-associated virus gene vector: short-term results of a phase I trial." Hum Gene Ther. 2008; 19(10): 979-990.
He, et al., "Alternative splicing of vascular endothelial growth factor (VEGF)-R1 (FLT-1) pre-mRNA is important for the regulation of VEGF activity." Mol Endocrinol. 1999; 13(4): 537-545.
Heinis, Christian, and Johnsson, Kai, "Using peptide loop insertion mutagenesis for the evolution of proteins." Methods Mol Biol. (2010); 634: 217-232.
Hellstrom, et al., "Cellular tropism and transduction properties of seven adeno-associated viral vector serotypes in adult retina after intravitreal injection." Gene Therapy (2009); 16: 521-532.
Hirsch, et al., "Directed Evolution of the AAV Capsid for Human Embryonic Stem Cell Transduction." Molecular Therapy; vol. 17, Supp. 1, S177-S178 (May 2009).
Hoess, R.H. et al., "The role of the loxP spacer region in P1 site-specific recombination." Nucleic Acids Research (1986); 14.5: 2287-2300.
Hoffman, et al., "Cell-mediated immune response and stability of intraocular transgene expression after adenovirus-mediated delivery." Invest Ophthalmol Vis Sci. 1997; 38(11): 2224-2233.
Honda, et al., "Experimental subretinal neovascularization is inhibited by adenovirus-mediated soluble VEGF/flt-1 receptor gene

(56) References Cited

OTHER PUBLICATIONS transfection: a role of VEGF and possible treatment for SRN in age-related macular degeneration." Gene Ther. 2000; 7(11): 978-985.
Hu, et al., "Design of retroviral vectors and helper cells for gene therapy." Pharmacol Rev. 2000; 52(4): 493-511.
Huang, et al., "Innate immune recognition of viruses and viral vectors." Hum Gene Ther. 2009; 20(4): 293-301.
Huttner, et al., "Genetic Modifications of the Adeno-Associated Virus Type 2 Capsid Reduce Affinity to Human Serum Antibodies and Overcome Potential Limitations of Neutralizing Antibodies for the Used in Human Gene Therapy"; Blood; vol. 100, No. 11, pp. Abstract No. 5548 (Nov. 16, 2002), 2 pgs.
Huttner, et al., "Genetic modifications of the adeno-associated virus type 2 capsid reduce the affinity and the neutralizing effects of human serum antibodies." Gene Ther; vol. 10, No. 26, pp. 2139-2147 (Dec. 2003).
Ibrahim, et al., "Heat shock and arsenite induce expression of the nonclassical class I histocompatibility HLA-G gene in tumor cell lines." Cell Stress Chaperones. 2000; 5(3): 207-218.
International Preliminary Report on Patentability for International Application No. PCT/US2010/048964, mailed Mar. 20, 2012, 14 pages.
International Preliminary Report on Patentability for International Application No. PCT/US2013/040011, mailed Nov. 18, 2014, 48 pages.
International Preliminary Report on Patentability for International Application No. PCT/US2013/045043, mailed Dec. 16, 2014, 9 pages.
International Preliminary Report on Patentability for International Application No. PCT/US2015/021087, mailed Sep. 20, 2016, 8 pages.
International Preliminary Report on Patentability for International Application No. PCT/US2016/068312, dated Jun. 26, 2018, 12 pages.
International Search Report and Written Opinion for International Application No. PCT/US2010/048964, mailed Jun. 17, 2011, 23 pages.
International Search Report and Written Opinion for International Application No. PCT/US2013/040011, mailed Dec. 17, 2013, 57 pages.
International Search Report and Written Opinion for International Application No. PCT/US2013/045043, mailed Nov. 12, 2013, 11 pages.
International Search Report and Written Opinion for International Application No. PCT/US2015/021087, mailed Aug. 12, 2015, 12 pages.
International Search Report and Written Opinion for International Application No. PCT/US2016/020482, mailed Aug. 8, 2016, 12 pages.
International Search Report and Written Opinion for International Application No. PCT/US2016/068312, mailed May 3, 2017, 22 pages.
Invitation to Pay Additional Fees for International Application No. PCT/US2013/040011, mailed Oct. 11, 2013, 5 pages.
Invitation to Pay Additional Fees for International Application No. PCT/US2015/021087, mailed Jun. 18, 2015, 3 pages.
Invitation to Pay Additional Fees for International Application No. PCT/US2016/020482, mailed May 6, 2016, 3 pages.
Jacobs, Gerald H., "A perspective on color vision in platyrrhine monkeys." Vision Research (1998); 38.21: 3307-3313.
Jacobs, Gerald H., et al. "Emergence of novel color vision in mice engineered to express a human cone photopigment." Science (2007); 315.5819: 1723-1725.
Jacobson, et al., "Safety in nonhuman primates of ocular AA V2-RPE65, a candidate treatment for blindness in Leber congenital amaurosis." Hum Gene Ther. 2006; 17(8): 845-858.
Jacobson, et al., "Safety of recombinant Adeno-associated virus type 2-RPE65 vector delivered by ocular subretinal injection", Mol Ther. (2006); 13(6):1074-1084.
Jacobson, et al., "Gene therapy for leber congenital amaurosis caused by RPE65 mutations: safety and efficacy in 15 children and adults followed up to 3 years." Arch Ophthalmol. (2012); 130(1): 9-24.
Jang, et al., "An evolved adeno-associated viral variant enhances gene delivery and gene targeting in neural stem cells." Mol Ther. (Apr. 2011); 19(4): 667-675.
Johnson-Saliba and Jans, "Gene Therapy: Optimising DNA Delivery to the Nucleus", Curr. Drug. Targets 2001; 2(4): 371-399.
Kaplitt, M.G. et al., "Long-term gene expression and phenotypic correction using adeno-associated virus vectors in the mammalian brain", Nature Genetics (1994); 6: 148-154.
Karp, et al., "An in vitro model of differentiated human airway epithelia. Methods for establishing primary cultures." Methods Mol Biol.; vol. 188, pp. 115-137 (2002).
Kendall, et al., "Identification of a natural soluble form of the vascular endothelial growth factor receptor, FLT-1, and its heterodimerization with KDR." Biochem Biophys Res Commun. 1996; 226(2): 324-328.
Kendall, et al., "Inhibition of vascular endothelial cell growth factor activity by an endogenously encoded soluble receptor." Proc Natl Acad Sci USA. (1993); 90(22): 10705-10709.
Kern, et al., "Identification of a heparin-binding motif on adeno-associated virus type 2 capsids." Journal of Virology; vol. 77, No. 20, pp. 11072-11081 (Oct. 2003).
Khabou, H. et al., "Insight Into the Mechanisms of Enhanced Retinal Transduction by the Engineered AAV2 Capsid Variant-7m8," Biotechnology and Bioengineering, vol. 113(12), 2016, pp. 2712-2724.
Khaliq, et al., "Increased expression of placenta growth factor in proliferative diabetic retinopathy." Lab Invest. 1998; 78(1): 109-116.
Khani, et al., "AAV-mediated expression targeting of rod and cone photoreceptors with a human rhodopsin kinase promoter." Investigative Ophthalmology & Visual Science. 2007; 48(9): 3954-3961.
Kiang, et al., "Cytoprotection and regulation of heat shock proteins induced by heat shock in human breast cancer T47-D cells: role of [Ca2+]i and protein kinases." FASEB J. 1998; 12(14): 1571-1579.
Klein, et al., "Fifteen-year cumulative incidence of age-related macular degeneration: the Beaver Dam Eye Study." Ophthalmology. 2007; 114(2): 253-262.
Klein, et al., "The relation of cardiovascular disease and its risk factors to the 5-year incidence of age-related maculopathy: the Beaver Dam Eye Study." Ophthalmology. 1997; 104(11): 1804-1812.
Kliffen, et al., "Increased expression of angiogenic growth factors in age-related maculopathy." Br J Ophthalmol. 1997; 81(2): 154-162.
Klimczak, et al., "A novel adeno-associated viral variant for efficient and selective intravitreal transduction of rat muller cells." PLoS One (Oct. 2009); 4(10): e7467.
Klimczak; "Molecular Evolution of Adeno-associated Virus for Improved Retinal Gene Therapies"; Dissertation submitted in partial fulfillment of the requirements for the degree of Doctor of Philosophy in Molecular and Cell Biology in the Graduate Division of University of California, Berkeley; 117 pages (2010).
Koerber, et al., "DNA Shuffling of Adeno-associated Virus Yields Functionally Diverse Viral Progeny." Mol Ther. (Oct. 2008); 16(10): 1703-1709. Epub Aug. 6, 2008.
Koerber, et al., "Engineering of a Novel AAV Vector In a Human Airway Model System for Cystic Fibrosis Gene Therapy"; AIChE Annual Meeting Abstract, 3 pages (Nov. 29, 2008).
Koerber, et al., "Molecular evolution of adeno-associated virus for enhanced glial gene delivery." Molecular Therapy (2009); vol. 17, No. 12, pp. 2088-2095.
Komaromy, et al., "Targeting gene expression to cones with human cone opsin promoters in recombinant AAV." Gene Ther. 2008; 15(14): 1049-1055.
Komromy, Andrs M., et al., "Gene therapy rescues cone function in congenital achromatopsia." Human Molecular Genetics (Jul. 2010); 19(13): 2581-2593. Epub Apr. 8, 2010.
Kong, et al., "Regional suppression of tumor growth by in vivo transfer of a cDNA encoding a secreted form of the extracellular

(56) References Cited

OTHER PUBLICATIONS domain of the flt-1 vascular endothelial growth factor receptor." Hum Gene Ther. 1998; 9(6): 823-833.
Kotterman and Schaffer, "Engineering adeno-associated viruses for clinical gene therapy." Nat Rev Genet. (Jul. 2014); 15(7): 445-451. Epub May 20, 2014.
Kozak, "Point mutations define a sequence flanking the AUG initiator codon that modulates translation by eukaryotic ribosomes", Cell (1986); 44(2): 283-292 (Abstract Only).
Krysiak, et al., "Soluble vascular endothelial growth factor receptor-1 (sFLT-1) mediates downregulation of FLT-1 and prevents activated neutrophils from women with preeclampsia from additional migration by VEGF." Circ Res. 2005; 97(12): 1253-1261.
Krzystolik, et al., "Prevention of experimental choroidal neovascularization with intravitreal anti-vascular endothelial growth factor antibody fragment." Arch Ophthalmol. 2002; 120(3):338-346.
Kuchenbecker, James A., et al. "Topography of the long-to middle-wavelength sensitive cone ratio in the human retina assessed with a wide-field color multifocal electroretinogram." Visual Neuroscience (2008); 25.03: 301-306.
Kvanta, et al., "Subfoveal fibrovascular membranes in age-related macular degeneration express vascular endothelial growth factor." Invest Ophthalmol Vis Sci. 1996; 37(9): 1929-1934.
Kvaratskhelia, Mamuka, et al., "Molecular mechanisms of retroviral integration site selection." Nucleic Acids Research (2014); 42.16: 10209-10225.
Kwak, et al., "VEGF is major stimulator in model of choroidal neovascularization." Invest Ophthalmol Vis Sci. 2000; 41(10): 3158-3164.
Kwon, et al.; "Designer gene delivery vectors: molecular engineering and evolution of adeno-associated viral vectors for enhanced gene transfer"; Pharmaceutical Research; vol. 25, No. 3, pp. 489-499 (Mar. 2008).
Lai, et al., "Generation of transgenic mice with mild and severe retinal neovascularisation." Br J Ophthalmol. 2005; 89(7): 911-916.
Lai, et al., "Inhibition of angiogenesis by adenovirus-mediated sFlt-1 expression in a rat model of corneal neovascularization." Hum Gene Ther. 2001; 12(10): 1299-1310.
Lai et al. "Long-Term Evaluation of AAV-Mediated sFlt-1 Gene Therapy for Ocular Neovascularization in Mice and Monkeys." Molecular Therapy (2005); 12:4, p. 659-668.
Lai, et al., "Potential long-term inhibition of ocular neovascularisation by recombinant Adeno-associated virus-mediated secretion gene therapy." Gene Ther. 2002; 9(12): 804-813.
Lai, et al., "Preclinical safety evaluation of subretinal AAV2.sF1t-1 in non-human primates." Gene Ther. 2012; 19(10): 999-1009. Epub Nov. 10, 2011.
Lai, et al., "rAAV.sFlt-1 Gene Therapy Achieves Lasting Reversal of Retinal Neovascularization in the Absence of a Strong Immune Response to the Viral Vector." Invest Ophthalmol Vis Sci. 2009; 50(9): 4279-4287.
Lai, et al., "Recombinant adeno-associated virus type 2-mediated gene delivery into the Rpe65-/-knockout mouse eye results in limited rescue." Genet Vaccines Ther. 2004; 2:3, 15 pages.
Lai, Timothy YY, et al., "The clinical applications of multifocal electroretinography: a systematic review." Survey of Ophthalmology (2007); 52.1: 61-96.
Lalwani, et al., "A variable-dosing regimen with intravitreal ranibizumab for neovascular age-related macular degeneration: year 2 of the PrONTO Study." Am J Ophthalmol. 2009; 148(1): 43-58.
Lane, et al.; "Production, purification, crystallization and preliminary X-ray analysis of adeno-associated virus serotype 8"; Acta Crystallographica; F61, pp. 558-561 (2005).
Langer, Stephen J., et al., "A genetic screen identifies novel noncompatible loxP sites." Nucleic Acids Research (2002); 30.14: 3067-3077.
Lavinksy, D. et al., "Modulation of transgene expression in retinal gene therapy by selective laser treatment." Investigative Ophthalmology & Visual Science. 2013; 54(3): 1873-1880.
Le Gal La Salle et al., "An Adenovirus Vector for Gene Transfer intoNeurons and Glia in the Brain," Science Feb. 12, 1993, vol. 259, 988-990.
Le Meur, et al., "Postsurgical assessment and long-term safety of recombinant adeno-associated virus-mediated gene transfer into the retinas of dogs and primates." Arch Ophthalmol. 2005; 123(4): 500-506.
Le Meur, et al., "Restoration of vision in RPE65-deficient Briard dogs using an AAV serotype 4 vector that specifically targets the retinal pigmented epithelium." Gene Ther. 2007; 14(4): 292-303.
Lebherz, et al., "Novel AAV serotypes for improved ocular gene transfer." J Gene Med. 2008; 10(4): 375-382.
Lee and Saito, "Role of nucleotide sequences of loxP spacer region in Cre-mediated recombination," Gene. Aug. 17, 1998;216(1):55-65.
Levine, et al., "Circulating angiogenic factors and the risk of preeclampsia." N Engl J Med. 2004; 350(7): 672-683.
Li, et al., "Cone-specific expression using a human red opsin promoter in recombinant AAV." Vision Res. 2008; 48(3): 332-338.
Li et al. "Engineering and Selection of Shuffled AAV Genomes: A New Strategy for Producing Targeted Biological Nanoparticles" Molecular Therapy, 16(7):1252-1260 (2008).
Li, et al., "Gene therapy following subretinal AAV5 vector delivery is not affected by a previous intravitreal AAV5 vector administration in the partner eye." Mol Vis. 2009; 15: 267-275.
Li, et al., "Generation of novel AAV variants by directed evolution for improved CFTR delivery to human ciliated airway epithelium." Molecular Therapy (2009), vol. 17, No. 12, pp. 2067-2077.
Li, et al., "Intraocular route of AAV2 vector administration defines humoral immune response and therapeutic potential." Mol Vis. 2008; 14: 1760-1769.
Lieber, et al., "Integrating adenovirus-adeno-associated virus hybrid vectors devoid of all viral genes." J Virol. 1999; 73(11): 9314-9324.
Limberis, et al., "Adeno-associated virus serotype 9 vectors transduce murine alveolar and nasal epithelia and can be readministered." (and Correction) Proc Natl Acad Sci USA; vol. 103, No. 35, pp. 12993-12998 (Aug. 29, 2006).
Lindenberg, Thomas, et al., "Cyclic summation versus m-sequence technique in the multifocal ERG." Graefe's Archive for Clinical and Experimental Ophthalmology (2003); 241.6: 505-510.
Liu, et al., "Gene therapy for ocular diseases." Br J Ophthalmol. 2011; 95(5): 604-612.
Liu, et al., "Soluble Fms-like tyrosine kinase-1 expression inhibits the growth of multiple myeloma in nude mice." Acta Biochim Biophys Sin (Shanghai). 2007; 39(7): 499-506.
Liu, Xiaomei, Han Ping, and Chun Zhang, "Rapid establishment of a HEK 293 cell line expressing FVIII-BDD using AAV site-specific integration plasmids." BMC Research Notes (2014); 7: 626, 6 pages.
Lochrie, et al., "Mutations on the External Surfaces of Adeno-Associated Virus Type 2 Capsids That Affect Transduction and Neutralization" Journal of Virology (Jan. 2006); 80(2): 821-834.
Loiler, et al., "Targeting recombinant adeno-associated virus vectors to enhance gene transfer to pancreatic islets and liver." Gene Ther.; vol. 10, pp. 1551-1558 (2003).
Lopez, et al., "Transdifferentiated retinal pigment epithelial cells are immunoreactive for vascular endothelial growth factor in surgically excised age-related macular degeneration-related choroidal neovascular membranes." Invest Ophthalmol Vis Sci. 1996; 37(5): 855-868.
Lu, et al., "Complete correction of hemophilia A with adeno-associated viral vectors containing a full-size expression cassette." Hum Gene Ther. (2008); 19(6):648-654. doi: 10.1089/hum.2007.0182.
Lukason, et al., "Inhibition of choroidal neovascularization in a nonhuman primate model by intravitreal administration of an AAV2 vector expressing a novel anti-VEGF molecule." Mol Ther. (Feb. 2011); 19(2): 260-265. Epub Oct. 26, 2010.
Lundstrom, "Alphavirus vectors: applications for DNA vaccine production and gene expression." Intervirology. 2000; 43(4-6): 247-257.
Luo and Saltzman, "Synthetic DNA delivery systems", Nature Biotechnol. 2000; 18(1): 33-37.

(56) References Cited

OTHER PUBLICATIONS

Luthert, et al., "Photoreceptor rescue." Eye (Lond). 1998; 12(Pt 3b): 591-596.
MacLachlan, et al., "Preclinical safety evaluation of AAV2-sFLT01—a gene therapy for age-related macular degeneration." Mol Ther. 2011; 19(2): 326-334. Epub Nov. 30, 2010.
Mae, et al., "Gene transfer of the vascular endothelial growth factor receptor flt-1suppresses pulmonary metastasis associated with lung growth." Am J Respir Cell Mol Biol. 2005; 33(6): 629-635.
Maguire, A.M. et al., "Safety and efficacy of gene transfer for Leber's congenital amaurosis", N. Engl J Med (2008); 358: 2240-2248.
Maguire, et al., "Age-dependent effects of RPE65 gene therapy for Leber's congenital amaurosis: a phase 1 dose-escalation trial." Lancet. 2009; 374(9701): 1597-1605.
Maguire, et al., "Directed evolution of adeno-associated virus for glioma cell transduction." J. Neurooncol.; vol. 96, pp. 337-347 (2010).
Mahasreshti, et al., "Adenovirus-mediated soluble FLT-1 gene therapy for ovarian carcinoma." Clin Cancer Res. 2001; 7(7): 2057-2066.
Mahasreshti, et al., "Intravenous delivery of adenovirus-mediated soluble FLT-1 results in liver toxicity." Clin Cancer Res. 2003; 9(7): 2701-2710.
Maheshri, Narendra, et al. "Directed evolution of adeno-associated virus yields enhanced gene delivery vectors." Nature Biotechnology (2006); 24.2: 198-204.
Makous, Walter. "Comment on "emergence of novel color vision in mice engineered to express a human cone photopigment"." Science (2007); 318.5848: 196b-196b.
Malamos, et al., "Correlation of high-definition optical coherence tomography and fluorescein angiography imaging in neovascular macular degeneration." Invest. Ophthalmol Vis Sci. 2009; 50(10): 4926-4933.
Mancuso et al., "An adaptation of the Cambridge Colour Test for use with animals." Visual Neuroscience (2006); 23.3-4: 695-701.
Mancuso et al., "Colorblindness Cure: Gene Therapy Confers a New Sensation", Investigative Opthamology & Visual Science (2008), 49: E-Abstract 3252 (Meeting Abstract).
Mancuso et al., "Gene therapy treatment of color blindness in adult primates." Journal of Vision (2007); 7(15): 15a. (Abstract).
Mancuso et al. "Progress in Developing a Gene Therapy Approach for Treating Color Blindness." Investigative Ophthalmology & Visual Science 46.13 (2005): 4565-4565 & 2005 Annual Meeting of the Association for Research in Vision and Ophthalmology, FL. Lauderdale, FL, 46(Supp S): 4565 (2005).
Mancuso et al., "Recombinant adenO-associated virus targets passenger gene expression to cones in primate retina", Journal of the Optical Society of America A (2007); 24(5): 1411-1416.
Mancuso, Katherine, et al. "Gene therapy for red-green colour blindness in adult primates." Nature (2009); 461.7265: 784-787.
Manno, et al., "Successful transduction of liver in hemophilia by AAV-Factor IX and limitations imposed by the host immune response." Nat Med. 2006; 12(3): 342-347.
Mao, Yanxiong, et al. "Persistent Suppression of Ocular Neovascularization with Intravitreal Administration of AAVrh.10 Coding for Bevacizumab." Human Gene Therapy (2011); 22(12): 1525-1535.
Marmor M.F., et al., "Retinitis Pigmentosa. A Symposium on Terminology and Methods of Examination," Ophthalmology, Feb. 1983, vol. 90 (2), pp. 126-131.
Martin et al., "Gene delivery to the eye using adeno-associated viral vectors", Methods (2002); 28: 267-275.
Mauck, et al., "Longitudinal in vivo Characterization of Expression of Viral Delivered Genes for L-opsin and Green Fluorescent Protein in Cone Photoreceptors of Gerbils." Investigative Ophthalmology & Visual Science (2006); 47.13: 4071-4071.
Mauck, Matthew C., et al., "Longitudinal evaluation of expression of virally delivered transgenes in gerbil cone photoreceptors." Visual Neuroscience (2008); 25(3): 273-282.
Maynard, et al., "Excess placental soluble fms-like tyrosine kinase 1 (sFlt1) may contribute to endothelial dysfunction, hypertension, and proteinuria in preeclampsia." J Clin Invest. 2003; 111(5): 649-658.
McCullum, et al., "Random Mutagenesis by Error-Prone PCR." Jeff Braman (ed.), In Vitro Mutagenesis Protocols: Third Edition, Methods in Molecular Biology (2010); vol. 634, pp. 103-109.
McGee Sanftner, et al., "Glial Cell Line Derived Neurotrophic Factor Delays Photoreceptor in a Transgenic Rat Model of Retinitis Pigmentosa." Molecular Therapy; vol. 4, No. 6, pp. 622-629 (Dec. 2001).
McLeod, Maureen, et al. "Identification of the crossover site during FLP-mediated recombination in the *Saccharomyces cerevisiae* plasmid 2 microns circle." Molecular and Cellular Biology (1986); 6.10: 3357-3367.
Merigan, et al., "Tracking Transfection of Macaque Retinal Ganglion Cells With AAV2 Viral Vectors; In vivo Imaging Reveals Differences Between Two Promoters." ARVO Annual Meeting Abstract (May 2008); Investigative Ophthalmology & Visual Science. 2008; vol. 49: 4514.
Michel, et al., "Stress-induced transcription of the clusterin/apoJ gene." Biochem J. 1997; 328 ( Pt 1): 45-50.
Michelfelder, et al., "Successful Expansion but Not Complete Restriction of Tropism of Adeno-Associated Virus by In Vivo Biopanning of Random Virus Display Peptide Libraries." PLoS One; vol. 4, No. 4, pp. 1-13 (Apr. 2009).
Michelfelder, et al., "Vectors selected from adeno-associated viral display peptide libraries for leukemia cell-targeted cytotoxic gene therapy." Experimental Hematology; vol. 35, pp. 1766-1776 (2007).
Miller, et al., "Human effector and memory CD8+ T cell responses to smallpox and yellow fever vaccines." Immunity. 2008; 28(5): 710-722.
Miller et al. "Production, purification and preliminary X-ray crystallographic studies of adeno-associated virus serotype 1" Acta Crystallographica Section F: Structural Biology and Crystallization Communications, 62(Pt 12):1271-1274 (2006).
Mitchell, et al., "AAV's anatomy: Roadmap for optimizing vectors for translational success." Curr Gene Ther. (2010); vol. 10, No. 5, pp. 319-340.
Mitchell, et al., "Cost effectiveness of treatments for wet age-related macular degeneration." PharmacoEconomics 2011; 29(2): 107-131.
Mitchell, et al., "Ranibizumab (Lucentis) in neovascular age-related macular degeneration: evidence from clinical trials." Br J Ophthalmol. 2010; 94(1): 2-13.
Miyamoto, et al., "Prevention of leukostasis and vascular leakage in streptozotocin induced diabetic retinopathy via intercellular adhesion molecule-1 inhibition." Proc Natl Acad Sci USA. 1999; 96(19): 10836-10841.
Miyoshi, H. et al. "Development of a self-inactivating lentivirus vector." J Virol. Oct. 1998;72(10):8150-7. doi: 10.1128/JVI.72.10.8150-8157.1998.
Müller, et al., "Random peptide libraries displayed on adeno-associated virus to select for targeted gene therapy vectors." Nature Biotechnology (2003); 21.9: 1040-1046.
Moskalenko, et al., "Epitope mapping of human anti-adeno-associated virus type 2 neutralizing antibodies: Implications for gene therapy and virus structure." J. Virol. (Feb. 2000.); 74(4): 1761-1766.
Nakai, et al., "AAV serotype 2 vectors preferentially integrate into active genes in mice." Nature Genetics (2003); 34 (3): 297-302.
Naldini et al., "Efficient transfer, integration, and sustained long-term expression of the transgene in adult rat brains injected with a lentiviral vector," Proc Natl Acad Sci USA., Oct. 1996;93(21):11382-11388.
Naldini et al., "Lentiviruses as gene transfer agents for delivery to non-dividing cells," Curr Opin Biotechnol. (1998); 9(5): 457-463.
Naldini, L. et al., "In vivo gene delivery and stable transduction of nondividing cells by alentiviral vector", Science (1996) Apr. 12;272(5259):263-7.
Narfstrom, et al., "Assessment of structure and function over a 3-year period after gene transfer in RPE65-/-dogs." Doc Ophthalmol. 2005; 111(1): 39-48.

(56) References Cited

OTHER PUBLICATIONS

Narfstrom, et al., "Functional and structural recovery of the retina after gene therapy in the RPE65 null mutation dog." Invest Ophthalmol Vis Sci. 2003; 44(4):1663-1672.
Narfstrom, et al., "In vivo gene therapy in young and adult RPE65-/- dogs produces long-term visual improvement." J Hered. 2003; 94(1): 31-37.
Nathans, et al., "Molecular genetics of human blue cone monochromacy." Science. 1989; 245(4920): 831-838.
Nathans, J., et al. "Molecular genetics of human color vision: the genes encoding blue, green, and red pigments." Science (1986); 232(4747): 193-202.
Nathans, J., et al. "Molecular genetics of inherited variation in human color vision." Science (1986); 232.4747: 203-210.
NCBI Reference Sequence NM_000513.2, by Gen Bank, on line published and documented at https://www.ncbi.nlm.nih.gov/nuccore/NM_000513.2/, printed Jun. 23, 2020, 5 pages. (Year: 2020).
Neitz, Maureen, et al. "Spectral tuning of pigments underlying red-green color vision." Science (1991); 252.5008: 971-974.
Nemerow, "A new link between virus cell entry and inflammation: adenovirus interaction with integrins induces specific pro inflammatory responses." Mol Ther. 2009; 17(9): 1490-1491.
Neufeld, et al., "Vascular endothelial growth factor (VEGF) and its receptors." FASEB J. 1999; 13(1): 9-22.
Nguyen, et al., "Convection-enhanced delivery of AAV-2 combined with heparin increases TK gene transfer in the rat brain." Neuroreport; vol. 12, No. 9, pp. 1961-1964 (Jul. 3, 2001).
Nicklin, et al., "Efficient and selective AAV2-mediated gene transfer directed to human vascular endothelial cells." Molecular Therapy (2001); vol. 4, No. 2, pp. 174-181.
Niederkorn, et al., "See No. evil, hear No. evil, do No. evil: the lessons of immune privilege." Nat Immunol. 2006; 7(4): 354-359.
Nietz, et al., "pMNTC Is a Cone-Specific Regulatory Cassette Designed To Treat Cone-Associated Disorders". Molecular Therapy, vol. 23 (Suppl 1): S80, Abstract 202, May 2015, 1 page.
Nork, et al., "Prevention of Experimental Choroidal Neovascularization and Resolution of Active Lesions by VEGF Trap in Nonhuman Primates." Archives of Ophthalmology (2011); 129 (8): 1042-1052.
Novartis, Application for inclusion in the WHO Essential Medicines List, Section 21, Ophthalmological Preparations Ranibizumab (Lucentis)—Addition. Webpage [online]. Nov. 28, 2014; Retrieved from the Internet: URL:http://www.selleckchem.com/products/lmk-235.html; 49 pages.
Ohno-Matsui, et al., "Novel mechanism for age-related macular degeneration: an equilibrium shift between the angiogenesis factors VEGF and PEDF." J Cell Physiol. 2001; 189(3): 323-333.
Oikawa, et al., "Three novel synthetic retinoids, Re 80, Am 580 and Am 80, all exhibit anti-angiogenic activity in vivo." Eur J Pharmacol. 1993; 249(1): 113-116.
Opie, et al., "Identification of Amino Acid Residues in the Capsid Proteins of Adeno-Associated Virus Type 2 that Contribute to Heparan Sulfate Proteoglycan Binding." Journal of Virology; vol. 77, No. 12, pp. 6995-7006 (Jun. 2003).
Ortolano, et al., "Present and future of adeno associated virus based gene therapy approaches". Recent Pat Endocr Metab Immune Drug Discov. (Jan. 2012); 6(1): 47-66.
Paddison, et al., "Stable suppression of gene expression by RNAI in mammalian cells." Proc. Nat'l Acad. Sci. USA; vol. 99, No. 3, pp. 1443-1448 (Feb. 5, 2002).
Padron et al. "Structure of adeno-Associated Virus Type 4" Journal of Virology 79(8):5047-5058 (2005).
Palu, G. et al., In pursuit of new developments for gene therapy of human diseases. J Biotechnol. Feb. 5, 1999;68 (1):1-13.
Pang, Ji-jing, et al. "Gene therapy restores vision-dependent behavior as well as retinal structure and function in a mouse model of RPE65 Leber congenital amaurosis." Molecular Therapy (2006); 13.3: 565-572.
Papadakis et al. "Promoters and Control Elements: Designing Expression Cassettes for Gene Therapy." Current Gene Therapy (2004); 4(1): 89-113.
Park, et al., "Intravitreal delivery of AAV8 retinoschisin results in cell type-specific gene expression and retinal rescue in the Rs1-KO mouse." Gene Therapy (2009); 16(7): 916-926.
Park, et al., "The fourth immunoglobulin-like loop in the extracellular domain of FLT-1, a VEGF receptor, includes a major heparin-binding site." Biochem Biophys Res. Commun. 1999; 264(3): 730-734.
Paulus, et al., "Selective retinal therapy with microsecond exposures using a continuous line scanning laser." Retina. 2011 ; 31(2): 380-388.
Pechan, et al. "Novel anti-VEGF chimeric molecules delivered by AAV vectors for inhibition of retinal neovascularization." Gene Therapy (2009); 16, p. 10-16.
Perabo, et al., "Combinatorial engineering of a gene therapy vector: directed evolution of adeno-associated virus." The Journal of Gene Medicine (2006); vol. 8, pp. 155-162.
Perabo, et al., "Heparan Sulfate Proteoglycan Binding Properties of Adeno-Associated Virus Retargeting Mutants and Consequences for Their In Vitro Tropism." Journal of Virology; vol. 80, No. 14, pp. 7265-7269 (Jul. 2006).
Perabo, et al., "In Vitro Selection of Viral Vectors with Modified Tropism: The Adeno-associated Virus Display." Molecular Therapy; vol. 8, No. 1, pp. 151-157 (Jul. 2003).
Perri, et al., "Replicon vectors derived from Sindbis virus and Semliki forest virus that establish persistent replication in host cells." J Virol. 2000; 74(20): 9802-9807.
Petrs-Silva, et al., "High-efficiency transduction of the mouse retina by tyrosine-mutant AAV serotype vectors." Molecular Therapy (2009); 17(3): 463-471.
Petrs-Silva, et al., "Novel properties of tyrosine-mutant AAV2 vectors in the mouse retina." Mol Ther. (Feb. 2001); 19(2): 293-301.
Pfeifer et al., "Gene therapy: promises and problems." Annu Rev Genomics Hum Genet. (2001); 2: 177-211.
Pieramici, et al., "Age-related macular degeneration and risk factors for the development of choroidal neovascularization in the fellow eye." Curr Opin Ophthalmol. 1998; 9(3): 38-46.
Pitcher, et al., "Development and homeostasis of T cell memory in rhesus macaque." J Immunol. 2002; 168(1): 29-43.
Pollock, et al., "Delivery of a stringent dimerizer-regulated gene expression system in a single retroviral vector." Proceedings of the National Academy of Sciences of the United States of America. 2000; 97(24): 13221-6.
Popa-Wagner, et al., "Impact of VP1-Specific Protein Sequence Motifs on Adeno-Associated Virus Type 2 Intracellular Trafficking and Nuclear Entry". Journal of Virology (Sep. 2012); 86(17): 9163-9174. Epub Jun. 13, 2012.
Provost, et al., "Biodistribution of rAAV vectors following intraocular administration: evidence for the presence and persistence of vector DNA in the optic nerve and in the brain." Mol Ther. 2005; 11(2): 275-83.
Pshenichkin, et al., "Heat shock enhances CMV-IE promoter-driven metabotropic glutamate receptor expression and toxicity in transfected cells." Neuropharmacology. 2011; 60: 1292-1300.
Quantin, et al., "Adenovirus as an expression vector in muscle cells in vivo." Proc Natl Acad Sci USA. (1992); 89(7): 2581-2584.
Rabinowitz, et al., "Building a Better Vector: The Manipulation of AAV Virions." Virology; vol. 278, pp. 301-308 (2000).
Rabinowitz, et al., "Insertional mutagenesis of AAV2 capsid and the production of recombinant virus." Virology; vol. 265, No. 2, pp. 274-285 (Dec. 20, 1999).
Rapti, Kleopatra, et al. "Neutralizing antibodies against AAV serotypes 1, 2, 6, and 9 in sera of commonly used animal models." Molecular Therapy (2012); 20.1: 73-83.
Rayaprolu, et al., "Comparative analysis of adeno-associated virus capsid stability and dynamics". Journal of Virology (Dec. 2013); 87(24): 13150-13160. Epub Sep. 25, 2013.
Recchia, Alessandra, et al. "Site-specific integration of functional transgenes into the human genome by adeno/AAV hybrid vectors." Molecular Therapy (2004); 10.4: 660-670.
Reffin, J. P., et al. "Trials of a computer-controlled colour vision test that preserves the advantages of pseudoisochromatic plates." Colour Vision Deficiencies X. Springer Netherlands (1991); pp. 69-76.

(56) References Cited

OTHER PUBLICATIONS

Regan, Benedict C., et al. "Luminance noise and the rapid determination of discrimination ellipses in colour deficiency." Vision Research (1994); 34.10: 1279-1299.
Regeneron press release, Bayer and Regeneron Report Positive Top-Line Results of Two Phase 3 Studies with VEGF Trap-Eye in Wet Age-related Macular Degeneration. Nov. 22, 2010.http://newsroom.regeneron.com/releasedetail.cfm?ReleaseiD=532099 (last accessed Nov. 24, 2010).
Regillo, et al., "Randomized, double-masked, sham-controlled trial of ranibizumab for neovascular age-related macular degeneration: PIER Study year 1." Am J Ophthalmol. 2008; 145(2): 239-248.
Rein, et al., "Forecasting age-related macular degeneration through the year 2050: the potential impact of new treatments." Arch Ophthalmol. 2009; 127(4): 533-540.
Response to request under 27 CFR 1.1 05, dated Apr. 27, 2015, in U.S. Appl. No. 10/075,415, pp. 8-10 (3 pages).
Ried, et al., "Adeno-associated virus capsids displaying immunoglobulin-binding domains permit antibody-mediated vector retargeting to specific cell surface receptors." J. Virol.; vol. 76, No. 9, pp. 4559-4566 (May 2002).
Roberts, et al., "Pathogenesis and genetics of pre-eclampsia." Lancet. 2001; 357(9249): 53-56.
Robinson, et al., "The splice variants of vascular endothelial growth factor (VEGF) and their receptors." J Cell Sci. 2001; 114(Pt 5): 853-865.
Rolling, et al., "Long-term real-time monitoring of adeno-associated virus-mediated gene expression in the rat retina." Clin Experiment Ophthalmol. 2000; 28(5): 382-386.
Romano, et al., "Latest developments in gene transfer technology: achievements, perspectives, and controversies over therapeutic applications." Stem Cells. 2000; 18(1): 19-39.
Rome, C., et al., "Spatial and temporal control of expression of therapeutic genes using heat shock protein promoters." Methods (2005); 35.2: 188-198.
Rosenfeld et al., "In vivo transfer of the human cystic fibrosis transmembrane conductance regulator gene to the airway epithelium," Cell, Jan. 10, 1992; vol. 68: 143-155.
Rosenfeld, et al., "Ranibizumab for neovascular age-related macular degeneration." N Engl J Med. 2006; 355(14): 1419-1431.
Ryals, et al., "Quantifying transduction efficiencies of unmodified and tyrosine capsid mutant AAV vectors in vitro using two ocular cell lines." Mol Vision (Apr. 2011); 7: 1090-1102.
Saishin, et al., "VEGF-TRAP(R1R2) suppresses choroidal neovascularization and VEGF-induced breakdown of the blood-retinal barrier." J Cell Physiol. 2003; 195(2): 241-248.
Salam, et al., "Treatment of proliferative diabetic retinopathy with anti-VEGF agents." Acta Ophthalmol. 2011; 89(5): 405-411.
Samulski, et al., "Helper-Free Stocks of Recombinant Adeno-Associated Viruses: Normal Integration Does Not Require Viral Gene Expression." Journal of Virology (1989); 63.9: 3822-3828.
Santiago-Ortiz, et al., "AAV ancestral reconstruction library enables selection of broadly infectious viral variants". Gene Ther. (Dec. 2015); 22(12): 934-946. Epub Jul. 17, 2015.
Sauer, B. "Site-specific recombination: developments and applications", Curr OpinBiotechnol. (1994); 5(5): 521-7.
Schaffer, et al.; "Directed evolution of AAV vector mutants for enhanced gene delivery"; Abstracts of Papers American Chemical Society; vol. 227, Part 1, Abstract 172, p. U214 (Mar. 28-Apr. 1, 2004), 2 pages.
Schiefer U., et al., "Centrally Tinted Contact Lenses. A Useful Visual Aid for Patients with Achromatopsia," German Journal of Ophthalmology, 1995, vol. 4(1), pp. 52-56.
Schlake et al., "Use of mutated FLP recognition target (FRT) sites for the exchange of expression cassettes at defined chromosomal loci." Biochemistry (1994); 33(43): 12746-12751.
Schmidt, Michael, et al., "Adeno-associated virus type 2 Rep78 induces apoptosis through caspase activation independently of p53." Journal of Virology (2000); 74.20: 9441-9450.
Schmidt-Erfurth, "Clinical safety of ranibizumab in age-related macular degeneration." Expert Opin Drug Saf. 2010; 9(1):149-165.
Schmidt-Erfurth, et al., "Efficacy and safety of monthly versus quarterly ranibizumab treatment in neovascular age-related macular degeneration: the EXCITE study." Ophthalmology. 2011; 118(5): 831-839.
Schuele, et al., "RPE damage thresholds and mechanisms for laser exposure in the microsecond-to-millisecond time regimen." Invest Ophthalmol Vis Sci. 2005; 46: 714-719.
Schwartz, et al., "Embryonic stem cell trials for macular degeneration: a preliminary report." Lancet. 2012; 379(9817): 713-720.
Score Search Result 33 for Arbetman et al.WO2004112727-A2, Dec. 29, 2004, 3 pages.
Score Search Results / Report for Per SEQ ID No. 17 per US2002/0192823 (U.S. Appl. No. 10/038,972) to Bartlett Published Dec. 19, 2002, 2 pages.
Search Report (English translation) in Chinese Application No. 2013800375773, dated Nov. 24, 2016, 2 pages.
Search result 9, run by the STIC search facility, 2016, 2 pages.
Seddon, et al., "Validation of a prediction algorithm for progression to advanced macular degeneration subtypes." JAMA Ophthalmol. 2013; 131(4): 448-455.
Senecoff, Julie F., et al., "DNA recognition by the FLP recombinase of the yeast 2 plasmid: a mutational analysis of the FLP binding site." Journal of Molecular Biology (1988); 201.2: 405-421.
Shaaban, Salam A., et al. "Transgenic mice expressing a functional human photopigment." Investigative Ophthalmology & Visual Science (1998); 39.6: 1036-1043.
Shah et al., "Outcomes and risk factors associated with endophthalmitis after intravitreal injection of anti-vascular endothelial growth factor agents." Jefferson Digital Commons. 2011; pp. 1-14.
Shapley, Robert. "Specificity of cone connections in the retina and color vision. Focus on "specificity of cone inputs to macaque retinal ganglion cells"." Journal of Neurophysiology (2006); 95.2: 587-588.
Shen, et al., "Multiple roles for sialylated glycans in determining the cardiopulmonary tropism of adeno-associated virus 4." J Virol. (Dec. 2013); 87(24): 13206-13213. Epub Sep. 25, 2013.
Shen, X. et al. "Characterization of the Relationship of AAV Capsid Domain Swapping to Liver Transduction Efficiency," Mol. Ther. (Nov. 2007, e-pub. Aug. 28, 2007); 15(11):1955-1962.
Sheridan, C., "Gene therapy finds its niche." Nat Biotechnol. 2011; 29(2): 121-128.
Shi, et al., "Capsid modifications overcome low heterogeneous expression of heparan sulfate proteoglycan that limits AAV2-mediated gene transfer and therapeutic efficacy in human ovarian carcinoma." Gynecol. Oncol.; vol. 103, pp. 1054-1062 (2006).
Shi, et al., "Insertional mutagenesis of the adeno-associated virus type 2 (AAV2) capsid gene and generation of AAV2 vectors targeted to alternative cell-surface receptors", Hum Gene Ther (2001); vol. 12, No. 14, pp. 1697-1711.
Shi et al. "Insertional Mutagenesis at Positions 520 and 584 of adeno-Associated Virus Type 2 (AAV2). Capsid Gene and Generation of AAV2 Vectors with Eliminated Heparin- Binding Ability and Introduced Novel Tropism" Human Gene Therapy 17:353-361 (2006).
Shi, et al., "RGD inclusion in VP3 provides adeno-associated virus type 2 (AAV2)-based vectors with a heparan sulfate-independent cell entry mechanism." Mol. Ther.; vol. No. 4, pp. 515-525 (Apr. 2003).
Shiose, et al., "Gene transfer of a soluble receptor of VEGF inhibits the growth of experimental eyelid malignant melanoma" Invest Ophthalmol Vis Sci. 2000; 41(9): 2395-2403.
Shoji and Nakashima, "Current Status of Delivery Systems to Improve Target Efficacy of Oligonu-cleotides", Current Pharmaceutical Design. (2004); 10(7): 785-796.
Silva, et al., "Age-related macular degeneration and risk factors for the development of choroidal neovascularisation in the fellow eye: a 3-year follow-up study." Ophthalmologica. 2011; 226(3): 110-118.
Simonelli, et al., "Gene therapy for Leber's congenital amaurosis is safe and effective through 1.5 years after vector administration." Mol Ther. 2010; 18(3): 643-650.

(56) References Cited

OTHER PUBLICATIONS

Sonntag et al. "Adeno-Associated Virus Type 2 Capsids with Externalized VP1NP2 Trafficking Domains Are Generated prior to Passage through the Cytoplasm and Are Maintained until Uncoating Occurs in the Nucleus" Journal of Virology, 80(22):11040-11054 (2006).
Sramek, C. et al., "Non-damaging retinal phototherapy: Dynamic range of heat shock protein expression." Investigative Ophthalmology & Visual Science. 2011; 52(3):1780-1787.
Stefansson, et al., "Metabolic physiology in age related macular degeneration." Prog Retin Eye Res. 2011; 30(1): 72-80.
Steinbach, et al., "Assembly of adeno-associated virus type 2 capsids in vitro." J of Gen Virology; vol. 78, pp. 1453-1462 (1997).
Stellmach, et al., "Prevention of ischemia-induced retinopathy by the natural ocular antiangiogenic agent pigment epithelium-derived factor." Proc Natl Acad Sci USA. 2001; 98(5): 2593-2597.
Stieger, et al., "AAV-mediated gene therapy for retinal disorders in large animal models." ILAR J. (2009); 50(2): 206-224.
Stieger, et al., "In vivo gene regulation using tetracycline- regulatable systems." Advanced Drug Delivery Reviews. 2009; 61(7-8): 527-41.
Stout, et al., "Surgical approaches to gene and stem cell therapy for retinal disease." Hum Gene Ther. 2011; 22(5): 531-535.
Stratford-Perricaudet, et al., "Widespread long-term gene transfer to mouse skeletal muscles and heart." J Clin Invest. 1992; 90(2): 626-630.
Streilein, et al., "Immunobiology and privilege of neuronal retina and pigment epithelium transplants." Vision Res. 2002; 42(4): 487-495.
Sullivan, et al., "Rationally designed AAV2 and AAVrh8R capsids provide improved transduction in the retina and brain." Gene Ther. (Jun. 2018); 25(3): 205-219. Epub May 22, 2018.
Sun, et al., "Immune response to adeno-associated virus and its recombinant vectors." Gene Therapy; vol. 10, pp. 964-976 (2003).
Surace, et al., "Delivery of Adeno-Associated Virus Vectors to the Fetal Retina: Impact of Viral Capsid Proteins on Retinal Neuronal Progenitor Transduction." Journal of Virology; vol. 77, No. 14, pp. 7957-7963 (Jul. 2003).
Sutter, Erich E. "The fast m-transform: a fast computation of cross-correlations with binary m-sequences." SIAM Journal on Computing (1991); 20.4: 686-694.
Swanson, William H., et al. "Temporal modulation sensitivity and pulse-detection thresholds for chromatic and luminance perturbations." Josa A (1987); 4.10: 1992-2005.
Szewczenko-Pawlikowski, et al., "Heat shock-regulated expression of calreticulin in retinal pigment epithelium." Mol Cell Biochem. 1997; 177(1-2): 145-52.
Takada, et al., "Synaptic Pathology in Retinoschisis Knockout (Rs1-/y) Mouse Retina and Modification by 4 rAAV-Rs1 Gene Delivery." Investigative Ophthalmology & Visual Science; vol. 49, No. 8, pp. 3677-3678 (Aug. 2008).
Takayama, et al., "Suppression of tumor angiogenesis and growth by gene transfer of a soluble form of vascular endothelial growth factor receptor into a remote organ." Cancer Res. 2000; 60(8): 2169-2177.
Tal, "Adeno-Associated Virus-Based Vectors in Gene Therapy." Journal of Biomedical Science; vol. 7, No. 4, pp. 279-291 (Jul. 2000).
Thyagarajan, Bhaskar, et al. "Site-specific genomic integration in mammalian cells mediated by phage C31 integrase." Molecular and Cellular Biology (2001); 21.12: 3926-3934.
Tolentino, et al., "Vascular endothelial growth factor is sufficient to produce iris neovascularization and neovascular glaucoma in a nonhuman primate." Arch Ophthalmol. 1996; 114(8): 964-670.
Tomar, et al., "Use of Adeno-Associated Viral Vector for Delivery of Small Interfering RNA." Oncogene; vol. 22, No. 36, pp. 5712-5715 (Aug. 28, 2003).
Tse L.V., et al., "Structure-Guided Evolution of Antigenically Distinct Adeno-Associated Virus Variants for Immune Evasion," Proceedings of the National Academy of Sciences, Jun. 2017, vol. 114(24), pp. E4812-E4821, XP055590029.
Ueyama, Hisao, et al. "Analysis of introns and promoters of L/M visual pigment genes in relation to deutan color-vision deficiency with an array of normal gene orders." Journal of Human Genetics (2009); 54.9: 525-530.
UniProtKB database: B4Y881_9VIRU; "Capsid protein VP1, adeno-associated virus"; 6 pages (Sep. 23, 2008).
Urabe et al. "Insect Cells as a Factory to Produce adeno-Associated Virus Type 2 Vectors" Human Gene Therapy 13:1935-1943 (2002).
US National Health Institute: "Safety and Efficacy Study of rAAV. sFlt-1 in Patients With Exudative Age-Related Macular Degeneration", NCT01494805, Clinical Trials, Updated Dec. 16, 2011; XP002751808, Retrieved from the Internet: URL:https:jjclinicaltrials.govjarchivejNCT01494805/2011_12_16 [retrieved on-Dec. 4, 2015].
US National Institute of Health: "Safety and Tolerability Study of AAV2-sFLT01 in Patients With Neovascular Age-Related Macular Degeneration (AMD)", NCT01024998, Clinical Trials, Updated Apr. 13, 2012; XP002751809, Retrieved from the Internet: URL:https:jjclinicaltrials.govjarchive/NCT01024998/2012_04_13 [retrieved on-Dec. 4, 2015].
Van Vliet, et al., "Proteolytic mapping of the adeno-associated virus capsid." Mol Ther. (Dec. 2006); 14(6): 809-821.
Venkatakrishnan, et al., "Structure and Dynamics of Adeno-Associated Virus Serotype 1 VP1-Unique N-Terminal Domain and Its Role in Capsid Trafficking". Journal of Virology (Apr. 2013); 87 (9): 4974-4984.
Verma and Somia, "Gene therapy—promises, problems and prospects", Nature 1997; 389: 239-242.
Viard, et al., "Clusterin gene expression mediates resistance to apoptotic cell death induced by heat shock and oxidative stress." J Invest Dermatol. 1999; 112(3): 290-296.
Vigna, et al., "Lentiviral vectors: excellent tools for experimental gene transfer and promising candidates for gene therapy." J Gene Med. 2000; 2(5): 308-316.
Wada, et al., "Expression of vascular endothelial growth factor and its receptor(KDR/flk-1) mRNA in experimental choroidal neovascularization." Curr Eye Res. 1999; 18(3): 203-213.
Walters et al. "Structure of adeno-Associated Virus Serotype 5" Journal of Virology 78(7):3361-3371 (2004).
Wang, et al., "A locus control region adjacent to the human red and green visual pigment genes." Neuron. 1992; 9(3): 429-440.
Wang, et al., "Spatiotemporal control of gene expression by a light-switchable transgene system." Nature Methods. 2012; 9(3): 266-269.
Watanabe, et al., "Tropisms of AAV for Subretinal Delivery to the Neonatal Mouse Retina and Its Application for In Vivo Rescue of Developmental Photoreceptor Disorders". PLoS ONE (Jan. 2013); 8(1): E54146, pp. 1-12.
Waterkamp, et al., "Isolation of targeted AAV2 vectors from novel virus display libraries." J. Gene. Med.; vol. 8, pp. 1307-1319 (Sep. 6, 2006).
Wells, et al., "Levels of vascular endothelial growth factor are elevated in the vitreous of patients with subretinal neovascularisation." Br J Ophthalmol. 1996; 80(4): 363-366.
Wenkel, et al., "Analysis of immune deviation elicited by antigens injected into the subretinal space." Invest Ophthalmol Vis Sci. 1998; 39(10): 1823-1834.
Wenkel, et al., "Evidence that retinal pigment epithelium functions as an immune-privileged tissue." Invest Ophthalmol Vis Sci. 2000; 41(11): 3467-73.
White, et al., "Genetic modification of adeno-associated viral vector type 2 capsid enhances gene transfer efficiency in polarized human airway epithelial cells." Human Gene Therapy; vol. 19, pp. 1407-1414 (Dec. 2008).
White, et al., "Targeted gene delivery to vascular tissue in vivo by tropism-modified adeno-associated virus vectors." Circulation; vol. 109, pp. 513-519 (Feb. 3, 2004).
Wickham, et al., "Increased in vitro and in vivo gene transfer be adenovirus vectors containing chimeric fiber proteins." Journal of Virology; vol. 71, No. 11, pp. 8221-8229 (Nov. 1997).

(56) References Cited

OTHER PUBLICATIONS

Wiesel, Torsten N., and Hubel, David H. "Single-cell responses in striate cortex of kittens deprived of vision in one eye." J Neurophysiol (1963); 26.6: 1003-1017.
Wiesmann, et al., "Crystal Structure at 1.7 Resolution of VEGF in Complex with Domain 2 of the Flt-1 Receptor". Cell (Nov. 28, 1997); 91(5): 695-704.
Winderickx, et al., "Defective Colour Vision Associated With a Missense Mutation in the Human Green Visual Pigment Gene". Nat Genet. (Jul. 1992); 1(4): 251-256.
Wobus, et al., "Monoclonal antibodies against the adeno-associated virus type 2 (AAV-2) capsid: epitope mapping and identification of capsid domains involved in AAV-2-cell interaction and neutralization of AAV-2 infection." J. Virol.; vol. 74, No. 19, pp. 9281-9293 (Oct. 2000).
Wolf, et al., "Preeclampsia and future cardiovascular disease: potential role of altered angiogenesis and insulin resistance." J Clin Endocrinol Metab. 2004; 89(12): 6239-6243.
Wong, et al., "Intravitreal VEGF and bFGF produce florid retinal neovascularization and hemorrhage in the rabbit." Curr Eye Res. 2001; 22(2): 140-147.
Work, et al., "Vascular bed-targeted in vivo gene delivery using tropism-modified adeno-associated viruses." Mol. Ther.; vol. 13, No. 4, pp. 683-693 (Apr. 2006).
Wu et al. "alpha2,3 and alpha2,6 N-Linked Sialic Acids Facilitate Efficient Binding and Transduction by Adeno-Associated Virus Types 1 and 6" Journal of Virology, 80(18):9093-9103 (2006).
Wu, et al., "Self-complementary recombinant adeno-associated viral vectors: packaging capacity and the role of rep proteins in vector purity." Hum Gene Ther. 2007; 18(2): 171-182.
Wu et al. "Single Amino Acid Changes Can Influence Titer, Heparin Binding, and Tissue Tropism in Different adeno-Associated Virus Serotypes" Journal of Virology, 80(22):11393-11397 (2006).
Wu, et al., "Mutational analysis of the adeno-associated virus type 2 (AAV2) capsid gene and construction of AAV2 vectors with altered tropism." Journal of Virology (2000); vol. 71, No. 18, pp. 8635-8647.
Wulff, et al., "Luteal angiogenesis: prevention and intervention by treatment with vascular endothelial growth factor trap(A40)." J Clin Endocrinol Metab. 2001; 86(7): 3377-3386.
Wykoff, et al., "Perioperative management of patients with reported povidone-iodine or penicillin/cephalosporin allergies." Presented at the Annual Meeting for the Association for Research in Vision and Opthalmology. Fort Lauderdale, Fl. May 5, 2011; Abstract No. 6416/D880.
Xiao, et al.; "Adenovirus-facilitated nuclear translocation of adeno-associated virus type 2." Journal of Virology; vol. 76, No. 22, pp. 11505-11517 (Nov. 2002).
Xiao, et al., "Production of high-titer recombinant adeno-associated virus vectors in the absence of helper adenovirus." J. Virol. 1998; 72(3): 2224-2232.
Xie et al. "The atomic structure of adeno-associated Virus (AAV-2)., a vector for human gene therapy" Proceeding of the National Academy of Sciences 99(16):10405-10410 (2002).
Xu, Zhengyao, et al. "Accuracy and efficiency define Bxb1 integrase as the best of fifteen candidate serine recombinases for the integration of DNA into the human genome." BMC Biotechnology (2013); 13: 87, 17 pages.
Yang, et al., "A myocardium tropic adeno-associated virus (AAV) evolved by DNA shuffling and in vivo selection." PNAS; vol. 106, No. 10, pp. 3946-3951 (Mar. 10, 2009).
Yang, et al., "Cellular and humoral immune responses to viral antigens create barriers to lung-directed gene therapy with recombinant adenoviruses." J Virol. 1995; 69(4): 2004-2015.
Yang, et al., "Directed Evolution of Adeno=Associated Virus (AAV) as Vector for Muscle Gene Therapy." Methods in Molecular Biology; vol. 709, pp. 127-139 (2011).
Ye, et al., "sFlt-1 gene therapy of follicular thyroid carcinoma." Endocrinology. 2004; 145(2): 817-822.
Ye, Guo-jie, et al. "Development and Evaluation of Cone-Specific Promoters in Non-human Primates for Gene Therapy of Congenital Cone Diseases Including Achromatopsia." ARVO Annual Meeting Abstract, Investigative Ophthalmology & Visual Science (2014); 55.13: 837-837, 5 pages.
Yero, et al., "Immunization of mice with Neisseria meningitides serogroup B genomic expression libraries elicits functional antibodies and reduces the level of bacteremia in an infant rat infection model", Vaccine (2005); 23(7): 932-939.
Yin, et al., "Intravitreal injection of AAV2 transduces macaque inner retina." Invest Ophthalmol Vis Sci. 2011; 52(5): 2775-2783.
Zabner, et al., "Adeno-associated virus type 5 (AAV5) but not AAV2 binds to the apical surfaces of airway epithelia and facilitates gene transfer." J Virol.; No. 74, No. 8, pp. 3852-3858 (Apr. 2000).
Zhang, et al., "AAV-mediated Gene Therapy Restores Cone Function In A Rat With An M-cone Opsin Deficiency, A Model For Blue Cone Monochromacy", Investigative Opthamology & Visual Science (2011); ARVO Annual Meeting Abstract, 52:1403.
Zhang, et al., "Suppression of tumor growth by oncolytic adenovirus-mediated delivery of an antiangiogenic gene, soluble Flt-1." Mol Ther. 2005; 11(4): 553-562.
Zhao, et al., "Molecular evolution by staggered extension process (StEP) in vitro recombination". Nature Biotechnology (Mar. 1998); 16(3): 258-261.
Zheng, et al., "Genomic integration and gene expression by a modified adenoviral vector." Nat Biotechnol. 2000; 18(2): 176-180.
Zolotukhin, et al., "Recombinant adeno-associated virus purification using novel methods improves infectious titer and yield." Gene Therapy (1999); vol. 6, pp. 973-985.
Zufferey et al., "Multiply attenuated lentiviral vector achieves efficient gene delivery in vivo", Nat Biotechnol. (1997), 15(9): 871-875.

* cited by examiner

SEQUENCE LISTING

<160> NUMBER OF SEQ ID NOS: 103

<210> SEQ ID NO 1
<211> LENGTH: 494
<212> TYPE: DNA
<213> ORGANISM: Homo sapiens

<400> SEQUENCE: 1
ggatccggtt ccaggcctcg gccctaaata gtctccctgg gctttcaaga gaaccacatg 60
agaaaggagg attcgggctc tgagcagttt caccacccac cccccagtct gcaaatcctg 120
acccgtgggt ccacctgccc caaaggcgga cgcaggacag tagaagggaa cagagaacac 180
ataaacacag agagggccac agcggctccc acagtcaccg ccaccttcct ggcggggatg 240
ggtggggcgt ctgagtttgg ttcccagcaa atccctctga gccgcccttg cgggctcgcc 300
tcaggagcag gggagcaaga ggtgggagga ggaggtctaa gtcccaggcc caattaagag 360
atcaggtagt gtagggtttg ggagctttta aggtgaagag gcccgggctg atcccacagg 420
ccagtataaa gcgccgtgac cctcaggtga tgcgccaggg ccggctgccg tcggggacag 480
ggctttccat agcc 494

<210> SEQ ID NO 2
<211> LENGTH: 494
<212> TYPE: DNA
<213> ORGANISM: Homo sapiens

<400> SEQUENCE: 2
ttatttagta gaaacggggt ttcaccatgt tagtcaggct ggtcgggaac tcctgacctc 60
aggagatcta cccgccttgg cctcccaaag tgctgggatt acaggcgtgt gccactgtgc 120
ccagccactt ttttttagac agagtcttgg tctgttgccc aggctagagt tcagtggcgc 180
catctcagct cactgcaacc tccgcctccc agattcaagc gattctcctg cctcgacctc 240
ccagtagctg ggattacagg tttccagcaa atccctctga gccgccccccg ggggctcgcc 300 tcaggagcaa ggaagcaagg ggtgggagga ggaggtctaa gtcccaggcc caattaagag 360
atcagatggt gtaggatttg ggagctttta aggtgaagag gcccgggctg atcccactgg 420
ccggtataaa gcaccgtgac cctcaggtga cgcaccaggg ccggctgccg tcggggacag 480
ggctttccat agcc 494

<210> SEQ ID NO 3
<211> LENGTH: 568
<212> TYPE: DNA
<213> ORGANISM: Homo sapiens

<400> SEQUENCE: 3
ctaggcattg tcaagttgcc taagtcctgt tccatcaagg ctgtttactg atgtgcttcc 60
agggcactcc ccactcccag ccctttcctg cagcccaggg ctggttccta gcctctcagc 120
agacttaaga tgggcacctt ccacaaaggg gcagatgagt tgaggaaaac ttaactgata 180
cagttgtgcc agaagccaaa ataagaggcg tgccctttct atagccccat taaaagaaca 240
aaaaagtgga agcatcttca gtgaatatgg gtcagcacct cccagacctc agggagtcca 300
cttctgttca tcccagcacc cagcattgca tatccagatt atttgagccc aatctcttat 360
cctctgaaga acacaatcgg ctttggggcc acaaaaggtt taggtagtgg tttagggatt 420
tctaatccca aactttgtcc ttgggaggtt taggattagt attgatcatt cacagagccc 480
aagtgttttt agaggagggg ttttgtgggg tgggaggatc acctataaga ggactcagag 540
gggggtgtgg ggcatccatg agaaaaat 568

<210> SEQ ID NO 4
<211> LENGTH: 1555
<212> TYPE: DNA
<213> ORGANISM: Homo sapiens

<400> SEQUENCE: 4
ccagggtgag attatgaggc tgagctgaga atatcaagac tgtaccgagt agggggcctt 60
ggcaagtgtg gagagcccgg cagctggggc agagggcgga gtacggtgtg cgtttacgga 120
cctcttcaaa cgaggtagga aggtcagaag tcaaaaaggg aacaaatgat gtttaaccac 180
acaaaaatga aaatccaatg gttggatatc cattccaaat acacaaaggc aacggataag 240
tgatccgggc caggcacaga aggccatgca cccgtaggat tgcactcaga gctcccaaat 300
gcataggaat agaagggtgg gtgcaggagg ctgaggggtg gggaaagggc atgggtgttt 360
catgaggaca gagcttccgt ttcatgcaat gaaaagagtt tggagacgga tggtggtgac 420
tggactatac acttacacac ggtagcgatg gtacactttg tattatgtat attttaccac 480
gatcttttta aagtgtcaaa ggcaaatggc caaatggttc cttgtcctat agctgtagca 540
gccatcggct gttagtgaca aagcccctga gtcaagatga cagcagcccc cataactcct 600
aatcggctct cccgcgtgga gtcatttagg agtagtcgca ttagagacaa gtccaacatc 660
taatcttcca ccctggccag ggccccagct ggcagcgagg gtgggagact ccgggcagag 720
cagagggcgc tgacattggg gcccggcctg gcttgggtcc ctctggcctt tccccagggg 780
ccctctttcc ttggggcttt cttgggccgc cactgctccc gctcctctcc ccccatccca 840
ccccctcacc ccctcgttct tcatatcctt ctctagtgct ccctccactt tcatccaccc 900
ttctgcaaga gtgtgggacc acaaatgagt tttcacctgg cctggggaca cacgtgcccc 960
cacaggtgct gagtgacttt ctaggacagt aatctgcttt aggctaaaat gggacttgat 1020
cttctgttag ccctaatcat caattagcag agccggtgaa ggtgcagaac ctaccgcctt 1080
tccaggcctc ctcccacctc tgccacctcc actctccttc ctgggatgtg ggggctggca 1140
cacgtgtggc ccagggcatt ggtgggattg cactgagctg ggtcattagc gtaatcctgg 1200
acaagggcag acagggcgag cggagggcca gctccggggc tcaggcaagg ctgggggctt 1260
cccccagaca ccccactcct cctctgctgg acccccactt catagggcac ttcgtgttct 1320
caaagggctt ccaaatagca tggtggcctt ggatgcccag ggaagcctca gagttgctta 1380
tctccctcta gacagaaggg gaatctcggt caagagggag aggtcgccct gttcaaggcc 1440
acccagccag ctcatggcgg taatgggaca aggctggcca gccatcccac cctcagaagg 1500
gacccggtgg ggcaggtgat ctcagaggag gctcacttct gggtctcaca ttctt 1555

<210> SEQ ID NO 5
<211> LENGTH: 189
<212> TYPE: DNA
<213> ORGANISM: Artificial Sequence
<220> FEATURE:
<223> OTHER INFORMATION: Modified SV40 intron

<400> SEQUENCE: 5
gatccggtac tcgaggaact gaaaaaccag aaagttaact ggtaagttta gtctttttgt 60
cttttatttc aggtcccgga tccggtggtg gtgcaaatca aagaactgct cctcagtgga 120
tgttgccttt acttctaggc ctgtacggaa gtgttacttc tgctctaaaa gctgcggaat 180

-continued

```
tgtacccgc                                                          189


<210> SEQ ID NO 6
<211> LENGTH: 1114
<212> TYPE: DNA
<213> ORGANISM: Homo sapiens

<400> SEQUENCE: 6

atgagaaaaa tgtcggagga agagttttat ctgttcaaaa atatctcttc agtggggccg     60

tgggatgggc ctcagtacca cattgcccct gtctgggcct tctacctcca ggcagctttc    120

atgggcactg tcttccttat agggttccca ctcaatgcca tggtgctggt ggccacactg    180

cgctacaaaa agttgcggca gcccctcaac tacattctgg tcaacgtgtc cttcggaggc    240

ttcctcctct gcatcttctc tgtcttccct gtcttcgtcg ccagctgtaa cggatacttc    300

gtcttcggtc gccatgtttg tgctttggag ggcttcctgg gcactgtagc aggtctggtt    360

acaggatggt cactggcctt cctggccttt gagcgctaca ttgtcatctg taagcccttc    420

ggcaacttcc gcttcagctc caagcatgca ctgacggtgg tcctggctac ctggaccatt    480

ggtattggcg tctccatccc acccttcttt ggctggagcc ggttcatccc tgagggcctg    540

cagtgttcct gtggccctga ctggtacacc gtgggcacca aataccgcag cgagtcctat    600

acgtggttcc tcttcatctt ctgcttcatt gtgcctctct ccctcatctg cttctcctac    660

actcagctgc tgagggccct gaaagctgtt gcagctcagc agcaggagtc agctacgacc    720

cagaaggctg aacgggaggt gagccgcatg gtggttgtga tggtaggatc cttctgtgtc    780

tgctacgtgc cctacgcggc cttcgccatg tacatggtca acaaccgtaa ccatgggctg    840

gacttacggc ttgtcaccat tccttcattc ttctccaaga gtgcttgcat ctacaatccc    900

atcatctact gcttcatgaa taagcagttc caagcttgca tcatgaagat ggtgtgtggg    960

aaggccatga cagatgaatc cgacacatgc agctcccaga aaacagaagt ttctactgtc   1020

tcgtctaccc aagttggccc caactgagga cccaatattg gcctgtttgc aacagctaga   1080

attaaatttt acttttaaaa aaaaaaaaaa aaaa                               1114


<210> SEQ ID NO 7
<211> LENGTH: 348
<212> TYPE: PRT
<213> ORGANISM: Homo sapiens

<400> SEQUENCE: 7

Met Arg Lys Met Ser Glu Glu Glu Phe Tyr Leu Phe Lys Asn Ile Ser
1               5                   10                  15

Ser Val Gly Pro Trp Asp Gly Pro Gln Tyr His Ile Ala Pro Val Trp
            20                  25                  30

Ala Phe Tyr Leu Gln Ala Ala Phe Met Gly Thr Val Phe Leu Ile Gly
        35                  40                  45

Phe Pro Leu Asn Ala Met Val Leu Val Ala Thr Leu Arg Tyr Lys Lys
    50                  55                  60

Leu Arg Gln Pro Leu Asn Tyr Ile Leu Val Asn Val Ser Phe Gly Gly
65                  70                  75                  80

Phe Leu Leu Cys Ile Phe Ser Val Phe Pro Val Phe Val Ala Ser Cys
                85                  90                  95

Asn Gly Tyr Phe Val Phe Gly Arg His Val Cys Ala Leu Glu Gly Phe
            100                 105                 110

Leu Gly Thr Val Ala Gly Leu Val Thr Gly Trp Ser Leu Ala Phe Leu
        115                 120                 125
```

-continued

```
Ala Phe Glu Arg Tyr Ile Val Ile Cys Lys Pro Phe Gly Asn Phe Arg
    130                 135                 140

Phe Ser Ser Lys His Ala Leu Thr Val Val Leu Ala Thr Trp Thr Ile
145                 150                 155                 160

Gly Ile Gly Val Ser Ile Pro Pro Phe Phe Gly Trp Ser Arg Phe Ile
                165                 170                 175

Pro Glu Gly Leu Gln Cys Ser Cys Gly Pro Asp Trp Tyr Thr Val Gly
            180                 185                 190

Thr Lys Tyr Arg Ser Glu Ser Tyr Thr Trp Phe Leu Phe Ile Phe Cys
        195                 200                 205

Phe Ile Val Pro Leu Ser Leu Ile Cys Phe Ser Tyr Thr Gln Leu Leu
    210                 215                 220

Arg Ala Leu Lys Ala Val Ala Ala Gln Gln Gln Glu Ser Ala Thr Thr
225                 230                 235                 240

Gln Lys Ala Glu Arg Glu Val Ser Arg Met Val Val Val Met Val Gly
                245                 250                 255

Ser Phe Cys Val Cys Tyr Val Pro Tyr Ala Ala Phe Ala Met Tyr Met
            260                 265                 270

Val Asn Asn Arg Asn His Gly Leu Asp Leu Arg Leu Val Thr Ile Pro
        275                 280                 285

Ser Phe Phe Ser Lys Ser Ala Cys Ile Tyr Asn Pro Ile Ile Tyr Cys
    290                 295                 300

Phe Met Asn Lys Gln Phe Gln Ala Cys Ile Met Lys Met Val Cys Gly
305                 310                 315                 320

Lys Ala Met Thr Asp Glu Ser Asp Thr Cys Ser Ser Gln Lys Thr Glu
                325                 330                 335

Val Ser Thr Val Ser Ser Thr Gln Val Gly Pro Asn
            340                 345
```

<210> SEQ ID NO 8
<211> LENGTH: 1998
<212> TYPE: DNA
<213> ORGANISM: Homo sapiens

<400> SEQUENCE: 8

```
cccactggcc ggtataaagc accgtgaccc tcaggtgacg caccagggcc ggctgccgtc      60

ggggacaggg ctttccatag ccatggccca gcagtggagc ctccaaaggc tcgcaggccg     120

ccatccgcag gacagctatg aggacagcac ccagtccagc atcttcacct acaccaacag     180

caactccacc agaggcccct tcgaaggccc gaattaccac atcgctccca gatgggtgta     240

ccacctcacc agtgtctgga tgatctttgt ggtcattgca tccgtcttca caaatgggct     300

tgtgctggcg gccaccatga agttcaagaa gctgcgccac ccgctgaact ggatcctggt     360

gaacctggcg gtcgctgacc tggcagagac cgtcatcgcc agcactatca gcgttgtgaa     420

ccaggtctat ggctacttcg tgctgggcca ccctatgtgt gtcctggagg gctacaccgt     480

ctccctgtgt gggatcacag gtctctggtc tctggccatc atttcctggg agagatggat     540

ggtggtctgc aagccctttg gcaatgtgag atttgatgcc aagctggcca tcgtgggcat     600

tgccttctcc tggatctggg ctgctgtgtg gacagccccg cccatctttg gttggagcag     660

gtactggccc cacggcctga agacttcatg cggcccagac gtgttcagcg gcagctcgta     720

ccccggggtg cagtcttaca tgattgtcct catggtcacc tgctgcatca ccccactcag     780

catcatcgtg ctctgctacc tccaagtgtg gctggccatc cgagcggtgg caaagcagca     840
```

-continued

```
gaaagagtct gaatccaccc agaaggcaga gaaggaagtg acgcgcatgg tggtggtgat     900

ggtcctggca ttctgcttct gctggggacc atacgccttc ttcgcatgct ttgctgctgc     960

caaccctggc taccccttcc accctttgat ggctgccctg ccggccttct ttgccaaaag    1020

tgccactatc tacaaccccg ttatctatgt ctttatgaac cggcagtttc gaaactgcat    1080

cttgcagctt ttcgggaaga aggttgacga tggctctgaa ctctccagcg cctccaaaac    1140

ggaggtctca tctgtgtcct cggtatcgcc tgcatgaggt ctgcctccta cccatcccgc    1200

ccaccggggc tttggccacc tctcctttcc ccctccttct ccatccctgt aaaataaatg    1260

taatttatct ttgccaaaac caacaaagtc acagaggctt tcactgcagt gtgggaccac    1320

ctgagcctct gcgtgtgcag gcactgggtc tcgagagggt gcaaggggga taaagaggag    1380

agagcgcttc atagacttta agttttcccg agcctcatgt ctaccgatgg cgtgaaagga    1440

tcctggcaaa acagaagtgt gaggcaggtg ggcgtctata tccatttcac caggctggtg    1500

gttacataat cggcaagcaa gagctgtgga ggggcttgct ggatgccctc agcacccagg    1560

aggagggagg gagctagcaa gctaaggcag gtggccctcc tggcccctta aggtccatct    1620

gctggaggcc cagagtcctt ggagtacagt ctacacctgg aggggaccca ttcctgccag    1680

tctgtggcag ggatggcgcg ccacctctgc caggccagga ccccaagccc gatcagcatc    1740

agcatggtgc aggtgcacag gcgtgagctg atcagtgacg aggggcaggc acacaaggtg    1800

gagacaaaga ccaagaggac ggttgccagt gagaggcgcg gactcaggaa cttgaacaac    1860

atctgcgggg gacggctttg gaggtgctcc gctgcctcca gttgggtgac ttgctgtagc    1920

atctccagct tggatattcg gctcttgaag gtctccgtga tctcctgcag gagacgaaaa    1980

tgcacgcacc agaagtca                                                  1998
```

<210> SEQ ID NO 9
<211> LENGTH: 364
<212> TYPE: PRT
<213> ORGANISM: Homo sapiens

<400> SEQUENCE: 9

```
Met Ala Gln Gln Trp Ser Leu Gln Arg Leu Ala Gly Arg His Pro Gln
1               5                   10                  15

Asp Ser Tyr Glu Asp Ser Thr Gln Ser Ser Ile Phe Thr Tyr Thr Asn
            20                  25                  30

Ser Asn Ser Thr Arg Gly Pro Phe Glu Gly Pro Asn Tyr His Ile Ala
        35                  40                  45

Pro Arg Trp Val Tyr His Leu Thr Ser Val Trp Met Ile Phe Val Val
    50                  55                  60

Ile Ala Ser Val Phe Thr Asn Gly Leu Val Leu Ala Ala Thr Met Lys
65                  70                  75                  80

Phe Lys Lys Leu Arg His Pro Leu Asn Trp Ile Leu Val Asn Leu Ala
                85                  90                  95

Val Ala Asp Leu Ala Glu Thr Val Ile Ala Ser Thr Ile Ser Val Val
            100                 105                 110

Asn Gln Val Tyr Gly Tyr Phe Val Leu Gly His Pro Met Cys Val Leu
        115                 120                 125

Glu Gly Tyr Thr Val Ser Leu Cys Gly Ile Thr Gly Leu Trp Ser Leu
    130                 135                 140

Ala Ile Ile Ser Trp Glu Arg Trp Met Val Val Cys Lys Pro Phe Gly
145                 150                 155                 160

Asn Val Arg Phe Asp Ala Lys Leu Ala Ile Val Gly Ile Ala Phe Ser
```

```
                165                 170                 175

Trp Ile Trp Ala Ala Val Trp Thr Ala Pro Pro Ile Phe Gly Trp Ser
            180                 185                 190

Arg Tyr Trp Pro His Gly Leu Lys Thr Ser Cys Gly Pro Asp Val Phe
        195                 200                 205

Ser Gly Ser Ser Tyr Pro Gly Val Gln Ser Tyr Met Ile Val Leu Met
    210                 215                 220

Val Thr Cys Cys Ile Thr Pro Leu Ser Ile Ile Val Leu Cys Tyr Leu
225                 230                 235                 240

Gln Val Trp Leu Ala Ile Arg Ala Val Ala Lys Gln Gln Lys Glu Ser
                245                 250                 255

Glu Ser Thr Gln Lys Ala Glu Lys Glu Val Thr Arg Met Val Val Val
            260                 265                 270

Met Val Leu Ala Phe Cys Phe Cys Trp Gly Pro Tyr Ala Phe Phe Ala
        275                 280                 285

Cys Phe Ala Ala Ala Asn Pro Gly Tyr Pro Phe His Pro Leu Met Ala
    290                 295                 300

Ala Leu Pro Ala Phe Phe Ala Lys Ser Ala Thr Ile Tyr Asn Pro Val
305                 310                 315                 320

Ile Tyr Val Phe Met Asn Arg Gln Phe Arg Asn Cys Ile Leu Gln Leu
                325                 330                 335

Phe Gly Lys Lys Val Asp Asp Gly Ser Glu Leu Ser Ser Ala Ser Lys
            340                 345                 350

Thr Glu Val Ser Ser Val Ser Ser Val Ser Pro Ala
        355                 360


<210> SEQ ID NO 10
<211> LENGTH: 1234
<212> TYPE: DNA
<213> ORGANISM: Homo sapiens

<400> SEQUENCE: 10

cggctgccgt cggggacagg gctttccata gccatggccc agcagtggag cctccaaagg      60

ctcgcaggcc gccatccgca ggacagctat gaggacagca cccagtccag catcttcacc     120

tacaccaaca gcaactccac cagaggcccc ttcgaaggcc cgaattacca catcgctccc     180

agatgggtgt accacctcac cagtgtctgg atgatctttg tggtcactgc atccgtcttc     240

acaaatgggc ttgtgctggc ggccaccatg aagttcaaga agctgcgcca cccgctgaac     300

tggatcctgg tgaacctggc ggtcgctgac ctagcagaga ccgtcatcgc cagcactatc     360

agcattgtga accaggtctc tggctacttc gtgctgggcc accctatgtg tgtcctggag     420

ggctacaccg tctccctgtg tgggatcaca ggtctctggt ctctggccat catttcctgg     480

gagaggtggc tggtggtgtg caagcccttt ggcaatgtga gatttgatgc caagctggcc     540

atcgtgggca ttgccttctc ctggatctgg tctgctgtgt ggacagcccc gcccatcttt     600

ggttggagca ggtactggcc ccacggcctg aagacttcat gcggcccaga cgtgttcagc     660

ggcagctcgt accccggggt gcagtcttac atgattgtcc tcatggtcac ctgctgcatc     720

atcccactcg ctatcatcat gctctgctac ctccaagtgt ggctggccat ccgagcggtg     780

gcaaagcagc agaaagagtc tgaatccacc cagaaggcag agaaggaagt gacgcgcatg     840

gtggtggtga tgatctttgc gtactgcgtc tgctggggac cctacacctt cttcgcatgc     900

tttgctgctg ccaaccctgg ttacgccttc caccctttga tggctgccct gccggcctac     960

tttgccaaaa gtgccactat ctacaacccc gttatctatg tctttatgaa ccggcagttt    1020
```

```
cgaaactgca tcttgcagct tttcgggaag aaggttgacg atggctctga actctccagc   1080

gcctccaaaa cggaggtctc atctgtgtcc tcggtatcgc ctgcatgagg tctgcctcct   1140

acccatcccg cccaccgggg ctttggccac ctctcctttc cccctccttc tccatccctg   1200

taaaataaat gtaatttatc tttgccaaaa ccaa                               1234


<210> SEQ ID NO 11
<211> LENGTH: 364
<212> TYPE: PRT
<213> ORGANISM: Homo sapiens

<400> SEQUENCE: 11

Met Ala Gln Gln Trp Ser Leu Gln Arg Leu Ala Gly Arg His Pro Gln
1               5                   10                  15

Asp Ser Tyr Glu Asp Ser Thr Gln Ser Ser Ile Phe Thr Tyr Thr Asn
            20                  25                  30

Ser Asn Ser Thr Arg Gly Pro Phe Glu Gly Pro Asn Tyr His Ile Ala
        35                  40                  45

Pro Arg Trp Val Tyr His Leu Thr Ser Val Trp Met Ile Phe Val Val
    50                  55                  60

Thr Ala Ser Val Phe Thr Asn Gly Leu Val Leu Ala Ala Thr Met Lys
65                  70                  75                  80

Phe Lys Lys Leu Arg His Pro Leu Asn Trp Ile Leu Val Asn Leu Ala
                85                  90                  95

Val Ala Asp Leu Ala Glu Thr Val Ile Ala Ser Thr Ile Ser Ile Val
            100                 105                 110

Asn Gln Val Ser Gly Tyr Phe Val Leu Gly His Pro Met Cys Val Leu
        115                 120                 125

Glu Gly Tyr Thr Val Ser Leu Cys Gly Ile Thr Gly Leu Trp Ser Leu
    130                 135                 140

Ala Ile Ile Ser Trp Glu Arg Trp Leu Val Val Cys Lys Pro Phe Gly
145                 150                 155                 160

Asn Val Arg Phe Asp Ala Lys Leu Ala Ile Val Gly Ile Ala Phe Ser
                165                 170                 175

Trp Ile Trp Ser Ala Val Trp Thr Ala Pro Pro Ile Phe Gly Trp Ser
            180                 185                 190

Arg Tyr Trp Pro His Gly Leu Lys Thr Ser Cys Gly Pro Asp Val Phe
        195                 200                 205

Ser Gly Ser Ser Tyr Pro Gly Val Gln Ser Tyr Met Ile Val Leu Met
    210                 215                 220

Val Thr Cys Cys Ile Ile Pro Leu Ala Ile Ile Met Leu Cys Tyr Leu
225                 230                 235                 240

Gln Val Trp Leu Ala Ile Arg Ala Val Ala Lys Gln Gln Lys Glu Ser
                245                 250                 255

Glu Ser Thr Gln Lys Ala Glu Lys Glu Val Thr Arg Met Val Val Val
            260                 265                 270

Met Ile Phe Ala Tyr Cys Val Cys Trp Gly Pro Tyr Thr Phe Phe Ala
        275                 280                 285

Cys Phe Ala Ala Ala Asn Pro Gly Tyr Ala Phe His Pro Leu Met Ala
    290                 295                 300

Ala Leu Pro Ala Tyr Phe Ala Lys Ser Ala Thr Ile Tyr Asn Pro Val
305                 310                 315                 320

Ile Tyr Val Phe Met Asn Arg Gln Phe Arg Asn Cys Ile Leu Gln Leu
                325                 330                 335
```

```
Phe Gly Lys Lys Val Asp Asp Gly Ser Glu Leu Ser Ser Ala Ser Lys
            340                 345                 350

Thr Glu Val Ser Ser Val Ser Ser Val Ser Pro Ala
        355                 360


<210> SEQ ID NO 12
<211> LENGTH: 7326
<212> TYPE: DNA
<213> ORGANISM: Homo sapiens

<400> SEQUENCE: 12

aggacacagc gtccggagcc agaggcgctc ttaacggcgt ttatgtcctt tgctgtctga     60

ggggcctcag ctctgaccaa tctggtcttc gtgtggtcat tagcatgggc ttcgtgagac    120

agatacagct tttgctctgg aagaactgga ccctgcggaa aaggcaaaag attcgctttg    180

tggtggaact cgtgtggcct ttatctttat ttctggtctt gatctggtta aggaatgcca    240

acccgctcta cagccatcat gaatgccatt tccccaacaa ggcgatgccc tcagcaggaa    300

tgctgccgtg gctccagggg atcttctgca atgtgaacaa tccctgtttt caaagcccca    360

ccccaggaga atctcctgga attgtgtcaa actataacaa ctccatcttg gcaagggtat    420

atcgagattt tcaagaactc ctcatgaatg caccagagag ccagcacctt ggccgtattt    480

ggacagagct acacatcttg tcccaattca tggacaccct ccggactcac ccggagagaa    540

ttgcaggaag aggaatacga ataagggata tcttgaaaga tgaagaaaca ctgacactat    600

ttctcattaa aaacatcggc ctgtctgact cagtggtcta ccttctgatc aactctcaag    660

tccgtccaga gcagttcgct catggagtcc cggacctggc gctgaaggac atcgcctgca    720

gcgaggccct cctggagcgc ttcatcatct tcagccagag acgcggggca aagacggtgc    780

gctatgccct gtgctccctc tcccagggca ccctacagtg gatagaagac actctgtatg    840

ccaacgtgga cttcttcaag ctcttccgtg tgcttcccac actcctagac agccgttctc    900

aaggtatcaa tctgagatct tggggaggaa tattatctga tatgtcacca agaattcaag    960

agtttatcca tcggccgagt atgcaggact tgctgtgggt gaccaggccc ctcatgcaga   1020

atggtggtcc agagaccttt acaaagctga tgggcatcct gtctgacctc ctgtgtggct   1080

accccgaggg aggtggctct cgggtgctct ccttcaactg gtatgaagac aataactata   1140

aggcctttct ggggattgac tccacaagga aggatcctat ctattcttat gacagaagaa   1200

caacatcctt ttgtaatgca ttgatccaga gcctggagtc aaatccttta accaaaatcg   1260

cttggagggc ggcaaagcct ttgctgatgg gaaaaatcct gtacactcct gattcacctg   1320

cagcacgaag gatactgaag aatgccaact caacttttga agaactggaa cacgttagga   1380

agttggtcaa agcctgggaa gaagtagggc cccagatctg gtacttcttt gacaacagca   1440

cacagatgaa catgatcaga gataccctgg ggaacccaac agtaaaagac tttttgaata   1500

ggcagcttgg tgaagaaggt attactgctg aagccatcct aaacttcctc tacaagggcc   1560

ctcgggaaag ccaggctgac gacatggcca acttcgactg gagggacata tttaacatca   1620

ctgatcgcac cctccgcctg gtcaatcaat acctggagtg cttggtcctg gataagtttg   1680

aaagctacaa tgatgaaact cagctcaccc aacgtgccct ctctctactg gaggaaaaca   1740

tgttctgggc cggagtggta ttccctgaca tgtatccctg gaccagctct ctaccacccc   1800

acgtgaagta taagatccga atggacatag acgtggtgga gaaaaccaat aagattaaag   1860

acaggtattg ggattctggt cccagagctg atcccgtgga agatttccgg tacatctggg   1920
```

-continued

```
gcgggtttgc ctatctgcag gacatggttg aacaggggat cacaaggagc caggtgcagg   1980
cggaggctcc agttggaatc tacctccagc agatgcccta cccctgcttc gtggacgatt   2040
ctttcatgat catcctgaac cgctgtttcc ctatcttcat ggtgctggca tggatctact   2100
ctgtctccat gactgtgaag agcatcgtct tggagaagga gttgcgactg aaggagacct   2160
tgaaaaatca gggtgtctcc aatgcagtga tttggtgtac ctggttcctg gacagcttct   2220
ccatcatgtc gatgagcatc ttcctcctga cgatattcat catgcatgga agaatcctac   2280
attacagcga cccattcatc ctcttcctgt tcttgttggc tttctccact gccaccatca   2340
tgctgtgctt tctgctcagc accttcttct ccaaggccag tctggcagca gcctgtagtg   2400
gtgtcatcta tttcaccctc tacctgccac acatcctgtg cttcgcctgg caggaccgca   2460
tgaccgctga gctgaagaag gctgtgagct tactgtctcc ggtggcattt ggatttggca   2520
ctgagtacct ggttcgcttt gaagagcaag gcctggggct gcagtggagc aacatcggga   2580
acagtcccac ggaaggggac gaattcagct tcctgctgtc catgcagatg atgctccttg   2640
atgctgctgt ctatggctta ctcgcttggt accttgatca ggtgtttcca ggagactatg   2700
gaaccccact tccttggtac tttcttctac aagagtcgta ttggcttggc ggtgaagggt   2760
gttcaaccag agaagaaaga gccctggaaa agaccgagcc cctaacagag gaaacggagg   2820
atccagagca cccagaagga atacacgact ccttctttga acgtgagcat ccagggtggg   2880
ttcctggggt atgcgtgaag aatctggtaa agatttttga gccctgtggc cggccagctg   2940
tggaccgtct gaacatcacc ttctacgaga accagatcac cgcattcctg ggccacaatg   3000
gagctgggaa aaccaccacc ttgtccatcc tgacgggtct gttgccacca acctctggga   3060
ctgtgctcgt tgggggaagg gacattgaaa ccagcctgga tgcagtccgg cagagccttg   3120
gcatgtgtcc acagcacaac atcctgttcc accacctcac ggtggctgag cacatgctgt   3180
tctatgccca gctgaaagga aagtcccagg aggaggccca gctggagatg gaagccatgt   3240
tggaggacac aggcctccac cacaagcgga atgaagaggc tcaggaccta tcaggtggca   3300
tgcagagaaa gctgtcggtt gccattgcct ttgtgggaga tgccaaggtg gtgattctgg   3360
acgaacccac ctctggggtg gacccttact cgagacgctc aatctgggat ctgctcctga   3420
agtatcgctc aggcagaacc atcatcatgt ccactcacca catggacgag gccgacctcc   3480
ttggggaccg cattgccatc attgcccagg gaaggctcta ctgctcaggc accccactct   3540
tcctgaagaa ctgctttggc acaggcttgt acttaacctt ggtgcgcaag atgaaaaaca   3600
tccagagcca aaggaaaggc agtgagggga cctgcagctg ctcgtctaag ggtttctcca   3660
ccacgtgtcc agcccacgtc gatgacctaa ctccagaaca agtcctggat ggggatgtaa   3720
atgagctgat ggatgtagtt ctccaccatg ttccagaggc aaagctggtg gagtgcattg   3780
gtcaagaact tatcttcctt cttccaaata agaacttcaa gcacagagca tatgccagcc   3840
ttttcagaga gctggaggag acgctggctg accttggtct cagcagtttt ggaatttctg   3900
acactcccct ggaagagatt tttctgaagg tcacggagga ttctgattca ggacctctgt   3960
ttgcgggtgg cgctcagcag aaaagagaaa acgtcaaccc ccgacacccc tgcttgggtc   4020
ccagagagaa ggctggacag acaccccagg actccaatgt ctgctcccca ggggcgccgg   4080
ctgctcaccc agagggccag cctcccccag agccagagtg cccaggcccg cagctcaaca   4140
cggggacaca gctggtcctc cagcatgtgc aggcgctgct ggtcaagaga ttccaacaca   4200
ccatccgcag ccacaaggac ttcctggcgc agatcgtgct cccggctacc tttgtgtttt   4260
tggctctgat gctttctatt gttatccctc cttttggcga ataccccgct ttgacccttc   4320
```

-continued

```
accccctggat atatgggcag cagtacacct tcttcagcat ggatgaacca ggcagtgagc   4380
agttcacggt acttgcagac gtcctcctga ataagccagg ctttggcaac cgctgcctga   4440
aggaagggtg gcttccggag taccccctgtg gcaactcaac accctggaag actccttctg   4500
tgtccccaaa catcacccag ctgttccaga agcagaaatg gacacaggtc aacccttcac   4560
catcctgcag gtgcagcacc agggagaagc tcaccatgct gccagagtgc cccgagggtg   4620
ccgggggcct cccgcccccc cagagaacac agcgcagcac ggaaattcta caagacctga   4680
cggacaggaa catctccgac ttcttggtaa aaacgtatcc tgctcttata agaagcagct   4740
taaagagcaa attctgggtc aatgaacaga ggtatggagg aatttccatt ggaggaaagc   4800
tcccagtcgt ccccatcacg ggggaagcac ttgttgggtt tttaagcgac cttggccgga   4860
tcatgaatgt gagcgggggc cctatcacta gagaggcctc taaagaaata cctgatttcc   4920
ttaaacatct agaaactgaa gacaacatta aggtgtggtt taataacaaa ggctggcatg   4980
ccctggtcag ctttctcaat gtggcccaca acgccatctt acgggccagc ctgcctaagg   5040
acaggagccc cgaggagtat ggaatcaccg tcattagcca accccctgaac ctgaccaagg   5100
agcagctctc agagattaca gtgctgacca cttcagtgga tgctgtggtt gccatctgcg   5160
tgattttctc catgtccttc gtcccagcca gctttgtcct ttatttgatc caggagcggg   5220
tgaacaaatc caagcacctc cagtttatca gtggagtgag ccccaccacc tactgggtga   5280
ccaacttcct ctgggacatc atgaattatt ccgtgagtgc tgggctggtg gtgggcatct   5340
tcatcgggtt tcagaagaaa gcctacactt ctccagaaaa ccttcctgcc cttgtggcac   5400
tgctcctgct gtatggatgg gcggtcattc ccatgatgta cccagcatcc ttcctgtttg   5460
atgtccccag cacagcctat gtggctttat cttgtgctaa tctgttcatc ggcatcaaca   5520
gcagtgctat taccttcatc ttggaattat ttgagaataa ccggacgctg ctcaggttca   5580
acgccgtgct gaggaagctg ctcattgtct tccccccactt ctgcctgggc cggggcctca   5640
ttgaccttgc actgagccag gctgtgacag atgtctatgc ccggtttggt gaggagcact   5700
ctgcaaatcc gttccactgg gacctgattg ggaagaacct gtttgccatg gtggtggaag   5760
gggtggtgta cttcctcctg accctgctgg tccagcgcca cttcttcctc tcccaatgga   5820
ttgccgagcc cactaaggag cccattgttg atgaagatga tgatgtggct gaagaaagac   5880
aaagaattat tactggtgga aataaaactg acatcttaag gctacatgaa ctaaccaaga   5940
tttatccagg cacctccagc ccagcagtgg acaggctgtg tgtcggagtt cgccctggag   6000
agtgctttgg cctcctggga gtgaatggtg ccggcaaaac aaccacattc aagatgctca   6060
ctggggacac cacagtgacc tcaggggatg ccaccgtagc aggcaagagt attttaacca   6120
atatttctga agtccatcaa aatatgggct actgtcctca gtttgatgca attgatgagc   6180
tgctcacagg acgagaacat ctttaccttt atgcccggct tcgaggtgta ccagcagaag   6240
aaatcgaaaa ggttgcaaac tggagtatta agagcctggg cctgactgtc tacgccgact   6300
gcctggctgg cacgtacagt gggggcaaca agcggaaact ctccacagcc atcgcactca   6360
ttggctgccc accgctggtg ctgctggatg agcccaccac agggatggac ccccaggcac   6420
gccgcatgct gtggaacgtc atcgtgagca tcatcagaga agggagggct gtggtcctca   6480
catcccacag catggaagaa tgtgaggcac tgtgtacccg gctggccatc atggtaaagg   6540
gcgcctttcg atgtatgggc accattcagc atctcaagtc caaatttgga gatggctata   6600
tcgtcacaat gaagatcaaa tccccgaagg acgacctgct tcctgacctg aaccctgtgg   6660
```

-continued

```
agcagttctt ccaggggaac ttcccaggca gtgtgcagag ggagaggcac tacaacatgc   6720

tccagttcca ggtctcctcc tcctccctgg cgaggatctt ccagctcctc ctctcccaca   6780

aggacagcct gctcatcgag gagtactcag tcacacagac cacactggac caggtgtttg   6840

taaattttgc taaacagcag actgaaagtc atgacctccc tctgcaccct cgagctgctg   6900

gagccagtcg acaagcccag gactgatctt tcacaccgct cgttcctgca gccagaaagg   6960

aactctgggc agctggaggc gcaggagcct gtgcccatat ggtcatccaa atggactggc   7020

cagcgtaaat gaccccactg cagcagaaaa caaacacacg aggagcatgc agcgaattca   7080

gaaagaggtc tttcagaagg aaaccgaaac tgacttgctc acctggaaca cctgatggtg   7140

aaaccaaaca aatacaaaat ccttctccag accccagaac tagaaacccc gggccatccc   7200

actagcagct ttggcctcca tattgctctc atttcaagca gatctgcttt tctgcatgtt   7260

tgtctgtgtg tctgcgttgt gtgtgatttt catggaaaaa taaaatgcaa atgcactcat   7320

cacaaa                                                              7326
```

<210> SEQ ID NO 13
<211> LENGTH: 2273
<212> TYPE: PRT
<213> ORGANISM: Homo sapiens

<400> SEQUENCE: 13

```
Met Gly Phe Val Arg Gln Ile Gln Leu Leu Leu Trp Lys Asn Trp Thr
1               5                   10                  15

Leu Arg Lys Arg Gln Lys Ile Arg Phe Val Val Glu Leu Val Trp Pro
            20                  25                  30

Leu Ser Leu Phe Leu Val Leu Ile Trp Leu Arg Asn Ala Asn Pro Leu
        35                  40                  45

Tyr Ser His His Glu Cys His Phe Pro Asn Lys Ala Met Pro Ser Ala
    50                  55                  60

Gly Met Leu Pro Trp Leu Gln Gly Ile Phe Cys Asn Val Asn Asn Pro
65                  70                  75                  80

Cys Phe Gln Ser Pro Thr Pro Gly Glu Ser Pro Gly Ile Val Ser Asn
                85                  90                  95

Tyr Asn Asn Ser Ile Leu Ala Arg Val Tyr Arg Asp Phe Gln Glu Leu
            100                 105                 110

Leu Met Asn Ala Pro Glu Ser Gln His Leu Gly Arg Ile Trp Thr Glu
        115                 120                 125

Leu His Ile Leu Ser Gln Phe Met Asp Thr Leu Arg Thr His Pro Glu
    130                 135                 140

Arg Ile Ala Gly Arg Gly Ile Arg Ile Arg Asp Ile Leu Lys Asp Glu
145                 150                 155                 160

Glu Thr Leu Thr Leu Phe Leu Ile Lys Asn Ile Gly Leu Ser Asp Ser
                165                 170                 175

Val Val Tyr Leu Leu Ile Asn Ser Gln Val Arg Pro Glu Gln Phe Ala
            180                 185                 190

His Gly Val Pro Asp Leu Ala Leu Lys Asp Ile Ala Cys Ser Glu Ala
        195                 200                 205

Leu Leu Glu Arg Phe Ile Ile Phe Ser Gln Arg Arg Gly Ala Lys Thr
    210                 215                 220

Val Arg Tyr Ala Leu Cys Ser Leu Ser Gln Gly Thr Leu Gln Trp Ile
225                 230                 235                 240

Glu Asp Thr Leu Tyr Ala Asn Val Asp Phe Phe Lys Leu Phe Arg Val
                245                 250                 255
```

```
Leu Pro Thr Leu Leu Asp Ser Arg Ser Gln Gly Ile Asn Leu Arg Ser
            260                 265                 270

Trp Gly Gly Ile Leu Ser Asp Met Ser Pro Arg Ile Gln Glu Phe Ile
        275                 280                 285

His Arg Pro Ser Met Gln Asp Leu Leu Trp Val Thr Arg Pro Leu Met
    290                 295                 300

Gln Asn Gly Gly Pro Glu Thr Phe Thr Lys Leu Met Gly Ile Leu Ser
305                 310                 315                 320

Asp Leu Leu Cys Gly Tyr Pro Glu Gly Gly Gly Ser Arg Val Leu Ser
                325                 330                 335

Phe Asn Trp Tyr Glu Asp Asn Asn Tyr Lys Ala Phe Leu Gly Ile Asp
            340                 345                 350

Ser Thr Arg Lys Asp Pro Ile Tyr Ser Tyr Asp Arg Arg Thr Thr Ser
        355                 360                 365

Phe Cys Asn Ala Leu Ile Gln Ser Leu Glu Ser Asn Pro Leu Thr Lys
    370                 375                 380

Ile Ala Trp Arg Ala Ala Lys Pro Leu Leu Met Gly Lys Ile Leu Tyr
385                 390                 395                 400

Thr Pro Asp Ser Pro Ala Ala Arg Arg Ile Leu Lys Asn Ala Asn Ser
                405                 410                 415

Thr Phe Glu Glu Leu Glu His Val Arg Lys Leu Val Lys Ala Trp Glu
            420                 425                 430

Glu Val Gly Pro Gln Ile Trp Tyr Phe Phe Asp Asn Ser Thr Gln Met
        435                 440                 445

Asn Met Ile Arg Asp Thr Leu Gly Asn Pro Thr Val Lys Asp Phe Leu
    450                 455                 460

Asn Arg Gln Leu Gly Glu Glu Gly Ile Thr Ala Glu Ala Ile Leu Asn
465                 470                 475                 480

Phe Leu Tyr Lys Gly Pro Arg Glu Ser Gln Ala Asp Asp Met Ala Asn
                485                 490                 495

Phe Asp Trp Arg Asp Ile Phe Asn Ile Thr Asp Arg Thr Leu Arg Leu
            500                 505                 510

Val Asn Gln Tyr Leu Glu Cys Leu Val Leu Asp Lys Phe Glu Ser Tyr
        515                 520                 525

Asn Asp Glu Thr Gln Leu Thr Gln Arg Ala Leu Ser Leu Leu Glu Glu
    530                 535                 540

Asn Met Phe Trp Ala Gly Val Val Phe Pro Asp Met Tyr Pro Trp Thr
545                 550                 555                 560

Ser Ser Leu Pro Pro His Val Lys Tyr Lys Ile Arg Met Asp Ile Asp
                565                 570                 575

Val Val Glu Lys Thr Asn Lys Ile Lys Asp Arg Tyr Trp Asp Ser Gly
            580                 585                 590

Pro Arg Ala Asp Pro Val Glu Asp Phe Arg Tyr Ile Trp Gly Gly Phe
        595                 600                 605

Ala Tyr Leu Gln Asp Met Val Glu Gln Gly Ile Thr Arg Ser Gln Val
    610                 615                 620

Gln Ala Glu Ala Pro Val Gly Ile Tyr Leu Gln Gln Met Pro Tyr Pro
625                 630                 635                 640

Cys Phe Val Asp Asp Ser Phe Met Ile Ile Leu Asn Arg Cys Phe Pro
                645                 650                 655

Ile Phe Met Val Leu Ala Trp Ile Tyr Ser Val Ser Met Thr Val Lys
            660                 665                 670
```

-continued

```
Ser Ile Val Leu Glu Lys Glu Leu Arg Leu Lys Glu Thr Leu Lys Asn
        675                 680                 685

Gln Gly Val Ser Asn Ala Val Ile Trp Cys Thr Trp Phe Leu Asp Ser
    690                 695                 700

Phe Ser Ile Met Ser Met Ser Ile Phe Leu Leu Thr Ile Phe Ile Met
705                 710                 715                 720

His Gly Arg Ile Leu His Tyr Ser Asp Pro Phe Ile Leu Phe Leu Phe
                725                 730                 735

Leu Leu Ala Phe Ser Thr Ala Thr Ile Met Leu Cys Phe Leu Leu Ser
            740                 745                 750

Thr Phe Phe Ser Lys Ala Ser Leu Ala Ala Ala Cys Ser Gly Val Ile
        755                 760                 765

Tyr Phe Thr Leu Tyr Leu Pro His Ile Leu Cys Phe Ala Trp Gln Asp
    770                 775                 780

Arg Met Thr Ala Glu Leu Lys Lys Ala Val Ser Leu Leu Ser Pro Val
785                 790                 795                 800

Ala Phe Gly Phe Gly Thr Glu Tyr Leu Val Arg Phe Glu Glu Gln Gly
                805                 810                 815

Leu Gly Leu Gln Trp Ser Asn Ile Gly Asn Ser Pro Thr Glu Gly Asp
            820                 825                 830

Glu Phe Ser Phe Leu Leu Ser Met Gln Met Met Leu Leu Asp Ala Ala
        835                 840                 845

Val Tyr Gly Leu Leu Ala Trp Tyr Leu Asp Gln Val Phe Pro Gly Asp
    850                 855                 860

Tyr Gly Thr Pro Leu Pro Trp Tyr Phe Leu Leu Gln Glu Ser Tyr Trp
865                 870                 875                 880

Leu Gly Gly Glu Gly Cys Ser Thr Arg Glu Glu Arg Ala Leu Glu Lys
                885                 890                 895

Thr Glu Pro Leu Thr Glu Glu Thr Glu Asp Pro Glu His Pro Glu Gly
            900                 905                 910

Ile His Asp Ser Phe Phe Glu Arg Glu His Pro Gly Trp Val Pro Gly
        915                 920                 925

Val Cys Val Lys Asn Leu Val Lys Ile Phe Glu Pro Cys Gly Arg Pro
    930                 935                 940

Ala Val Asp Arg Leu Asn Ile Thr Phe Tyr Glu Asn Gln Ile Thr Ala
945                 950                 955                 960

Phe Leu Gly His Asn Gly Ala Gly Lys Thr Thr Thr Leu Ser Ile Leu
                965                 970                 975

Thr Gly Leu Leu Pro Pro Thr Ser Gly Thr Val Leu Val Gly Gly Arg
            980                 985                 990

Asp Ile Glu Thr Ser Leu Asp Ala  Val Arg Gln Ser Leu  Gly Met Cys
        995                 1000                 1005

Pro Gln  His Asn Ile Leu Phe  His His Leu Thr Val  Ala Glu His
    1010                 1015                 1020

Met Leu  Phe Tyr Ala Gln Leu  Lys Gly Lys Ser Gln  Glu Glu Ala
    1025                 1030                 1035

Gln Leu  Glu Met Glu Ala Met  Leu Glu Asp Thr Gly  Leu His His
    1040                 1045                 1050

Lys Arg  Asn Glu Glu Ala Gln  Asp Leu Ser Gly Gly  Met Gln Arg
    1055                 1060                 1065

Lys Leu  Ser Val Ala Ile Ala  Phe Val Gly Asp Ala  Lys Val Val
    1070                 1075                 1080

Ile Leu  Asp Glu Pro Thr Ser  Gly Val Asp Pro Tyr  Ser Arg Arg
```

```
    1085                1090                1095

Ser Ile  Trp Asp Leu Leu Leu  Lys Tyr Arg Ser Gly  Arg Thr Ile
    1100                1105                1110

Ile Met  Ser Thr His His Met  Asp Glu Ala Asp Leu  Leu Gly Asp
    1115                1120                1125

Arg Ile  Ala Ile Ile Ala Gln  Gly Arg Leu Tyr Cys  Ser Gly Thr
    1130                1135                1140

Pro Leu  Phe Leu Lys Asn Cys  Phe Gly Thr Gly Leu  Tyr Leu Thr
    1145                1150                1155

Leu Val  Arg Lys Met Lys Asn  Ile Gln Ser Gln Arg  Lys Gly Ser
    1160                1165                1170

Glu Gly  Thr Cys Ser Cys Ser  Ser Lys Gly Phe Ser  Thr Thr Cys
    1175                1180                1185

Pro Ala  His Val Asp Asp Leu  Thr Pro Glu Gln Val  Leu Asp Gly
    1190                1195                1200

Asp Val  Asn Glu Leu Met Asp  Val Val Leu His His  Val Pro Glu
    1205                1210                1215

Ala Lys  Leu Val Glu Cys Ile  Gly Gln Glu Leu Ile  Phe Leu Leu
    1220                1225                1230

Pro Asn  Lys Asn Phe Lys His  Arg Ala Tyr Ala Ser  Leu Phe Arg
    1235                1240                1245

Glu Leu  Glu Glu Thr Leu Ala  Asp Leu Gly Leu Ser  Ser Phe Gly
    1250                1255                1260

Ile Ser  Asp Thr Pro Leu Glu  Glu Ile Phe Leu Lys  Val Thr Glu
    1265                1270                1275

Asp Ser  Asp Ser Gly Pro Leu  Phe Ala Gly Gly Ala  Gln Gln Lys
    1280                1285                1290

Arg Glu  Asn Val Asn Pro Arg  His Pro Cys Leu Gly  Pro Arg Glu
    1295                1300                1305

Lys Ala  Gly Gln Thr Pro Gln  Asp Ser Asn Val Cys  Ser Pro Gly
    1310                1315                1320

Ala Pro  Ala Ala His Pro Glu  Gly Gln Pro Pro Pro  Glu Pro Glu
    1325                1330                1335

Cys Pro  Gly Pro Gln Leu Asn  Thr Gly Thr Gln Leu  Val Leu Gln
    1340                1345                1350

His Val  Gln Ala Leu Leu Val  Lys Arg Phe Gln His  Thr Ile Arg
    1355                1360                1365

Ser His  Lys Asp Phe Leu Ala  Gln Ile Val Leu Pro  Ala Thr Phe
    1370                1375                1380

Val Phe  Leu Ala Leu Met Leu  Ser Ile Val Ile Pro  Pro Phe Gly
    1385                1390                1395

Glu Tyr  Pro Ala Leu Thr Leu  His Pro Trp Ile Tyr  Gly Gln Gln
    1400                1405                1410

Tyr Thr  Phe Phe Ser Met Asp  Glu Pro Gly Ser Glu  Gln Phe Thr
    1415                1420                1425

Val Leu  Ala Asp Val Leu Leu  Asn Lys Pro Gly Phe  Gly Asn Arg
    1430                1435                1440

Cys Leu  Lys Glu Gly Trp Leu  Pro Glu Tyr Pro Cys  Gly Asn Ser
    1445                1450                1455

Thr Pro  Trp Lys Thr Pro Ser  Val Ser Pro Asn Ile  Thr Gln Leu
    1460                1465                1470

Phe Gln  Lys Gln Lys Trp Thr  Gln Val Asn Pro Ser  Pro Ser Cys
    1475                1480                1485
```

-continued

```
Arg Cys  Ser Thr Arg Glu Lys  Leu Thr Met Leu Pro  Glu Cys Pro
    1490                 1495                 1500

Glu Gly  Ala Gly Gly Leu Pro  Pro Pro Gln Arg Thr  Gln Arg Ser
    1505                 1510                 1515

Thr Glu  Ile Leu Gln Asp Leu  Thr Asp Arg Asn Ile  Ser Asp Phe
    1520                 1525                 1530

Leu Val  Lys Thr Tyr Pro Ala  Leu Ile Arg Ser Ser  Leu Lys Ser
    1535                 1540                 1545

Lys Phe  Trp Val Asn Glu Gln  Arg Tyr Gly Gly Ile  Ser Ile Gly
    1550                 1555                 1560

Gly Lys  Leu Pro Val Val Pro  Ile Thr Gly Glu Ala  Leu Val Gly
    1565                 1570                 1575

Phe Leu  Ser Asp Leu Gly Arg  Ile Met Asn Val Ser  Gly Gly Pro
    1580                 1585                 1590

Ile Thr  Arg Glu Ala Ser Lys  Glu Ile Pro Asp Phe  Leu Lys His
    1595                 1600                 1605

Leu Glu  Thr Glu Asp Asn Ile  Lys Val Trp Phe Asn  Asn Lys Gly
    1610                 1615                 1620

Trp His  Ala Leu Val Ser Phe  Leu Asn Val Ala His  Asn Ala Ile
    1625                 1630                 1635

Leu Arg  Ala Ser Leu Pro Lys  Asp Arg Ser Pro Glu  Glu Tyr Gly
    1640                 1645                 1650

Ile Thr  Val Ile Ser Gln Pro  Leu Asn Leu Thr Lys  Glu Gln Leu
    1655                 1660                 1665

Ser Glu  Ile Thr Val Leu Thr  Thr Ser Val Asp Ala  Val Val Ala
    1670                 1675                 1680

Ile Cys  Val Ile Phe Ser Met  Ser Phe Val Pro Ala  Ser Phe Val
    1685                 1690                 1695

Leu Tyr  Leu Ile Gln Glu Arg  Val Asn Lys Ser Lys  His Leu Gln
    1700                 1705                 1710

Phe Ile  Ser Gly Val Ser Pro  Thr Thr Tyr Trp Val  Thr Asn Phe
    1715                 1720                 1725

Leu Trp  Asp Ile Met Asn Tyr  Ser Val Ser Ala Gly  Leu Val Val
    1730                 1735                 1740

Gly Ile  Phe Ile Gly Phe Gln  Lys Lys Ala Tyr Thr  Ser Pro Glu
    1745                 1750                 1755

Asn Leu  Pro Ala Leu Val Ala  Leu Leu Leu Leu Tyr  Gly Trp Ala
    1760                 1765                 1770

Val Ile  Pro Met Met Tyr Pro  Ala Ser Phe Leu Phe  Asp Val Pro
    1775                 1780                 1785

Ser Thr  Ala Tyr Val Ala Leu  Ser Cys Ala Asn Leu  Phe Ile Gly
    1790                 1795                 1800

Ile Asn  Ser Ser Ala Ile Thr  Phe Ile Leu Glu Leu  Phe Glu Asn
    1805                 1810                 1815

Asn Arg  Thr Leu Leu Arg Phe  Asn Ala Val Leu Arg  Lys Leu Leu
    1820                 1825                 1830

Ile Val  Phe Pro His Phe Cys  Leu Gly Arg Gly Leu  Ile Asp Leu
    1835                 1840                 1845

Ala Leu  Ser Gln Ala Val Thr  Asp Val Tyr Ala Arg  Phe Gly Glu
    1850                 1855                 1860

Glu His  Ser Ala Asn Pro Phe  His Trp Asp Leu Ile  Gly Lys Asn
    1865                 1870                 1875
```

-continued

```
Leu Phe  Ala Met Val Val Glu  Gly Val Val Tyr Phe  Leu Leu Thr
    1880                 1885                 1890

Leu Leu  Val Gln Arg His Phe  Phe Leu Ser Gln Trp  Ile Ala Glu
    1895                 1900                 1905

Pro Thr  Lys Glu Pro Ile Val  Asp Glu Asp Asp Asp  Val Ala Glu
    1910                 1915                 1920

Glu Arg  Gln Arg Ile Ile Thr  Gly Gly Asn Lys Thr  Asp Ile Leu
    1925                 1930                 1935

Arg Leu  His Glu Leu Thr Lys  Ile Tyr Pro Gly Thr  Ser Ser Pro
    1940                 1945                 1950

Ala Val  Asp Arg Leu Cys Val  Gly Val Arg Pro Gly  Glu Cys Phe
    1955                 1960                 1965

Gly Leu  Leu Gly Val Asn Gly  Ala Gly Lys Thr Thr  Thr Phe Lys
    1970                 1975                 1980

Met Leu  Thr Gly Asp Thr Thr  Val Thr Ser Gly Asp  Ala Thr Val
    1985                 1990                 1995

Ala Gly  Lys Ser Ile Leu Thr  Asn Ile Ser Glu Val  His Gln Asn
    2000                 2005                 2010

Met Gly  Tyr Cys Pro Gln Phe  Asp Ala Ile Asp Glu  Leu Leu Thr
    2015                 2020                 2025

Gly Arg  Glu His Leu Tyr Leu  Tyr Ala Arg Leu Arg  Gly Val Pro
    2030                 2035                 2040

Ala Glu  Glu Ile Glu Lys Val  Ala Asn Trp Ser Ile  Lys Ser Leu
    2045                 2050                 2055

Gly Leu  Thr Val Tyr Ala Asp  Cys Leu Ala Gly Thr  Tyr Ser Gly
    2060                 2065                 2070

Gly Asn  Lys Arg Lys Leu Ser  Thr Ala Ile Ala Leu  Ile Gly Cys
    2075                 2080                 2085

Pro Pro  Leu Val Leu Leu Asp  Glu Pro Thr Thr Gly  Met Asp Pro
    2090                 2095                 2100

Gln Ala  Arg Arg Met Leu Trp  Asn Val Ile Val Ser  Ile Ile Arg
    2105                 2110                 2115

Glu Gly  Arg Ala Val Val Leu  Thr Ser His Ser Met  Glu Glu Cys
    2120                 2125                 2130

Glu Ala  Leu Cys Thr Arg Leu  Ala Ile Met Val Lys  Gly Ala Phe
    2135                 2140                 2145

Arg Cys  Met Gly Thr Ile Gln  His Leu Lys Ser Lys  Phe Gly Asp
    2150                 2155                 2160

Gly Tyr  Ile Val Thr Met Lys  Ile Lys Ser Pro Lys  Asp Asp Leu
    2165                 2170                 2175

Leu Pro  Asp Leu Asn Pro Val  Glu Gln Phe Phe Gln  Gly Asn Phe
    2180                 2185                 2190

Pro Gly  Ser Val Gln Arg Glu  Arg His Tyr Asn Met  Leu Gln Phe
    2195                 2200                 2205

Gln Val  Ser Ser Ser Ser Leu  Ala Arg Ile Phe Gln  Leu Leu Leu
    2210                 2215                 2220

Ser His  Lys Asp Ser Leu Leu  Ile Glu Glu Tyr Ser  Val Thr Gln
    2225                 2230                 2235

Thr Thr  Leu Asp Gln Val Phe  Val Asn Phe Ala Lys  Gln Gln Thr
    2240                 2245                 2250

Glu Ser  His Asp Leu Pro Leu  His Pro Arg Ala Ala  Gly Ala Ser
    2255                 2260                 2265

Arg Gln  Ala Gln Asp
```

2270

<210> SEQ ID NO 14
<211> LENGTH: 2608
<212> TYPE: DNA
<213> ORGANISM: Homo sapiens

<400> SEQUENCE: 14

```
tccttcttca ttctgcagtt ggtgccagaa ctctggatcc tgaactggaa gaaaatgtct     60

atccaggttg agcatcctgc tggtggttac aagaaactgt ttgaaactgt ggaggaactg    120

tcctcgccgc tcacagctca tgtaacaggc aggatccccc tctggctcac cggcagtctc    180

cttcgatgtg ggccaggact ctttgaagtt ggatctgagc cattttacca cctgtttgat    240

gggcaagccc tcctgcacaa gtttgacttt aaagaaggac atgtcacata ccacagaagg    300

ttcatccgca ctgatgctta cgtacgggca atgactgaga aaaggatcgt cataacagaa    360

tttggcacct gtgctttccc agatccctgc aagaatatat tttccaggtt tttttcttac    420

tttcgaggag tagaggttac tgacaatgcc cttgttaatg tctacccagt gggggaagat    480

tactacgctt gcacagagac caactttatt acaaagatta atccagagac cttggagaca    540

attaagcagg ttgatctttg caactatgtc tctgtcaatg gggccactgc tcacccccac    600

attgaaaatg atggaaccgt ttacaatatt ggtaattgct ttggaaaaaa tttttcaatt    660

gcctacaaca ttgtaaagat cccaccactg caagcagaca aggaagatcc aataagcaag    720

tcagagatcg ttgtacaatt cccctgcagt gaccgattca agccatctta cgttcatagt    780

tttggtctga ctcccaacta tatcgttttt gtggagacac cagtcaaaat taacctgttc    840

aagttccttt cttcatggag tctttgggga gccaactaca tggattgttt tgagtccaat    900

gaaaccatgg gggtttggct tcatattgct gacaaaaaaa ggaaaaagta cctcaataat    960

aaatacagaa cttctccttt caacctcttc catcacatca acacctatga agacaatggg   1020

tttctgattg tggatctctg ctgctggaaa ggatttgagt ttgtttataa ttacttatat   1080

ttagccaatt tacgtgagaa ctgggaagag gtgaaaaaaa atgccagaaa ggctccccaa   1140

cctgaagtta ggagatatgt acttcctttg aatattgaca aggctgacac aggcaagaat   1200

ttagtcacgc tccccaatac aactgccact gcaattctgt gcagtgacga gactatctgg   1260

ctggagcctg aagttctctt ttcagggcct cgtcaagcat ttgagtttcc tcaaatcaat   1320

taccagaagt attgtgggaa accttacaca tatgcgtatg gacttggctt gaatcacttt   1380

gttccagata ggctctgtaa gctgaatgtc aaaactaaag aaacttgggt ttggcaagag   1440

cctgattcat acccatcaga acccatcttt gtttctcacc cagatgcctt ggaagaagat   1500

gatggtgtag ttctgagtgt ggtggtgagc ccaggagcag gacaaaagcc tgcttatctc   1560

ctgattctga atgccaagga cttaagtgaa gttgcccggg ctgaagtgga gattaacatc   1620

cctgtcacct ttcatggact gttcaaaaaa tcttgagcat actccagcaa gatatgtttt   1680

tggtagcaaa actgagaaaa tcagcttcag gtctgcaatc aaattctgtt caattttagc   1740

ctgctatatg tcatggtttt aacttgcaga tgcgcacaat tttgcaatgt tttacagaaa   1800

gcactgagtt gagcaagcaa ttcctttatt taaaaaaaaa agtacgtatt tagataatca   1860

tacttcctct gtgagacagg ccataactga aaaactctta aatatttagc aatcaaatag   1920

gaaatgaatg tggacttact aaatggcttt taattcctat tataagagca tattttaggt   1980

acctatctgc tccaattata tttttaacat ttaaaaacca aagtcctcta cacttgattt   2040

atattatatg tggctttgct gagtcaagga agtatcatgc aataaggctt aattactaaa   2100
```

-continued

```
tgtcaaacca aactttttct caaaccaggg actatcatct aagattaatt acagtaatta   2160

ttttgcgtat acgtaactgc tcaaagatta tgaatcttat gaatgttaac ctttccgttt   2220

attacaagca agtactatta tttctgattt tataataaga aaatctgtgt ttaatcaact   2280

gaggcctctc aaccaaataa catctcagag attaagttat atattaaaag cttatgtaac   2340

ataaaagcaa gtacatatag tagtgactat atttaaaaaa acagcataaa atgcttaaaa   2400

atgtaatatt tactaaaatc agattatggg ataatgttgc aggattatac tttattgcat   2460

ctttttttgtt taattgtatt taagcattgt gcaatcactt gggaaaaata ttaaattatt   2520

aacattgagg tattaataca ttttaagcct tttgttttta aatttctttt cttccagaga   2580

ttgtttaaaa ataaatattg acaaaaat                                      2608


<210> SEQ ID NO 15
<211> LENGTH: 533
<212> TYPE: PRT
<213> ORGANISM: Homo sapiens

<400> SEQUENCE: 15

Met Ser Ile Gln Val Glu His Pro Ala Gly Gly Tyr Lys Lys Leu Phe
1               5                   10                  15

Glu Thr Val Glu Glu Leu Ser Ser Pro Leu Thr Ala His Val Thr Gly
            20                  25                  30

Arg Ile Pro Leu Trp Leu Thr Gly Ser Leu Leu Arg Cys Gly Pro Gly
        35                  40                  45

Leu Phe Glu Val Gly Ser Glu Pro Phe Tyr His Leu Phe Asp Gly Gln
    50                  55                  60

Ala Leu Leu His Lys Phe Asp Phe Lys Glu Gly His Val Thr Tyr His
65                  70                  75                  80

Arg Arg Phe Ile Arg Thr Asp Ala Tyr Val Arg Ala Met Thr Glu Lys
                85                  90                  95

Arg Ile Val Ile Thr Glu Phe Gly Thr Cys Ala Phe Pro Asp Pro Cys
            100                 105                 110

Lys Asn Ile Phe Ser Arg Phe Phe Ser Tyr Phe Arg Gly Val Glu Val
        115                 120                 125

Thr Asp Asn Ala Leu Val Asn Val Tyr Pro Val Gly Glu Asp Tyr Tyr
    130                 135                 140

Ala Cys Thr Glu Thr Asn Phe Ile Thr Lys Ile Asn Pro Glu Thr Leu
145                 150                 155                 160

Glu Thr Ile Lys Gln Val Asp Leu Cys Asn Tyr Val Ser Val Asn Gly
                165                 170                 175

Ala Thr Ala His Pro His Ile Glu Asn Asp Gly Thr Val Tyr Asn Ile
            180                 185                 190

Gly Asn Cys Phe Gly Lys Asn Phe Ser Ile Ala Tyr Asn Ile Val Lys
        195                 200                 205

Ile Pro Pro Leu Gln Ala Asp Lys Glu Asp Pro Ile Ser Lys Ser Glu
    210                 215                 220

Ile Val Val Gln Phe Pro Cys Ser Asp Arg Phe Lys Pro Ser Tyr Val
225                 230                 235                 240

His Ser Phe Gly Leu Thr Pro Asn Tyr Ile Val Phe Val Glu Thr Pro
                245                 250                 255

Val Lys Ile Asn Leu Phe Lys Phe Leu Ser Ser Trp Ser Leu Trp Gly
            260                 265                 270

Ala Asn Tyr Met Asp Cys Phe Glu Ser Asn Glu Thr Met Gly Val Trp
```

-continued

```
        275                 280                 285

Leu His Ile Ala Asp Lys Lys Arg Lys Lys Tyr Leu Asn Asn Lys Tyr
    290                 295                 300

Arg Thr Ser Pro Phe Asn Leu Phe His His Ile Asn Thr Tyr Glu Asp
305                 310                 315                 320

Asn Gly Phe Leu Ile Val Asp Leu Cys Cys Trp Lys Gly Phe Glu Phe
                325                 330                 335

Val Tyr Asn Tyr Leu Tyr Leu Ala Asn Leu Arg Glu Asn Trp Glu Glu
            340                 345                 350

Val Lys Lys Asn Ala Arg Lys Ala Pro Gln Pro Glu Val Arg Arg Tyr
        355                 360                 365

Val Leu Pro Leu Asn Ile Asp Lys Ala Asp Thr Gly Lys Asn Leu Val
    370                 375                 380

Thr Leu Pro Asn Thr Thr Ala Thr Ala Ile Leu Cys Ser Asp Glu Thr
385                 390                 395                 400

Ile Trp Leu Glu Pro Glu Val Leu Phe Ser Gly Pro Arg Gln Ala Phe
                405                 410                 415

Glu Phe Pro Gln Ile Asn Tyr Gln Lys Tyr Cys Gly Lys Pro Tyr Thr
            420                 425                 430

Tyr Ala Tyr Gly Leu Gly Leu Asn His Phe Val Pro Asp Arg Leu Cys
        435                 440                 445

Lys Leu Asn Val Lys Thr Lys Glu Thr Trp Val Trp Gln Glu Pro Asp
    450                 455                 460

Ser Tyr Pro Ser Glu Pro Ile Phe Val Ser His Pro Asp Ala Leu Glu
465                 470                 475                 480

Glu Asp Asp Gly Val Val Leu Ser Val Val Val Ser Pro Gly Ala Gly
                485                 490                 495

Gln Lys Pro Ala Tyr Leu Leu Ile Leu Asn Ala Lys Asp Leu Ser Glu
            500                 505                 510

Val Ala Arg Ala Glu Val Glu Ile Asn Ile Pro Val Thr Phe His Gly
        515                 520                 525

Leu Phe Lys Lys Ser
    530


<210> SEQ ID NO 16
<211> LENGTH: 1752
<212> TYPE: DNA
<213> ORGANISM: Homo sapiens

<400> SEQUENCE: 16

gagcccgatt taacggaaac tgtgggcggt gagaagttcc ttatgacaca ctaatcccaa     60

cctgctgacc ggaccacgcc tccagcggag ggaacctcta gagctccagg acattcaggt    120

accaggtagc cccaaggagg agctgccgac ctggcaggga acaaccaaga ctggggttaa    180

atctcacagc ctgcaagtgg aagagaagaa cttgaaccca ggtccaactt ttgcgccaca    240

gcaggctgcc tcttggtcct gacaggaagt cacaacttgg ccctgacttc ctatcctagg    300

gaaggggccg gctggagagg ccaggacaga gaaagcagat cccttctttt tccaaggact    360

ctgtgtcttc cataggcaac atgtcagaag gggtgggcac gttccgcatg gtacctgaag    420

aggaacagga gctccgtgcc caactggagc agctcacaac caaggaccat ggacctgtct    480

ttggcccgtg cagccagctg ccccgccaca ccttgcagaa ggccaaggat gagctgaacg    540

agagagagga gacccgggag gaggcagtgc gagagctgca ggagatggtg caggcgcagg    600

cggcctcggg ggaggagctg gcggtggccg tggcggagag ggtgcaagag aaggacagcg    660
```

```
gcttcttcct gcgcttcatc cgcgcacgga agttcaacgt gggccgtgcc tatgagctgc    720
tcagaggcta tgtgaatttc cggctgcagt accctgagct ctttgacagc ctgtccccag    780
aggctgtccg ctgcaccatt gaagctggct accctggtgt cctctctagt cgggacaagt    840
atggccgagt ggtcatgctc ttcaacattg agaactggca aagtcaagaa atcacctttg    900
atgagatctt gcaggcatat tgcttcatcc tggagaagct gctggagaat gaggaaactc    960
aaatcaatgg cttctgcatc attgagaact tcaagggctt taccatgcag caggctgcta   1020
gtctccggac ttcagatctc aggaagatgg tggacatgct ccaggattcc ttcccagccc   1080
ggttcaaagc catccacttc atccaccagc catggtactt caccacgacc tacaatgtgg   1140
tcaagccctt cttgaagagc aagctgcttg agagggtctt tgtccacggg gatgaccttt   1200
ctggtttcta ccaggagatc gatgagaaca tcctgccctc tgacttcggg ggcacgctgc   1260
ccaagtatga tggcaaggcc gttgctgagc agctctttgg cccccaggcc caagctgaga   1320
acacagcctt ctgaaaacat ctcctgccag ctgaactgta gttagaatct ctgggcctct   1380
cctcaactgt cctggaccca aggctaggaa agggctgctt gagatgactg tggtcccccc   1440
ttagactccc taagcccgag tgagctcagg tgtcaccctg ttctcaagtt gggggatggg   1500
taataaagga gggggaattc ccttgaacaa gaagaactgg ggatagttat atttccacct   1560
gcccttgaag ctttaagaca gtgatttttg tgtaaggttg tatttcaaag actcgaattc   1620
atttctcag tcatttcctt tgtaacagag ttttacgact tagagtctgt gaaaacaggc   1680
aaggagcccg ggttaaaata tccccctatt cgcccccaaa atgcaataaa agaagataaa   1740
agagagagga ta                                                       1752
```

<210> SEQ ID NO 17
<211> LENGTH: 317
<212> TYPE: PRT
<213> ORGANISM: Homo sapiens

<400> SEQUENCE: 17

```
Met Ser Glu Gly Val Gly Thr Phe Arg Met Val Pro Glu Glu Glu Gln
1               5                   10                  15

Glu Leu Arg Ala Gln Leu Glu Gln Leu Thr Thr Lys Asp His Gly Pro
            20                  25                  30

Val Phe Gly Pro Cys Ser Gln Leu Pro Arg His Thr Leu Gln Lys Ala
        35                  40                  45

Lys Asp Glu Leu Asn Glu Arg Glu Glu Thr Arg Glu Glu Ala Val Arg
    50                  55                  60

Glu Leu Gln Glu Met Val Gln Ala Gln Ala Ala Ser Gly Glu Glu Leu
65                  70                  75                  80

Ala Val Ala Val Ala Glu Arg Val Gln Glu Lys Asp Ser Gly Phe Phe
                85                  90                  95

Leu Arg Phe Ile Arg Ala Arg Lys Phe Asn Val Gly Arg Ala Tyr Glu
            100                 105                 110

Leu Leu Arg Gly Tyr Val Asn Phe Arg Leu Gln Tyr Pro Glu Leu Phe
        115                 120                 125

Asp Ser Leu Ser Pro Glu Ala Val Arg Cys Thr Ile Glu Ala Gly Tyr
    130                 135                 140

Pro Gly Val Leu Ser Ser Arg Asp Lys Tyr Gly Arg Val Val Met Leu
145                 150                 155                 160

Phe Asn Ile Glu Asn Trp Gln Ser Gln Glu Ile Thr Phe Asp Glu Ile
                165                 170                 175
```

-continued

```
Leu Gln Ala Tyr Cys Phe Ile Leu Glu Lys Leu Leu Glu Asn Glu Glu
            180                 185                 190

Thr Gln Ile Asn Gly Phe Cys Ile Ile Glu Asn Phe Lys Gly Phe Thr
        195                 200                 205

Met Gln Gln Ala Ala Ser Leu Arg Thr Ser Asp Leu Arg Lys Met Val
    210                 215                 220

Asp Met Leu Gln Asp Ser Phe Pro Ala Arg Phe Lys Ala Ile His Phe
225                 230                 235                 240

Ile His Gln Pro Trp Tyr Phe Thr Thr Thr Tyr Asn Val Val Lys Pro
                245                 250                 255

Phe Leu Lys Ser Lys Leu Leu Glu Arg Val Phe Val His Gly Asp Asp
            260                 265                 270

Leu Ser Gly Phe Tyr Gln Glu Ile Asp Glu Asn Ile Leu Pro Ser Asp
        275                 280                 285

Phe Gly Gly Thr Leu Pro Lys Tyr Asp Gly Lys Ala Val Ala Glu Gln
    290                 295                 300

Leu Phe Gly Pro Gln Ala Gln Ala Glu Asn Thr Ala Phe
305                 310                 315


<210> SEQ ID NO 18
<211> LENGTH: 3027
<212> TYPE: DNA
<213> ORGANISM: Homo sapiens

<400> SEQUENCE: 18

cagcgttcag gctgcccctt cttggctggg aagggcgctg aagaaacaac gcccaggacc      60

aggactatcc cctgctcaag ctgtgattcc gagacccctg ccaccactac tgcattcacg     120

gggatcccag gctagtggga ctcgacatgg gtagccccca gggcagctcc ctacagcttg     180

ggccatctgc acttttccca aggccctaag tctccgcctc tgggctcgtt aaggtttggg     240

gtgggagctg tgctgtggga agcaacccgg actacacttg gcaagcatgg cgctactgaa     300

agtcaagttt gaccagaaga agcgggtcaa gttggcccaa gggctctggc tcatgaactg     360

gttctccgtg ttggctggca tcatcatctt cagcctagga ctgttcctga agattgaact     420

ccgaaagagg agcgatgtga tgaataattc tgagagccat tttgtgccca actcattgat     480

agggatgggg gtgctatcct gtgtcttcaa ctcgctggct gggaagatct gctacgacgc     540

cctggaccca gccaagtatg ccagatggaa gccctggctg aagccgtacc tggctatctg     600

tgttctcttc aacatcatcc tcttccttgt ggctctctgc tgctttctgc ttcggggctc     660

gctggagaac accctgggcc aagggctcaa gaacggcatg aagtactacc gggacacaga     720

cacccctggc aggtgtttca tgaagaagac catcgacatg ctgcagatcg agttcaaatg     780

ctgcggcaac aacggttttc gggactggtt tgagattcag tggatcagca atcgctacct     840

ggacttttcc tccaaagaag tcaaagatcg aatcaagagc aacgtggatg ggcggtacct     900

ggtggacggc gtccctttca gctgctgcaa tcctagctcg ccacggccct gcatccagta     960

tcagatcacc aacaactcag cacactacag ttacgaccac cagacggagg agctcaacct    1020

gtgggtgcgt ggctgcaggg ctgccctgct gagctactac agcagcctca tgaactccat    1080

gggtgtcgtc acgctcctca tttggctctt cgaggtgacc attacaattg ggctgcgcta    1140

cctacagacg tcgctggatg gtgtgtccaa ccccgaggaa tctgagagcg agagccaggg    1200

ctggctgctg gagaggagcg tgccggagac ctggaaggcc tttctggaga gtgtgaagaa    1260

gctgggcaag ggcaaccagg tggaagccga gggcgcagac gcaggccagg ccccagaggc    1320
```

```
tggctgaggg ccctggggcc cctcccctcc cgaacactga gaaatagtgc actccaagaa   1380
acgtggatct ccccctcatc caactccgaa agtctgaatc tcccaaggag ggcaccatct   1440
tacagagact ctccctgacg gtggaattta agtttagggt ccctaaaagc atttgacaca   1500
cagttgttga atgactgacc caaaatgtga atgaagctaa tgtgaatgtg agtgaagctc   1560
ccttcaggcc cgctgcccta ggatatgccc tcctggtgac tcgggggctg tctcagacga   1620
ctagcccagg acccatcttt ctcacacgga tttagtccca ccctatggcc actggccgta   1680
tctgagggct gctccccttt tagaatttac ctcttatgag ctccatgttg cttcactcta   1740
tccaaagtgt cacttggtgc ataagcacag aaatctgaaa aatggccatg ttgtcttttt   1800
ttttttttt taatgccaag attgacaggt tggccgtttg cttaatgcca gaagttgggg    1860
gaaagttacg cttttctaag aataatggac tcttaaggca ttgagggctc taaacaggat   1920
tctttaatca tggagcaaga gaatttcaag gcaggggatt ttatcccccca ccaaaaacac  1980
agtgaaaggc ctgcttttgt gtcccattca catgccctcg gtcactgagt ctggagtgaa   2040
ccacgggttg aggaagtcag gctgttggcg tgtcccagca ccacaccacc cctaaagtgc   2100
caggtgatct cctgtggctc atcggtggaa gcagtggggt aggctgctgc cctgctgtgg   2160
aagaggagca acaatcagac atgagtccac cctttggaga ccaggcctca gctcttggtg   2220
ggcccaggga cacccacaca ggtggccatc acagccccat ggacaacact aattgtccac   2280
agcaaagggc aaggaatcct ctgggagctt cttccgtttc ttccccccag atacccatct   2340
tgaaaaacac tatttctgga atgcttctgc atcaaaggag attctttgag atagcccatc   2400
ttcctgagct agcaaataca ggagttttca ctttctttag gaaagagaag ctttcagggg   2460
aaggagagaa tgattttgct gacttcccaa gccctggtga ccagaccaag gcagggccca   2520
gcataattcc tccagttgga tgaacattca agagagctcg ttcctacctg gctggagacc   2580
gaggccagaa ggcaaaaacc agaaagggaa cagtccataa cttacctctg cttctgaccg   2640
atggtgtttg ggaataggtt actttggact gagtttgggt tctctgctgt cctaagaact   2700
tcagtgtaga gaaaataaga cttctggtgc tgctggggta tgttctgggc ttaattcccc   2760
caagcagaag accagatcca agatgtttgg acaccctgtc agacgttggt cccaagttta   2820
attagatttc tgaatctcgt tgaggccaag gaatgatcca tactgaaaaa atgctgagcc   2880
agccatcttt ggcaaaggtc cctgagctct tgctatctct caagagtgct gagaaccacg   2940
gtgaaagtgc tgctctaggc ccacaagtgt aactatgctg ttaacagctg tcaatagata   3000
attaaaattc atactgtatg aaaatca                                       3027
```

<210> SEQ ID NO 19
<211> LENGTH: 346
<212> TYPE: PRT
<213> ORGANISM: Homo sapiens

<400> SEQUENCE: 19

```
Met Ala Leu Leu Lys Val Lys Phe Asp Gln Lys Lys Arg Val Lys Leu
1               5                   10                  15

Ala Gln Gly Leu Trp Leu Met Asn Trp Phe Ser Val Leu Ala Gly Ile
            20                  25                  30

Ile Ile Phe Ser Leu Gly Leu Phe Leu Lys Ile Glu Leu Arg Lys Arg
        35                  40                  45

Ser Asp Val Met Asn Asn Ser Glu Ser His Phe Val Pro Asn Ser Leu
    50                  55                  60
```

-continued

```
Ile Gly Met Gly Val Leu Ser Cys Val Phe Asn Ser Leu Ala Gly Lys
65                  70                  75                  80

Ile Cys Tyr Asp Ala Leu Asp Pro Ala Lys Tyr Ala Arg Trp Lys Pro
                85                  90                  95

Trp Leu Lys Pro Tyr Leu Ala Ile Cys Val Leu Phe Asn Ile Ile Leu
            100                 105                 110

Phe Leu Val Ala Leu Cys Cys Phe Leu Leu Arg Gly Ser Leu Glu Asn
        115                 120                 125

Thr Leu Gly Gln Gly Leu Lys Asn Gly Met Lys Tyr Tyr Arg Asp Thr
    130                 135                 140

Asp Thr Pro Gly Arg Cys Phe Met Lys Lys Thr Ile Asp Met Leu Gln
145                 150                 155                 160

Ile Glu Phe Lys Cys Cys Gly Asn Asn Gly Phe Arg Asp Trp Phe Glu
                165                 170                 175

Ile Gln Trp Ile Ser Asn Arg Tyr Leu Asp Phe Ser Ser Lys Glu Val
            180                 185                 190

Lys Asp Arg Ile Lys Ser Asn Val Asp Gly Arg Tyr Leu Val Asp Gly
        195                 200                 205

Val Pro Phe Ser Cys Cys Asn Pro Ser Ser Pro Arg Pro Cys Ile Gln
    210                 215                 220

Tyr Gln Ile Thr Asn Asn Ser Ala His Tyr Ser Tyr Asp His Gln Thr
225                 230                 235                 240

Glu Glu Leu Asn Leu Trp Val Arg Gly Cys Arg Ala Ala Leu Leu Ser
                245                 250                 255

Tyr Tyr Ser Ser Leu Met Asn Ser Met Gly Val Val Thr Leu Leu Ile
            260                 265                 270

Trp Leu Phe Glu Val Thr Ile Thr Ile Gly Leu Arg Tyr Leu Gln Thr
        275                 280                 285

Ser Leu Asp Gly Val Ser Asn Pro Glu Glu Ser Glu Ser Glu Ser Gln
    290                 295                 300

Gly Trp Leu Leu Glu Arg Ser Val Pro Glu Thr Trp Lys Ala Phe Leu
305                 310                 315                 320

Glu Ser Val Lys Lys Leu Gly Lys Gly Asn Gln Val Glu Ala Glu Gly
                325                 330                 335

Ala Asp Ala Gly Gln Ala Pro Glu Ala Gly
            340                 345


<210> SEQ ID NO 20
<211> LENGTH: 1767
<212> TYPE: DNA
<213> ORGANISM: Homo sapiens

<400> SEQUENCE: 20

gtcagctggg tgactcatac atctgtgaga ccctccgtat ggagaccggg gcggggggtg      60

ttgcttaatg cttagaactg ctgaaactac cagttcactg tctcagcact aatccaactc     120

tgctccttaa gtgggatttg gcttttagac attgagacct ggatgctggg catcctcgct     180

agatccccta caaattcccc acatacgtag gccaggagcc tcagcggtgc cccttcaggc     240

tcatctggca agacggtacc agcttgctca gaacaggggc tggctattca tcatctcaga     300

gcatagagac cctctccttg ccacccggcc cttcccacct ggttggtgac aaatcacaag     360

gtggtagaag ttgccaggga cagataacat ggcagccagc gggaagacca gcaagtccga     420

accgaaccat gttatcttca agaagatctc ccgggacaaa tcggtgacca tctacctggg     480

gaacagagac tacatagacc atgtcagcca agtccagcct gtggatggtg tcgtgttggt     540
```

```
tgatcctgat cttgtgaagg gaaagaaagt gtatgtcact ctgacctgcg ccttccgcta    600

tggccaagag gacattgacg tgatcggctt gaccttccgc agggacctgt acttctcccg    660

ggtccaggtg tatcctcctg tgggggccgc gagcaccccc acaaaactgc aagagagcct    720

gcttaaaaag ctggggagca acacgtaccc ctttctcctg acgtttcctg actacttgcc    780

ctgttcagtg atgttgcagc cagctccaca agattcaggg aagtcctgtg ggggttgactt   840

tgaggtcaaa gcattcgcca cagacagcac cgatgccgaa gaggacaaaa tccccaagaa    900

gagctccgtg cgattactga tccgcaaagt acagcatgcc ccacttgaga tgggtcccca    960

gccccgagct gaggcggcct ggcagttctt catgtctgac aagcccctgc accttgcggt   1020

ctctctcaac aaagagatct atttccatgg ggagcccatc cctgtgaccg tgactgtcac   1080

caataacaca gagaagaccg tgaagaagat taaagcattc gtggaacagg tggccaatgt   1140

ggttctctac tcgagtgatt attacgtcaa gcccgtggct atggaggaag cgcaagaaaa   1200

agtgccacca aacagcactt tgaccaagac gctgacgctg ctgcccttgc tggctaacaa   1260

tcgagaaagg agaggcattg ccctggatgg gaaaatcaag cacgaggaca caaaccttgc   1320

ctccagcacc atcattaagg agggcataga ccggaccgtc ctgggaatcc tggtgtctta   1380

ccagatcaag gtgaagctca cagtgtcagg ctttctggga gagctcacct ccagtgaagt   1440

cgccactgag gtcccattcc gcctcatgca ccctcagcct gaggacccag ctaaggaaag   1500

ttatcaggat gcaaatttag tttttgagga gtttgctcgc cataatctga aagatgcagg   1560

agaagctgag gaggggaaga gagacaagaa tgacgttgat gagtgaagat gtcggctcag   1620

gatgccggaa aatgacctgt agttaccagt gcaacgagca aagccccaca gtttagtcct   1680

ttggagttat gctgcgtatg aaaggatgag tcttcttccg agaaataaag cttgtttgtt   1740

ctcccctgga aaaaaaaaaa aaaaaaa                                       1767
```

<210> SEQ ID NO 21
<211> LENGTH: 405
<212> TYPE: PRT
<213> ORGANISM: Homo sapiens

<400> SEQUENCE: 21

```
Met Ala Ala Ser Gly Lys Thr Ser Lys Ser Glu Pro Asn His Val Ile
1               5                   10                  15

Phe Lys Lys Ile Ser Arg Asp Lys Ser Val Thr Ile Tyr Leu Gly Asn
            20                  25                  30

Arg Asp Tyr Ile Asp His Val Ser Gln Val Gln Pro Val Asp Gly Val
        35                  40                  45

Val Leu Val Asp Pro Asp Leu Val Lys Gly Lys Lys Val Tyr Val Thr
    50                  55                  60

Leu Thr Cys Ala Phe Arg Tyr Gly Gln Glu Asp Ile Asp Val Ile Gly
65                  70                  75                  80

Leu Thr Phe Arg Arg Asp Leu Tyr Phe Ser Arg Val Gln Val Tyr Pro
                85                  90                  95

Pro Val Gly Ala Ala Ser Thr Pro Thr Lys Leu Gln Glu Ser Leu Leu
            100                 105                 110

Lys Lys Leu Gly Ser Asn Thr Tyr Pro Phe Leu Leu Thr Phe Pro Asp
        115                 120                 125

Tyr Leu Pro Cys Ser Val Met Leu Gln Pro Ala Pro Gln Asp Ser Gly
    130                 135                 140

Lys Ser Cys Gly Val Asp Phe Glu Val Lys Ala Phe Ala Thr Asp Ser
```

-continued

```
145                 150                 155                 160

Thr Asp Ala Glu Glu Asp Lys Ile Pro Lys Lys Ser Ser Val Arg Leu
                165                 170                 175

Leu Ile Arg Lys Val Gln His Ala Pro Leu Glu Met Gly Pro Gln Pro
            180                 185                 190

Arg Ala Glu Ala Ala Trp Gln Phe Phe Met Ser Asp Lys Pro Leu His
        195                 200                 205

Leu Ala Val Ser Leu Asn Lys Glu Ile Tyr Phe His Gly Glu Pro Ile
    210                 215                 220

Pro Val Thr Val Thr Val Thr Asn Asn Thr Glu Lys Thr Val Lys Lys
225                 230                 235                 240

Ile Lys Ala Phe Val Glu Gln Val Ala Asn Val Val Leu Tyr Ser Ser
                245                 250                 255

Asp Tyr Tyr Val Lys Pro Val Ala Met Glu Glu Ala Gln Glu Lys Val
            260                 265                 270

Pro Pro Asn Ser Thr Leu Thr Lys Thr Leu Thr Leu Leu Pro Leu Leu
        275                 280                 285

Ala Asn Asn Arg Glu Arg Arg Gly Ile Ala Leu Asp Gly Lys Ile Lys
    290                 295                 300

His Glu Asp Thr Asn Leu Ala Ser Ser Thr Ile Ile Lys Glu Gly Ile
305                 310                 315                 320

Asp Arg Thr Val Leu Gly Ile Leu Val Ser Tyr Gln Ile Lys Val Lys
                325                 330                 335

Leu Thr Val Ser Gly Phe Leu Gly Glu Leu Thr Ser Ser Glu Val Ala
            340                 345                 350

Thr Glu Val Pro Phe Arg Leu Met His Pro Gln Pro Glu Asp Pro Ala
        355                 360                 365

Lys Glu Ser Tyr Gln Asp Ala Asn Leu Val Phe Glu Glu Phe Ala Arg
    370                 375                 380

His Asn Leu Lys Asp Ala Gly Glu Ala Glu Glu Gly Lys Arg Asp Lys
385                 390                 395                 400

Asn Asp Val Asp Glu
                405


<210> SEQ ID NO 22
<211> LENGTH: 2483
<212> TYPE: DNA
<213> ORGANISM: Homo sapiens

<400> SEQUENCE: 22

agttgattgc aggtcctcct ggggccagaa gggtgcctgg gaggccaggt tctggggatc      60

ccctccatcc agaagaacca cctgctcact ctgtcccttc gcctgctgct gggaccatgg     120

gggctggggc cagtgctgag gagaagcact ccagggagct ggaaaagaag ctgaaagagg     180

acgctgagaa ggatgctcga accgtgaagc tgctgcttct gggtgccggt gagtccggga     240

agagcaccat cgtcaagcag atgaagatta tccaccagga cgggtactcg ctggaagagt     300

gcctcgagtt tatcgccatc atctacggca acacgttgca gtccatcctg gccatcgtac     360

gcgccatgac cacactcaac atccagtacg gagactctgc acgccaggac gacgcccgga     420

agctgatgca catggcagac actatcgagg agggcacgat gcccaaggag atgtcggaca     480

tcatccagcg gctgtggaag gactccggta tccaggcctg ttttgagcgc gcctcggagt     540

accagctcaa cgactcggcg ggctactacc tctccgacct ggagcgcctg gtaaccccgg     600

gctacgtgcc caccgagcag gacgtgctgc gctcgcgagt caagaccact ggcatcatcg     660
```

```
agacgcagtt ctccttcaag gatctcaact tccggatgtt cgatgtgggc gggcagcgct    720

cggagcgcaa gaagtggatc cactgcttcg agggcgtgac ctgcatcatc ttcatcgcgg    780

cgctgagcgc ctacgacatg gtgctagtgg aggacgacga agtgaaccgc atgcacgaga    840

gcctgcacct gttcaacagc atctgcaacc accgctactt cgccacgacg tccatcgtgc    900

tcttccttaa caagaaggac gtcttcttcg agaagatcaa gaaggcgcac ctcagcatct    960

gtttcccgga ctacgatgga cccaacacct acgaggacgc cggcaactac atcaaggtgc   1020

agttcctcga gctcaacatg cggcgcgacg tgaaggagat ctattcccac atgacgtgcg   1080

ccaccgacac gcagaacgtc aaatttgtct tcgacgctgt caccgacatc atcatcaagg   1140

agaacctcaa agactgtggc ctcttctgag gccagggcct gtgctgcagt cggggacaag   1200

gagcttccgt ctggcaaggc cggggcacaa tttgcactcc cctcagctag acgcacagac   1260

tcagcaataa acctttgcat caggctccag ctgtcctttc ttggtggagg acttaattat   1320

cacaagtcat gggcatttat taagtgccca gtgctgggtt gggcatgaag tgggaagatg   1380

gcccctccca ggaagaagta cctggcctga caaggtgggg cactcttggg ggtatgggac   1440

caactcatgg cttttcacgg gagttgagga gagaggagct gtggaaaata ttcactggga   1500

cagtcttgga tcaagaggga gttttgaggt ggaggctcat tctggcaggg accgtagtgt   1560

ctaccagccc cagaaacatg ggcttatggc cacaggagtt cagtggagca agagcagggg   1620

aggagagacg tggacaggtg cccaaagcca gtcggagggc ctgggctttc tcagaaggtg   1680

atggagagtc ttggaagccc tcgaggcagg aacataattg cagggctggg attagggtga   1740

gggaagtgag gcacactcac cttgggtgca acatttaagg cgatgccaaa aaatttagta   1800

accaaggtaa ataatattag gataatattt ttaaaaatca aatgaatgca aaaccccaca   1860

atgaatgaaa tatcaaaatc caacagagga tcaaacagag gcatgctaag atatattggg   1920

gcttgaagca aagggaaaac tatttgttgc tatatgtttg tagggatttt ttgccagttt   1980

taaaaataca tgtatcataa agtttactat ctcagccact tgccggtgta tagtttggtg   2040

gtgttaagta cattcataat gttgtacaac caccgcaact gttcatctcc agaactcctt   2100

tcctcttgta aaactgtaac tctgtaccca tgaaaaaata accccccatt cctgccttcc   2160

cccggctcct ggcatccacc attctacttt ccatctctat gaatgtgact gctctaagtg   2220

cctcagatgt gtgggtccat gaagtctttg tctttttgca actggcttat ttcacttagc   2280

atcatgtctt caaggtttat tcatgtgtag catatggcag aatctccttc ctttttaagg   2340

ttgaataata ttccattgta tatattccac actttgttta tttattcatc tattgatgaa   2400

tggttacatc tgccttttgg ctattgtgaa taatgctgct atgaacatgg gtgtacaaat   2460

ctctcaaaaa aaaaaaaaaa aaa                                           2483
```

```
<210> SEQ ID NO 23
<211> LENGTH: 350
<212> TYPE: PRT
<213> ORGANISM: Homo sapiens

<400> SEQUENCE: 23

Met Gly Ala Gly Ala Ser Ala Glu Glu Lys His Ser Arg Glu Leu Glu
1               5                   10                  15

Lys Lys Leu Lys Glu Asp Ala Glu Lys Asp Ala Arg Thr Val Lys Leu
            20                  25                  30

Leu Leu Leu Gly Ala Gly Glu Ser Gly Lys Ser Thr Ile Val Lys Gln
        35                  40                  45
```

Met Lys Ile Ile His Gln Asp Gly Tyr Ser Leu Glu Glu Cys Leu Glu
    50                  55                  60

Phe Ile Ala Ile Ile Tyr Gly Asn Thr Leu Gln Ser Ile Leu Ala Ile
65                  70                  75                  80

Val Arg Ala Met Thr Thr Leu Asn Ile Gln Tyr Gly Asp Ser Ala Arg
                85                  90                  95

Gln Asp Asp Ala Arg Lys Leu Met His Met Ala Asp Thr Ile Glu Glu
            100                 105                 110

Gly Thr Met Pro Lys Glu Met Ser Asp Ile Ile Gln Arg Leu Trp Lys
        115                 120                 125

Asp Ser Gly Ile Gln Ala Cys Phe Glu Arg Ala Ser Glu Tyr Gln Leu
    130                 135                 140

Asn Asp Ser Ala Gly Tyr Tyr Leu Ser Asp Leu Glu Arg Leu Val Thr
145                 150                 155                 160

Pro Gly Tyr Val Pro Thr Glu Gln Asp Val Leu Arg Ser Arg Val Lys
                165                 170                 175

Thr Thr Gly Ile Ile Glu Thr Gln Phe Ser Phe Lys Asp Leu Asn Phe
            180                 185                 190

Arg Met Phe Asp Val Gly Gly Gln Arg Ser Glu Arg Lys Lys Trp Ile
        195                 200                 205

His Cys Phe Glu Gly Val Thr Cys Ile Ile Phe Ile Ala Ala Leu Ser
    210                 215                 220

Ala Tyr Asp Met Val Leu Val Glu Asp Asp Glu Val Asn Arg Met His
225                 230                 235                 240

Glu Ser Leu His Leu Phe Asn Ser Ile Cys Asn His Arg Tyr Phe Ala
                245                 250                 255

Thr Thr Ser Ile Val Leu Phe Leu Asn Lys Lys Asp Val Phe Phe Glu
            260                 265                 270

Lys Ile Lys Lys Ala His Leu Ser Ile Cys Phe Pro Asp Tyr Asp Gly
        275                 280                 285

Pro Asn Thr Tyr Glu Asp Ala Gly Asn Tyr Ile Lys Val Gln Phe Leu
    290                 295                 300

Glu Leu Asn Met Arg Arg Asp Val Lys Glu Ile Tyr Ser His Met Thr
305                 310                 315                 320

Cys Ala Thr Asp Thr Gln Asn Val Lys Phe Val Phe Asp Ala Val Thr
                325                 330                 335

Asp Ile Ile Ile Lys Glu Asn Leu Lys Asp Cys Gly Leu Phe
            340                 345                 350

<210> SEQ ID NO 24
<211> LENGTH: 201
<212> TYPE: PRT
<213> ORGANISM: Homo sapiens

<400> SEQUENCE: 24

Met Gly Asn Val Met Glu Gly Lys Ser Val Glu Glu Leu Ser Ser Thr
1               5                   10                  15

Glu Cys His Gln Trp Tyr Lys Lys Phe Met Thr Glu Cys Pro Ser Gly
            20                  25                  30

Gln Leu Thr Leu Tyr Glu Phe Arg Gln Phe Phe Gly Leu Lys Asn Leu
        35                  40                  45

Ser Pro Ser Ala Ser Gln Tyr Val Glu Gln Met Phe Glu Thr Phe Asp
    50                  55                  60

Phe Asn Lys Asp Gly Tyr Ile Asp Phe Met Glu Tyr Val Ala Ala Leu

```
65                  70                  75                  80

Ser Leu Val Leu Lys Gly Lys Val Glu Gln Lys Leu Arg Trp Tyr Phe
                85                  90                  95

Lys Leu Tyr Asp Val Asp Gly Asn Gly Cys Ile Asp Arg Asp Glu Leu
            100                 105                 110

Leu Thr Ile Ile Gln Ala Ile Arg Ala Ile Asn Pro Cys Ser Asp Thr
        115                 120                 125

Thr Met Thr Ala Glu Glu Phe Thr Asp Thr Val Phe Ser Lys Ile Asp
    130                 135                 140

Val Asn Gly Asp Gly Glu Leu Ser Leu Glu Glu Phe Ile Glu Gly Val
145                 150                 155                 160

Gln Lys Asp Gln Met Leu Leu Asp Thr Leu Thr Arg Ser Leu Asp Leu
                165                 170                 175

Thr Arg Ile Val Arg Arg Leu Gln Asn Gly Glu Gln Asp Glu Glu Gly
            180                 185                 190

Ala Asp Glu Ala Ala Glu Ala Ala Gly
        195                 200


<210> SEQ ID NO 25
<211> LENGTH: 1103
<212> TYPE: PRT
<213> ORGANISM: Homo sapiens

<400> SEQUENCE: 25

Met Thr Ala Cys Ala Arg Arg Ala Gly Gly Leu Pro Asp Pro Gly Leu
1               5                   10                  15

Cys Gly Pro Ala Trp Trp Ala Pro Ser Leu Pro Arg Leu Pro Arg Ala
            20                  25                  30

Leu Pro Arg Leu Pro Leu Leu Leu Leu Leu Leu Leu Leu Gln Pro Pro
        35                  40                  45

Ala Leu Ser Ala Val Phe Thr Val Gly Val Leu Gly Pro Trp Ala Cys
    50                  55                  60

Asp Pro Ile Phe Ser Arg Ala Arg Pro Asp Leu Ala Ala Arg Leu Ala
65                  70                  75                  80

Ala Ala Arg Leu Asn Arg Asp Pro Gly Leu Ala Gly Gly Pro Arg Phe
                85                  90                  95

Glu Val Ala Leu Leu Pro Glu Pro Cys Arg Thr Pro Gly Ser Leu Gly
            100                 105                 110

Ala Val Ser Ser Ala Leu Ala Arg Val Ser Gly Leu Val Gly Pro Val
        115                 120                 125

Asn Pro Ala Ala Cys Arg Pro Ala Glu Leu Leu Ala Glu Glu Ala Gly
    130                 135                 140

Ile Ala Leu Val Pro Trp Gly Cys Pro Trp Thr Gln Ala Glu Gly Thr
145                 150                 155                 160

Thr Ala Pro Ala Val Thr Pro Ala Ala Asp Ala Leu Tyr Ala Leu Leu
                165                 170                 175

Arg Ala Phe Gly Trp Ala Arg Val Ala Leu Val Thr Ala Pro Gln Asp
            180                 185                 190

Leu Trp Val Glu Ala Gly Arg Ser Leu Ser Thr Ala Leu Arg Ala Arg
        195                 200                 205

Gly Leu Pro Val Ala Ser Val Thr Ser Met Glu Pro Leu Asp Leu Ser
    210                 215                 220

Gly Ala Arg Glu Ala Leu Arg Lys Val Arg Asp Gly Pro Arg Val Thr
225                 230                 235                 240
```

-continued

```
Ala Val Ile Met Val Met His Ser Val Leu Leu Gly Gly Glu Glu Gln
                245                 250                 255

Arg Tyr Leu Leu Glu Ala Ala Glu Glu Leu Gly Leu Thr Asp Gly Ser
            260                 265                 270

Leu Val Phe Leu Pro Phe Asp Thr Ile His Tyr Ala Leu Ser Pro Gly
        275                 280                 285

Pro Glu Ala Leu Ala Ala Leu Ala Asn Ser Ser Gln Leu Arg Arg Ala
    290                 295                 300

His Asp Ala Val Leu Thr Leu Thr Arg His Cys Pro Ser Glu Gly Ser
305                 310                 315                 320

Val Leu Asp Ser Leu Arg Arg Ala Gln Glu Arg Arg Glu Leu Pro Ser
                325                 330                 335

Asp Leu Asn Leu Gln Gln Val Ser Pro Leu Phe Gly Thr Ile Tyr Asp
            340                 345                 350

Ala Val Phe Leu Leu Ala Arg Gly Val Ala Glu Ala Arg Ala Ala Ala
        355                 360                 365

Gly Gly Arg Trp Val Ser Gly Ala Ala Val Ala Arg His Ile Arg Asp
    370                 375                 380

Ala Gln Val Pro Gly Phe Cys Gly Asp Leu Gly Gly Asp Glu Glu Pro
385                 390                 395                 400

Pro Phe Val Leu Leu Asp Thr Asp Ala Ala Gly Asp Arg Leu Phe Ala
                405                 410                 415

Thr Tyr Met Leu Asp Pro Ala Arg Gly Ser Phe Leu Ser Ala Gly Thr
            420                 425                 430

Arg Met His Phe Pro Arg Gly Gly Ser Ala Pro Gly Pro Asp Pro Ser
        435                 440                 445

Cys Trp Phe Asp Pro Asn Asn Ile Cys Gly Gly Gly Leu Glu Pro Gly
    450                 455                 460

Leu Val Phe Leu Gly Phe Leu Leu Val Val Gly Met Gly Leu Ala Gly
465                 470                 475                 480

Ala Phe Leu Ala His Tyr Val Arg His Arg Leu Leu His Met Gln Met
                485                 490                 495

Val Ser Gly Pro Asn Lys Ile Ile Leu Thr Val Asp Asp Ile Thr Phe
            500                 505                 510

Leu His Pro His Gly Gly Thr Ser Arg Lys Val Ala Gln Gly Ser Arg
        515                 520                 525

Ser Ser Leu Gly Ala Arg Ser Met Ser Asp Ile Arg Ser Gly Pro Ser
    530                 535                 540

Gln His Leu Asp Ser Pro Asn Ile Gly Val Tyr Glu Gly Asp Arg Val
545                 550                 555                 560

Trp Leu Lys Lys Phe Pro Gly Asp Gln His Ile Ala Ile Arg Pro Ala
                565                 570                 575

Thr Lys Thr Ala Phe Ser Lys Leu Gln Glu Leu Arg His Glu Asn Val
            580                 585                 590

Ala Leu Tyr Leu Gly Leu Phe Leu Ala Arg Gly Ala Glu Gly Pro Ala
        595                 600                 605

Ala Leu Trp Glu Gly Asn Leu Ala Val Val Ser Glu His Cys Thr Arg
    610                 615                 620

Gly Ser Leu Gln Asp Leu Leu Ala Gln Arg Glu Ile Lys Leu Asp Trp
625                 630                 635                 640

Met Phe Lys Ser Ser Leu Leu Leu Asp Leu Ile Lys Gly Ile Arg Tyr
                645                 650                 655

Leu His His Arg Gly Val Ala His Gly Arg Leu Lys Ser Arg Asn Cys
```

-continued

```
            660                 665                 670

Ile Val Asp Gly Arg Phe Val Leu Lys Ile Thr Asp His Gly His Gly
        675                 680                 685

Arg Leu Leu Glu Ala Gln Lys Val Leu Pro Glu Pro Pro Arg Ala Glu
    690                 695                 700

Asp Gln Leu Trp Thr Ala Pro Glu Leu Leu Arg Asp Pro Ala Leu Glu
705                 710                 715                 720

Arg Arg Gly Thr Leu Ala Gly Asp Val Phe Ser Leu Ala Ile Ile Met
                725                 730                 735

Gln Glu Val Val Cys Arg Ser Ala Pro Tyr Ala Met Leu Glu Leu Thr
            740                 745                 750

Pro Glu Glu Val Val Gln Arg Val Arg Ser Pro Pro Pro Leu Cys Arg
        755                 760                 765

Pro Leu Val Ser Met Asp Gln Ala Pro Val Glu Cys Ile Leu Leu Met
    770                 775                 780

Lys Gln Cys Trp Ala Glu Gln Pro Glu Leu Arg Pro Ser Met Asp His
785                 790                 795                 800

Thr Phe Asp Leu Phe Lys Asn Ile Asn Lys Gly Arg Lys Thr Asn Ile
                805                 810                 815

Ile Asp Ser Met Leu Arg Met Leu Glu Gln Tyr Ser Ser Asn Leu Glu
            820                 825                 830

Asp Leu Ile Arg Glu Arg Thr Glu Glu Leu Glu Leu Glu Lys Gln Lys
        835                 840                 845

Thr Asp Arg Leu Leu Thr Gln Met Leu Pro Pro Ser Val Ala Glu Ala
    850                 855                 860

Leu Lys Thr Gly Thr Pro Val Glu Pro Glu Tyr Phe Glu Gln Val Thr
865                 870                 875                 880

Leu Tyr Phe Ser Asp Ile Val Gly Phe Thr Thr Ile Ser Ala Met Ser
                885                 890                 895

Glu Pro Ile Glu Val Val Asp Leu Leu Asn Asp Leu Tyr Thr Leu Phe
            900                 905                 910

Asp Ala Ile Ile Gly Ser His Asp Val Tyr Lys Val Glu Thr Ile Gly
        915                 920                 925

Asp Ala Tyr Met Val Ala Ser Gly Leu Pro Gln Arg Asn Gly Gln Arg
    930                 935                 940

His Ala Ala Glu Ile Ala Asn Met Ser Leu Asp Ile Leu Ser Ala Val
945                 950                 955                 960

Gly Thr Phe Arg Met Arg His Met Pro Glu Val Pro Val Arg Ile Arg
                965                 970                 975

Ile Gly Leu His Ser Gly Pro Cys Val Ala Gly Val Val Gly Leu Thr
            980                 985                 990

Met Pro Arg Tyr Cys Leu Phe Gly  Asp Thr Val Asn Thr  Ala Ser Arg
        995                 1000                1005

Met Glu  Ser Thr Gly Leu Pro  Tyr Arg Ile His Val  Asn Leu Ser
    1010                 1015                 1020

Thr Val  Gly Ile Leu Arg Ala  Leu Asp Ser Gly Tyr  Gln Val Glu
    1025                 1030                 1035

Leu Arg  Gly Arg Thr Glu Leu  Lys Gly Lys Gly Ala  Glu Asp Thr
    1040                 1045                 1050

Phe Trp  Leu Val Gly Arg Arg  Gly Phe Asn Lys Pro  Ile Pro Lys
    1055                 1060                 1065

Pro Pro  Asp Leu Gln Pro Gly  Ser Ser Asn His Gly  Ile Ser Leu
    1070                 1075                 1080
```

```
Gln Glu  Ile Pro Pro Glu Arg  Arg Arg Lys Leu Glu  Lys Ala Arg
    1085                 1090                 1095

Pro Gly  Gln Phe Ser
    1100


<210> SEQ ID NO 26
<211> LENGTH: 676
<212> TYPE: PRT
<213> ORGANISM: Homo sapiens

<400> SEQUENCE: 26

Met Ala Lys Ile Asn Thr Gln Tyr Ser His Pro Ser Arg Thr His Leu
1               5                   10                  15

Lys Val Lys Thr Ser Asp Arg Asp Leu Asn Arg Ala Glu Asn Gly Leu
            20                  25                  30

Ser Arg Ala His Ser Ser Ser Glu Glu Thr Ser Ser Val Leu Gln Pro
        35                  40                  45

Gly Ile Ala Met Glu Thr Arg Gly Leu Ala Asp Ser Gly Gln Gly Ser
    50                  55                  60

Phe Thr Gly Gln Gly Ile Ala Arg Leu Ser Arg Leu Ile Phe Leu Leu
65                  70                  75                  80

Arg Arg Trp Ala Ala Arg His Val His His Gln Asp Gln Gly Pro Asp
                85                  90                  95

Ser Phe Pro Asp Arg Phe Arg Gly Ala Glu Leu Lys Glu Val Ser Ser
            100                 105                 110

Gln Glu Ser Asn Ala Gln Ala Asn Val Gly Ser Gln Glu Pro Ala Asp
        115                 120                 125

Arg Gly Arg Arg Lys Lys Thr Lys Lys Lys Asp Ala Ile Val Val Asp
    130                 135                 140

Pro Ser Ser Asn Leu Tyr Tyr Arg Trp Leu Thr Ala Ile Ala Leu Pro
145                 150                 155                 160

Val Phe Tyr Asn Trp Tyr Leu Leu Ile Cys Arg Ala Cys Phe Asp Glu
                165                 170                 175

Leu Gln Ser Glu Tyr Leu Met Leu Trp Leu Val Leu Asp Tyr Ser Ala
            180                 185                 190

Asp Val Leu Tyr Val Leu Asp Val Leu Val Arg Ala Arg Thr Gly Phe
        195                 200                 205

Leu Glu Gln Gly Leu Met Val Ser Asp Thr Asn Arg Leu Trp Gln His
    210                 215                 220

Tyr Lys Thr Thr Thr Gln Phe Lys Leu Asp Val Leu Ser Leu Val Pro
225                 230                 235                 240

Thr Asp Leu Ala Tyr Leu Lys Val Gly Thr Asn Tyr Pro Glu Val Arg
                245                 250                 255

Phe Asn Arg Leu Leu Lys Phe Ser Arg Leu Phe Glu Phe Phe Asp Arg
            260                 265                 270

Thr Glu Thr Arg Thr Asn Tyr Pro Asn Met Phe Arg Ile Gly Asn Leu
        275                 280                 285

Val Leu Tyr Ile Leu Ile Ile Ile His Trp Asn Ala Cys Ile Tyr Phe
    290                 295                 300

Ala Ile Ser Lys Phe Ile Gly Phe Gly Thr Asp Ser Trp Val Tyr Pro
305                 310                 315                 320

Asn Ile Ser Ile Pro Glu His Gly Arg Leu Ser Arg Lys Tyr Ile Tyr
                325                 330                 335

Ser Leu Tyr Trp Ser Thr Leu Thr Leu Thr Thr Ile Gly Glu Thr Pro
```

```
            340                 345                 350

Pro Pro Val Lys Asp Glu Glu Tyr Leu Phe Val Val Val Asp Phe Leu
        355                 360                 365

Val Gly Val Leu Ile Phe Ala Thr Ile Val Gly Asn Val Gly Ser Met
    370                 375                 380

Ile Ser Asn Met Asn Ala Ser Arg Ala Glu Phe Gln Ala Lys Ile Asp
385                 390                 395                 400

Ser Ile Lys Gln Tyr Met Gln Phe Arg Lys Val Thr Lys Asp Leu Glu
                405                 410                 415

Thr Arg Val Ile Arg Trp Phe Asp Tyr Leu Trp Ala Asn Lys Lys Thr
            420                 425                 430

Val Asp Glu Lys Glu Val Leu Lys Ser Leu Pro Asp Lys Leu Lys Ala
        435                 440                 445

Glu Ile Ala Ile Asn Val His Leu Asp Thr Leu Lys Lys Val Arg Ile
    450                 455                 460

Phe Gln Asp Cys Glu Ala Gly Leu Leu Val Glu Leu Val Leu Lys Leu
465                 470                 475                 480

Arg Pro Thr Val Phe Ser Pro Gly Asp Tyr Ile Cys Lys Lys Gly Asp
                485                 490                 495

Ile Gly Lys Glu Met Tyr Ile Ile Asn Glu Gly Lys Leu Ala Val Val
            500                 505                 510

Ala Asp Asp Gly Val Thr Gln Phe Val Val Leu Ser Asp Gly Ser Tyr
        515                 520                 525

Phe Gly Glu Ile Ser Ile Leu Asn Ile Lys Gly Ser Lys Ser Gly Asn
    530                 535                 540

Arg Arg Thr Ala Asn Ile Arg Ser Ile Gly Tyr Ser Asp Leu Phe Cys
545                 550                 555                 560

Leu Ser Lys Asp Asp Leu Met Glu Ala Leu Thr Glu Tyr Pro Glu Ala
                565                 570                 575

Lys Lys Ala Leu Glu Glu Lys Gly Arg Gln Ile Leu Met Lys Asp Asn
            580                 585                 590

Leu Ile Asp Glu Glu Leu Ala Arg Ala Gly Ala Asp Pro Lys Asp Leu
        595                 600                 605

Glu Glu Lys Val Glu Gln Leu Gly Ser Ser Leu Asp Thr Leu Gln Thr
    610                 615                 620

Arg Phe Ala Arg Leu Leu Ala Glu Tyr Asn Ala Thr Gln Met Lys Met
625                 630                 635                 640

Lys Gln Arg Leu Ser Gln Leu Glu Ser Gln Val Lys Gly Gly Gly Asp
                645                 650                 655

Lys Pro Leu Ala Asp Gly Glu Val Pro Gly Asp Ala Thr Lys Thr Glu
            660                 665                 670

Asp Lys Gln Gln
        675


<210> SEQ ID NO 27
<211> LENGTH: 694
<212> TYPE: PRT
<213> ORGANISM: Homo sapiens

<400> SEQUENCE: 27

Met Ala Lys Ile Asn Thr Gln Tyr Ser His Pro Ser Arg Thr His Leu
1               5                   10                  15

Lys Val Lys Thr Ser Asp Arg Asp Leu Asn Arg Ala Glu Asn Gly Leu
            20                  25                  30
```

-continued

```
Ser Arg Ala His Ser Ser Ser Glu Glu Thr Ser Ser Val Leu Gln Pro
        35                  40                  45

Gly Ile Ala Met Glu Thr Arg Gly Leu Ala Asp Ser Gly Gln Gly Ser
    50                  55                  60

Phe Thr Gly Gln Gly Ile Ala Arg Leu Ser Arg Leu Ile Phe Leu Leu
65                  70                  75                  80

Arg Arg Trp Ala Ala Arg His Val His His Gln Asp Gln Gly Pro Asp
                85                  90                  95

Ser Phe Pro Asp Arg Phe Arg Gly Ala Glu Leu Lys Glu Val Ser Ser
            100                 105                 110

Gln Glu Ser Asn Ala Gln Ala Asn Val Gly Ser Gln Glu Pro Ala Asp
        115                 120                 125

Arg Gly Arg Ser Ala Trp Pro Leu Ala Lys Cys Asn Thr Asn Thr Ser
    130                 135                 140

Asn Asn Thr Glu Glu Glu Lys Lys Thr Lys Lys Lys Asp Ala Ile Val
145                 150                 155                 160

Val Asp Pro Ser Ser Asn Leu Tyr Tyr Arg Trp Leu Thr Ala Ile Ala
                165                 170                 175

Leu Pro Val Phe Tyr Asn Trp Tyr Leu Leu Ile Cys Arg Ala Cys Phe
            180                 185                 190

Asp Glu Leu Gln Ser Glu Tyr Leu Met Leu Trp Leu Val Leu Asp Tyr
        195                 200                 205

Ser Ala Asp Val Leu Tyr Val Leu Asp Val Leu Val Arg Ala Arg Thr
    210                 215                 220

Gly Phe Leu Glu Gln Gly Leu Met Val Ser Asp Thr Asn Arg Leu Trp
225                 230                 235                 240

Gln His Tyr Lys Thr Thr Thr Gln Phe Lys Leu Asp Val Leu Ser Leu
                245                 250                 255

Val Pro Thr Asp Leu Ala Tyr Leu Lys Val Gly Thr Asn Tyr Pro Glu
            260                 265                 270

Val Arg Phe Asn Arg Leu Leu Lys Phe Ser Arg Leu Phe Glu Phe Phe
        275                 280                 285

Asp Arg Thr Glu Thr Arg Thr Asn Tyr Pro Asn Met Phe Arg Ile Gly
    290                 295                 300

Asn Leu Val Leu Tyr Ile Leu Ile Ile Ile His Trp Asn Ala Cys Ile
305                 310                 315                 320

Tyr Phe Ala Ile Ser Lys Phe Ile Gly Phe Gly Thr Asp Ser Trp Val
                325                 330                 335

Tyr Pro Asn Ile Ser Ile Pro Glu His Gly Arg Leu Ser Arg Lys Tyr
            340                 345                 350

Ile Tyr Ser Leu Tyr Trp Ser Thr Leu Thr Leu Thr Thr Ile Gly Glu
        355                 360                 365

Thr Pro Pro Pro Val Lys Asp Glu Glu Tyr Leu Phe Val Val Val Asp
    370                 375                 380

Phe Leu Val Gly Val Leu Ile Phe Ala Thr Ile Val Gly Asn Val Gly
385                 390                 395                 400

Ser Met Ile Ser Asn Met Asn Ala Ser Arg Ala Glu Phe Gln Ala Lys
                405                 410                 415

Ile Asp Ser Ile Lys Gln Tyr Met Gln Phe Arg Lys Val Thr Lys Asp
            420                 425                 430

Leu Glu Thr Arg Val Ile Arg Trp Phe Asp Tyr Leu Trp Ala Asn Lys
        435                 440                 445

Lys Thr Val Asp Glu Lys Glu Val Leu Lys Ser Leu Pro Asp Lys Leu
```

```
    450                 455                 460

Lys Ala Glu Ile Ala Ile Asn Val His Leu Asp Thr Leu Lys Lys Val
465                 470                 475                 480

Arg Ile Phe Gln Asp Cys Glu Ala Gly Leu Leu Val Glu Leu Val Leu
                485                 490                 495

Lys Leu Arg Pro Thr Val Phe Ser Pro Gly Asp Tyr Ile Cys Lys Lys
            500                 505                 510

Gly Asp Ile Gly Lys Glu Met Tyr Ile Ile Asn Glu Gly Lys Leu Ala
        515                 520                 525

Val Val Ala Asp Asp Gly Val Thr Gln Phe Val Val Leu Ser Asp Gly
    530                 535                 540

Ser Tyr Phe Gly Glu Ile Ser Ile Leu Asn Ile Lys Gly Ser Lys Ser
545                 550                 555                 560

Gly Asn Arg Arg Thr Ala Asn Ile Arg Ser Ile Gly Tyr Ser Asp Leu
                565                 570                 575

Phe Cys Leu Ser Lys Asp Asp Leu Met Glu Ala Leu Thr Glu Tyr Pro
            580                 585                 590

Glu Ala Lys Lys Ala Leu Glu Glu Lys Gly Arg Gln Ile Leu Met Lys
        595                 600                 605

Asp Asn Leu Ile Asp Glu Glu Leu Ala Arg Ala Gly Ala Asp Pro Lys
    610                 615                 620

Asp Leu Glu Glu Lys Val Glu Gln Leu Gly Ser Ser Leu Asp Thr Leu
625                 630                 635                 640

Gln Thr Arg Phe Ala Arg Leu Leu Ala Glu Tyr Asn Ala Thr Gln Met
                645                 650                 655

Lys Met Lys Gln Arg Leu Ser Gln Leu Glu Ser Gln Val Lys Gly Gly
            660                 665                 670

Gly Asp Lys Pro Leu Ala Asp Gly Glu Val Pro Gly Asp Ala Thr Lys
        675                 680                 685

Thr Glu Asp Lys Gln Gln
    690


<210> SEQ ID NO 28
<211> LENGTH: 354
<212> TYPE: PRT
<213> ORGANISM: Homo sapiens

<400> SEQUENCE: 28

Met Gly Ser Gly Ala Ser Ala Glu Asp Lys Glu Leu Ala Lys Arg Ser
1               5                   10                  15

Lys Glu Leu Glu Lys Lys Leu Gln Glu Asp Ala Asp Lys Glu Ala Lys
            20                  25                  30

Thr Val Lys Leu Leu Leu Leu Gly Ala Gly Glu Ser Gly Lys Ser Thr
        35                  40                  45

Ile Val Lys Gln Met Lys Ile Ile His Gln Asp Gly Tyr Ser Pro Glu
    50                  55                  60

Glu Cys Leu Glu Phe Lys Ala Ile Ile Tyr Gly Asn Val Leu Gln Ser
65                  70                  75                  80

Ile Leu Ala Ile Ile Arg Ala Met Thr Thr Leu Gly Ile Asp Tyr Ala
                85                  90                  95

Glu Pro Ser Cys Ala Asp Asp Gly Arg Gln Leu Asn Asn Leu Ala Asp
            100                 105                 110

Ser Ile Glu Glu Gly Thr Met Pro Pro Glu Leu Val Glu Val Ile Arg
        115                 120                 125
```

-continued

```
Arg Leu Trp Lys Asp Gly Gly Val Gln Ala Cys Phe Glu Arg Ala Ala
    130                 135                 140

Glu Tyr Gln Leu Asn Asp Ser Ala Ser Tyr Tyr Leu Asn Gln Leu Glu
145                 150                 155                 160

Arg Ile Thr Asp Pro Glu Tyr Leu Pro Ser Glu Gln Asp Val Leu Arg
                165                 170                 175

Ser Arg Val Lys Thr Thr Gly Ile Ile Glu Thr Lys Phe Ser Val Lys
            180                 185                 190

Asp Leu Asn Phe Arg Met Phe Asp Val Gly Gly Gln Arg Ser Glu Arg
        195                 200                 205

Lys Lys Trp Ile His Cys Phe Glu Gly Val Thr Cys Ile Ile Phe Cys
    210                 215                 220

Ala Ala Leu Ser Ala Tyr Asp Met Val Leu Val Glu Asp Asp Glu Val
225                 230                 235                 240

Asn Arg Met His Glu Ser Leu His Leu Phe Asn Ser Ile Cys Asn His
                245                 250                 255

Lys Phe Phe Ala Ala Thr Ser Ile Val Leu Phe Leu Asn Lys Lys Asp
            260                 265                 270

Leu Phe Glu Glu Lys Ile Lys Lys Val His Leu Ser Ile Cys Phe Pro
        275                 280                 285

Glu Tyr Asp Gly Asn Asn Ser Tyr Asp Asp Ala Gly Asn Tyr Ile Lys
    290                 295                 300

Ser Gln Phe Leu Asp Leu Asn Met Arg Lys Asp Val Lys Glu Ile Tyr
305                 310                 315                 320

Ser His Met Thr Cys Ala Thr Asp Thr Gln Asn Val Lys Phe Val Phe
                325                 330                 335

Asp Ala Val Thr Asp Ile Ile Ile Lys Glu Asn Leu Lys Asp Cys Gly
            340                 345                 350

Leu Phe


<210> SEQ ID NO 29
<211> LENGTH: 858
<212> TYPE: PRT
<213> ORGANISM: Homo sapiens

<400> SEQUENCE: 29

Met Gly Glu Ile Asn Gln Val Ala Val Glu Lys Tyr Leu Glu Glu Asn
1               5                   10                  15

Pro Gln Phe Ala Lys Glu Tyr Phe Asp Arg Lys Leu Arg Val Glu Val
            20                  25                  30

Leu Gly Glu Ile Phe Lys Asn Ser Gln Val Pro Val Gln Ser Ser Met
        35                  40                  45

Ser Phe Ser Glu Leu Thr Gln Val Glu Glu Ser Ala Leu Cys Leu Glu
    50                  55                  60

Leu Leu Trp Thr Val Gln Glu Glu Gly Gly Thr Pro Glu Gln Gly Val
65                  70                  75                  80

His Arg Ala Leu Gln Arg Leu Ala His Leu Leu Gln Ala Asp Arg Cys
                85                  90                  95

Ser Met Phe Leu Cys Arg Ser Arg Asn Gly Ile Pro Glu Val Ala Ser
            100                 105                 110

Arg Leu Leu Asp Val Thr Pro Thr Ser Lys Phe Glu Asp Asn Leu Val
        115                 120                 125

Gly Pro Asp Lys Glu Val Val Phe Pro Leu Asp Ile Gly Ile Val Gly
    130                 135                 140
```

-continued

```
Trp Ala Ala His Thr Lys Lys Thr His Asn Val Pro Asp Val Lys Lys
145                 150                 155                 160

Asn Ser His Phe Ser Asp Phe Met Asp Lys Gln Thr Gly Tyr Val Thr
                165                 170                 175

Lys Asn Leu Leu Ala Thr Pro Ile Val Val Gly Lys Glu Val Leu Ala
            180                 185                 190

Val Ile Met Ala Val Asn Lys Val Asn Ala Ser Glu Phe Ser Lys Gln
        195                 200                 205

Asp Glu Glu Val Phe Ser Lys Tyr Leu Asn Phe Val Ser Ile Ile Leu
    210                 215                 220

Arg Leu His His Thr Ser Tyr Met Tyr Asn Ile Glu Ser Arg Arg Ser
225                 230                 235                 240

Gln Ile Leu Met Trp Ser Ala Asn Lys Val Phe Glu Glu Leu Thr Asp
                245                 250                 255

Val Glu Arg Gln Phe His Lys Ala Leu Tyr Thr Val Arg Ser Tyr Leu
            260                 265                 270

Asn Cys Glu Arg Tyr Ser Ile Gly Leu Leu Asp Met Thr Lys Glu Lys
        275                 280                 285

Glu Phe Tyr Asp Glu Trp Pro Ile Lys Leu Gly Glu Val Glu Pro Tyr
    290                 295                 300

Lys Gly Pro Lys Thr Pro Asp Gly Arg Glu Val Asn Phe Tyr Lys Ile
305                 310                 315                 320

Ile Asp Tyr Ile Leu His Gly Lys Glu Glu Ile Lys Val Ile Pro Thr
                325                 330                 335

Pro Pro Ala Asp His Trp Thr Leu Ile Ser Gly Leu Pro Thr Tyr Val
            340                 345                 350

Ala Glu Asn Gly Phe Ile Cys Asn Met Met Asn Ala Pro Ala Asp Glu
        355                 360                 365

Tyr Phe Thr Phe Gln Lys Gly Pro Val Asp Glu Thr Gly Trp Val Ile
    370                 375                 380

Lys Asn Val Leu Ser Leu Pro Ile Val Asn Lys Lys Glu Asp Ile Val
385                 390                 395                 400

Gly Val Ala Thr Phe Tyr Asn Arg Lys Asp Gly Lys Pro Phe Asp Glu
                405                 410                 415

His Asp Glu Tyr Ile Thr Glu Thr Leu Thr Gln Phe Leu Gly Trp Ser
            420                 425                 430

Leu Leu Asn Thr Asp Thr Tyr Asp Lys Met Asn Lys Leu Glu Asn Arg
        435                 440                 445

Lys Asp Ile Ala Gln Glu Met Leu Met Asn Gln Thr Lys Ala Thr Pro
    450                 455                 460

Glu Glu Ile Lys Ser Ile Leu Lys Phe Gln Glu Lys Leu Asn Val Asp
465                 470                 475                 480

Val Ile Asp Asp Cys Glu Glu Lys Gln Leu Val Ala Ile Leu Lys Glu
                485                 490                 495

Asp Leu Pro Asp Pro Arg Ser Ala Glu Leu Tyr Glu Phe Arg Phe Ser
            500                 505                 510

Asp Phe Pro Leu Thr Glu His Gly Leu Ile Lys Cys Gly Ile Arg Leu
        515                 520                 525

Phe Phe Glu Ile Asn Val Val Glu Lys Phe Lys Val Pro Val Glu Val
    530                 535                 540

Leu Thr Arg Trp Met Tyr Thr Val Arg Lys Gly Tyr Arg Ala Val Thr
545                 550                 555                 560

Tyr His Asn Trp Arg His Gly Phe Asn Val Gly Gln Thr Met Phe Thr
```

-continued

```
                565                 570                 575

Leu Leu Met Thr Gly Arg Leu Lys Lys Tyr Tyr Thr Asp Leu Glu Ala
            580                 585                 590

Phe Ala Met Leu Ala Ala Ala Phe Cys His Asp Ile Asp His Arg Gly
        595                 600                 605

Thr Asn Asn Leu Tyr Gln Met Lys Ser Thr Ser Pro Leu Ala Arg Leu
    610                 615                 620

His Gly Ser Ser Ile Leu Glu Arg His His Leu Glu Tyr Ser Lys Thr
625                 630                 635                 640

Leu Leu Gln Asp Glu Ser Leu Asn Ile Phe Gln Asn Leu Asn Lys Arg
                645                 650                 655

Gln Phe Glu Thr Val Ile His Leu Phe Glu Val Ala Ile Ile Ala Thr
            660                 665                 670

Asp Leu Ala Leu Tyr Phe Lys Lys Arg Thr Met Phe Gln Lys Ile Val
        675                 680                 685

Asp Ala Cys Glu Gln Met Gln Thr Glu Glu Glu Ala Ile Lys Tyr Val
    690                 695                 700

Thr Val Asp Pro Thr Lys Lys Glu Ile Ile Met Ala Met Met Met Thr
705                 710                 715                 720

Ala Cys Asp Leu Ser Ala Ile Thr Lys Pro Trp Glu Val Gln Ser Gln
                725                 730                 735

Val Ala Leu Met Val Ala Asn Glu Phe Trp Glu Gln Gly Asp Leu Glu
            740                 745                 750

Arg Thr Val Leu Gln Gln Gln Pro Ile Pro Met Met Asp Arg Asn Lys
        755                 760                 765

Arg Asp Glu Leu Pro Lys Leu Gln Val Gly Phe Ile Asp Phe Val Cys
    770                 775                 780

Thr Phe Val Tyr Lys Glu Phe Ser Arg Phe His Lys Glu Ile Thr Pro
785                 790                 795                 800

Met Leu Ser Gly Leu Gln Asn Asn Arg Val Glu Trp Lys Ser Leu Ala
                805                 810                 815

Asp Glu Tyr Asp Ala Lys Met Lys Val Ile Glu Glu Glu Ala Lys Lys
            820                 825                 830

Gln Glu Gly Gly Ala Glu Lys Ala Ala Glu Asp Ser Gly Gly Gly Asp
        835                 840                 845

Asp Lys Lys Ser Lys Thr Cys Leu Met Leu
    850                 855


<210> SEQ ID NO 30
<211> LENGTH: 83
<212> TYPE: PRT
<213> ORGANISM: Homo sapiens

<400> SEQUENCE: 30

Met Ser Asp Asn Thr Thr Leu Pro Ala Pro Ala Ser Asn Gln Gly Pro
1               5                   10                  15

Thr Thr Pro Arg Lys Gly Pro Pro Lys Phe Lys Gln Arg Gln Thr Arg
            20                  25                  30

Gln Phe Lys Ser Lys Pro Pro Lys Lys Gly Val Lys Gly Phe Gly Asp
        35                  40                  45

Asp Ile Pro Gly Met Glu Gly Leu Gly Thr Asp Ile Thr Val Ile Cys
    50                  55                  60

Pro Trp Glu Ala Phe Ser His Leu Glu Leu His Glu Leu Ala Gln Phe
65                  70                  75                  80
```

Gly Ile Ile

<210> SEQ ID NO 31
<211> LENGTH: 299
<212> TYPE: PRT
<213> ORGANISM: Homo sapiens

<400> SEQUENCE: 31

```
Met Met Ala Tyr Met Asn Pro Gly Pro His Tyr Ser Val Asn Ala Leu
1               5                   10                  15

Ala Leu Ser Gly Pro Ser Val Asp Leu Met His Gln Ala Val Pro Tyr
            20                  25                  30

Pro Ser Ala Pro Arg Lys Gln Arg Arg Glu Arg Thr Thr Phe Thr Arg
        35                  40                  45

Ser Gln Leu Glu Glu Leu Glu Ala Leu Phe Ala Lys Thr Gln Tyr Pro
    50                  55                  60

Asp Val Tyr Ala Arg Glu Glu Val Ala Leu Lys Ile Asn Leu Pro Glu
65                  70                  75                  80

Ser Arg Val Gln Val Trp Phe Lys Asn Arg Arg Ala Lys Cys Arg Gln
                85                  90                  95

Gln Arg Gln Gln Gln Lys Gln Gln Gln Gln Pro Pro Gly Gly Gln Ala
            100                 105                 110

Lys Ala Arg Pro Ala Lys Arg Lys Ala Gly Thr Ser Pro Arg Pro Ser
        115                 120                 125

Thr Asp Val Cys Pro Asp Pro Leu Gly Ile Ser Asp Ser Tyr Ser Pro
    130                 135                 140

Pro Leu Pro Gly Pro Ser Gly Ser Pro Thr Thr Ala Val Ala Thr Val
145                 150                 155                 160

Ser Ile Trp Ser Pro Ala Ser Glu Ser Pro Leu Pro Glu Ala Gln Arg
                165                 170                 175

Ala Gly Leu Val Ala Ser Gly Pro Ser Leu Thr Ser Ala Pro Tyr Ala
            180                 185                 190

Met Thr Tyr Ala Pro Ala Ser Ala Phe Cys Ser Ser Pro Ser Ala Tyr
        195                 200                 205

Gly Ser Pro Ser Ser Tyr Phe Ser Gly Leu Asp Pro Tyr Leu Ser Pro
    210                 215                 220

Met Val Pro Gln Leu Gly Gly Pro Ala Leu Ser Pro Leu Ser Gly Pro
225                 230                 235                 240

Ser Val Gly Pro Ser Leu Ala Gln Ser Pro Thr Ser Leu Ser Gly Gln
                245                 250                 255

Ser Tyr Gly Ala Tyr Ser Pro Val Asp Ser Leu Glu Phe Lys Asp Pro
            260                 265                 270

Thr Gly Thr Trp Lys Phe Thr Tyr Asn Pro Met Asp Pro Leu Asp Tyr
        275                 280                 285

Lys Asp Gln Ser Ala Trp Lys Phe Gln Ile Leu
    290                 295
```

<210> SEQ ID NO 32
<211> LENGTH: 809
<212> TYPE: PRT
<213> ORGANISM: Homo sapiens

<400> SEQUENCE: 32

```
Met Phe Lys Ser Leu Thr Lys Val Asn Lys Val Lys Pro Ile Gly Glu
1               5                   10                  15

Asn Asn Glu Asn Glu Gln Ser Ser Arg Arg Asn Glu Glu Gly Ser His
```

-continued

```
            20                  25                  30

Pro Ser Asn Gln Ser Gln Gln Thr Thr Ala Gln Glu Glu Asn Lys Gly
        35                  40                  45

Glu Glu Lys Ser Leu Lys Thr Lys Ser Thr Pro Val Thr Ser Glu Glu
    50                  55                  60

Pro His Thr Asn Ile Gln Asp Lys Leu Ser Lys Lys Asn Ser Ser Gly
65                  70                  75                  80

Asp Leu Thr Thr Asn Pro Asp Pro Gln Asn Ala Ala Glu Pro Thr Gly
                85                  90                  95

Thr Val Pro Glu Gln Lys Glu Met Asp Pro Gly Lys Glu Gly Pro Asn
            100                 105                 110

Ser Pro Gln Asn Lys Pro Pro Ala Ala Pro Val Ile Asn Glu Tyr Ala
        115                 120                 125

Asp Ala Gln Leu His Asn Leu Val Lys Arg Met Arg Gln Arg Thr Ala
    130                 135                 140

Leu Tyr Lys Lys Lys Leu Val Glu Gly Asp Leu Ser Ser Pro Glu Ala
145                 150                 155                 160

Ser Pro Gln Thr Ala Lys Pro Thr Ala Val Pro Pro Val Lys Glu Ser
                165                 170                 175

Asp Asp Lys Pro Thr Glu His Tyr Tyr Arg Leu Leu Trp Phe Lys Val
            180                 185                 190

Lys Lys Met Pro Leu Thr Glu Tyr Leu Lys Arg Ile Lys Leu Pro Asn
        195                 200                 205

Ser Ile Asp Ser Tyr Thr Asp Arg Leu Tyr Leu Leu Trp Leu Leu Leu
    210                 215                 220

Val Thr Leu Ala Tyr Asn Trp Asn Cys Trp Phe Ile Pro Leu Arg Leu
225                 230                 235                 240

Val Phe Pro Tyr Gln Thr Ala Asp Asn Ile His Tyr Trp Leu Ile Ala
                245                 250                 255

Asp Ile Ile Cys Asp Ile Ile Tyr Leu Tyr Asp Met Leu Phe Ile Gln
            260                 265                 270

Pro Arg Leu Gln Phe Val Arg Gly Gly Asp Ile Ile Val Asp Ser Asn
        275                 280                 285

Glu Leu Arg Lys His Tyr Arg Thr Ser Thr Lys Phe Gln Leu Asp Val
    290                 295                 300

Ala Ser Ile Ile Pro Phe Asp Ile Cys Tyr Leu Phe Phe Gly Phe Asn
305                 310                 315                 320

Pro Met Phe Arg Ala Asn Arg Met Leu Lys Tyr Thr Ser Phe Phe Glu
                325                 330                 335

Phe Asn His His Leu Glu Ser Ile Met Asp Lys Ala Tyr Ile Tyr Arg
            340                 345                 350

Val Ile Arg Thr Thr Gly Tyr Leu Leu Phe Ile Leu His Ile Asn Ala
        355                 360                 365

Cys Val Tyr Tyr Trp Ala Ser Asn Tyr Glu Gly Ile Gly Thr Thr Arg
    370                 375                 380

Trp Val Tyr Asp Gly Glu Gly Asn Glu Tyr Leu Arg Cys Tyr Tyr Trp
385                 390                 395                 400

Ala Val Arg Thr Leu Ile Thr Ile Gly Gly Leu Pro Glu Pro Gln Thr
                405                 410                 415

Leu Phe Glu Ile Val Phe Gln Leu Leu Asn Phe Phe Ser Gly Val Phe
            420                 425                 430

Val Phe Ser Ser Leu Ile Gly Gln Met Arg Asp Val Ile Gly Ala Ala
        435                 440                 445
```

-continued

```
Thr Ala Asn Gln Asn Tyr Phe Arg Ala Cys Met Asp Asp Thr Ile Ala
    450                 455                 460

Tyr Met Asn Asn Tyr Ser Ile Pro Lys Leu Val Gln Lys Arg Val Arg
465                 470                 475                 480

Thr Trp Tyr Glu Tyr Thr Trp Asp Ser Gln Arg Met Leu Asp Glu Ser
                485                 490                 495

Asp Leu Leu Lys Thr Leu Pro Thr Thr Val Gln Leu Ala Leu Ala Ile
            500                 505                 510

Asp Val Asn Phe Ser Ile Ile Ser Lys Val Asp Leu Phe Lys Gly Cys
        515                 520                 525

Asp Thr Gln Met Ile Tyr Asp Met Leu Leu Arg Leu Lys Ser Val Leu
    530                 535                 540

Tyr Leu Pro Gly Asp Phe Val Cys Lys Lys Gly Glu Ile Gly Lys Glu
545                 550                 555                 560

Met Tyr Ile Ile Lys His Gly Glu Val Gln Val Leu Gly Gly Pro Asp
                565                 570                 575

Gly Thr Lys Val Leu Val Thr Leu Lys Ala Gly Ser Val Phe Gly Glu
            580                 585                 590

Ile Ser Leu Leu Ala Ala Gly Gly Gly Asn Arg Arg Thr Ala Asn Val
        595                 600                 605

Val Ala His Gly Phe Ala Asn Leu Leu Thr Leu Asp Lys Lys Thr Leu
    610                 615                 620

Gln Glu Ile Leu Val His Tyr Pro Asp Ser Glu Arg Ile Leu Met Lys
625                 630                 635                 640

Lys Ala Arg Val Leu Leu Lys Gln Lys Ala Lys Thr Ala Glu Ala Thr
                645                 650                 655

Pro Pro Arg Lys Asp Leu Ala Leu Leu Phe Pro Pro Lys Glu Glu Thr
            660                 665                 670

Pro Lys Leu Phe Lys Thr Leu Leu Gly Gly Thr Gly Lys Ala Ser Leu
        675                 680                 685

Ala Arg Leu Leu Lys Leu Lys Arg Glu Gln Ala Ala Gln Lys Lys Glu
    690                 695                 700

Asn Ser Glu Gly Gly Glu Glu Glu Gly Lys Glu Asn Glu Asp Lys Gln
705                 710                 715                 720

Lys Glu Asn Glu Asp Lys Gln Lys Glu Asn Glu Asp Lys Gly Lys Glu
                725                 730                 735

Asn Glu Asp Lys Asp Lys Gly Arg Glu Pro Glu Glu Lys Pro Leu Asp
            740                 745                 750

Arg Pro Glu Cys Thr Ala Ser Pro Ile Ala Val Glu Glu Glu Pro His
        755                 760                 765

Ser Val Arg Arg Thr Val Leu Pro Arg Gly Thr Ser Arg Gln Ser Leu
    770                 775                 780

Ile Ile Ser Met Ala Pro Ser Ala Glu Gly Gly Glu Glu Val Leu Thr
785                 790                 795                 800

Ile Glu Val Lys Glu Lys Ala Lys Gln
                805
```

<210> SEQ ID NO 33
<211> LENGTH: 610
<212> TYPE: PRT
<213> ORGANISM: Homo sapiens

<400> SEQUENCE: 33

```
Met Pro Leu Thr Glu Tyr Leu Lys Arg Ile Lys Leu Pro Asn Ser Ile
```

-continued

```
1               5                   10                  15

Asp Ser Tyr Thr Asp Arg Leu Tyr Leu Leu Trp Leu Leu Leu Val Thr
            20                  25                  30

Leu Ala Tyr Asn Trp Asn Cys Cys Phe Ile Pro Leu Arg Leu Val Phe
        35                  40                  45

Pro Tyr Gln Thr Ala Asp Asn Ile His Tyr Trp Leu Ile Ala Asp Ile
    50                  55                  60

Ile Cys Asp Ile Ile Tyr Leu Tyr Asp Met Leu Phe Ile Gln Pro Arg
65                  70                  75                  80

Leu Gln Phe Val Arg Gly Gly Asp Ile Ile Val Asp Ser Asn Glu Leu
                85                  90                  95

Arg Lys His Tyr Arg Thr Ser Thr Lys Phe Gln Leu Asp Val Ala Ser
            100                 105                 110

Ile Ile Pro Phe Asp Ile Cys Tyr Leu Phe Phe Gly Phe Asn Pro Met
        115                 120                 125

Phe Arg Ala Asn Arg Met Leu Lys Tyr Thr Ser Phe Phe Glu Phe Asn
    130                 135                 140

His His Leu Glu Ser Ile Met Asp Lys Ala Tyr Ile Tyr Arg Val Ile
145                 150                 155                 160

Arg Thr Thr Gly Tyr Leu Leu Phe Ile Leu His Ile Asn Ala Cys Val
                165                 170                 175

Tyr Tyr Trp Ala Ser Asn Tyr Glu Gly Ile Gly Thr Thr Arg Trp Val
            180                 185                 190

Tyr Asp Gly Glu Gly Asn Glu Tyr Leu Arg Cys Tyr Tyr Trp Ala Val
        195                 200                 205

Arg Thr Leu Ile Thr Ile Gly Gly Leu Pro Glu Pro Gln Thr Leu Phe
    210                 215                 220

Glu Ile Val Phe Gln Leu Leu Asn Phe Phe Ser Gly Val Phe Val Phe
225                 230                 235                 240

Ser Ser Leu Ile Gly Gln Met Arg Asp Val Ile Gly Ala Ala Thr Ala
                245                 250                 255

Asn Gln Asn Tyr Phe Arg Ala Cys Met Asp Asp Thr Ile Ala Tyr Met
            260                 265                 270

Asn Asn Tyr Ser Ile Pro Lys Leu Val Gln Lys Arg Val Arg Thr Trp
        275                 280                 285

Tyr Glu Tyr Thr Trp Asp Ser Gln Arg Met Leu Asp Glu Ser Asp Leu
    290                 295                 300

Leu Lys Thr Leu Pro Thr Thr Val Gln Leu Ala Leu Ala Ile Asp Val
305                 310                 315                 320

Asn Phe Ser Ile Ile Ser Lys Val Asp Leu Phe Lys Gly Cys Asp Thr
                325                 330                 335

Gln Met Ile Tyr Asp Met Leu Leu Arg Leu Lys Ser Val Leu Tyr Leu
            340                 345                 350

Pro Gly Asp Phe Val Cys Lys Lys Gly Glu Ile Gly Lys Glu Met Tyr
        355                 360                 365

Ile Ile Lys His Gly Glu Val Gln Val Leu Gly Gly Pro Asp Gly Thr
    370                 375                 380

Lys Val Leu Val Thr Leu Lys Ala Gly Ser Val Leu Leu Ala Ala Gly
385                 390                 395                 400

Gly Gly Asn Arg Arg Thr Ala Asn Val Val Ala His Gly Phe Ala Asn
                405                 410                 415

Leu Leu Thr Leu Asp Lys Lys Thr Leu Gln Glu Ile Leu Val His Tyr
            420                 425                 430
```

```
Pro Asp Ser Glu Arg Ile Leu Met Lys Lys Ala Arg Val Leu Leu Lys
        435                 440                 445

Gln Lys Ala Lys Thr Ala Glu Ala Thr Pro Pro Arg Lys Asp Leu Ala
    450                 455                 460

Leu Leu Phe Pro Pro Lys Glu Glu Thr Pro Lys Leu Phe Lys Thr Leu
465                 470                 475                 480

Leu Gly Gly Thr Gly Lys Ala Ser Leu Ala Arg Leu Leu Lys Leu Lys
                485                 490                 495

Arg Glu Gln Ala Ala Gln Lys Lys Glu Asn Ser Glu Gly Gly Glu Glu
            500                 505                 510

Glu Gly Lys Glu Asn Glu Asp Lys Gln Lys Glu Asn Glu Asp Lys Gln
        515                 520                 525

Lys Glu Asn Glu Asp Lys Gly Lys Glu Asn Glu Asp Lys Asp Lys Gly
    530                 535                 540

Arg Glu Pro Glu Glu Lys Pro Leu Asp Arg Pro Glu Cys Thr Ala Ser
545                 550                 555                 560

Pro Ile Ala Val Glu Glu Glu Pro His Ser Val Arg Arg Thr Val Leu
                565                 570                 575

Pro Arg Gly Thr Ser Arg Gln Ser Leu Ile Ile Ser Met Ala Pro Ser
            580                 585                 590

Ala Glu Gly Gly Glu Glu Val Leu Thr Ile Glu Val Lys Glu Lys Ala
        595                 600                 605

Lys Gln
    610
```

<210> SEQ ID NO 34
<211> LENGTH: 7100
<212> TYPE: DNA
<213> ORGANISM: Homo sapiens

<400> SEQUENCE: 34

```
gacatactga gaataaatcc aaagacatta gtttctttgc acgaaatgag gttacatatc     60

cagtgacatt tatttgagct atttaaacaa cttaaacatc tttttctttt cttaataagg    120

gacgtttcaa gttgtggtct cagccaaaat gagtgatacc ccttctactg gtttttccat    180

cattcatcct acgtcttctg aaggtcaagt tccacccccct cgccatttga gcctcactca    240

tcctgttgtg gccaagcgaa tcagtttcta caagagcgga gaccccccaat tcggcggggt    300

cagggtggtg gtcaaccctc gctcctttaa gtcctttgat gctctgctgg ataacttgtc    360

caggaaggtg cccctccctt ttggagtgag gaacatcagc acccctcggg gcaggcacag    420

catcacgcgc ctggaggagc tggaggacgg cgagtcctac ctatgttccc acggcaggaa    480

ggtgcagcct gtagacctgg acaaagcccg tcggcgcccg cggccctggc tcagcagccg    540

ggccattagc gcgcactcac cgccccaccc cgtagccgtc gctgctcccg gcatgccccg    600

ccccccacgg agcctagtgg tcttcaggaa tggcgacccg aagacgaggc gtgcggttct    660

tctgagcagg agggtcaccc agagcttcga ggcatttcta cagcacctga cagaggtcat    720

gcagcgccct gtggtcaagc tgtacgctac ggacggaagg agggttccca gcctccaggc    780

agtgatcctg agctctggag ctgtggtggc ggcaggaagg gagccattta aaccaggaaa    840

ttatgacatc caaaaatact tgcttcctgc tagattacca gggatctctc agcgtgtgta    900

ccccaaggga aatgcaaagt cagaaagcag aaagataagc acacatatgt cttcaagctc    960

aaggtcccag atttattctg tttcttctga gaaaacacat aataatgatt gctacttaga   1020
```

```
ctattctttt gttcctgaaa agtacttggc cttagaaaag aatgattctc agaatttacc   1080
aatatatcct tctgaagatg atattgagaa atcaattatt tttaatcaag acggcactat   1140
gacagttgag atgaaagttc gattcagaat aaaagaggaa gaaaccataa aatggacaac   1200
tactgtcagt aaaactggtc cttctaataa tgatgaaaag agtgagatga gttttccagg   1260
aagaacagaa agtcgatcat ctggtttaaa gcttgcagca tgttcattct ctgcagatgt   1320
gtcacctatg gagcgaagca gtaatcaaga gggcagtttg gcagaggaga taaacattca   1380
aatgacagat caagtggctg aaacttgcag ttctgctagt tgggagaatg ctactgtgga   1440
cacagatatc atccagggaa ctcaagacca agcaaagcat cgtttttata ggcccccctac   1500
acctggacta agaagagtga gacaaaagaa atctgtgatt ggcagtgtga ccttagtatc   1560
tgaaactgag gttcaagaga aaatgattgg acagttttca tatagtgaag aaagggaaag   1620
tggggaaaac aagtctgagt atcacatgtt tacacattct tgcagtaaaa tgtcatcagt   1680
atctaacaaa ccagtacttg ttcagatcaa taacaatgat caaatggagg agtcatcatt   1740
agaaagaaaa aaggaaaaca gtctgcttaa gtcaagtgca ataagtgctg gtgttataga   1800
aattacaagt cagaagatgt tagagatgtc acataataat ggtttgccat caactatatc   1860
aaataactca attgtggagg aagatgtagt tgattgtgtg gtattggaca acaaaactgg   1920
tatcaagaac ttcaaaactt atggtaacac caatgatagg ttcagtccta tttcagcaga   1980
tgcaacccat ttttcaagta ataactctgg aactgacaaa aatatttctg aggctccagc   2040
ttcagaagca tcctctactg tcactgcaag aattgacaga ctaattaatg aatttgctca   2100
gtgtggttta acaaaacttc caaaaaatga aaagaagatt ttgtcatctg ttgccagcaa   2160
aaagaagaaa aaatctcgac agcaagcaat aaattccagg tatcaagatg gacagcttgc   2220
aaccaaagga attcttaata agaatgagag aataaacaca aaaggtagaa ttacaaagga   2280
aatgatagtg caagattcag atagtcccct taaaggaggg atactttgtg aggaagacct   2340
ccagaaaagt gatactgtaa ttgaatcaaa tactttttgt tccaaaagta atctcaattc   2400
cacgatttcc aagaatttcc atagaaataa attaaatact actcaaaatt ccaaggttca   2460
aggactttta accaaaagaa aatctagatc actaaataaa ataagcttag gagcacctaa   2520
aaaaagagaa atcggtcaaa gagataaagt gtttcctcac aatgaatcta aatattgcaa   2580
aagtactttt gaaaacaaaa gtttatttca tgtatttaac atccttgagc aaaaacccaa   2640
agatttttat gcaccgcaat ctcaagcaga agtggcatct gggtatttga gaggaatggc   2700
aaagaagagt ttagtttcaa aagttactga ttcacacata actttaaaaa gccagaaaaa   2760
acgtaaaggg gataaagtga aagcaagtgc tattttaagt aaacaacatg ctacaaccag   2820
ggcaaattct ttagcttctt tgaaaaaacc tgattttcct gaggctattg ctcatcattc   2880
aattcaaaat tatatacaga gttggttgca gaacataaat ccatatccaa ctttaaagcc   2940
tataaaatca gctccagtat gtagaaatga aacgagtgtg gtaaattgta gcaataatag   3000
tttttcaggg aatgatcccc atacaaattc tggaaaaata agtaattttg ttatggaaag   3060
taataagcac ataactaaaa ttgccggttt gacaggagat aatctatgta aagagggaga   3120
taagtctttt attgccaatg acactggtga agaagatctc catgagacac aggttggatc   3180
tctgaatgat gcttatttgg ttcccctgca tgaacactgt actttgtcac agtcagctat   3240
taatgatcat aatactaaaa gtcatatagc tgctgaaaaa tcaggaccag agaaaaaact   3300
tgtttaccag gaaataaacc tagctagaaa aaggcaaagt gtagaggctg ccattcaagt   3360
agatcctata gaagaggaaa ctccaaaaga cctcttacca gtcctgatgc ttcaccaatt   3420
```

-continued

```
gcaagcttca gttcctggta ttcacaagac tcagaatgga gttgttcaaa tgccaggttc   3480
acttgcaggt gttccctttc attctgcaat atgtaattca tccactaatc tccttctagc   3540
ttggctcttg gtgctaaacc taaagggaag tatgaatagc ttctgtcaag ttgatgctca   3600
caaggctacc aacaaatctt cagaaacact tgcattgttg gagattctaa agcacatagc   3660
tatcacagag gaagctgatg acttgaaagc tgctgttgcc aatttagtgg agtcaactac   3720
aagccacttt ggactcagtg agaaagaaca agacatggtt ccaatagatc tttctgcaaa   3780
ttgttccacg gtcaacattc agagtgttcc taagtgcagt gaaaatgaaa gaacacaagg   3840
aatctcctct ttggatggag gttgctctgc cagtgaggca tgtgcccctg aagtctgtgt   3900
tttggaagtg acttgctctc catgtgagat gtgcactgta aataaggctt attctccaaa   3960
agagacatgt aaccccagtg acactttttt tcctagtgat ggttatggtg tggatcagac   4020
ttctatgaat aaggcttgtt tcctaggaga ggtctgttca cttactgata ctgtgttttc   4080
tgataaggct tgtgctcaaa aggagaacca tacctatgag ggagcttgcc caattgatga   4140
gacctacgtt cctgtcaatg tctgcaatac cattgacttt ttaaactcca aagaaaacac   4200
atatactgat aacttggatt caactgaaga gttagaaaga ggtgatgaca ttcagaaaga   4260
tctaaatatt ttgacagacc ctgaatataa aaatggattt aatacattgg tgtcacatca   4320
aaatgtcagt aatttaagct cctgtggcct ttgcctaagt gaaaaagaag cagaacttga   4380
taagaaacat agttctctag atgattttga aaattgttca ctaaggaagt ttcaggatga   4440
aaatgcatat acttcctttg atatggaaga accacggact tctgaagaac caggctcaat   4500
aaccaacagc atgacatcaa gtgaaagaaa catttcagaa ttggaatctt ttgaagaatt   4560
agaaaaccat gacactgata tctttaatac agtggtaaat ggaggagagc aagccactga   4620
agaattaatc caagaagagg tagaggctag taaaacttta gaattgatag acatctctag   4680
taagaatatt atggaagaaa aaagaatgaa cggtataatt tatgaaataa tcagtaagag   4740
gctggcaaca ccaccatctt tagatttttg ctatgattct aagcaaaata gtgaaaagga   4800
gaccaatgaa ggagaaacta agatggtaaa aatgatggtg aaaactatgg aaactggaag   4860
ttattcagag tcctctcctg atttaaaaaa atgcatcaaa agtccagtga cttctgattg   4920
gtcagactat cggcctgaca gtgacagtga gcagccatat aaaacatcca gtgatgatcc   4980
caatgacagt ggcgaactta cccaagagaa agaatataac ataggatttg ttaaaagggc   5040
aatagaaaaa ctgtacggta aagcagatat tatcaaacca tctttttttc ctgggtctac   5100
ccgcaaatct caggtttgtc cttataattc tgtggaattt cagtgttcca ggaaagcaag   5160
tctttatgat tctgaagggc agtcatttgg ctcttctgaa caggtatcta gtagttcatc   5220
tatgttgcag gaattccagg aggaaagaca agataagtgt gatgttagtg ctgtgaggga   5280
caattattgt aggggtgaca ttgtagaacc tggtacaaaa caaaatgatg atagcagaat   5340
cctcacagac atagaggaag gagtactgat tgacaaaggc aaatggcttc tgaaagaaaa   5400
tcatttgcta aggatgtcat ctgaaaatcc tggcatgtgt ggcaatgcag acaccacatc   5460
agtggacacc ctacttgata ataacagcag tgaggtacca tattcacatt ttggtaattt   5520
ggccccaggc ccaacgatgg atgaactctc ctcttcagaa ctcgaggaac tgactcaacc   5580
ccttgaacta aaatgcaatt actttaacat gcctcatggt agtgactcag aaccttttca   5640
tgaggacttg ctggatgttc gcaatgaaac ctgtgccaag gaaagaatag caaatcatca   5700
tacagaggag aagggtagtc atcagtcaga aagagtatgc acatctgtca ctcattcctt   5760
```

tatttctgct ggtaacaaag tctaccctgt ctctgatgat gctattaaaa accaaccatt 5820
gcctggcagt aatatgattc atggtacact tcaggaagct gactctttgg ataaactgta 5880
tgctctttgt ggtcaacatt gcccaatact aactgttatt atccaaccca tgaatgagga 5940
agaccgagga tttgcatatc gcaaagaatc tgatattgaa aatttcttgg gtttttattt 6000
atggatgaaa atacacccat atttacttca gacagacaaa aatgtgttca gggaagagaa 6060
caataaagca agtatgagac aaaatcttat tgataatgcc attggtgata tatttgatca 6120
gttttatttc agtaacacat ttgacttgat gggtaaaaga agaaaacaaa aaagaattaa 6180
cttcttgggg ttagaggaag aaggtaattt aaagaaattt caaccagatt tgaaggaaag 6240
gttttgtatg aatttcttgc acacatcatt gttagttgtg ggtaatgtgg attcaaatac 6300
acaagacctc agcggtcaga caaatgaaat ctttaaagca gtcgatgaga ataacaactt 6360
attaaataac agattccagg gctcaagaac aaatctcaac caagtagtaa gagaaaatat 6420
caactgtcat tacttctttg aaatgcttgg tcaagcttgc ctcttagata tttgccaagt 6480
tgagacctcc ttaaatatta gcaacagaaa tattttagaa ctttgtatgt ttgagggtga 6540
aaatcttttc atttgggaag aggaagacat attaaattta actgatcttg aaagcagtag 6600
agaacaagaa gatttataat ttcaatatca gcacactcat tctttgtcaa ttcatttttt 6660
cccatgagat gaagcacatg tgacgaatac ggactagata acctctaaga attttccact 6720
tcttcaaaat gaacttactc tagaaagctt acccttggat aaccagtttg actttcataa 6780
tgtctctgtt ttttgttttt ccaacaatta cagactcagg ttctcttatt ttggaagttt 6840
ctatctggtt ttgttctgaa cttacatttt tttttttttt ggtatctatg attttttttg 6900
ctcagggcat caaaatgtgc taaggacaag aattatatcc tttttaaaaa atgttgttag 6960
cttggtgtaa aatgtatatt gactgtattg gtgaataaat tgaatagaca taacctcaaa 7020
gtacttcact tattcttttt aactactgat ttgataaaaa gtatgattat aagatatcca 7080
cgacaatctc atagtttctt 7100

<210> SEQ ID NO 35
<211> LENGTH: 2156
<212> TYPE: PRT
<213> ORGANISM: Homo sapiens

<400> SEQUENCE: 35

Met Ser Asp Thr Pro Ser Thr Gly Phe Ser Ile Ile His Pro Thr Ser
1 5 10 15

Ser Glu Gly Gln Val Pro Pro Pro Arg His Leu Ser Leu Thr His Pro
20 25 30

Val Val Ala Lys Arg Ile Ser Phe Tyr Lys Ser Gly Asp Pro Gln Phe
35 40 45

Gly Gly Val Arg Val Val Val Asn Pro Arg Ser Phe Lys Ser Phe Asp
50 55 60

Ala Leu Leu Asp Asn Leu Ser Arg Lys Val Pro Leu Pro Phe Gly Val
65 70 75 80

Arg Asn Ile Ser Thr Pro Arg Gly Arg His Ser Ile Thr Arg Leu Glu
85 90 95

Glu Leu Glu Asp Gly Glu Ser Tyr Leu Cys Ser His Gly Arg Lys Val
100 105 110

Gln Pro Val Asp Leu Asp Lys Ala Arg Arg Arg Pro Arg Pro Trp Leu
115 120 125

Ser Ser Arg Ala Ile Ser Ala His Ser Pro Pro His Pro Val Ala Val

```
    130                 135                 140

Ala Ala Pro Gly Met Pro Arg Pro Pro Arg Ser Leu Val Val Phe Arg
145                 150                 155                 160

Asn Gly Asp Pro Lys Thr Arg Arg Ala Val Leu Leu Ser Arg Arg Val
                165                 170                 175

Thr Gln Ser Phe Glu Ala Phe Leu Gln His Leu Thr Glu Val Met Gln
            180                 185                 190

Arg Pro Val Val Lys Leu Tyr Ala Thr Asp Gly Arg Arg Val Pro Ser
        195                 200                 205

Leu Gln Ala Val Ile Leu Ser Ser Gly Ala Val Val Ala Ala Gly Arg
    210                 215                 220

Glu Pro Phe Lys Pro Gly Asn Tyr Asp Ile Gln Lys Tyr Leu Leu Pro
225                 230                 235                 240

Ala Arg Leu Pro Gly Ile Ser Gln Arg Val Tyr Pro Lys Gly Asn Ala
                245                 250                 255

Lys Ser Glu Ser Arg Lys Ile Ser Thr His Met Ser Ser Ser Ser Arg
            260                 265                 270

Ser Gln Ile Tyr Ser Val Ser Ser Glu Lys Thr His Asn Asn Asp Cys
        275                 280                 285

Tyr Leu Asp Tyr Ser Phe Val Pro Glu Lys Tyr Leu Ala Leu Glu Lys
    290                 295                 300

Asn Asp Ser Gln Asn Leu Pro Ile Tyr Pro Ser Glu Asp Asp Ile Glu
305                 310                 315                 320

Lys Ser Ile Ile Phe Asn Gln Asp Gly Thr Met Thr Val Glu Met Lys
                325                 330                 335

Val Arg Phe Arg Ile Lys Glu Glu Glu Thr Ile Lys Trp Thr Thr Thr
            340                 345                 350

Val Ser Lys Thr Gly Pro Ser Asn Asn Asp Glu Lys Ser Glu Met Ser
        355                 360                 365

Phe Pro Gly Arg Thr Glu Ser Arg Ser Ser Gly Leu Lys Leu Ala Ala
    370                 375                 380

Cys Ser Phe Ser Ala Asp Val Ser Pro Met Glu Arg Ser Ser Asn Gln
385                 390                 395                 400

Glu Gly Ser Leu Ala Glu Glu Ile Asn Ile Gln Met Thr Asp Gln Val
                405                 410                 415

Ala Glu Thr Cys Ser Ser Ala Ser Trp Glu Asn Ala Thr Val Asp Thr
            420                 425                 430

Asp Ile Ile Gln Gly Thr Gln Asp Gln Ala Lys His Arg Phe Tyr Arg
        435                 440                 445

Pro Pro Thr Pro Gly Leu Arg Arg Val Arg Gln Lys Lys Ser Val Ile
    450                 455                 460

Gly Ser Val Thr Leu Val Ser Glu Thr Glu Val Gln Glu Lys Met Ile
465                 470                 475                 480

Gly Gln Phe Ser Tyr Ser Glu Glu Arg Glu Ser Gly Glu Asn Lys Ser
                485                 490                 495

Glu Tyr His Met Phe Thr His Ser Cys Ser Lys Met Ser Ser Val Ser
            500                 505                 510

Asn Lys Pro Val Leu Val Gln Ile Asn Asn Asn Asp Gln Met Glu Glu
        515                 520                 525

Ser Ser Leu Glu Arg Lys Lys Glu Asn Ser Leu Leu Lys Ser Ser Ala
    530                 535                 540

Ile Ser Ala Gly Val Ile Glu Ile Thr Ser Gln Lys Met Leu Glu Met
545                 550                 555                 560
```

-continued

```
Ser His Asn Asn Gly Leu Pro Ser Thr Ile Ser Asn Asn Ser Ile Val
                565                 570                 575

Glu Glu Asp Val Val Asp Cys Val Val Leu Asp Asn Lys Thr Gly Ile
            580                 585                 590

Lys Asn Phe Lys Thr Tyr Gly Asn Thr Asn Asp Arg Phe Ser Pro Ile
        595                 600                 605

Ser Ala Asp Ala Thr His Phe Ser Ser Asn Asn Ser Gly Thr Asp Lys
    610                 615                 620

Asn Ile Ser Glu Ala Pro Ala Ser Glu Ala Ser Ser Thr Val Thr Ala
625                 630                 635                 640

Arg Ile Asp Arg Leu Ile Asn Glu Phe Ala Gln Cys Gly Leu Thr Lys
                645                 650                 655

Leu Pro Lys Asn Glu Lys Lys Ile Leu Ser Ser Val Ala Ser Lys Lys
            660                 665                 670

Lys Lys Lys Ser Arg Gln Gln Ala Ile Asn Ser Arg Tyr Gln Asp Gly
        675                 680                 685

Gln Leu Ala Thr Lys Gly Ile Leu Asn Lys Asn Glu Arg Ile Asn Thr
    690                 695                 700

Lys Gly Arg Ile Thr Lys Glu Met Ile Val Gln Asp Ser Asp Ser Pro
705                 710                 715                 720

Leu Lys Gly Gly Ile Leu Cys Glu Glu Asp Leu Gln Lys Ser Asp Thr
                725                 730                 735

Val Ile Glu Ser Asn Thr Phe Cys Ser Lys Ser Asn Leu Asn Ser Thr
            740                 745                 750

Ile Ser Lys Asn Phe His Arg Asn Lys Leu Asn Thr Thr Gln Asn Ser
        755                 760                 765

Lys Val Gln Gly Leu Leu Thr Lys Arg Lys Ser Arg Ser Leu Asn Lys
    770                 775                 780

Ile Ser Leu Gly Ala Pro Lys Lys Arg Glu Ile Gly Gln Arg Asp Lys
785                 790                 795                 800

Val Phe Pro His Asn Glu Ser Lys Tyr Cys Lys Ser Thr Phe Glu Asn
                805                 810                 815

Lys Ser Leu Phe His Val Phe Asn Ile Leu Glu Gln Lys Pro Lys Asp
            820                 825                 830

Phe Tyr Ala Pro Gln Ser Gln Ala Glu Val Ala Ser Gly Tyr Leu Arg
        835                 840                 845

Gly Met Ala Lys Lys Ser Leu Val Ser Lys Val Thr Asp Ser His Ile
    850                 855                 860

Thr Leu Lys Ser Gln Lys Lys Arg Lys Gly Asp Lys Val Lys Ala Ser
865                 870                 875                 880

Ala Ile Leu Ser Lys Gln His Ala Thr Thr Arg Ala Asn Ser Leu Ala
                885                 890                 895

Ser Leu Lys Lys Pro Asp Phe Pro Glu Ala Ile Ala His His Ser Ile
            900                 905                 910

Gln Asn Tyr Ile Gln Ser Trp Leu Gln Asn Ile Asn Pro Tyr Pro Thr
        915                 920                 925

Leu Lys Pro Ile Lys Ser Ala Pro Val Cys Arg Asn Glu Thr Ser Val
    930                 935                 940

Val Asn Cys Ser Asn Asn Ser Phe Ser Gly Asn Asp Pro His Thr Asn
945                 950                 955                 960

Ser Gly Lys Ile Ser Asn Phe Val Met Glu Ser Asn Lys His Ile Thr
                965                 970                 975
```

-continued

```
Lys Ile Ala Gly Leu Thr Gly Asp Asn Leu Cys Lys Glu Gly Asp Lys
            980                 985                 990

Ser Phe Ile Ala Asn Asp Thr Gly  Glu Glu Asp Leu His  Glu Thr Gln
        995                 1000                 1005

Val Gly  Ser Leu Asn Asp Ala  Tyr Leu Val Pro Leu  His Glu His
    1010                 1015                 1020

Cys Thr  Leu Ser Gln Ser Ala  Ile Asn Asp His Asn  Thr Lys Ser
    1025                 1030                 1035

His Ile  Ala Ala Glu Lys Ser  Gly Pro Glu Lys Lys  Leu Val Tyr
    1040                 1045                 1050

Gln Glu  Ile Asn Leu Ala Arg  Lys Arg Gln Ser Val  Glu Ala Ala
    1055                 1060                 1065

Ile Gln  Val Asp Pro Ile Glu  Glu Glu Thr Pro Lys  Asp Leu Leu
    1070                 1075                 1080

Pro Val  Leu Met Leu His Gln  Leu Gln Ala Ser Val  Pro Gly Ile
    1085                 1090                 1095

His Lys  Thr Gln Asn Gly Val  Val Gln Met Pro Gly  Ser Leu Ala
    1100                 1105                 1110

Gly Val  Pro Phe His Ser Ala  Ile Cys Asn Ser Ser  Thr Asn Leu
    1115                 1120                 1125

Leu Leu  Ala Trp Leu Leu Val  Leu Asn Leu Lys Gly  Ser Met Asn
    1130                 1135                 1140

Ser Phe  Cys Gln Val Asp Ala  His Lys Ala Thr Asn  Lys Ser Ser
    1145                 1150                 1155

Glu Thr  Leu Ala Leu Leu Glu  Ile Leu Lys His Ile  Ala Ile Thr
    1160                 1165                 1170

Glu Glu  Ala Asp Asp Leu Lys  Ala Ala Val Ala Asn  Leu Val Glu
    1175                 1180                 1185

Ser Thr  Thr Ser His Phe Gly  Leu Ser Glu Lys Glu  Gln Asp Met
    1190                 1195                 1200

Val Pro  Ile Asp Leu Ser Ala  Asn Cys Ser Thr Val  Asn Ile Gln
    1205                 1210                 1215

Ser Val  Pro Lys Cys Ser Glu  Asn Glu Arg Thr Gln  Gly Ile Ser
    1220                 1225                 1230

Ser Leu  Asp Gly Gly Cys Ser  Ala Ser Glu Ala Cys  Ala Pro Glu
    1235                 1240                 1245

Val Cys  Val Leu Glu Val Thr  Cys Ser Pro Cys Glu  Met Cys Thr
    1250                 1255                 1260

Val Asn  Lys Ala Tyr Ser Pro  Lys Glu Thr Cys Asn  Pro Ser Asp
    1265                 1270                 1275

Thr Phe  Phe Pro Ser Asp Gly  Tyr Gly Val Asp Gln  Thr Ser Met
    1280                 1285                 1290

Asn Lys  Ala Cys Phe Leu Gly  Glu Val Cys Ser Leu  Thr Asp Thr
    1295                 1300                 1305

Val Phe  Ser Asp Lys Ala Cys  Ala Gln Lys Glu Asn  His Thr Tyr
    1310                 1315                 1320

Glu Gly  Ala Cys Pro Ile Asp  Glu Thr Tyr Val Pro  Val Asn Val
    1325                 1330                 1335

Cys Asn  Thr Ile Asp Phe Leu  Asn Ser Lys Glu Asn  Thr Tyr Thr
    1340                 1345                 1350

Asp Asn  Leu Asp Ser Thr Glu  Glu Leu Glu Arg Gly  Asp Asp Ile
    1355                 1360                 1365

Gln Lys  Asp Leu Asn Ile Leu  Thr Asp Pro Glu Tyr  Lys Asn Gly
```

-continued

```
    1370                1375                1380

Phe Asn  Thr Leu Val Ser His  Gln Asn Val Ser Asn  Leu Ser Ser
    1385                1390                1395

Cys Gly  Leu Cys Leu Ser Glu  Lys Glu Ala Glu Leu  Asp Lys Lys
    1400                1405                1410

His Ser  Ser Leu Asp Asp Phe  Glu Asn Cys Ser Leu  Arg Lys Phe
    1415                1420                1425

Gln Asp  Glu Asn Ala Tyr Thr  Ser Phe Asp Met Glu  Glu Pro Arg
    1430                1435                1440

Thr Ser  Glu Glu Pro Gly Ser  Ile Thr Asn Ser Met  Thr Ser Ser
    1445                1450                1455

Glu Arg  Asn Ile Ser Glu Leu  Glu Ser Phe Glu Glu  Leu Glu Asn
    1460                1465                1470

His Asp  Thr Asp Ile Phe Asn  Thr Val Val Asn Gly  Gly Glu Gln
    1475                1480                1485

Ala Thr  Glu Glu Leu Ile Gln  Glu Glu Val Glu Ala  Ser Lys Thr
    1490                1495                1500

Leu Glu  Leu Ile Asp Ile Ser  Ser Lys Asn Ile Met  Glu Glu Lys
    1505                1510                1515

Arg Met  Asn Gly Ile Ile Tyr  Glu Ile Ile Ser Lys  Arg Leu Ala
    1520                1525                1530

Thr Pro  Pro Ser Leu Asp Phe  Cys Tyr Asp Ser Lys  Gln Asn Ser
    1535                1540                1545

Glu Lys  Glu Thr Asn Glu Gly  Glu Thr Lys Met Val  Lys Met Met
    1550                1555                1560

Val Lys  Thr Met Glu Thr Gly  Ser Tyr Ser Glu Ser  Ser Pro Asp
    1565                1570                1575

Leu Lys  Lys Cys Ile Lys Ser  Pro Val Thr Ser Asp  Trp Ser Asp
    1580                1585                1590

Tyr Arg  Pro Asp Ser Asp Ser  Glu Gln Pro Tyr Lys  Thr Ser Ser
    1595                1600                1605

Asp Asp  Pro Asn Asp Ser Gly  Glu Leu Thr Gln Glu  Lys Glu Tyr
    1610                1615                1620

Asn Ile  Gly Phe Val Lys Arg  Ala Ile Glu Lys Leu  Tyr Gly Lys
    1625                1630                1635

Ala Asp  Ile Ile Lys Pro Ser  Phe Phe Pro Gly Ser  Thr Arg Lys
    1640                1645                1650

Ser Gln  Val Cys Pro Tyr Asn  Ser Val Glu Phe Gln  Cys Ser Arg
    1655                1660                1665

Lys Ala  Ser Leu Tyr Asp Ser  Glu Gly Gln Ser Phe  Gly Ser Ser
    1670                1675                1680

Glu Gln  Val Ser Ser Ser Ser  Ser Met Leu Gln Glu  Phe Gln Glu
    1685                1690                1695

Glu Arg  Gln Asp Lys Cys Asp  Val Ser Ala Val Arg  Asp Asn Tyr
    1700                1705                1710

Cys Arg  Gly Asp Ile Val Glu  Pro Gly Thr Lys Gln  Asn Asp Asp
    1715                1720                1725

Ser Arg  Ile Leu Thr Asp Ile  Glu Glu Gly Val Leu  Ile Asp Lys
    1730                1735                1740

Gly Lys  Trp Leu Leu Lys Glu  Asn His Leu Leu Arg  Met Ser Ser
    1745                1750                1755

Glu Asn  Pro Gly Met Cys Gly  Asn Ala Asp Thr Thr  Ser Val Asp
    1760                1765                1770
```

```
Thr Leu  Leu Asp Asn Asn Ser  Ser Glu Val Pro Tyr  Ser His Phe
    1775                 1780                 1785

Gly Asn  Leu Ala Pro Gly Pro  Thr Met Asp Glu Leu  Ser Ser Ser
    1790                 1795                 1800

Glu Leu  Glu Glu Leu Thr Gln  Pro Leu Glu Leu Lys  Cys Asn Tyr
    1805                 1810                 1815

Phe Asn  Met Pro His Gly Ser  Asp Ser Glu Pro Phe  His Glu Asp
    1820                 1825                 1830

Leu Leu  Asp Val Arg Asn Glu  Thr Cys Ala Lys Glu  Arg Ile Ala
    1835                 1840                 1845

Asn His  His Thr Glu Glu Lys  Gly Ser His Gln Ser  Glu Arg Val
    1850                 1855                 1860

Cys Thr  Ser Val Thr His Ser  Phe Ile Ser Ala Gly  Asn Lys Val
    1865                 1870                 1875

Tyr Pro  Val Ser Asp Asp Ala  Ile Lys Asn Gln Pro  Leu Pro Gly
    1880                 1885                 1890

Ser Asn  Met Ile His Gly Thr  Leu Gln Glu Ala Asp  Ser Leu Asp
    1895                 1900                 1905

Lys Leu  Tyr Ala Leu Cys Gly  Gln His Cys Pro Ile  Leu Thr Val
    1910                 1915                 1920

Ile Ile  Gln Pro Met Asn Glu  Glu Asp Arg Gly Phe  Ala Tyr Arg
    1925                 1930                 1935

Lys Glu  Ser Asp Ile Glu Asn  Phe Leu Gly Phe Tyr  Leu Trp Met
    1940                 1945                 1950

Lys Ile  His Pro Tyr Leu Leu  Gln Thr Asp Lys Asn  Val Phe Arg
    1955                 1960                 1965

Glu Glu  Asn Asn Lys Ala Ser  Met Arg Gln Asn Leu  Ile Asp Asn
    1970                 1975                 1980

Ala Ile  Gly Asp Ile Phe Asp  Gln Phe Tyr Phe Ser  Asn Thr Phe
    1985                 1990                 1995

Asp Leu  Met Gly Lys Arg Arg  Lys Gln Lys Arg Ile  Asn Phe Leu
    2000                 2005                 2010

Gly Leu  Glu Glu Glu Gly Asn  Leu Lys Lys Phe Gln  Pro Asp Leu
    2015                 2020                 2025

Lys Glu  Arg Phe Cys Met Asn  Phe Leu His Thr Ser  Leu Leu Val
    2030                 2035                 2040

Val Gly  Asn Val Asp Ser Asn  Thr Gln Asp Leu Ser  Gly Gln Thr
    2045                 2050                 2055

Asn Glu  Ile Phe Lys Ala Val  Asp Glu Asn Asn Asn  Leu Leu Asn
    2060                 2065                 2070

Asn Arg  Phe Gln Gly Ser Arg  Thr Asn Leu Asn Gln  Val Val Arg
    2075                 2080                 2085

Glu Asn  Ile Asn Cys His Tyr  Phe Phe Glu Met Leu  Gly Gln Ala
    2090                 2095                 2100

Cys Leu  Leu Asp Ile Cys Gln  Val Glu Thr Ser Leu  Asn Ile Ser
    2105                 2110                 2115

Asn Arg  Asn Ile Leu Glu Leu  Cys Met Phe Glu Gly  Glu Asn Leu
    2120                 2125                 2130

Phe Ile  Trp Glu Glu Glu Asp  Ile Leu Asn Leu Thr  Asp Leu Glu
    2135                 2140                 2145

Ser Ser  Arg Glu Gln Glu Asp  Leu
    2150                 2155
```

<210> SEQ ID NO 36
<211> LENGTH: 3950
<212> TYPE: DNA
<213> ORGANISM: Homo sapiens

<400> SEQUENCE: 36

```
atgtcacatc tggtggaccc tacatcagga gacttgccag ttagagacat agatgctata     60
cctctggtgc taccagcctc aaaaggtaag aatatgaaaa ctcaaccacc cttgagcagg    120
atgaaccggg aggaattgga ggacagtttc tttcgacttc gcgaagatca catgttggtg    180
aaggagcttt cttggaagca acaggatgag atcaaaaggc tgaggaccac cttgctgcgg    240
ttgaccgctg ctggccggga cctgcgggtc gcggaggagg cggcgccgct ctcggagacc    300
gcaaggcgcg ggcagaaggc gggatggcgg cagcgcctct ccatgcacca gcgcccccag    360
atgcaccgac tgcaagggca tttccactgc gtcggccctg ccagcccccg ccgcgcccag    420
cctcgcgtcc aagtgggaca cagacagctc cacacagccg gtgcaccggt gccggagaaa    480
cccaagaggg ggccaaggga caggctgagc tacacagccc ctccatcgtt taaggagcat    540
gcgacaaatg aaaacagagg tgaagtagcc agtaaaccca gtgaacttgt ttctggttct    600
aacagcataa tttctttcag cagtgtcata agtatggcta aacccattgg tctatgcatg    660
cctaacagtg cccacatcat ggccagcaat accatgcaag tggaagagcc acccaagtct    720
cctgagaaaa tgtggcctaa agatgaaaat tttgaacaga gaagctcatt ggagtgtgct    780
cagaaggctg cagagcttcg agcttccatt aaagagaagg tagagctgat tcgacttaag    840
aagctcttac atgaaagaaa tgcttcattg gttatgacaa aagcacaatt aacagaagtt    900
caagaggcat acgaaacctt gctccagaag aatcagggaa tcctgagtgc agcccatgag    960
gccctcctca agcaagtgaa tgagctcagg gcagagctga aggaagaaag caagaaggct   1020
gtgagcttga agagccaact ggaagatgtg tctatcttgc agatgactct gaaggagttt   1080
caggagagag ttgaagattt ggaaaaagaa cgaaaattgc tgaatgacaa ttatgacaaa   1140
ctcttagaaa gcatgctgga cagcagtgac agctccagtc agccccactg gagcaacgag   1200
ctcatagcgg aacagctaca gcagcaagtc tctcagctgc aggatcagct ggatgctgag   1260
ctggaggaca agagaaaagt tttacttgag ctgtccaggg agaaagccca aaatgaggat   1320
ctgaagcttg aagtcaccaa catacttcag aagcataaac aggaagtaga gctcctccaa   1380
aatgcagcca caatttccca acctcctgac aggcaatctg aaccagccac tcacccagct   1440
gtattgcaag agaacactca gatcgagcca agtgaaccca aaaaccaaga agaaaagaaa   1500
ctgtcccagg tgctaaatga gttgcaagta tcacacgcag agaccacatt ggaactagaa   1560
aagaccaggg acatgcttat tctgcagcgc aaaatcaacg tgtgttatca ggaggaactg   1620
gaggcaatga tgacaaaagc tgacaatgat aatagagatc acaaagaaaa gctggagagg   1680
ttgactcgac tactagacct caagaataac cgtatcaagc agctggaagg tattttaaga   1740
agccatgacc ttccaacatc tgaacagctc aaagatgttg cttatggcac ccgaccgttg   1800
tcgttatgtt tggaaacact gccagcccat ggagatgagg ataaagtgga tatttctctg   1860
ctgcatcagg gtgagaatct tttgaactg cacatccacc aggccttcct gacatctgcc    1920
gccctagctc aggctggaga tacccaacct accactttct gcacctattc cttctatgac   1980
tttgaaaccc actgtacccc attatctgtg gggccacagc ccctctatga cttcacctcc   2040
cagtatgtga tggagacaga ttcgcttttc ttacactacc ttcaagaggc ttcagcccgg   2100
cttgacatac accaggccat ggccagtgaa cacagcactc ttgctgcagg atggatttgc   2160
```

```
tttgacaggg tgctagagac tgtggagaaa gtccatggct tggccacact gattggagct   2220
ggtggagaag agttcggggt tctagagtac tggatgaggc tgcgtttccc cataaaaccc   2280
agcctacagg cgtgcaataa acgaaagaaa gcccaggtct acctgtcaac cgatgtgctt   2340
ggaggccgga aggcccagga agaggagttc agatcggagt cttgggaacc tcagaacgag   2400
ctgtggattg aaatcaccaa gtgctgtggc ctccggagtc gatggctggg aactcaaccc   2460
agtccatatg ctgtgtaccg cttcttcacc ttttctgacc atgacactgc catcattcca   2520
gccagtaaca acccctactt tagagaccag gctcgattcc cagtgcttgt gacctctgac   2580
ctggaccatt atctgagacg ggaggccttg tctatacatg tttttgatga tgaagactta   2640
gagcctggct cgtatcttgg ccgagcccga gtgcctttac tgcctcttgc aaaaaatgaa   2700
tctatcaaag gtgattttaa cctcactgac cctgcagaga aacccaacgg atctattcaa   2760
gtgcaactgg attggaagtt tccctacata ccccctgaga gcttcctgaa accagaagct   2820
cagactaagg ggaaggatac caaggacagt tcaaagatct catctgaaga ggaaaaggct   2880
tcatttcctt cccaggatca gatggcatct cctgaggttc ccattgaagc tggccagtat   2940
cgatctaaga gaaaacctcc tcatggggga gaaagaaagg agaaggagca ccaggttgtg   3000
agctactcaa gaagaaaaca tggcaaaaga ataggtgttc aaggaaagaa tagaatggag   3060
tatcttagcc ttaacatctt aaatggaaat acaccagagc aggtgaatta cactgagtgg   3120
aagttctcag agactaacag cttcataggt gatggcttta aaaatcagca cgaggaagag   3180
gaaatgacat tatcccattc agcactgaaa cagaaggaac ctctacatcc tgtaaatgac   3240
aaagaatcct ctgaacaagg ttctgaagtc agtgaagcac aaactaccga cagtgatgat   3300
gtcatagtgc cacccatgtc tcagaaatat cctaaggcag attcagagaa gatgtgcatt   3360
gaaattgtct ccctggcctt ctacccagag gcagaagtga tgtctgatga gaacataaaa   3420
caggtgtatg tggagtacaa attctacgac ctacccttgt cggagacaga gactccagtg   3480
tccctaagga agcctagggc aggagaagaa atccactttc actttagcaa ggtaatagac   3540
ctggacccac aggagcagca aggccgaagg cggtttctgt tcgacatgct gaatggacaa   3600
gatcctgatc aaggacattt aaagtttaca gtggtaagtg atcctctgga tgaagaaaag   3660
aaagaatgtg aagaagtggg atatgcatat cttcaactgt ggcagatcct ggagtcagga   3720
agagatattc tagagcaaga gctagacatt gttagccctg aagatctggc taccccaata   3780
ggaaggctga aggtttccct tcaagcagct gctgtcctcc atgctattta caaggagatg   3840
actgaagatt tgttttcatg aaggaacaag tgctattcca atctaaaagt ctctgaggga   3900
accatagtaa aaagtctctt ataaagttag cttgctataa catgaaaaaa              3950
```

<210> SEQ ID NO 37
<211> LENGTH: 1286
<212> TYPE: PRT
<213> ORGANISM: Homo sapiens

<400> SEQUENCE: 37

```
Met Ser His Leu Val Asp Pro Thr Ser Gly Asp Leu Pro Val Arg Asp
1               5                   10                  15

Ile Asp Ala Ile Pro Leu Val Leu Pro Ala Ser Lys Gly Lys Asn Met
            20                  25                  30

Lys Thr Gln Pro Pro Leu Ser Arg Met Asn Arg Glu Glu Leu Glu Asp
        35                  40                  45

Ser Phe Phe Arg Leu Arg Glu Asp His Met Leu Val Lys Glu Leu Ser
```

```
    50                  55                  60

Trp Lys Gln Gln Asp Glu Ile Lys Arg Leu Arg Thr Thr Leu Leu Arg
65                  70                  75                  80

Leu Thr Ala Ala Gly Arg Asp Leu Arg Val Ala Glu Glu Ala Ala Pro
                85                  90                  95

Leu Ser Glu Thr Ala Arg Arg Gly Gln Lys Ala Gly Trp Arg Gln Arg
            100                 105                 110

Leu Ser Met His Gln Arg Pro Gln Met His Arg Leu Gln Gly His Phe
        115                 120                 125

His Cys Val Gly Pro Ala Ser Pro Arg Arg Ala Gln Pro Arg Val Gln
    130                 135                 140

Val Gly His Arg Gln Leu His Thr Ala Gly Ala Pro Val Pro Glu Lys
145                 150                 155                 160

Pro Lys Arg Gly Pro Arg Asp Arg Leu Ser Tyr Thr Ala Pro Pro Ser
                165                 170                 175

Phe Lys Glu His Ala Thr Asn Glu Asn Arg Gly Glu Val Ala Ser Lys
            180                 185                 190

Pro Ser Glu Leu Val Ser Gly Ser Asn Ser Ile Ile Ser Phe Ser Ser
        195                 200                 205

Val Ile Ser Met Ala Lys Pro Ile Gly Leu Cys Met Pro Asn Ser Ala
    210                 215                 220

His Ile Met Ala Ser Asn Thr Met Gln Val Glu Glu Pro Pro Lys Ser
225                 230                 235                 240

Pro Glu Lys Met Trp Pro Lys Asp Glu Asn Phe Glu Gln Arg Ser Ser
                245                 250                 255

Leu Glu Cys Ala Gln Lys Ala Ala Glu Leu Arg Ala Ser Ile Lys Glu
            260                 265                 270

Lys Val Glu Leu Ile Arg Leu Lys Lys Leu Leu His Glu Arg Asn Ala
        275                 280                 285

Ser Leu Val Met Thr Lys Ala Gln Leu Thr Glu Val Gln Glu Ala Tyr
    290                 295                 300

Glu Thr Leu Leu Gln Lys Asn Gln Gly Ile Leu Ser Ala Ala His Glu
305                 310                 315                 320

Ala Leu Leu Lys Gln Val Asn Glu Leu Arg Ala Glu Leu Lys Glu Glu
                325                 330                 335

Ser Lys Lys Ala Val Ser Leu Lys Ser Gln Leu Glu Asp Val Ser Ile
            340                 345                 350

Leu Gln Met Thr Leu Lys Glu Phe Gln Glu Arg Val Glu Asp Leu Glu
        355                 360                 365

Lys Glu Arg Lys Leu Leu Asn Asp Asn Tyr Asp Lys Leu Leu Glu Ser
    370                 375                 380

Met Leu Asp Ser Ser Asp Ser Ser Ser Gln Pro His Trp Ser Asn Glu
385                 390                 395                 400

Leu Ile Ala Glu Gln Leu Gln Gln Gln Val Ser Gln Leu Gln Asp Gln
                405                 410                 415

Leu Asp Ala Glu Leu Glu Asp Lys Arg Lys Val Leu Leu Glu Leu Ser
            420                 425                 430

Arg Glu Lys Ala Gln Asn Glu Asp Leu Lys Leu Glu Val Thr Asn Ile
        435                 440                 445

Leu Gln Lys His Lys Gln Glu Val Glu Leu Leu Gln Asn Ala Ala Thr
    450                 455                 460

Ile Ser Gln Pro Pro Asp Arg Gln Ser Glu Pro Ala Thr His Pro Ala
465                 470                 475                 480
```

-continued

```
Val Leu Gln Glu Asn Thr Gln Ile Glu Pro Ser Glu Pro Lys Asn Gln
                485                 490                 495

Glu Glu Lys Lys Leu Ser Gln Val Leu Asn Glu Leu Gln Val Ser His
            500                 505                 510

Ala Glu Thr Thr Leu Glu Leu Glu Lys Thr Arg Asp Met Leu Ile Leu
        515                 520                 525

Gln Arg Lys Ile Asn Val Cys Tyr Gln Glu Glu Leu Glu Ala Met Met
    530                 535                 540

Thr Lys Ala Asp Asn Asp Asn Arg Asp His Lys Glu Lys Leu Glu Arg
545                 550                 555                 560

Leu Thr Arg Leu Leu Asp Leu Lys Asn Asn Arg Ile Lys Gln Leu Glu
                565                 570                 575

Gly Ile Leu Arg Ser His Asp Leu Pro Thr Ser Glu Gln Leu Lys Asp
            580                 585                 590

Val Ala Tyr Gly Thr Arg Pro Leu Ser Leu Cys Leu Glu Thr Leu Pro
        595                 600                 605

Ala His Gly Asp Glu Asp Lys Val Asp Ile Ser Leu Leu His Gln Gly
    610                 615                 620

Glu Asn Leu Phe Glu Leu His Ile His Gln Ala Phe Leu Thr Ser Ala
625                 630                 635                 640

Ala Leu Ala Gln Ala Gly Asp Thr Gln Pro Thr Thr Phe Cys Thr Tyr
                645                 650                 655

Ser Phe Tyr Asp Phe Glu Thr His Cys Thr Pro Leu Ser Val Gly Pro
            660                 665                 670

Gln Pro Leu Tyr Asp Phe Thr Ser Gln Tyr Val Met Glu Thr Asp Ser
        675                 680                 685

Leu Phe Leu His Tyr Leu Gln Glu Ala Ser Ala Arg Leu Asp Ile His
    690                 695                 700

Gln Ala Met Ala Ser Glu His Ser Thr Leu Ala Ala Gly Trp Ile Cys
705                 710                 715                 720

Phe Asp Arg Val Leu Glu Thr Val Glu Lys Val His Gly Leu Ala Thr
                725                 730                 735

Leu Ile Gly Ala Gly Gly Glu Glu Phe Gly Val Leu Glu Tyr Trp Met
            740                 745                 750

Arg Leu Arg Phe Pro Ile Lys Pro Ser Leu Gln Ala Cys Asn Lys Arg
        755                 760                 765

Lys Lys Ala Gln Val Tyr Leu Ser Thr Asp Val Leu Gly Gly Arg Lys
    770                 775                 780

Ala Gln Glu Glu Glu Phe Arg Ser Glu Ser Trp Glu Pro Gln Asn Glu
785                 790                 795                 800

Leu Trp Ile Glu Ile Thr Lys Cys Cys Gly Leu Arg Ser Arg Trp Leu
                805                 810                 815

Gly Thr Gln Pro Ser Pro Tyr Ala Val Tyr Arg Phe Phe Thr Phe Ser
            820                 825                 830

Asp His Asp Thr Ala Ile Ile Pro Ala Ser Asn Asn Pro Tyr Phe Arg
        835                 840                 845

Asp Gln Ala Arg Phe Pro Val Leu Val Thr Ser Asp Leu Asp His Tyr
    850                 855                 860

Leu Arg Arg Glu Ala Leu Ser Ile His Val Phe Asp Asp Glu Asp Leu
865                 870                 875                 880

Glu Pro Gly Ser Tyr Leu Gly Arg Ala Arg Val Pro Leu Leu Pro Leu
                885                 890                 895
```

-continued

```
Ala Lys Asn Glu Ser Ile Lys Gly Asp Phe Asn Leu Thr Asp Pro Ala
            900                 905                 910

Glu Lys Pro Asn Gly Ser Ile Gln Val Gln Leu Asp Trp Lys Phe Pro
        915                 920                 925

Tyr Ile Pro Pro Glu Ser Phe Leu Lys Pro Glu Ala Gln Thr Lys Gly
    930                 935                 940

Lys Asp Thr Lys Asp Ser Ser Lys Ile Ser Ser Glu Glu Glu Lys Ala
945                 950                 955                 960

Ser Phe Pro Ser Gln Asp Gln Met Ala Ser Pro Glu Val Pro Ile Glu
                965                 970                 975

Ala Gly Gln Tyr Arg Ser Lys Arg Lys Pro Pro His Gly Gly Glu Arg
            980                 985                 990

Lys Glu Lys Glu His Gln Val Val  Ser Tyr Ser Arg Arg  Lys His Gly
        995                 1000                1005

Lys Arg  Ile Gly Val Gln Gly  Lys Asn Arg Met Glu  Tyr Leu Ser
    1010                 1015                 1020

Leu Asn  Ile Leu Asn Gly Asn  Thr Pro Glu Gln Val  Asn Tyr Thr
    1025                 1030                 1035

Glu Trp  Lys Phe Ser Glu Thr  Asn Ser Phe Ile Gly  Asp Gly Phe
    1040                 1045                 1050

Lys Asn  Gln His Glu Glu Glu  Glu Met Thr Leu Ser  His Ser Ala
    1055                 1060                 1065

Leu Lys  Gln Lys Glu Pro Leu  His Pro Val Asn Asp  Lys Glu Ser
    1070                 1075                 1080

Ser Glu  Gln Gly Ser Glu Val  Ser Glu Ala Gln Thr  Thr Asp Ser
    1085                 1090                 1095

Asp Asp  Val Ile Val Pro Pro  Met Ser Gln Lys Tyr  Pro Lys Ala
    1100                 1105                 1110

Asp Ser  Glu Lys Met Cys Ile  Glu Ile Val Ser Leu  Ala Phe Tyr
    1115                 1120                 1125

Pro Glu  Ala Glu Val Met Ser  Asp Glu Asn Ile Lys  Gln Val Tyr
    1130                 1135                 1140

Val Glu  Tyr Lys Phe Tyr Asp  Leu Pro Leu Ser Glu  Thr Glu Thr
    1145                 1150                 1155

Pro Val  Ser Leu Arg Lys Pro  Arg Ala Gly Glu Glu  Ile His Phe
    1160                 1165                 1170

His Phe  Ser Lys Val Ile Asp  Leu Asp Pro Gln Glu  Gln Gln Gly
    1175                 1180                 1185

Arg Arg  Arg Phe Leu Phe Asp  Met Leu Asn Gly Gln  Asp Pro Asp
    1190                 1195                 1200

Gln Gly  His Leu Lys Phe Thr  Val Val Ser Asp Pro  Leu Asp Glu
    1205                 1210                 1215

Glu Lys  Lys Glu Cys Glu Glu  Val Gly Tyr Ala Tyr  Leu Gln Leu
    1220                 1225                 1230

Trp Gln  Ile Leu Glu Ser Gly  Arg Asp Ile Leu Glu  Gln Glu Leu
    1235                 1240                 1245

Asp Ile  Val Ser Pro Glu Asp  Leu Ala Thr Pro Ile  Gly Arg Leu
    1250                 1255                 1260

Lys Val  Ser Leu Gln Ala Ala  Ala Val Leu His Ala  Ile Tyr Lys
    1265                 1270                 1275

Glu Met  Thr Glu Asp Leu Phe  Ser
    1280                 1285
```

-continued

<210> SEQ ID NO 38
<211> LENGTH: 7221
<212> TYPE: DNA
<213> ORGANISM: Homo sapiens

<400> SEQUENCE: 38
cgggcggcct cttgtgtgag ggcctgtggg attctccgga tatggccgga gtgtttcctt 60
atcgagggcc gggtaacccg gtgcctggcc ctctagcccc gctaccggac tacatgtcgg 120
aggagaagct gcaggagaaa gctcgaaaat ggcagcaatt gcaggccaag cgctatgcag 180
aaaagcggaa gtttgggttt gtggatgccc agaaggaaga catgccccca gaacatgtca 240
gggagatcat tcgagaccat ggagacatga ccaacaggaa gttccgccat gacaaaaggg 300
tttacttggg tgccctaaag tacatgcccc acgcagtcct caaactcctg gagaacatgc 360
ctatgccttg ggagcagatt cgggatgtgc ccgtgctgta ccacatcact ggagccattt 420
ccttcgtcaa tgagattccc tgggtcattg aacctgtcta catctcccag tgggggtcaa 480
tgtggattat gatgcgccga gaaaaaagag ataggaggca tttcaagaga atgcgttttc 540
cccctttga tgatgaggag ccgccccttgg actatgctga caacatccta aatgttgagc 600
cactggaggc cattcagcta gagctggacc ctgaggagga cgcccctgtg ttggactggt 660
tctatgacca ccagccgttg agggacagca ggaagtatgt aaatggctcc acttaccagc 720
gctggcagtt cacactacct atgatgtcaa ctctctaccg cctggctaat cagctcctga 780
cagacttggt ggatgacaac tacttctacc tgtttgattt gaaggccttc tttacgtcca 840
aggcactcaa tatggccatt cctggaggcc ccaaatttga acctcttgtt cgagacatca 900
acctacagga tgaagactgg aatgaattca atgatattaa caagattatc atccggcagc 960
ctatccggac tgagtacaag attgcttttc cttacttgta caacaatctt ccacaccatg 1020
tccacctcac ctggtaccat actcccaatg ttgtattcat caaaactgaa gatcctgact 1080
tgccagcttt ctactttgac cctttgatca acccaatctc ccataggcac tcagtcaaga 1140
gccaggaacc attgccggat gatgatgagg aatttgagct cccggagttt gtggagccct 1200
tcctgaagga cacacccctc tatacagaca atacagccaa tggcattgcc ctgctctggg 1260
ccccgcggcc cttcaaccta cgctctggtc gcacccgtcg ggccctggac atacccttg 1320
tcaagaactg gtatcgggag cattgtcctg ccgggcagcc tgtgaaagtg agggtctcct 1380
accagaagct gcttaagtac tatgtgctga atgccctgaa gcatcggccc cctaaggctc 1440
aaaagaagag gtatttgttc cgctccttca aagccaccaa attctttcag tccacaaagc 1500
tggactgggt ggagggttgg ctccaggttt gccgccaggg ctacaacatg ctcaaccttc 1560
tcattcaccg caaaaacctc aactacctgc acctggacta caacttcaac ctcaagcctg 1620
tgaaaacgct caccaccaag gaaagaaaga aatctcgttt tgggaatgct ttccacctgt 1680
gtcgggaagt tctgcgtttg actaagctgg tggtggatag tcacgtgcag tatcggctgg 1740
gcaatgtgga tgccttccag ctggcagatg gattgcagta tatatttgcc catgttgggc 1800
agttgacggg catgtatcga tacaaataca agctgatgcg acagattcgc gtgtgcaagg 1860
acctgaagca tctcatctat tatcgtttca acacaggccc tgtagggaag ggtcctggct 1920
gtggcttctg ggctgccggt tggcgagtct ggctcttttt catgcgtggc attacccctt 1980
tattagagcg atggcttggc aacctcctgg cccggcagtt tgaaggtcga cactcaaagg 2040
gggtggcaaa gacagtaaca aagcagcgag tggagtcaca ttttgacctt gagctgcggg 2100
cagctgtgat gcatgatatt ctggacatga tgcctgaggg gatcaagcag aacaaggccc 2160

-continued

```
ggacaatcct gcagcacctc agtgaagcct ggcgctgctg gaaagccaac attccctgga   2220
aggtccctgg gctgccgacg cccatagaga atatgatcct tcgatacgtg aaggccaagg   2280
ctgactggtg gaccaacact gcccactaca accgagaacg gatccgccga ggggccactg   2340
tggacaagac tgtttgtaaa aagaatctgg gccgcctcac ccggctctat ctgaaggcag   2400
aacaggagcg gcagcacaac tacctgaagg acgggcctta catcacagcg gaggaaacag   2460
tggcagtata taccaccaca gtgcattggt tggaaagccg caggttttca cccatcccat   2520
tccccccact ctcctataag catgacacca agttgctcat cttggcattg gagcggctca   2580
aggaagctta tagtgtgaag tctcggttga accagtctca gagggaggag ctaggtctga   2640
tcgagcaggc ctacgataac ctccacgagg cgctgtcccg cataaagcgt cacctcctca   2700
cacagagagc cttcaaagag gtgggcattg agttcatgga tctgtatagc cacctcgttc   2760
cagtatatga tgttgagccc ctggagaaga taactgatgc ttacctggac cagtacctgt   2820
ggtatgaagc cgacaagcgc cgcctgttcc caccctggat taagcctgca gacacagaac   2880
cacctccact gcttgtttac aagtggtgtc aaggcatcaa taacctgcag gacgtgtggg   2940
agacgagtga aggcgagtgc aatgtcatgc tggaatcccg ctttgagaag atgtatgaga   3000
agatcgactt gactctgctc aacaggctcg tgcgcctcat cgtggaccac aacatagccg   3060
actacatgac agccaagaac aacgtcgtca tcaactataa ggacatgaac catacgaatt   3120
catatgggat catcagaggc ctgcagtttg cctcattcat agtgcagtat tatggcctgg   3180
tgatggattt gcttgtattg ggattgcacc gggccagtga gatggctggg ccccctcaga   3240
tgccaaatga ctttctcagt ttccaggaca tagccactga ggctgcccac cccatccgtc   3300
tcttctgcag atacattgat cgcatccata tttttttcag gttcacagca gatgaggctc   3360
gggacctgat tcaacgttac ctgacagagc accctgaccc caataatgaa aacatcgttg   3420
gctataataa caagaagtgc tggccccgag atgcccgcat gcgcctcatg aaacatgatg   3480
ttaacttagg ccgggcggta ttctgggaca tcaagaaccg cttgccacgg tcagtgacta   3540
cagttcagtg ggagaacagc ttcgtgtctg tgtacagtaa ggacaacccc aacctgctgt   3600
tcaacatgtg tggcttcgag tgccgcatcc tgcctaagtg ccgcaccagc tatgaggagt   3660
tcacccacaa ggacggggtc tggaacctgc agaatgaggt tactaaggag cgcacagctc   3720
agtgtttcct gcgtgtggac gatgagtcaa tgcagcgctt ccacaaccgc gtgcgtcaga   3780
ttctcatggc ctctgggtcc accaccttca ccaagattgt gaataagtgg aatacagctc   3840
tcattggcct tatgacatac tttcgggagg ctgtggtgaa cacccaagag ctcttggact   3900
tactggtgaa gtgtgagcac aaaatccaga cacgtatcaa gattggactc aactccaaga   3960
tgccaagtcg gttccccccg gttgtgttct acaccccctaa ggagttgggt ggactcggca   4020
tgctctcaat gggccatgtg ctcatccccc aatccgacct caggtggtcc aaacagacag   4080
atgtaggtat cacacacttt cgttcaggaa tgagccatga agaagaccag ctcattccca   4140
acttgtaccg ctacatacag ccatgggaga gcgagttcat tgattctcag cgggtctggg   4200
ctgagtactc actcaagaga caagaggcca ttgctcagaa cagacgcctg actttagaag   4260
acctagaaga ttcatgggat cgtggcattc ctcgaatcaa taccctcttc cagaaggacc   4320
ggcacacact ggcttatgat aagggctggc gtgtcagaac tgactttaag cagtatcagg   4380
ttttgaagca gaatccgttc tggtggacac accagcggca tgatgggaag ctctggaacc   4440
tgaacaacta ccgtacagac atgatccagg ccctgggcgg tgtggaaggc attctggaac   4500
acacactctt taagggcact tacttcccta cctgggaggg gcttttctgg gagaaggcca   4560
```

```
gtggctttga ggaatctatg aagtggaaga agctaactaa tgctcagcga tcaggactga   4620
accagattcc caatcgtaga ttcaccctct ggtggtcccc gaccattaat cgagccaatg   4680
tatatgtagg ctttcaggtg cagctagacc tgacgggtat cttcatgcac ggcaagatcc   4740
ccacgctgaa gatctctctc atccagatct tccgagctca cttgtggcag aagatccatg   4800
agagcattgt tatggactta tgtcaggtgt ttgaccagga acttgatgca ctggaaattg   4860
agacagtaca aaaggagaca atccatcccc gaaagtcata taagatgaac tcttcctgtg   4920
cagatatcct gctctttgcc tcctataagt ggaatgtctc ccggccctca ttgctggctg   4980
actccaagga tgtgatggac agcaccacca cccagaaata ctggattgac atccagttgc   5040
gctgggggga ctatgattcc cacgacattg agcgctacgc ccgggccaag ttcctggact   5100
acaccaccga caacatgagt atctaccctt cgcccacagg tgtactcatc gccattgacc   5160
tggcctataa cttgcacagt gcctatggaa actggttccc aggcagcaag cctctcatac   5220
aacaggccat ggccaagatc atgaaggcaa accctgccct gtatgtgtta cgtgaacgga   5280
tccgcaaggg gctacagctc tattcatctg aacccactga gccttatttg tcttctcaga   5340
actatggtga gctcttctcc aaccagatta tctggtttgt ggatgacacc aacgtctaca   5400
gagtgactat tcacaagacc tttgaaggga acttgacaac caagcccatc aacggagcca   5460
tcttcatctt caacccacgc acagggcagc tgttcctcaa gataatccac acgtccgtgt   5520
gggcgggaca gaagcgtttg gggcagttgg ctaagtggaa gacagctgag gaggtggccg   5580
ccctgatccg atctctgcct gtggaggagc agcccaagca gatcattgtc accaggaagg   5640
acatgctgga cccactggag gtgcacttac tggacttccc caatattgtc atcaaaggat   5700
cggagctcca actccctttc caggcgtgtc tcaaggtgga aaaattcggg gatctcatcc   5760
ttaaagccac tgagccccag atggttctct tcaacctcta tgacgactgg ctcaagacta   5820
tttcatctta cacggccttc tcccgtctca tcctgattct gcgtgcccta catgtgaaca   5880
acgatcgggc aaaagtgatc ctgaagccag acaagactac tattacagaa ccacaccaca   5940
tctggcccac tctgactgac gaagaatgga tcaaggtcga ggtgcagctc aaggatctga   6000
tcttggctga ctacggcaag aaaaacaatg tgaacgtggc atcactgaca caatcagaaa   6060
ttcgagacat catcctgggt atggagatct cggcaccgtc acagcagcgg cagcagatcg   6120
ctgagatcga gaagcagacc aaggaacaat cgcagctgac ggcaacacag actcgcactg   6180
tcaacaagca tggcgatgag atcatcacct ccaccaccag caactatgag acccagactt   6240
tctcatccaa gactgagtgg agggtcaggg ccatctctgc tgccaacctg cacctaagga   6300
ccaatcacat ctatgtttca tctgacgaca tcaaggagac tggctacacc tacatccttc   6360
ccaagaatgt gcttaagaag ttcatctgca tatctgacct tcgggcccaa attgcaggat   6420
acctatatgg ggtgagccca ccagataacc cccaggtgaa ggagatccgc tgcattgtga   6480
tggtgccgca gtggggcact caccagaccg tgcacctgcc tggccagctg ccccagcatg   6540
agtacctcaa ggagatggaa cccttaggtt ggatccacac tcagcccaat gagtccccgc   6600
agttatcacc ccaggatgtc accacccatg ccaagatcat ggctgacaac ccatcttggg   6660
atggcgagaa gaccattatc atcacatgca gcttcacgcc aggctcctgt acactgacgg   6720
cctacaagct gacccctagt ggctacgaat ggggccgcca gaacacagac aagggcaaca   6780
accccaaggg ctacctgcct tcacactatg agagggtgca gatgctgctg tcggaccgtt   6840
tccttggctt cttcatggtc cctgcccagt cctcgtggaa ctacaacttc atgggtgttc   6900
```

-continued ggcatgaccc caacatgaaa tatgagctac agctggcgaa ccccaaagag ttctaccacg 6960
aggtgcacag gccctctcac ttcctcaact ttgctctcct gcaggagggg gaggtttact 7020
ctgcggatcg ggaggacctg tatgcctgac cgtttccctg cctcctgctt cagcctcccg 7080
aggccgaagc ctcagcccct ccagacaggc cgctgacatt cagcagtttg gcctctttcc 7140
ctctgtctgt gcttgtgttg ttgacctcct gatggcttgt catcctgaat aaaatataat 7200
aataaatttt gtataaatag g 7221

<210> SEQ ID NO 39
<211> LENGTH: 2335
<212> TYPE: PRT
<213> ORGANISM: Homo sapiens

<400> SEQUENCE: 39

Met Ala Gly Val Phe Pro Tyr Arg Gly Pro Gly Asn Pro Val Pro Gly
1 5 10 15

Pro Leu Ala Pro Leu Pro Asp Tyr Met Ser Glu Glu Lys Leu Gln Glu
20 25 30

Lys Ala Arg Lys Trp Gln Gln Leu Gln Ala Lys Arg Tyr Ala Glu Lys
35 40 45

Arg Lys Phe Gly Phe Val Asp Ala Gln Lys Glu Asp Met Pro Pro Glu
50 55 60

His Val Arg Glu Ile Ile Arg Asp His Gly Asp Met Thr Asn Arg Lys
65 70 75 80

Phe Arg His Asp Lys Arg Val Tyr Leu Gly Ala Leu Lys Tyr Met Pro
85 90 95

His Ala Val Leu Lys Leu Leu Glu Asn Met Pro Met Pro Trp Glu Gln
100 105 110

Ile Arg Asp Val Pro Val Leu Tyr His Ile Thr Gly Ala Ile Ser Phe
115 120 125

Val Asn Glu Ile Pro Trp Val Ile Glu Pro Val Tyr Ile Ser Gln Trp
130 135 140

Gly Ser Met Trp Ile Met Met Arg Arg Glu Lys Arg Asp Arg Arg His
145 150 155 160

Phe Lys Arg Met Arg Phe Pro Pro Phe Asp Asp Glu Glu Pro Pro Leu
165 170 175

Asp Tyr Ala Asp Asn Ile Leu Asn Val Glu Pro Leu Glu Ala Ile Gln
180 185 190

Leu Glu Leu Asp Pro Glu Glu Asp Ala Pro Val Leu Asp Trp Phe Tyr
195 200 205

Asp His Gln Pro Leu Arg Asp Ser Arg Lys Tyr Val Asn Gly Ser Thr
210 215 220

Tyr Gln Arg Trp Gln Phe Thr Leu Pro Met Met Ser Thr Leu Tyr Arg
225 230 235 240

Leu Ala Asn Gln Leu Leu Thr Asp Leu Val Asp Asp Asn Tyr Phe Tyr
245 250 255

Leu Phe Asp Leu Lys Ala Phe Phe Thr Ser Lys Ala Leu Asn Met Ala
260 265 270

Ile Pro Gly Gly Pro Lys Phe Glu Pro Leu Val Arg Asp Ile Asn Leu
275 280 285

Gln Asp Glu Asp Trp Asn Glu Phe Asn Asp Ile Asn Lys Ile Ile Ile
290 295 300

Arg Gln Pro Ile Arg Thr Glu Tyr Lys Ile Ala Phe Pro Tyr Leu Tyr
305 310 315 320

-continued

```
Asn Asn Leu Pro His His Val His Leu Thr Trp Tyr His Thr Pro Asn
                325                 330                 335

Val Val Phe Ile Lys Thr Glu Asp Pro Asp Leu Pro Ala Phe Tyr Phe
            340                 345                 350

Asp Pro Leu Ile Asn Pro Ile Ser His Arg His Ser Val Lys Ser Gln
        355                 360                 365

Glu Pro Leu Pro Asp Asp Asp Glu Glu Phe Glu Leu Pro Glu Phe Val
    370                 375                 380

Glu Pro Phe Leu Lys Asp Thr Pro Leu Tyr Thr Asp Asn Thr Ala Asn
385                 390                 395                 400

Gly Ile Ala Leu Leu Trp Ala Pro Arg Pro Phe Asn Leu Arg Ser Gly
                405                 410                 415

Arg Thr Arg Arg Ala Leu Asp Ile Pro Leu Val Lys Asn Trp Tyr Arg
            420                 425                 430

Glu His Cys Pro Ala Gly Gln Pro Val Lys Val Arg Val Ser Tyr Gln
        435                 440                 445

Lys Leu Leu Lys Tyr Tyr Val Leu Asn Ala Leu Lys His Arg Pro Pro
    450                 455                 460

Lys Ala Gln Lys Lys Arg Tyr Leu Phe Arg Ser Phe Lys Ala Thr Lys
465                 470                 475                 480

Phe Phe Gln Ser Thr Lys Leu Asp Trp Val Glu Gly Trp Leu Gln Val
                485                 490                 495

Cys Arg Gln Gly Tyr Asn Met Leu Asn Leu Leu Ile His Arg Lys Asn
            500                 505                 510

Leu Asn Tyr Leu His Leu Asp Tyr Asn Phe Asn Leu Lys Pro Val Lys
        515                 520                 525

Thr Leu Thr Thr Lys Glu Arg Lys Lys Ser Arg Phe Gly Asn Ala Phe
    530                 535                 540

His Leu Cys Arg Glu Val Leu Arg Leu Thr Lys Leu Val Val Asp Ser
545                 550                 555                 560

His Val Gln Tyr Arg Leu Gly Asn Val Asp Ala Phe Gln Leu Ala Asp
                565                 570                 575

Gly Leu Gln Tyr Ile Phe Ala His Val Gly Gln Leu Thr Gly Met Tyr
            580                 585                 590

Arg Tyr Lys Tyr Lys Leu Met Arg Gln Ile Arg Val Cys Lys Asp Leu
        595                 600                 605

Lys His Leu Ile Tyr Tyr Arg Phe Asn Thr Gly Pro Val Gly Lys Gly
    610                 615                 620

Pro Gly Cys Gly Phe Trp Ala Ala Gly Trp Arg Val Trp Leu Phe Phe
625                 630                 635                 640

Met Arg Gly Ile Thr Pro Leu Leu Glu Arg Trp Leu Gly Asn Leu Leu
                645                 650                 655

Ala Arg Gln Phe Glu Gly Arg His Ser Lys Gly Val Ala Lys Thr Val
            660                 665                 670

Thr Lys Gln Arg Val Glu Ser His Phe Asp Leu Glu Leu Arg Ala Ala
        675                 680                 685

Val Met His Asp Ile Leu Asp Met Met Pro Glu Gly Ile Lys Gln Asn
    690                 695                 700

Lys Ala Arg Thr Ile Leu Gln His Leu Ser Glu Ala Trp Arg Cys Trp
705                 710                 715                 720

Lys Ala Asn Ile Pro Trp Lys Val Pro Gly Leu Pro Thr Pro Ile Glu
                725                 730                 735
```

```
Asn Met Ile Leu Arg Tyr Val Lys Ala Lys Ala Asp Trp Trp Thr Asn
            740                 745                 750

Thr Ala His Tyr Asn Arg Glu Arg Ile Arg Arg Gly Ala Thr Val Asp
        755                 760                 765

Lys Thr Val Cys Lys Lys Asn Leu Gly Arg Leu Thr Arg Leu Tyr Leu
    770                 775                 780

Lys Ala Glu Gln Glu Arg Gln His Asn Tyr Leu Lys Asp Gly Pro Tyr
785                 790                 795                 800

Ile Thr Ala Glu Glu Thr Val Ala Val Tyr Thr Thr Thr Val His Trp
                805                 810                 815

Leu Glu Ser Arg Arg Phe Ser Pro Ile Pro Phe Pro Pro Leu Ser Tyr
            820                 825                 830

Lys His Asp Thr Lys Leu Leu Ile Leu Ala Leu Glu Arg Leu Lys Glu
        835                 840                 845

Ala Tyr Ser Val Lys Ser Arg Leu Asn Gln Ser Gln Arg Glu Glu Leu
    850                 855                 860

Gly Leu Ile Glu Gln Ala Tyr Asp Asn Leu His Glu Ala Leu Ser Arg
865                 870                 875                 880

Ile Lys Arg His Leu Leu Thr Gln Arg Ala Phe Lys Glu Val Gly Ile
                885                 890                 895

Glu Phe Met Asp Leu Tyr Ser His Leu Val Pro Val Tyr Asp Val Glu
            900                 905                 910

Pro Leu Glu Lys Ile Thr Asp Ala Tyr Leu Asp Gln Tyr Leu Trp Tyr
        915                 920                 925

Glu Ala Asp Lys Arg Arg Leu Phe Pro Pro Trp Ile Lys Pro Ala Asp
    930                 935                 940

Thr Glu Pro Pro Pro Leu Leu Val Tyr Lys Trp Cys Gln Gly Ile Asn
945                 950                 955                 960

Asn Leu Gln Asp Val Trp Glu Thr Ser Glu Gly Glu Cys Asn Val Met
                965                 970                 975

Leu Glu Ser Arg Phe Glu Lys Met Tyr Glu Lys Ile Asp Leu Thr Leu
            980                 985                 990

Leu Asn Arg Leu Val Arg Leu Ile  Val Asp His Asn Ile  Ala Asp Tyr
        995                 1000                1005

Met Thr  Ala Lys Asn Asn Val  Val Ile Asn Tyr Lys  Asp Met Asn
    1010                1015                1020

His Thr  Asn Ser Tyr Gly Ile  Ile Arg Gly Leu Gln  Phe Ala Ser
    1025                1030                1035

Phe Ile  Val Gln Tyr Tyr Gly  Leu Val Met Asp Leu  Leu Val Leu
    1040                1045                1050

Gly Leu  His Arg Ala Ser Glu  Met Ala Gly Pro Pro  Gln Met Pro
    1055                1060                1065

Asn Asp  Phe Leu Ser Phe Gln  Asp Ile Ala Thr Glu  Ala Ala His
    1070                1075                1080

Pro Ile  Arg Leu Phe Cys Arg  Tyr Ile Asp Arg Ile  His Ile Phe
    1085                1090                1095

Phe Arg  Phe Thr Ala Asp Glu  Ala Arg Asp Leu Ile  Gln Arg Tyr
    1100                1105                1110

Leu Thr  Glu His Pro Asp Pro  Asn Asn Glu Asn Ile  Val Gly Tyr
    1115                1120                1125

Asn Asn  Lys Lys Cys Trp Pro  Arg Asp Ala Arg Met  Arg Leu Met
    1130                1135                1140

Lys His  Asp Val Asn Leu Gly  Arg Ala Val Phe Trp  Asp Ile Lys
```

```
    1145                1150                1155

Asn Arg  Leu Pro Arg Ser Val  Thr Thr Val Gln Trp  Glu Asn Ser
    1160                1165                1170

Phe Val  Ser Val Tyr Ser Lys  Asp Asn Pro Asn Leu  Leu Phe Asn
    1175                1180                1185

Met Cys  Gly Phe Glu Cys Arg  Ile Leu Pro Lys Cys  Arg Thr Ser
    1190                1195                1200

Tyr Glu  Glu Phe Thr His Lys  Asp Gly Val Trp Asn  Leu Gln Asn
    1205                1210                1215

Glu Val  Thr Lys Glu Arg Thr  Ala Gln Cys Phe Leu  Arg Val Asp
    1220                1225                1230

Asp Glu  Ser Met Gln Arg Phe  His Asn Arg Val Arg  Gln Ile Leu
    1235                1240                1245

Met Ala  Ser Gly Ser Thr Thr  Phe Thr Lys Ile Val  Asn Lys Trp
    1250                1255                1260

Asn Thr  Ala Leu Ile Gly Leu  Met Thr Tyr Phe Arg  Glu Ala Val
    1265                1270                1275

Val Asn  Thr Gln Glu Leu Leu  Asp Leu Leu Val Lys  Cys Glu His
    1280                1285                1290

Lys Ile  Gln Thr Arg Ile Lys  Ile Gly Leu Asn Ser  Lys Met Pro
    1295                1300                1305

Ser Arg  Phe Pro Pro Val Val  Phe Tyr Thr Pro Lys  Glu Leu Gly
    1310                1315                1320

Gly Leu  Gly Met Leu Ser Met  Gly His Val Leu Ile  Pro Gln Ser
    1325                1330                1335

Asp Leu  Arg Trp Ser Lys Gln  Thr Asp Val Gly Ile  Thr His Phe
    1340                1345                1350

Arg Ser  Gly Met Ser His Glu  Glu Asp Gln Leu Ile  Pro Asn Leu
    1355                1360                1365

Tyr Arg  Tyr Ile Gln Pro Trp  Glu Ser Glu Phe Ile  Asp Ser Gln
    1370                1375                1380

Arg Val  Trp Ala Glu Tyr Ser  Leu Lys Arg Gln Glu  Ala Ile Ala
    1385                1390                1395

Gln Asn  Arg Arg Leu Thr Leu  Glu Asp Leu Glu Asp  Ser Trp Asp
    1400                1405                1410

Arg Gly  Ile Pro Arg Ile Asn  Thr Leu Phe Gln Lys  Asp Arg His
    1415                1420                1425

Thr Leu  Ala Tyr Asp Lys Gly  Trp Arg Val Arg Thr  Asp Phe Lys
    1430                1435                1440

Gln Tyr  Gln Val Leu Lys Gln  Asn Pro Phe Trp Trp  Thr His Gln
    1445                1450                1455

Arg His  Asp Gly Lys Leu Trp  Asn Leu Asn Asn Tyr  Arg Thr Asp
    1460                1465                1470

Met Ile  Gln Ala Leu Gly Gly  Val Glu Gly Ile Leu  Glu His Thr
    1475                1480                1485

Leu Phe  Lys Gly Thr Tyr Phe  Pro Thr Trp Glu Gly  Leu Phe Trp
    1490                1495                1500

Glu Lys  Ala Ser Gly Phe Glu  Glu Ser Met Lys Trp  Lys Lys Leu
    1505                1510                1515

Thr Asn  Ala Gln Arg Ser Gly  Leu Asn Gln Ile Pro  Asn Arg Arg
    1520                1525                1530

Phe Thr  Leu Trp Trp Ser Pro  Thr Ile Asn Arg Ala  Asn Val Tyr
    1535                1540                1545
```

-continued

```
Val Gly  Phe Gln Val Gln Leu  Asp Leu Thr Gly Ile  Phe Met His
    1550                 1555                 1560

Gly Lys  Ile Pro Thr Leu Lys  Ile Ser Leu Ile Gln  Ile Phe Arg
    1565                 1570                 1575

Ala His  Leu Trp Gln Lys Ile  His Glu Ser Ile Val  Met Asp Leu
    1580                 1585                 1590

Cys Gln  Val Phe Asp Gln Glu  Leu Asp Ala Leu Glu  Ile Glu Thr
    1595                 1600                 1605

Val Gln  Lys Glu Thr Ile His  Pro Arg Lys Ser Tyr  Lys Met Asn
    1610                 1615                 1620

Ser Ser  Cys Ala Asp Ile Leu  Leu Phe Ala Ser Tyr  Lys Trp Asn
    1625                 1630                 1635

Val Ser  Arg Pro Ser Leu Leu  Ala Asp Ser Lys Asp  Val Met Asp
    1640                 1645                 1650

Ser Thr  Thr Thr Gln Lys Tyr  Trp Ile Asp Ile Gln  Leu Arg Trp
    1655                 1660                 1665

Gly Asp  Tyr Asp Ser His Asp  Ile Glu Arg Tyr Ala  Arg Ala Lys
    1670                 1675                 1680

Phe Leu  Asp Tyr Thr Thr Asp  Asn Met Ser Ile Tyr  Pro Ser Pro
    1685                 1690                 1695

Thr Gly  Val Leu Ile Ala Ile  Asp Leu Ala Tyr Asn  Leu His Ser
    1700                 1705                 1710

Ala Tyr  Gly Asn Trp Phe Pro  Gly Ser Lys Pro Leu  Ile Gln Gln
    1715                 1720                 1725

Ala Met  Ala Lys Ile Met Lys  Ala Asn Pro Ala Leu  Tyr Val Leu
    1730                 1735                 1740

Arg Glu  Arg Ile Arg Lys Gly  Leu Gln Leu Tyr Ser  Ser Glu Pro
    1745                 1750                 1755

Thr Glu  Pro Tyr Leu Ser Ser  Gln Asn Tyr Gly Glu  Leu Phe Ser
    1760                 1765                 1770

Asn Gln  Ile Ile Trp Phe Val  Asp Asp Thr Asn Val  Tyr Arg Val
    1775                 1780                 1785

Thr Ile  His Lys Thr Phe Glu  Gly Asn Leu Thr Thr  Lys Pro Ile
    1790                 1795                 1800

Asn Gly  Ala Ile Phe Ile Phe  Asn Pro Arg Thr Gly  Gln Leu Phe
    1805                 1810                 1815

Leu Lys  Ile Ile His Thr Ser  Val Trp Ala Gly Gln  Lys Arg Leu
    1820                 1825                 1830

Gly Gln  Leu Ala Lys Trp Lys  Thr Ala Glu Glu Val  Ala Ala Leu
    1835                 1840                 1845

Ile Arg  Ser Leu Pro Val Glu  Glu Gln Pro Lys Gln  Ile Ile Val
    1850                 1855                 1860

Thr Arg  Lys Asp Met Leu Asp  Pro Leu Glu Val His  Leu Leu Asp
    1865                 1870                 1875

Phe Pro  Asn Ile Val Ile Lys  Gly Ser Glu Leu Gln  Leu Pro Phe
    1880                 1885                 1890

Gln Ala  Cys Leu Lys Val Glu  Lys Phe Gly Asp Leu  Ile Leu Lys
    1895                 1900                 1905

Ala Thr  Glu Pro Gln Met Val  Leu Phe Asn Leu Tyr  Asp Asp Trp
    1910                 1915                 1920

Leu Lys  Thr Ile Ser Ser Tyr  Thr Ala Phe Ser Arg  Leu Ile Leu
    1925                 1930                 1935
```

-continued

```
Ile Leu Arg Ala Leu His Val Asn Asn Asp Arg Ala Lys Val Ile
    1940                1945                1950

Leu Lys Pro Asp Lys Thr Thr Ile Thr Glu Pro His His Ile Trp
    1955                1960                1965

Pro Thr Leu Thr Asp Glu Glu Trp Ile Lys Val Glu Val Gln Leu
    1970                1975                1980

Lys Asp Leu Ile Leu Ala Asp Tyr Gly Lys Lys Asn Asn Val Asn
    1985                1990                1995

Val Ala Ser Leu Thr Gln Ser Glu Ile Arg Asp Ile Ile Leu Gly
    2000                2005                2010

Met Glu Ile Ser Ala Pro Ser Gln Gln Arg Gln Gln Ile Ala Glu
    2015                2020                2025

Ile Glu Lys Gln Thr Lys Glu Gln Ser Gln Leu Thr Ala Thr Gln
    2030                2035                2040

Thr Arg Thr Val Asn Lys His Gly Asp Glu Ile Ile Thr Ser Thr
    2045                2050                2055

Thr Ser Asn Tyr Glu Thr Gln Thr Phe Ser Ser Lys Thr Glu Trp
    2060                2065                2070

Arg Val Arg Ala Ile Ser Ala Ala Asn Leu His Leu Arg Thr Asn
    2075                2080                2085

His Ile Tyr Val Ser Ser Asp Asp Ile Lys Glu Thr Gly Tyr Thr
    2090                2095                2100

Tyr Ile Leu Pro Lys Asn Val Leu Lys Lys Phe Ile Cys Ile Ser
    2105                2110                2115

Asp Leu Arg Ala Gln Ile Ala Gly Tyr Leu Tyr Gly Val Ser Pro
    2120                2125                2130

Pro Asp Asn Pro Gln Val Lys Glu Ile Arg Cys Ile Val Met Val
    2135                2140                2145

Pro Gln Trp Gly Thr His Gln Thr Val His Leu Pro Gly Gln Leu
    2150                2155                2160

Pro Gln His Glu Tyr Leu Lys Glu Met Glu Pro Leu Gly Trp Ile
    2165                2170                2175

His Thr Gln Pro Asn Glu Ser Pro Gln Leu Ser Pro Gln Asp Val
    2180                2185                2190

Thr Thr His Ala Lys Ile Met Ala Asp Asn Pro Ser Trp Asp Gly
    2195                2200                2205

Glu Lys Thr Ile Ile Ile Thr Cys Ser Phe Thr Pro Gly Ser Cys
    2210                2215                2220

Thr Leu Thr Ala Tyr Lys Leu Thr Pro Ser Gly Tyr Glu Trp Gly
    2225                2230                2235

Arg Gln Asn Thr Asp Lys Gly Asn Asn Pro Lys Gly Tyr Leu Pro
    2240                2245                2250

Ser His Tyr Glu Arg Val Gln Met Leu Leu Ser Asp Arg Phe Leu
    2255                2260                2265

Gly Phe Phe Met Val Pro Ala Gln Ser Ser Trp Asn Tyr Asn Phe
    2270                2275                2280

Met Gly Val Arg His Asp Pro Asn Met Lys Tyr Glu Leu Gln Leu
    2285                2290                2295

Ala Asn Pro Lys Glu Phe Tyr His Glu Val His Arg Pro Ser His
    2300                2305                2310

Phe Leu Asn Phe Ala Leu Leu Gln Glu Gly Glu Val Tyr Ser Ala
    2315                2320                2325

Asp Arg Glu Asp Leu Tyr Ala
```

2330 2335

<210> SEQ ID NO 40
<211> LENGTH: 7972
<212> TYPE: DNA
<213> ORGANISM: Homo sapiens

<400> SEQUENCE: 40
atttgaagtc ctcgttccac gccttctcat catcctgaac accgagctct gggactccgg 60
cggagaatct aaacgtaaag catcacccac ggtcgtgaac tgtaggctct cctggcatcc 120
gggatcttat tctggccttg gcggagttgg ggatggtgtc gcctagcagc cgctgccgct 180
ttggcttgct cgggaccatt tggctggacc cagagtccgc gtggaaccgc gatagggatc 240
tgtcagggcc cgcggccggg tccagcttgg tggttgcggt agtgagaggc ctccgctggt 300
tgccaggctt ggtctagagg tggagcacag tgaaagaatt caagatgcca cctaatataa 360
actggaaaga aataatgaaa gttgacccag atgacctgcc ccgtcaagaa gaactggcag 420
ataatttatt gatttcctta tccaaggtgg aagtaaatga gctaaaaagt gaaaagcaag 480
aaaatgtgat acaccttttc agaattactc agtcactaat gaagatgaaa gctcaagaag 540
tggagctggc tttggaagaa gtagaaaaag ctggagaaga acaagcaaaa tttgaaaatc 600
aattaaaaac taaagtaatg aaactggaaa atgaactgga gatggctcag cagtctgcag 660
gtggacgaga tactcggttt ttacgtaatg aaatttgcca acttgaaaaa caattagaac 720
aaaaagatag agaattggag gacatggaaa aggagttgga gaaagagaag aaagttaatg 780
agcaattggc tcttcgaaat gaggaggcag aaaatgaaaa cagcaaatta agaagagaga 840
acaaacgtct aaagaaaaag aatgaacaac tttgtcagga tattattgac taccagaaac 900
aaatagattc acagaaagaa acacttttat caagaagagg ggaagacagt gactaccgat 960
cacagttgtc taaaaaaaac tatgagctta tccaatatct tgatgaaatt cagactttaa 1020
cagaagctaa tgagaaaatt gaagttcaga atcaagaaat gagaaaaaat ttagaagagt 1080
ctgtacagga aatggagaag atgactgatg aatataatag aatgaaagct attgtgcatc 1140
agacagataa tgtaatagat cagttaaaaa aagaaaacga tcattatcaa cttcaagtgc 1200
aggagcttac agatcttctg aaatcaaaaa atgaagaaga tgatccaatt atggtagctg 1260
tcaatgcaaa agtagaagaa tggaagctaa ttttgtcttc taaagatgat gaaattattg 1320
agtatcagca aatgttacat aacctaaggg agaaacttaa gaatgctcag cttgatgctg 1380
ataaaagtaa tgttatggct ctacagcagg gtatacagga acgagacagt caaattaaga 1440
tgctcaccga acaagtagaa caatatacaa aagaaatgga aaagaatact tgtattattg 1500
aagatttgaa aaatgagctc caaagaaaca aaggtgcttc aaccctttct caacagactc 1560
atatgaaaat tcagtcaacg ttagacattt taaaagagaa aactaaagag gctgagagaa 1620
cagctgaact ggctgaggct gatgctaggg aaaaggataa agaattagtt gaggctctga 1680
agaggttaaa agattatgaa tcgggagtat atggtttaga agatgctgtc gttgaaataa 1740
agaattgtaa aaaccaaatt aaaataagag atcgagagat tgaaatatta acaaaggaaa 1800
tcaataaact tgaattgaag atcagtgatt tccttgatga aaatgaggca cttagagagc 1860
gtgtgggcct tgaaccaaag acaatgattg atttaactga atttagaaat agcaaacact 1920
taaaacagca gcagtacaga gctgaaaacc agattctttt gaaagagatt gaaagtctag 1980
aggaagaacg acttgatctg aaaaaaaaaa ttcgtcaaat ggctcaagaa agaggaaaaa 2040
gaagtgcaac ttcaggatta accactgagg acctgaacct aactgaaaac atttctcaag 2100

-continued

```
gagatagaat aagtgaaaga aaattggatt tattgagcct caaaaatatg agtgaagcac   2160
aatcaaagaa tgaatttctt tcaagagaac taattgaaaa agaaagagat ttagaaagga   2220
gtaggacagt gatagccaaa tttcagaata aattaaaaga attagttgaa gaaaataagc   2280
aacttgaaga aggtatgaaa gaaatattgc aagcaattaa ggaaatgcag aaagatcctg   2340
atgttaaagg aggagaaaca tctctaatta tccctagcct tgaaagacta gttaatgcta   2400
tagaatcaaa gaatgcagaa ggaatctttg atgcgagtct gcatttgaaa gcccaagttg   2460
atcagcttac cggaagaaat gaagaattaa gacaggagct cagggaatct cggaaagagg   2520
ctataaatta ttcacagcag ttggcaaaag ctaatttaaa gatagaccat cttgaaaaag   2580
aaactagtct tttacgacaa tcagaaggat cgaatgttgt ttttaaagga attgacttac   2640
ctgatgggat agcaccatct agtgccagta tcattaattc tcagaatgaa tatttaatac   2700
atttgttaca ggaactagaa aataaagaaa aaaagttaaa gaatttagaa gattctcttg   2760
aagattacaa cagaaaattt gctgtaattc gtcatcaaca aagtttgttg tataaagaat   2820
acctaagtga aaaggagacc tggaaaacag aatctaaaac aataaaagag gaaaagagaa   2880
aacttgagga tcaagtccaa caagatgcta taaaagtaaa agaatataat aatttgctca   2940
atgctcttca gatggattcg gatgaaatga aaaaaatact tgcagaaaat agtaggaaaa   3000
ttactgtttt gcaagtgaat gaaaaatcac ttataaggca atatacaacc ttagtagaat   3060
tggagcgaca acttagaaaa gaaaatgaga agcaaaagaa tgaattgttg tcaatggagg   3120
ctgaagtttg tgaaaaaatt gggtgtttgc aaagatttaa ggaaatggcc attttcaaga   3180
ttgcagctct ccaaaaagtt gtagataata gtgtttcttt gtctgaacta gaactggcta   3240
ataaacagta caatgaactg actgctaagt acagggacat cttgcaaaaa gataatatgc   3300
ttgttcaaag aacaagtaac ttggaacacc tggagtgtga aaacatctcc ttaaaagaac   3360
aagtggagtc tataaataaa gaactggaga ttaccaagga aaaacttcac actattgaac   3420
aagcctggga acaggaaact aaattaggta atgaatctag catggataag gcaaagaaat   3480
caataaccaa cagtgacatt gtttccattt caaaaaaaat aactatgctg gaaatgaagg   3540
aattaaatga aaggcagcgg gctgaacatt gtcaaaaaat gtatgaacac ttacggactt   3600
cgttaaagca aatggaggaa cgtaattttg aattggaaac caaatttgct gagcttacca   3660
aaatcaattt ggatgcacag aaggtggaac agatgttaag agatgaatta gctgatagtg   3720
tgagcaaggc agtaagtgat gctgataggc aacggattct agaattagag aagaatgaaa   3780
tggaactaaa agttgaagtg tcaaaactga gagagatttc tgatattgcc agaagacaag   3840
ttgaaatttt gaatgcacaa caacaatcta gggacaagga agtagagtcc ctcagaatgc   3900
aactgctaga ctatcaggca cagtctgatg aaaagtcgct cattgccaag ttgcaccaac   3960
ataatgtctc tcttcaactg agtgaggcta ctgctcttgg taagttggag tcaattacat   4020
ctaaactgca gaagatggag gcctacaact tgcgcttaga gcagaaactt gatgaaaaag   4080
aacaggctct ctattatgct cgtttggagg gaagaaacag agcaaaacat ctgcgccaaa   4140
caattcagtc tctacgacga cagtttagtg gagctttacc cttggcacaa caggaaaagt   4200
tctccaaaac aatgattcaa ctacaaaatg acaaacttaa gataatgcaa gaaatgaaaa   4260
attctcaaca agaacataga aatatggaga acaaaacatt ggagatggaa ttaaaattaa   4320
agggcctgga agagttaata agcactttaa aggataccaa aggagcccaa aaggtaatca   4380
actggcatat gaaaatagaa gaacttcgtc ttcaagaact taaactaaat cgggaattag   4440
```

```
tcaaggataa agaagaaata aaatatttga ataacataat ttctgaatat gaacgtacaa   4500
tcagcagtct tgaagaagaa attgtgcaac agaacaagtt tcatgaagaa agacaaatgg   4560
cctgggatca aagagaagtt gacctggaac gccaactaga catttttgac cgtcagcaaa   4620
atgaaatact aaatgcggca caaaagtttg aagaagctac aggatcaatc cctgacccta   4680
gtttgcccct tccaaatcaa cttgagatcg ctctaaggaa aattaaggag aacattcgaa   4740
taattctaga aacacgggca acttgcaaat cactagaaga gaaactaaaa gagaaagaat   4800
ctgctttaag gttagcagaa caaaatatac tgtcaagaga caaagtaatc aatgaactga   4860
ggcttcgatt gcctgccact gcagaaagag aaaagctcat agctgagcta ggcagaaaag   4920
agatggaacc aaaatctcac cacacattga aaattgctca tcaaaccatt gcaaacatgc   4980
aagcaaggtt aaatcaaaaa gaagaagtat taaagaagta tcaacgtctt ctagaaaaag   5040
ccagagagga gcaaagagaa attgtgaaga aacatgagga agaccttcat attcttcatc   5100
acagattaga actacaggct gatagttcac taaataaatt caaacaaacg gcttgggatt   5160
taatgaaaca gtctcccact ccagttccta ccaacaagca ttttattcgt ctggctgaga   5220
tggaacagac agtagcagaa caagatgact ctctttcctc actcttggtc aaactaaaga   5280
aagtatcaca agatttggag agacaaagag aaatcactga attaaaagta aaagaatttg   5340
aaaatatcaa attacagctt caagaaaacc atgaagatga agtgaaaaaa gtaaaagcgg   5400
aagtagagga tttaaagtat cttctggacc agtcacaaaa ggagtcacag tgtttaaaat   5460
ctgaacttca ggctcaaaaa gaagcaaatt caagagctcc aacaactaca atgagaaatc   5520
tagtagaacg gctaaagagc caattagcct tgaaggagaa acaacagaaa gcacttagtc   5580
gggcactttt agaactccgg gcagaaatga cagcagctgc tgaagaacgt attatttctg   5640
caacttctca aaaagaggcc catctcaatg ttcaacaaat cgttgatcga catactagag   5700
agctaaagac acaagttgaa gatttaaatg aaaatctttt aaaattgaaa gaagcactta   5760
aaacaagtaa aaacagagaa aactcactaa ctgataattt gaatgactta aataatgaac   5820
tgcaaaagaa acaaaaagcc tataataaaa tacttagaga gaaagaggaa attgatcaag   5880
agaatgatga actgaaaagg caaattaaaa gactaaccag tggattacag ggcaaacccc   5940
tgacagataa taaacaaagt ctaattgaag aactccaaag gaaagttaaa aaactagaga   6000
accaattaga gggaaaggtg gaggaagtag acctaaaacc tatgaaagaa aagaatgcta   6060
aagaagaatt aattaggtgg gaagaaggta aaaagtggca agccaaaata gaaggaattc   6120
gaaacaagtt aaaagagaaa gagggggaag tctttacttt aacaaagcag ttgaatactt   6180
tgaaggatct tttgccaaa gccgataaag agaaacttac tttgcagagg aaactaaaaa   6240
caactggcat gactgttgat caggttttgg gaatacgagc tttggagtca gaaaaagaat   6300
tggaagaatt aaaaaagaga aatcttgact tagaaaatga tatattgtat atgagggccc   6360
accaagctct tcctcgagat tctgttgtag aagatttaca tttacaaaat agatacctcc   6420
aagaaaaact tcatgcttta gaaaaacagt tttcaaagga tacatattct aagccttcaa   6480
tttcaggaat agagtcagat gatcattgtc agagagaaca ggagcttcag aaggaaaact   6540
tgaagttgtc atctgaaaat attgaactga aatttcagct tgaacaagca aataaagatt   6600
tgccaagatt aaagaatcaa gtcagagatt tgaaggaaat gtgtgaattt cttaagaaag   6660
aaaaagcaga agttcagcgg aaacttggcc atgttagagg gtctggtaga agtggaaaga   6720
caatcccaga actggaaaaa accattggtt taatgaaaaa agtagttgaa aaagtccaga   6780
gagaaaatga acagttgaaa aaagcatcag gaatattgac tagtgaaaaa atggctaata   6840
```

```
ttgagcagga aaatgaaaaa ttgaaggctg aattagaaaa acttaaagct catcttgggc   6900

atcagttgag catgcactat gaatccaaga ccaaaggcac agaaaaaatt attgctgaaa   6960

atgaaaggct tcgtaaagaa cttaaaaaag aaactgatgc tgcagagaaa ttacggatag   7020

caaagaataa tttagagata ttaaatgaga agatgacagt tcaactagaa gagactggta   7080

agagattgca gtttgcagaa agcagaggtc cacagcttga aggtgctgac agtaagagct   7140

ggaaatccat tgtggttaca agaatgtatg aaaccaagtt aaaagaattg gaaactgata   7200

ttgccaaaaa aaatcaaagc attactgacc ttaaacagct tgtaaaagaa gcaacagaga   7260

gagaacaaaa agttaacaaa tacaatgaag accttgaaca acagattaag attcttaaac   7320

atgttcctga aggtgctgag acagagcaag gccttaaacg ggagcttcaa gttcttagat   7380

tagctaatca tcagctggat aaagagaaag cagaattaat ccatcagata gaagctaaca   7440

aggaccaaag tggagctgaa agcaccatac ctgatgctga tcaactaaag gaaaaaataa   7500

aagatctaga gacacagctc aaaatgtcag atctagaaaa gcagcatttg aaggaggaaa   7560

taaagaagct gaaaaaagaa ctggaaaatt ttgatccttc atttttgaa gaaattgaag    7620

atcttaagta taattacaag gaagaagtga agaagaatat tctcttagaa gagaaggtaa   7680

aaaaactttc agaacaattg ggagttgaat taactagccc tgttgctgct tctgaagagt   7740

ttgaagatga agaagaaagt cctgttaatt tccccattta ctaaaggtca cctataaact   7800

ttgtttcatt taactattta ttaactttat aagttaaata tacttggaaa taagcagttc   7860

tccgaactgt agtatttcct tctcactacc ttgtaccttt atacttagat tggaattctt   7920

aataaataaa attatatgaa attttcaact tattaaaaaa aaaaaaaaaa aa           7972
```

<210> SEQ ID NO 41
<211> LENGTH: 2479
<212> TYPE: PRT
<213> ORGANISM: Homo sapiens

<400> SEQUENCE: 41

```
Met Pro Pro Asn Ile Asn Trp Lys Glu Ile Met Lys Val Asp Pro Asp
1               5                   10                  15

Asp Leu Pro Arg Gln Glu Glu Leu Ala Asp Asn Leu Leu Ile Ser Leu
            20                  25                  30

Ser Lys Val Glu Val Asn Glu Leu Lys Ser Glu Lys Gln Glu Asn Val
        35                  40                  45

Ile His Leu Phe Arg Ile Thr Gln Ser Leu Met Lys Met Lys Ala Gln
    50                  55                  60

Glu Val Glu Leu Ala Leu Glu Glu Val Glu Lys Ala Gly Glu Glu Gln
65                  70                  75                  80

Ala Lys Phe Glu Asn Gln Leu Lys Thr Lys Val Met Lys Leu Glu Asn
                85                  90                  95

Glu Leu Glu Met Ala Gln Gln Ser Ala Gly Gly Arg Asp Thr Arg Phe
            100                 105                 110

Leu Arg Asn Glu Ile Cys Gln Leu Glu Lys Gln Leu Glu Gln Lys Asp
        115                 120                 125

Arg Glu Leu Glu Asp Met Glu Lys Glu Leu Glu Lys Glu Lys Lys Val
    130                 135                 140

Asn Glu Gln Leu Ala Leu Arg Asn Glu Glu Ala Glu Asn Glu Asn Ser
145                 150                 155                 160

Lys Leu Arg Arg Glu Asn Lys Arg Leu Lys Lys Lys Asn Glu Gln Leu
                165                 170                 175
```

-continued

```
Cys Gln Asp Ile Ile Asp Tyr Gln Lys Gln Ile Asp Ser Gln Lys Glu
            180                 185                 190

Thr Leu Leu Ser Arg Arg Gly Glu Asp Ser Asp Tyr Arg Ser Gln Leu
        195                 200                 205

Ser Lys Lys Asn Tyr Glu Leu Ile Gln Tyr Leu Asp Glu Ile Gln Thr
    210                 215                 220

Leu Thr Glu Ala Asn Glu Lys Ile Glu Val Gln Asn Gln Glu Met Arg
225                 230                 235                 240

Lys Asn Leu Glu Glu Ser Val Gln Glu Met Glu Lys Met Thr Asp Glu
                245                 250                 255

Tyr Asn Arg Met Lys Ala Ile Val His Gln Thr Asp Asn Val Ile Asp
            260                 265                 270

Gln Leu Lys Lys Glu Asn Asp His Tyr Gln Leu Gln Val Gln Glu Leu
        275                 280                 285

Thr Asp Leu Leu Lys Ser Lys Asn Glu Glu Asp Asp Pro Ile Met Val
    290                 295                 300

Ala Val Asn Ala Lys Val Glu Glu Trp Lys Leu Ile Leu Ser Ser Lys
305                 310                 315                 320

Asp Asp Glu Ile Ile Glu Tyr Gln Gln Met Leu His Asn Leu Arg Glu
                325                 330                 335

Lys Leu Lys Asn Ala Gln Leu Asp Ala Asp Lys Ser Asn Val Met Ala
            340                 345                 350

Leu Gln Gln Gly Ile Gln Glu Arg Asp Ser Gln Ile Lys Met Leu Thr
        355                 360                 365

Glu Gln Val Glu Gln Tyr Thr Lys Glu Met Glu Lys Asn Thr Cys Ile
    370                 375                 380

Ile Glu Asp Leu Lys Asn Glu Leu Gln Arg Asn Lys Gly Ala Ser Thr
385                 390                 395                 400

Leu Ser Gln Gln Thr His Met Lys Ile Gln Ser Thr Leu Asp Ile Leu
                405                 410                 415

Lys Glu Lys Thr Lys Glu Ala Glu Arg Thr Ala Glu Leu Ala Glu Ala
            420                 425                 430

Asp Ala Arg Glu Lys Asp Lys Glu Leu Val Glu Ala Leu Lys Arg Leu
        435                 440                 445

Lys Asp Tyr Glu Ser Gly Val Tyr Gly Leu Glu Asp Ala Val Val Glu
    450                 455                 460

Ile Lys Asn Cys Lys Asn Gln Ile Lys Ile Arg Asp Arg Glu Ile Glu
465                 470                 475                 480

Ile Leu Thr Lys Glu Ile Asn Lys Leu Glu Leu Lys Ile Ser Asp Phe
                485                 490                 495

Leu Asp Glu Asn Glu Ala Leu Arg Glu Arg Val Gly Leu Glu Pro Lys
            500                 505                 510

Thr Met Ile Asp Leu Thr Glu Phe Arg Asn Ser Lys His Leu Lys Gln
        515                 520                 525

Gln Gln Tyr Arg Ala Glu Asn Gln Ile Leu Leu Lys Glu Ile Glu Ser
    530                 535                 540

Leu Glu Glu Glu Arg Leu Asp Leu Lys Lys Lys Ile Arg Gln Met Ala
545                 550                 555                 560

Gln Glu Arg Gly Lys Arg Ser Ala Thr Ser Gly Leu Thr Thr Glu Asp
                565                 570                 575

Leu Asn Leu Thr Glu Asn Ile Ser Gln Gly Asp Arg Ile Ser Glu Arg
            580                 585                 590
```

-continued

```
Lys Leu Asp Leu Leu Ser Leu Lys Asn Met Ser Glu Ala Gln Ser Lys
        595                 600                 605

Asn Glu Phe Leu Ser Arg Glu Leu Ile Glu Lys Glu Arg Asp Leu Glu
    610                 615                 620

Arg Ser Arg Thr Val Ile Ala Lys Phe Gln Asn Lys Leu Lys Glu Leu
625                 630                 635                 640

Val Glu Glu Asn Lys Gln Leu Glu Glu Gly Met Lys Glu Ile Leu Gln
                645                 650                 655

Ala Ile Lys Glu Met Gln Lys Asp Pro Asp Val Lys Gly Gly Glu Thr
            660                 665                 670

Ser Leu Ile Ile Pro Ser Leu Glu Arg Leu Val Asn Ala Ile Glu Ser
        675                 680                 685

Lys Asn Ala Glu Gly Ile Phe Asp Ala Ser Leu His Leu Lys Ala Gln
    690                 695                 700

Val Asp Gln Leu Thr Gly Arg Asn Glu Glu Leu Arg Gln Glu Leu Arg
705                 710                 715                 720

Glu Ser Arg Lys Glu Ala Ile Asn Tyr Ser Gln Gln Leu Ala Lys Ala
                725                 730                 735

Asn Leu Lys Ile Asp His Leu Glu Lys Glu Thr Ser Leu Leu Arg Gln
            740                 745                 750

Ser Glu Gly Ser Asn Val Val Phe Lys Gly Ile Asp Leu Pro Asp Gly
        755                 760                 765

Ile Ala Pro Ser Ser Ala Ser Ile Ile Asn Ser Gln Asn Glu Tyr Leu
    770                 775                 780

Ile His Leu Leu Gln Glu Leu Glu Asn Lys Glu Lys Lys Leu Lys Asn
785                 790                 795                 800

Leu Glu Asp Ser Leu Glu Asp Tyr Asn Arg Lys Phe Ala Val Ile Arg
                805                 810                 815

His Gln Gln Ser Leu Leu Tyr Lys Glu Tyr Leu Ser Glu Lys Glu Thr
            820                 825                 830

Trp Lys Thr Glu Ser Lys Thr Ile Lys Glu Glu Lys Arg Lys Leu Glu
        835                 840                 845

Asp Gln Val Gln Gln Asp Ala Ile Lys Val Lys Glu Tyr Asn Asn Leu
    850                 855                 860

Leu Asn Ala Leu Gln Met Asp Ser Asp Glu Met Lys Lys Ile Leu Ala
865                 870                 875                 880

Glu Asn Ser Arg Lys Ile Thr Val Leu Gln Val Asn Glu Lys Ser Leu
                885                 890                 895

Ile Arg Gln Tyr Thr Thr Leu Val Glu Leu Glu Arg Gln Leu Arg Lys
            900                 905                 910

Glu Asn Glu Lys Gln Lys Asn Glu Leu Leu Ser Met Glu Ala Glu Val
        915                 920                 925

Cys Glu Lys Ile Gly Cys Leu Gln Arg Phe Lys Glu Met Ala Ile Phe
    930                 935                 940

Lys Ile Ala Ala Leu Gln Lys Val Val Asp Asn Ser Val Ser Leu Ser
945                 950                 955                 960

Glu Leu Glu Leu Ala Asn Lys Gln Tyr Asn Glu Leu Thr Ala Lys Tyr
                965                 970                 975

Arg Asp Ile Leu Gln Lys Asp Asn Met Leu Val Gln Arg Thr Ser Asn
            980                 985                 990

Leu Glu His Leu Glu Cys Glu Asn  Ile Ser Leu Lys Glu  Gln Val Glu
        995                 1000                1005

Ser Ile  Asn Lys Glu Leu Glu  Ile Thr Lys Glu Lys  Leu His Thr
```

1010 1015 1020

Ile Glu Gln Ala Trp Glu Gln Glu Thr Lys Leu Gly Asn Glu Ser
1025 1030 1035

Ser Met Asp Lys Ala Lys Lys Ser Ile Thr Asn Ser Asp Ile Val
1040 1045 1050

Ser Ile Ser Lys Lys Ile Thr Met Leu Glu Met Lys Glu Leu Asn
1055 1060 1065

Glu Arg Gln Arg Ala Glu His Cys Gln Lys Met Tyr Glu His Leu
1070 1075 1080

Arg Thr Ser Leu Lys Gln Met Glu Glu Arg Asn Phe Glu Leu Glu
1085 1090 1095

Thr Lys Phe Ala Glu Leu Thr Lys Ile Asn Leu Asp Ala Gln Lys
1100 1105 1110

Val Glu Gln Met Leu Arg Asp Glu Leu Ala Asp Ser Val Ser Lys
1115 1120 1125

Ala Val Ser Asp Ala Asp Arg Gln Arg Ile Leu Glu Leu Glu Lys
1130 1135 1140

Asn Glu Met Glu Leu Lys Val Glu Val Ser Lys Leu Arg Glu Ile
1145 1150 1155

Ser Asp Ile Ala Arg Arg Gln Val Glu Ile Leu Asn Ala Gln Gln
1160 1165 1170

Gln Ser Arg Asp Lys Glu Val Glu Ser Leu Arg Met Gln Leu Leu
1175 1180 1185

Asp Tyr Gln Ala Gln Ser Asp Glu Lys Ser Leu Ile Ala Lys Leu
1190 1195 1200

His Gln His Asn Val Ser Leu Gln Leu Ser Glu Ala Thr Ala Leu
1205 1210 1215

Gly Lys Leu Glu Ser Ile Thr Ser Lys Leu Gln Lys Met Glu Ala
1220 1225 1230

Tyr Asn Leu Arg Leu Glu Gln Lys Leu Asp Glu Lys Glu Gln Ala
1235 1240 1245

Leu Tyr Tyr Ala Arg Leu Glu Gly Arg Asn Arg Ala Lys His Leu
1250 1255 1260

Arg Gln Thr Ile Gln Ser Leu Arg Arg Gln Phe Ser Gly Ala Leu
1265 1270 1275

Pro Leu Ala Gln Gln Glu Lys Phe Ser Lys Thr Met Ile Gln Leu
1280 1285 1290

Gln Asn Asp Lys Leu Lys Ile Met Gln Glu Met Lys Asn Ser Gln
1295 1300 1305

Gln Glu His Arg Asn Met Glu Asn Lys Thr Leu Glu Met Glu Leu
1310 1315 1320

Lys Leu Lys Gly Leu Glu Glu Leu Ile Ser Thr Leu Lys Asp Thr
1325 1330 1335

Lys Gly Ala Gln Lys Val Ile Asn Trp His Met Lys Ile Glu Glu
1340 1345 1350

Leu Arg Leu Gln Glu Leu Lys Leu Asn Arg Glu Leu Val Lys Asp
1355 1360 1365

Lys Glu Glu Ile Lys Tyr Leu Asn Asn Ile Ile Ser Glu Tyr Glu
1370 1375 1380

Arg Thr Ile Ser Ser Leu Glu Glu Glu Ile Val Gln Gln Asn Lys
1385 1390 1395

Phe His Glu Glu Arg Gln Met Ala Trp Asp Gln Arg Glu Val Asp
1400 1405 1410

```
Leu Glu  Arg Gln Leu Asp Ile  Phe Asp Arg Gln Gln  Asn Glu Ile
    1415                 1420                 1425

Leu Asn  Ala Ala Gln Lys Phe  Glu Glu Ala Thr Gly  Ser Ile Pro
    1430                 1435                 1440

Asp Pro  Ser Leu Pro Leu Pro  Asn Gln Leu Glu Ile  Ala Leu Arg
    1445                 1450                 1455

Lys Ile  Lys Glu Asn Ile Arg  Ile Ile Leu Glu Thr  Arg Ala Thr
    1460                 1465                 1470

Cys Lys  Ser Leu Glu Glu Lys  Leu Lys Glu Lys Glu  Ser Ala Leu
    1475                 1480                 1485

Arg Leu  Ala Glu Gln Asn Ile  Leu Ser Arg Asp Lys  Val Ile Asn
    1490                 1495                 1500

Glu Leu  Arg Leu Arg Leu Pro  Ala Thr Ala Glu Arg  Glu Lys Leu
    1505                 1510                 1515

Ile Ala  Glu Leu Gly Arg Lys  Glu Met Glu Pro Lys  Ser His His
    1520                 1525                 1530

Thr Leu  Lys Ile Ala His Gln  Thr Ile Ala Asn Met  Gln Ala Arg
    1535                 1540                 1545

Leu Asn  Gln Lys Glu Glu Val  Leu Lys Lys Tyr Gln  Arg Leu Leu
    1550                 1555                 1560

Glu Lys  Ala Arg Glu Glu Gln  Arg Glu Ile Val Lys  Lys His Glu
    1565                 1570                 1575

Glu Asp  Leu His Ile Leu His  His Arg Leu Glu Leu  Gln Ala Asp
    1580                 1585                 1590

Ser Ser  Leu Asn Lys Phe Lys  Gln Thr Ala Trp Asp  Leu Met Lys
    1595                 1600                 1605

Gln Ser  Pro Thr Pro Val Pro  Thr Asn Lys His Phe  Ile Arg Leu
    1610                 1615                 1620

Ala Glu  Met Glu Gln Thr Val  Ala Glu Gln Asp Asp  Ser Leu Ser
    1625                 1630                 1635

Ser Leu  Leu Val Lys Leu Lys  Lys Val Ser Gln Asp  Leu Glu Arg
    1640                 1645                 1650

Gln Arg  Glu Ile Thr Glu Leu  Lys Val Lys Glu Phe  Glu Asn Ile
    1655                 1660                 1665

Lys Leu  Gln Leu Gln Glu Asn  His Glu Asp Glu Val  Lys Lys Val
    1670                 1675                 1680

Lys Ala  Glu Val Glu Asp Leu  Lys Tyr Leu Leu Asp  Gln Ser Gln
    1685                 1690                 1695

Lys Glu  Ser Gln Cys Leu Lys  Ser Glu Leu Gln Ala  Gln Lys Glu
    1700                 1705                 1710

Ala Asn  Ser Arg Ala Pro Thr  Thr Thr Met Arg Asn  Leu Val Glu
    1715                 1720                 1725

Arg Leu  Lys Ser Gln Leu Ala  Leu Lys Glu Lys Gln  Gln Lys Ala
    1730                 1735                 1740

Leu Ser  Arg Ala Leu Leu Glu  Leu Arg Ala Glu Met  Thr Ala Ala
    1745                 1750                 1755

Ala Glu  Glu Arg Ile Ile Ser  Ala Thr Ser Gln Lys  Glu Ala His
    1760                 1765                 1770

Leu Asn  Val Gln Gln Ile Val  Asp Arg His Thr Arg  Glu Leu Lys
    1775                 1780                 1785

Thr Gln  Val Glu Asp Leu Asn  Glu Asn Leu Leu Lys  Leu Lys Glu
    1790                 1795                 1800
```

-continued

```
Ala Leu  Lys Thr Ser Lys Asn  Arg Glu Asn Ser Leu  Thr Asp Asn
    1805                 1810                 1815

Leu Asn  Asp Leu Asn Asn Glu  Leu Gln Lys Lys Gln  Lys Ala Tyr
    1820                 1825                 1830

Asn Lys  Ile Leu Arg Glu Lys  Glu Glu Ile Asp Gln  Glu Asn Asp
    1835                 1840                 1845

Glu Leu  Lys Arg Gln Ile Lys  Arg Leu Thr Ser Gly  Leu Gln Gly
    1850                 1855                 1860

Lys Pro  Leu Thr Asp Asn Lys  Gln Ser Leu Ile Glu  Glu Leu Gln
    1865                 1870                 1875

Arg Lys  Val Lys Lys Leu Glu  Asn Gln Leu Glu Gly  Lys Val Glu
    1880                 1885                 1890

Glu Val  Asp Leu Lys Pro Met  Lys Glu Lys Asn Ala  Lys Glu Glu
    1895                 1900                 1905

Leu Ile  Arg Trp Glu Glu Gly  Lys Lys Trp Gln Ala  Lys Ile Glu
    1910                 1915                 1920

Gly Ile  Arg Asn Lys Leu Lys  Glu Lys Glu Gly Glu  Val Phe Thr
    1925                 1930                 1935

Leu Thr  Lys Gln Leu Asn Thr  Leu Lys Asp Leu Phe  Ala Lys Ala
    1940                 1945                 1950

Asp Lys  Glu Lys Leu Thr Leu  Gln Arg Lys Leu Lys  Thr Thr Gly
    1955                 1960                 1965

Met Thr  Val Asp Gln Val Leu  Gly Ile Arg Ala Leu  Glu Ser Glu
    1970                 1975                 1980

Lys Glu  Leu Glu Glu Leu Lys  Lys Arg Asn Leu Asp  Leu Glu Asn
    1985                 1990                 1995

Asp Ile  Leu Tyr Met Arg Ala  His Gln Ala Leu Pro  Arg Asp Ser
    2000                 2005                 2010

Val Val  Glu Asp Leu His Leu  Gln Asn Arg Tyr Leu  Gln Glu Lys
    2015                 2020                 2025

Leu His  Ala Leu Glu Lys Gln  Phe Ser Lys Asp Thr  Tyr Ser Lys
    2030                 2035                 2040

Pro Ser  Ile Ser Gly Ile Glu  Ser Asp Asp His Cys  Gln Arg Glu
    2045                 2050                 2055

Gln Glu  Leu Gln Lys Glu Asn  Leu Lys Leu Ser Ser  Glu Asn Ile
    2060                 2065                 2070

Glu Leu  Lys Phe Gln Leu Glu  Gln Ala Asn Lys Asp  Leu Pro Arg
    2075                 2080                 2085

Leu Lys  Asn Gln Val Arg Asp  Leu Lys Glu Met Cys  Glu Phe Leu
    2090                 2095                 2100

Lys Lys  Glu Lys Ala Glu Val  Gln Arg Lys Leu Gly  His Val Arg
    2105                 2110                 2115

Gly Ser  Gly Arg Ser Gly Lys  Thr Ile Pro Glu Leu  Glu Lys Thr
    2120                 2125                 2130

Ile Gly  Leu Met Lys Lys Val  Val Glu Lys Val Gln  Arg Glu Asn
    2135                 2140                 2145

Glu Gln  Leu Lys Lys Ala Ser  Gly Ile Leu Thr Ser  Glu Lys Met
    2150                 2155                 2160

Ala Asn  Ile Glu Gln Glu Asn  Glu Lys Leu Lys Ala  Glu Leu Glu
    2165                 2170                 2175

Lys Leu  Lys Ala His Leu Gly  His Gln Leu Ser Met  His Tyr Glu
    2180                 2185                 2190

Ser Lys  Thr Lys Gly Thr Glu  Lys Ile Ile Ala Glu  Asn Glu Arg
```

```
    2195                2200                2205

Leu Arg  Lys Glu Leu Lys Lys  Glu Thr Asp Ala Ala  Glu Lys Leu
    2210                2215                2220

Arg Ile  Ala Lys Asn Asn Leu  Glu Ile Leu Asn Glu  Lys Met Thr
    2225                2230                2235

Val Gln  Leu Glu Glu Thr Gly  Lys Arg Leu Gln Phe  Ala Glu Ser
    2240                2245                2250

Arg Gly  Pro Gln Leu Glu Gly  Ala Asp Ser Lys Ser  Trp Lys Ser
    2255                2260                2265

Ile Val  Val Thr Arg Met Tyr  Glu Thr Lys Leu Lys  Glu Leu Glu
    2270                2275                2280

Thr Asp  Ile Ala Lys Lys Asn  Gln Ser Ile Thr Asp  Leu Lys Gln
    2285                2290                2295

Leu Val  Lys Glu Ala Thr Glu  Arg Glu Gln Lys Val  Asn Lys Tyr
    2300                2305                2310

Asn Glu  Asp Leu Glu Gln Gln  Ile Lys Ile Leu Lys  His Val Pro
    2315                2320                2325

Glu Gly  Ala Glu Thr Glu Gln  Gly Leu Lys Arg Glu  Leu Gln Val
    2330                2335                2340

Leu Arg  Leu Ala Asn His Gln  Leu Asp Lys Glu Lys  Ala Glu Leu
    2345                2350                2355

Ile His  Gln Ile Glu Ala Asn  Lys Asp Gln Ser Gly  Ala Glu Ser
    2360                2365                2370

Thr Ile  Pro Asp Ala Asp Gln  Leu Lys Glu Lys Ile  Lys Asp Leu
    2375                2380                2385

Glu Thr  Gln Leu Lys Met Ser  Asp Leu Glu Lys Gln  His Leu Lys
    2390                2395                2400

Glu Glu  Ile Lys Lys Leu Lys  Lys Glu Leu Glu Asn  Phe Asp Pro
    2405                2410                2415

Ser Phe  Phe Glu Glu Ile Glu  Asp Leu Lys Tyr Asn  Tyr Lys Glu
    2420                2425                2430

Glu Val  Lys Lys Asn Ile Leu  Leu Glu Glu Lys Val  Lys Lys Leu
    2435                2440                2445

Ser Glu  Gln Leu Gly Val Glu  Leu Thr Ser Pro Val  Ala Ala Ser
    2450                2455                2460

Glu Glu  Phe Glu Asp Glu Glu  Glu Ser Pro Val Asn  Phe Pro Ile
    2465                2470                2475

Tyr
```

<210> SEQ ID NO 42
<211> LENGTH: 2625
<212> TYPE: DNA
<213> ORGANISM: Homo sapiens

<400> SEQUENCE: 42

```
actcgaccgg gctgcgctca ctgcccagcc ggggccccgg gagcctccag gctcccgccc     60

gccctgagct gcggcctccg catggagggg ccactcactc caccaccgct gcagggaggc    120

ggagccgccg ctgttccgga gcccggagcc cggcaacacc cgggacacga gacggcggcg    180

cagcggtaca gcgcccgact gctgcaggcc ggctacgagc ccgagagccc tagattggac    240

ctcgctacac acccgacgac accccgttca gaactatctt cagtggtctt actggcaggt    300

gttggtgtcc agatggatcg ccttcgcagg gctagcatgg cggactacct gatcagcggc    360

ggcaccggct acgtgcccga ggatgggctc accgcgcagc agctcttcgc cagcgccgac    420
```

-continued

```
ggcctcacct acaacgactt cctgattctc ccaggattca tagacttcat agctgatgag     480
gtggacctga cctcagccct gacccggaag atcacgctga agacgccact gatctcctcc     540
cccatggaca ctgtgacaga ggctgacatg gccattgcca tggctctgat gggaggtatt     600
ggtttcattc accacaactg caccccagag ttccaggcca acgaggtgcg gaaggtcaag     660
aagtttgaac agggcttcat cacggaccct gtggtgctga gcccctcgca cactgtgggc     720
gatgtgctgg aggccaagat gcggcatggc ttctctggca tccccatcac tgagacgggc     780
accatgggca gcaagctggt gggcatcgtc acctcccgag acatcgactt tcttgctgag     840
aaggaccaca ccaccctcct cagtgaggtg atgacgccaa ggattgaact ggtggtggct     900
ccagcaggtg tgacgttgaa agaggcaaat gagatcctgc agcgtagcaa gaaagggaag     960
ctgcctatcg tcaatgattg cgatgagctg gtggccatca tcgcccgcac cgacctgaag    1020
aagaaccgag actaccctct ggcctccaag gattcccaga agcagctgct ctgtggggca    1080
gctgtgggca cccgtgagga tgacaaatac cgtctggacc tgctcaccca ggcgggcgtc    1140
gacgtcatag tcttggactc gtcccaaggg aattcggtgt atcagatcgc catggtgcat    1200
tacatcaaac agaagtaccc ccacctccag gtgattgggg ggaacgtggt gacagcagcc    1260
caggccaaga acctgattga tgctggtgtg gacgggctgc gcgtgggcat gggctgcggc    1320
tccatctgca tcacccagga agtgatggcc tgtggtcggc cccagggcac tgctgtgtac    1380
aaggtggctg agtatgcccg gcgctttggt gtgcccatca tagccgatgg cggcatccag    1440
accgtgggac acgtggtcaa ggccctggcc cttggagcct ccacagtgat gatgggctcc    1500
ctgctggccg ccactacgga ggcccctggc gagtacttct tctcagacgg ggtgcggctc    1560
aagaagtacc ggggcatggg ctcactggat gccatggaga agagcagcag cagccagaaa    1620
cgatacttca gcgaggggga taaagtgaag atcgcgcagg gtgtctcggg ctccatccag    1680
gacaaaggat ccattcagaa gttcgtgccc tacctcatag caggcatcca acacggctgc    1740
caggatatcg gggcccgcag cctgtctgtc cttcggtcca tgatgtactc aggagagctc    1800
aagtttgaga agcggaccat gtcggcccag attgagggtg gtgtccatgg cctgcactct    1860
tacgaaaagc ggctgtactg aggacagcgg tggaggccga ggtggtggag gggatgcacc    1920
ccagtgtcca cttttgggca cagcctccct ccataactga gtggtccaca gatttgcact    1980
acgggttctc cagctccttt ccaggcagag aggaggggag gtcctgaggg gactgctgcc    2040
cctcactcgg catcccctgc agagtcagga ctgctcccgg ggccaggctg ccctgggagc    2100
ccccctccga gcccagccag ccaggctctc aggccctgcg cctgcctcag gtctttcttg    2160
ctgcagcctg ctccagcctg gcccccaccc caggggcagg cggcccctcc tggcttctcc    2220
tgtagggcac ctccctgccc ctagcctccc aggaaatggt gctctcctgg ccctgcctct    2280
ggcccttccc gggccgctgc ccctcagcca tgtggcactt ctgagctcct gacctaggcc    2340
aaggggaggt ctctgccccc ttccccggcc ctgggctacc cttgggtcct gctcctcagg    2400
ccgctcccct gtccctggcc atgggtagga gactgccctg gtcatggccg cctgcctgtc    2460
attcctgact caccaccgtc cccaggtgaa ccattcctcc cttctcctca gctgcagtcg    2520
aaggctttaa ctttgcacac ttgggatcac agttgcgtca ttgtgtatta aatacttgga    2580
ataaatcaag caggtctcaa cgcctccact aaaaaaaaaa aaaaa                    2625
```

<210> SEQ ID NO 43
<211> LENGTH: 599
<212> TYPE: PRT

<213> ORGANISM: Homo sapiens

<400> SEQUENCE: 43

Met Glu Gly Pro Leu Thr Pro Pro Pro Leu Gln Gly Gly Gly Ala Ala
1 5 10 15

Ala Val Pro Glu Pro Gly Ala Arg Gln His Pro Gly His Glu Thr Ala
20 25 30

Ala Gln Arg Tyr Ser Ala Arg Leu Leu Gln Ala Gly Tyr Glu Pro Glu
35 40 45

Ser Pro Arg Leu Asp Leu Ala Thr His Pro Thr Thr Pro Arg Ser Glu
50 55 60

Leu Ser Ser Val Val Leu Leu Ala Gly Val Gly Val Gln Met Asp Arg
65 70 75 80

Leu Arg Arg Ala Ser Met Ala Asp Tyr Leu Ile Ser Gly Gly Thr Gly
85 90 95

Tyr Val Pro Glu Asp Gly Leu Thr Ala Gln Gln Leu Phe Ala Ser Ala
100 105 110

Asp Gly Leu Thr Tyr Asn Asp Phe Leu Ile Leu Pro Gly Phe Ile Asp
115 120 125

Phe Ile Ala Asp Glu Val Asp Leu Thr Ser Ala Leu Thr Arg Lys Ile
130 135 140

Thr Leu Lys Thr Pro Leu Ile Ser Ser Pro Met Asp Thr Val Thr Glu
145 150 155 160

Ala Asp Met Ala Ile Ala Met Ala Leu Met Gly Gly Ile Gly Phe Ile
165 170 175

His His Asn Cys Thr Pro Glu Phe Gln Ala Asn Glu Val Arg Lys Val
180 185 190

Lys Lys Phe Glu Gln Gly Phe Ile Thr Asp Pro Val Val Leu Ser Pro
195 200 205

Ser His Thr Val Gly Asp Val Leu Glu Ala Lys Met Arg His Gly Phe
210 215 220

Ser Gly Ile Pro Ile Thr Glu Thr Gly Thr Met Gly Ser Lys Leu Val
225 230 235 240

Gly Ile Val Thr Ser Arg Asp Ile Asp Phe Leu Ala Glu Lys Asp His
245 250 255

Thr Thr Leu Leu Ser Glu Val Met Thr Pro Arg Ile Glu Leu Val Val
260 265 270

Ala Pro Ala Gly Val Thr Leu Lys Glu Ala Asn Glu Ile Leu Gln Arg
275 280 285

Ser Lys Lys Gly Lys Leu Pro Ile Val Asn Asp Cys Asp Glu Leu Val
290 295 300

Ala Ile Ile Ala Arg Thr Asp Leu Lys Lys Asn Arg Asp Tyr Pro Leu
305 310 315 320

Ala Ser Lys Asp Ser Gln Lys Gln Leu Leu Cys Gly Ala Ala Val Gly
325 330 335

Thr Arg Glu Asp Asp Lys Tyr Arg Leu Asp Leu Leu Thr Gln Ala Gly
340 345 350

Val Asp Val Ile Val Leu Asp Ser Ser Gln Gly Asn Ser Val Tyr Gln
355 360 365

Ile Ala Met Val His Tyr Ile Lys Gln Lys Tyr Pro His Leu Gln Val
370 375 380

Ile Gly Gly Asn Val Val Thr Ala Ala Gln Ala Lys Asn Leu Ile Asp
385 390 395 400

```
Ala Gly Val Asp Gly Leu Arg Val Gly Met Gly Cys Gly Ser Ile Cys
                405                 410                 415

Ile Thr Gln Glu Val Met Ala Cys Gly Arg Pro Gln Gly Thr Ala Val
            420                 425                 430

Tyr Lys Val Ala Glu Tyr Ala Arg Arg Phe Gly Val Pro Ile Ile Ala
        435                 440                 445

Asp Gly Gly Ile Gln Thr Val Gly His Val Val Lys Ala Leu Ala Leu
    450                 455                 460

Gly Ala Ser Thr Val Met Met Gly Ser Leu Leu Ala Ala Thr Thr Glu
465                 470                 475                 480

Ala Pro Gly Glu Tyr Phe Phe Ser Asp Gly Val Arg Leu Lys Lys Tyr
                485                 490                 495

Arg Gly Met Gly Ser Leu Asp Ala Met Glu Lys Ser Ser Ser Ser Gln
            500                 505                 510

Lys Arg Tyr Phe Ser Glu Gly Asp Lys Val Lys Ile Ala Gln Gly Val
        515                 520                 525

Ser Gly Ser Ile Gln Asp Lys Gly Ser Ile Gln Lys Phe Val Pro Tyr
    530                 535                 540

Leu Ile Ala Gly Ile Gln His Gly Cys Gln Asp Ile Gly Ala Arg Ser
545                 550                 555                 560

Leu Ser Val Leu Arg Ser Met Met Tyr Ser Gly Glu Leu Lys Phe Glu
                565                 570                 575

Lys Arg Thr Met Ser Ala Gln Ile Glu Gly Gly Val His Gly Leu His
            580                 585                 590

Ser Tyr Glu Lys Arg Leu Tyr
        595
```

<210> SEQ ID NO 44
<211> LENGTH: 2981
<212> TYPE: DNA
<213> ORGANISM: Homo sapiens

<400> SEQUENCE: 44

```
gctgggtaaa tcccagagtc tcagccgcct aagtgtcttc cccggaggtg agattatctc     60

cgcctgtgct ggacacctcc ctttctcctg cagccatgga tgccgctctg ctcctgaacg    120

tggaaggggt caagaaaacc attctgcacg ggggcacggg cgagctccca aacttcatca    180

ccggatcccg agtgatcttt catttccgca ccatgaaatg tgatgaggag cggacagtca    240

ttgacgacag tcggcaggtg ggccagccca tgcacatcat catcggaaac atgttcaagc    300

tcgaggtctg ggagatcctg cttacctcca tgcgggtgca cgaggtggcc gagttctggt    360

gcgacaccat ccacacgggg gtctacccca tcctatcccg gagcctgagg cagatggccc    420

agggcaagga ccccacagag tggcacgtgc acacgtgcgg gctggccaac atgttcgcct    480

accacacgct gggctacgag gacctggacg agctgcagaa ggagcctcag cctctggtct    540

ttgtgatcga gctgctgcag gttgatgccc cgagtgatta ccagagggag acctggaacc    600

tgagcaatca tgagaagatg aaggcggtgc ccgtcctcca cggagaggga aatcggctct    660

tcaagctggg ccgctacgag gaggcctctt ccaagtacca ggaggccatc atctgcctaa    720

ggaacctgca gaccaaggag aagccatggg aggtgcagtg gctgaagctg gagaagatga    780

tcaatactct gatcctcaac tactgccagt gcctgctgaa gaaggaggag tactatgagg    840

tgctggagca caccagtgat attctccggc accacccagg catcgtgaag gcctactacg    900

tgcgtgcccg ggctcacgca gaggtgtgga atgaggccga ggccaaggcg gacctccaga    960
```

-continued

```
aagtgctgga gctggagccg tccatgcaga aggcggtgcg cagggagctg aggctgctgg   1020
agaaccgcat ggcggagaag caggaggagg agcggctgcg ctgccggaac atgctgagcc   1080
agggtgccac gcagcctccc gcagagccac ccacagagcc acccgcacag tcatccacag   1140
agccacctgc agagccaccc acagcaccat ctgcagagct gtccgcaggg ccccctgcag   1200
agccagccac agagccaccc ccgtccccag ggcactcgct gcagcactga gccccctgag   1260
gcccacagcc acccaggcag ggagcaagtg gcctggtcac ttctggttcg attgaccagg   1320
atcgtggtgt cactttttaa aatttaaaat taatttttga aatcaaagtc agacacaccc   1380
atggtaaaaa aaaaaaaaaa aacaatccca agggtacaga agagcttatg aataaaagta   1440
gttttctcct ctacccctct cattccttcc gtgccatggt tttaattgac cctgttttta   1500
attcttctgg tagttttctc tatttccaag taatctgttt aaatcagttt ctagatttta   1560
ccccatgtca atgacaaatg aggatttgat gctctgatcc tttctcatgc ctgatacccc   1620
tccctgtctc cccattttgg atagttacat ttgggggtca tctcggtgat ttttgtaact   1680
ttacgcagga cacttagagc tctctagaat cccactgact ttagtgggtc ttgatgtagg   1740
gtgggcaagc cccgacactg gagcttagcc tgagagggtt cttggcctcc cccaggaaag   1800
atttcaaagg caagcgccag tggtagggta gaagaaaaca gctgtggtcg ggcacggtgg   1860
ctcacgccta taatcccagc actttgggag gccgaggcgg gtggatcacc tgaggtcagg   1920
agttccagac cagcctggcc aacatggtga aacctcatct ctactaaaaa tacaaaaaaa   1980
ctagctgggc gtggtggcgg gcgcctataa tcccagctac ttgggaggct gaggcaggag   2040
aattgattga acctgggagg cggaggttgc agtgagccaa gatcacgtca ttgcactcca   2100
gcctggtcaa caagagtaaa acttcatctc aaaaaacaaa acaaaacaaa aacaacaaca   2160
aaaaacaaaa gaaaaacaaa caaaaccaaa accaaaacag ctgtattgaa gctgcagtgt   2220
tgcagctctg tgactgccct gcagagcagg gctaccccat aggcagcgag cagcagctca   2280
gggcagttct gcagtcagat ttatacccac ttttaattac atgtagatta aggagctgca   2340
tatacaaaga tttctaggga aggagtagta acttctgggt cctggggtct ttgccacgga   2400
acagggcagt atgccagggt gttgccacgg caatggtaaa ctgacatggc accctggggg   2460
tcatgcctta gggaaagccg cttccactcg cccctgtttt agctcatctt caagttagtc   2520
tggtgtccaa gctccaccgc ctgcctcagt ctggtgacct ccttctgtgt ctgatgagca   2580
tggcagcgtt gggaccttcc ccttccaact ctctccctcc tcttcgtcct ccctaaagga   2640
cgggtacgag gaggggctat cacgccagcg acatcctcta gcaccaccca ggtgtgtggg   2700
gtggggcagg ggggcgacga agtatccagc ccagggccac gtagtcaact gccaagggct   2760
tcctgggctt ctcttctgcc ccagagcttg tctccaccca gcaggggttc ccccagcgct   2820
aactgtatcc ctaaagttct gatgtacttt acttttccat cttccttgtt gttaacatct   2880
accttctgct ctgtaagcaa aactaaatct tctgtgcttt gtccataggt tgattctaca   2940
atctgaaaat caataaacag catttgcatg aaaaaaaaaa a                       2981
```

<210> SEQ ID NO 45
<211> LENGTH: 384
<212> TYPE: PRT
<213> ORGANISM: Homo sapiens

<400> SEQUENCE: 45

```
Met Asp Ala Ala Leu Leu Leu Asn Val Glu Gly Val Lys Lys Thr Ile
1               5                   10                  15
```

```
Leu His Gly Gly Thr Gly Glu Leu Pro Asn Phe Ile Thr Gly Ser Arg
            20                  25                  30

Val Ile Phe His Phe Arg Thr Met Lys Cys Asp Glu Glu Arg Thr Val
        35                  40                  45

Ile Asp Asp Ser Arg Gln Val Gly Gln Pro Met His Ile Ile Ile Gly
    50                  55                  60

Asn Met Phe Lys Leu Glu Val Trp Glu Ile Leu Leu Thr Ser Met Arg
65                  70                  75                  80

Val His Glu Val Ala Glu Phe Trp Cys Asp Thr Ile His Thr Gly Val
                85                  90                  95

Tyr Pro Ile Leu Ser Arg Ser Leu Arg Gln Met Ala Gln Gly Lys Asp
            100                 105                 110

Pro Thr Glu Trp His Val His Thr Cys Gly Leu Ala Asn Met Phe Ala
        115                 120                 125

Tyr His Thr Leu Gly Tyr Glu Asp Leu Asp Glu Leu Gln Lys Glu Pro
    130                 135                 140

Gln Pro Leu Val Phe Val Ile Glu Leu Leu Gln Val Asp Ala Pro Ser
145                 150                 155                 160

Asp Tyr Gln Arg Glu Thr Trp Asn Leu Ser Asn His Glu Lys Met Lys
                165                 170                 175

Ala Val Pro Val Leu His Gly Glu Gly Asn Arg Leu Phe Lys Leu Gly
            180                 185                 190

Arg Tyr Glu Glu Ala Ser Ser Lys Tyr Gln Glu Ala Ile Ile Cys Leu
        195                 200                 205

Arg Asn Leu Gln Thr Lys Glu Lys Pro Trp Glu Val Gln Trp Leu Lys
    210                 215                 220

Leu Glu Lys Met Ile Asn Thr Leu Ile Leu Asn Tyr Cys Gln Cys Leu
225                 230                 235                 240

Leu Lys Lys Glu Glu Tyr Tyr Glu Val Leu Glu His Thr Ser Asp Ile
                245                 250                 255

Leu Arg His His Pro Gly Ile Val Lys Ala Tyr Tyr Val Arg Ala Arg
            260                 265                 270

Ala His Ala Glu Val Trp Asn Glu Ala Glu Ala Lys Ala Asp Leu Gln
        275                 280                 285

Lys Val Leu Glu Leu Glu Pro Ser Met Gln Lys Ala Val Arg Arg Glu
    290                 295                 300

Leu Arg Leu Leu Glu Asn Arg Met Ala Glu Lys Gln Glu Glu Glu Arg
305                 310                 315                 320

Leu Arg Cys Arg Asn Met Leu Ser Gln Gly Ala Thr Gln Pro Pro Ala
                325                 330                 335

Glu Pro Pro Thr Glu Pro Pro Ala Gln Ser Ser Thr Glu Pro Pro Ala
            340                 345                 350

Glu Pro Pro Thr Ala Pro Ser Ala Glu Leu Ser Ala Gly Pro Pro Ala
        355                 360                 365

Glu Pro Ala Thr Glu Pro Pro Pro Ser Pro Gly His Ser Leu Gln His
    370                 375                 380
```

<210> SEQ ID NO 46
<211> LENGTH: 1934
<212> TYPE: DNA
<213> ORGANISM: Homo sapiens

<400> SEQUENCE: 46

```
gggcacaagc aatcctccct tctcagcttc ctgagtggcc aggactacag aggactgtat      60
```

-continued

```
gctgttctta aggactctct gcttcctgga caagctcaag ctaaggacta catctcccag    120

caggctgtgc tctgacagct cttggattta aataggattc tgggctctgc tcagagtcag    180

gctgctgctc agcacccagg acggagagga gcagagaagc agcagaagca gccaagagct    240

ggagccagac caggaacctg agccagagct ggggttgaag ctggagcagc agcaaaagca    300

acagcagcta cagaagttgg aacgatgctg gtcaccttgg gactgctcac ctccttcttc    360

tcgttcctgt atatggtagc tccatccatc aggaagttct ttgctggtgg agtgtgtaga    420

acaaatgtgc agcttcctgg caaggtagtg gtgatcactg gcgccaacac gggcattggc    480

aaggagacgg ccagagagct cgctagccga ggagcccgag tctatattgc ctgcagagat    540

gtactgaagg gggagtctgc tgccagtgaa atccgagtgg atacaaagaa ctcccaggtg    600

ctggtgcgga aattggacct atccgacacc aaatctatcc gagcctttgc tgagggcttt    660

ctggcagagg aaaagcagct ccatattctg atcaacaatg cgggagtaat gatgtgtcca    720

tattccaaga cagctgatgg ctttgaaacc cacctgggag tcaaccacct gggccacttc    780

ctcctcacct acctgctcct ggagcggcta aaggtgtctg cccctgcacg ggtggttaat    840

gtgtcctcgg tggctcacca cattggcaag attcccttcc acgacctcca gagcgagaag    900

cgctacagca ggggttttgc ctattgccac agcaagctgg ccaatgtgct tttactcgt     960

gagctggcca agaggctcca aggcaccggg gtcaccacct acgcagtgca cccaggcgtc   1020

gtccgctctg agctggtccg gcactcctcc ctgctctgcc tgctctggcg gctcttctcc   1080

ccctttgtca agacggcacg ggagggggcg cagaccagcc tgcactgcgc cctggctgag   1140

ggcctggagc ccctgagtgg caagtacttc agtgactgca agaggacctg ggtgtctcca   1200

agggcccgaa ataacaaaac agctgagcgc ctatggaatg tcagctgtga gcttctagga   1260

atccggtggg agtagctggt ggaagagctg cagctttatc aggcccaatc catgccataa   1320

tgaacaggga ccaaggagaa ggccaaccct aaaggattgt cctcttggcc agctggtgct   1380

gcgaatcctg cctgctctga tcctcttgac ccttctggga atgtttgcac acctgacact   1440

cttgtgagac tggcttatgg catgagttgt ggacacctat agagtgttct tctctaagac   1500

ctggaaagtc agcaaccctc tgggggcagc aggactgggc agatcccagg ctgggcatgg   1560

gggtggcaga agagcccgag aaattgggtc agttccctca tcagcaccag aggctcagct   1620

gaggcaagaa gagcaccatc actgcctatt tctaggggct atacactcca actcttggtt   1680

gatctctttc tttttaaaaa tatttgccac caccctggag tctagaccaa cacacaaaga   1740

tcctggctaa ccctggccta tttagattcc ttcctctcac ctggaccttc ccatttcaat   1800

catgcagatg gtttcttttt gtaaagagtt ccgtttgcct ttcaattttt agagaaaata   1860

aagactgcat tcatctcaaa aaaaaaaaaa aaaaaaaaaa aaaaaaaaaa aaaaaaaaaa   1920

aaaaaaaaaa aaaa                                                     1934
```

<210> SEQ ID NO 47
<211> LENGTH: 316
<212> TYPE: PRT
<213> ORGANISM: Homo sapiens

<400> SEQUENCE: 47

```
Met Leu Val Thr Leu Gly Leu Leu Thr Ser Phe Phe Ser Phe Leu Tyr
1               5                   10                  15

Met Val Ala Pro Ser Ile Arg Lys Phe Phe Ala Gly Gly Val Cys Arg
            20                  25                  30

Thr Asn Val Gln Leu Pro Gly Lys Val Val Val Ile Thr Gly Ala Asn
```

-continued

```
        35                  40                  45

Thr Gly Ile Gly Lys Glu Thr Ala Arg Glu Leu Ala Ser Arg Gly Ala
    50                  55                  60

Arg Val Tyr Ile Ala Cys Arg Asp Val Leu Lys Gly Glu Ser Ala Ala
65                  70                  75                  80

Ser Glu Ile Arg Val Asp Thr Lys Asn Ser Gln Val Leu Val Arg Lys
                85                  90                  95

Leu Asp Leu Ser Asp Thr Lys Ser Ile Arg Ala Phe Ala Glu Gly Phe
            100                 105                 110

Leu Ala Glu Glu Lys Gln Leu His Ile Leu Ile Asn Asn Ala Gly Val
        115                 120                 125

Met Met Cys Pro Tyr Ser Lys Thr Ala Asp Gly Phe Glu Thr His Leu
    130                 135                 140

Gly Val Asn His Leu Gly His Phe Leu Leu Thr Tyr Leu Leu Leu Glu
145                 150                 155                 160

Arg Leu Lys Val Ser Ala Pro Ala Arg Val Val Asn Val Ser Ser Val
                165                 170                 175

Ala His His Ile Gly Lys Ile Pro Phe His Asp Leu Gln Ser Glu Lys
            180                 185                 190

Arg Tyr Ser Arg Gly Phe Ala Tyr Cys His Ser Lys Leu Ala Asn Val
        195                 200                 205

Leu Phe Thr Arg Glu Leu Ala Lys Arg Leu Gln Gly Thr Gly Val Thr
    210                 215                 220

Thr Tyr Ala Val His Pro Gly Val Val Arg Ser Glu Leu Val Arg His
225                 230                 235                 240

Ser Ser Leu Leu Cys Leu Leu Trp Arg Leu Phe Ser Pro Phe Val Lys
                245                 250                 255

Thr Ala Arg Glu Gly Ala Gln Thr Ser Leu His Cys Ala Leu Ala Glu
            260                 265                 270

Gly Leu Glu Pro Leu Ser Gly Lys Tyr Phe Ser Asp Cys Lys Arg Thr
        275                 280                 285

Trp Val Ser Pro Arg Ala Arg Asn Asn Lys Thr Ala Glu Arg Leu Trp
    290                 295                 300

Asn Val Ser Cys Glu Leu Leu Gly Ile Arg Trp Glu
305                 310                 315


<210> SEQ ID NO 48
<211> LENGTH: 4729
<212> TYPE: DNA
<213> ORGANISM: Homo sapiens

<400> SEQUENCE: 48

agtctaggcc tccgcctccg ttaccctgga gcccaggtta ccgccgctgc cacccaggag      60

ccccgatcct cgcctctgtc ccatccttgt gttcaaacct cccgcatctc ggcaacctcg     120

gcacccgccc ggcagcctcc gcaggaacca ggcacccgct ctttggcggt cagacgccga     180

ggccccagct gggagtttgg tcctaagagg gaaggcaagg aggcgggacg ccgcatcggc     240

tctgctgaag agcctgcggg ttggaggtgg gctttgaagt gggcgtggag acggcggggg     300

aggtggaggt gcgagtataa atgatcaacc agaaattatc ttcaaaggaa taaaaccaga     360

agtatgtaaa taaaaagccc aagataaaga aacagaaaag ctgacactac atgaagcaga     420

gggcaaaaaa gtttatcttc tggatgccaa tgtgaattgt ggtctacaaa tacattgtgg     480

agaaaataga ttgcacagaa atgaatatta tcaggatctg aagactgtga aaatgttttt     540
```

```
cagtattgtc atagtctcct ctggagaaaa taatctgtga aattatgtga atagagacca    600
tttttcaaaa caatggggga aagagcagga agtccaggta ctgatcaaga aagaaaggca    660
ggcaaacacc attattctta cttatctgat tttgaaacgc cacagtcttc tggccgatca    720
tcgctggtca gttcttcacc tgcaagtgtt aggagaaaaa atcctaaaag acaaacttca    780
gatggccaag tacatcacca agcccctcgg aaaccaagcc ctaagggtct accaaacaga    840
aagggagtcc gagtgggatt tcgctcccag agcctcaata gagagccact tcggaaagat    900
actgatcttg ttacaaaacg gattctgtct gcaagactgc taaaaatcaa tgagttgcag    960
aatgaagtat ctgaactcca ggtcaagtta gctgagctgc taaaagaaaa taaatctttg   1020
aaaaggcttc agtacagaca ggagaaagcc ctgaataagt ttgaagatgc cgaaaatgaa   1080
atctcacaac ttatatttcg tcataacaat gagattacag cactcaaaga acgcttaaga   1140
aaatctcaag agaaagaacg ggcaactgag aaaagggtaa aagatacaga aagtgaacta   1200
tttaggacaa aattttcctt acagaaactg aaagagatct ctgaagctag acacctacct   1260
gaacgagatg atttggcaaa gaaactagtt tcagcagagt taaagttaga tgacaccgag   1320
agaagaatta aggagctatc gaaaaacctt gaactgagta ctaacagttt ccaacgacag   1380
ttgcttgctg aaaggaaaag ggcatatgag gctcatgatg aaaataaagt tcttcaaaag   1440
gaggtacagc gactatatca caaattaaag gaaaaggaga gagaactgga tataaaaaat   1500
atatattcta atcgtctgcc aaagtcctct ccaaataaag agaaagaact tgcattaaga   1560
aaaaatgctg catgccagag tgattttgca gacctgtgta caaaaggagt acaaaccatg   1620
gaagacttca agccagaaga atatccttta actccagaaa caattatgtg ttacgaaaac   1680
aaatgggaag aaccaggaca tcttactttg gacttgcaat ctcaaaagca agacaggcat   1740
ggagaagcag ggattctaaa cccaattatg gaaagagaag aaaaatttgt tacagatgaa   1800
gaactccatg tcgtaaaaca ggaggttgaa aagctggagg atgaatggga aagagaagaa   1860
cttgataaaa agcaaaaaga aaaggcatct ttactggaaa gagaagaaaa gccagagtgg   1920
gaaactggaa ggtaccaact aggaatgtat ccaattcaga atatggataa attgcaagga   1980
gaggaagaag aaagactgaa gagagaaatg ctacttgcta aactgaatga aattgacaga   2040
gaactccaag attctcgaaa tctaaaatac cctgttttgc cattgttacc tgattttgaa   2100
tcaaaactac actccccaga gagaagcccc aaaacataca ggttctctga atcctcagag   2160
agattattta atgggcatca tttgcaagac atcagtttct caactccaaa aggagaaggt   2220
cagaattcag gaaatgttag aagtccagcc tcccctaatg agttcgcatt tggtagctac   2280
gtgccttcgt ttgcaaaaac atcagagagg tcaaatccat ttagtcaaaa aagtagtttt   2340
ttggatttcc aaagaaacag tatggaaaaa cttagtaaag atggtgtaga tttaattaca   2400
agaaaagaga aaaaagctaa tttgatggaa cagttatttg gtgccagtgg tagcagcacc   2460
atttcctcca aaagcagtga cccaaattct gtggcttcca gtaaaggaga cattgaccct   2520
ctaaattttc tccctgggaa taaaggcagc agagatcaag aacatgatga agatgaaggc   2580
tttttcctca gtgaaggaag aagttttaat ccaaataggc accgattaaa acatgcagac   2640
gataaaccag cagtaaaagc agctgattct gtagaagatg aaattgaaga agtagcactg   2700
agatgactga ctagagtata cattttttct aattgtaaat attgaaatat tttaatacag   2760
tatttattat aaacatttag actttttaat gctaaaatgt ccttattaag gaatgatttt   2820
taatagctaa atacaatgca gttaaaaaga agtagatcat acatacacca catagatagt   2880
ttgccaagaa tgaaggaggc tttttgaat gaaaccaaaa ataaaaatat gtcttgaaaa   2940
```

-continued atgaaataga ttttaactct tcatccagtg ctatggcaag tttaactgca ctggaggtgg 3000
tattcctttt ctacttttat tcctatttat gtatttattt ttaatcatat tctcactgtg 3060
ctaaatacag tcttcccact aattgttgaa tgaaaattaa gggtgaaagt ctgtgttggg 3120
aagtgtagct ccggatggtg gagaaccagt gcttcttagg agcccttccc tttatggata 3180
gggccagggg tccctatctt acgtggcagt cctaagctac tcttgagtga tagcagtcac 3240
aacattggga tttcccattc ctctgaaagt acccacagct aaacactact catttcccaa 3300
tttcagtatt tactgaaatc acttacctac aattctgtta gaatattatg ttgagttcgg 3360
aagacatttc tctgtttgca aggacagtta gttgctctct gtcatagccc gcagaagctt 3420
ggctacagtg taattcctct ccttgttctc ctacactctt tgtatctcag tgactgggtg 3480
taagatttca tgccaaatgc aaggaatagt ggaaatacat accaactgca aagaatagaa 3540
aaactttatc ccaatatatt atagaaagat cttcagttca attatgtcca gagtaatata 3600
atttggcaat gttaatgctt ttaagatttg aacttgtcct caaaccaagg agacaacaat 3660
agtgtaatac tattggactt acaggattag ttttaaagca actttgaata gaagtgtttc 3720
agacatagga cttctgcctt gttgactaga gtggatagtt ttctgtttaa atgcattggt 3780
cttttggctg tttgtaattc acttcagctt atagagaagt tgatgacctt ggatcatgct 3840
gggtatgatt ggtctttaaa aagcagtaat ataccaccag cccaaggaga aaacattgtt 3900
aaaatgaaga gtggtggaaa tagtgtgttg ggaagaataa aaaatttaga ttggcactta 3960
ttctaaagtg agctgttttt ttcaagaatt tactagcatt tgctcgtagt atgatttctg 4020
acgccagtca tatatactga tgaggggaag gagttactgt gttattctga gttcttataa 4080
atgcatatta ttgaatttca ttgcatgact atttgtcaag acttacctgg ttaggtctcc 4140
aattaaaaga tgtaccacct gtcatcttct aaattgtgtt cctttcattt attgggaaca 4200
gaatctctca aaagtgctaa actatattaa aaagttttct taatagattt gtatgtctga 4260
tatgtataac catttactat aatatgttgc aaatcattct aatatatgta aaacaatatt 4320
atttgtaatg cagttattgg taaaatatta tgtaatgtta attttgttcc tagctgctaa 4380
tttttctgcc aaaagtattc taattttcag gttgttttaa aggcttttaa aactttttag 4440
ttaagttttt tattcacgtc atttaaatta gtttttttgct tttttctac ctgataatct 4500 ctttaacaag atgcaacaag acagaattat taaaattaaa cctaaagtta agttacagat 4560
ttaaaggcat tatgatatta agcattaaaa ttggagatta aaatgtacaa aacagggttt 4620
tccttatgaa caaaccttac agggtaaatt gtttttttt ctaaatgtca ttaaatttat 4680
ttgtactcag aactgttact aataaaaatt aaaaatgcaa aaaaaaaaa 4729

<210> SEQ ID NO 49
<211> LENGTH: 697
<212> TYPE: PRT
<213> ORGANISM: Homo sapiens

<400> SEQUENCE: 49

Met Gly Glu Arg Ala Gly Ser Pro Gly Thr Asp Gln Glu Arg Lys Ala
1 5 10 15

Gly Lys His His Tyr Ser Tyr Leu Ser Asp Phe Glu Thr Pro Gln Ser
20 25 30

Ser Gly Arg Ser Ser Leu Val Ser Ser Ser Pro Ala Ser Val Arg Arg
35 40 45

Lys Asn Pro Lys Arg Gln Thr Ser Asp Gly Gln Val His His Gln Ala

```
    50                  55                  60

Pro Arg Lys Pro Ser Pro Lys Gly Leu Pro Asn Arg Lys Gly Val Arg
65                  70                  75                  80

Val Gly Phe Arg Ser Gln Ser Leu Asn Arg Glu Pro Leu Arg Lys Asp
                85                  90                  95

Thr Asp Leu Val Thr Lys Arg Ile Leu Ser Ala Arg Leu Leu Lys Ile
            100                 105                 110

Asn Glu Leu Gln Asn Glu Val Ser Glu Leu Gln Val Lys Leu Ala Glu
        115                 120                 125

Leu Leu Lys Glu Asn Lys Ser Leu Lys Arg Leu Gln Tyr Arg Gln Glu
    130                 135                 140

Lys Ala Leu Asn Lys Phe Glu Asp Ala Glu Asn Glu Ile Ser Gln Leu
145                 150                 155                 160

Ile Phe Arg His Asn Asn Glu Ile Thr Ala Leu Lys Glu Arg Leu Arg
                165                 170                 175

Lys Ser Gln Glu Lys Glu Arg Ala Thr Glu Lys Arg Val Lys Asp Thr
            180                 185                 190

Glu Ser Glu Leu Phe Arg Thr Lys Phe Ser Leu Gln Lys Leu Lys Glu
        195                 200                 205

Ile Ser Glu Ala Arg His Leu Pro Glu Arg Asp Asp Leu Ala Lys Lys
    210                 215                 220

Leu Val Ser Ala Glu Leu Lys Leu Asp Asp Thr Glu Arg Arg Ile Lys
225                 230                 235                 240

Glu Leu Ser Lys Asn Leu Glu Leu Ser Thr Asn Ser Phe Gln Arg Gln
                245                 250                 255

Leu Leu Ala Glu Arg Lys Arg Ala Tyr Glu Ala His Asp Glu Asn Lys
            260                 265                 270

Val Leu Gln Lys Glu Val Gln Arg Leu Tyr His Lys Leu Lys Glu Lys
        275                 280                 285

Glu Arg Glu Leu Asp Ile Lys Asn Ile Tyr Ser Asn Arg Leu Pro Lys
    290                 295                 300

Ser Ser Pro Asn Lys Glu Lys Glu Leu Ala Leu Arg Lys Asn Ala Ala
305                 310                 315                 320

Cys Gln Ser Asp Phe Ala Asp Leu Cys Thr Lys Gly Val Gln Thr Met
                325                 330                 335

Glu Asp Phe Lys Pro Glu Glu Tyr Pro Leu Thr Pro Glu Thr Ile Met
            340                 345                 350

Cys Tyr Glu Asn Lys Trp Glu Glu Pro Gly His Leu Thr Leu Asp Leu
        355                 360                 365

Gln Ser Gln Lys Gln Asp Arg His Gly Glu Ala Gly Ile Leu Asn Pro
    370                 375                 380

Ile Met Glu Arg Glu Glu Lys Phe Val Thr Asp Glu Glu Leu His Val
385                 390                 395                 400

Val Lys Gln Glu Val Glu Lys Leu Glu Asp Glu Trp Glu Arg Glu Glu
                405                 410                 415

Leu Asp Lys Lys Gln Lys Glu Lys Ala Ser Leu Leu Glu Arg Glu Glu
            420                 425                 430

Lys Pro Glu Trp Glu Thr Gly Arg Tyr Gln Leu Gly Met Tyr Pro Ile
        435                 440                 445

Gln Asn Met Asp Lys Leu Gln Gly Glu Glu Glu Glu Arg Leu Lys Arg
    450                 455                 460

Glu Met Leu Leu Ala Lys Leu Asn Glu Ile Asp Arg Glu Leu Gln Asp
465                 470                 475                 480
```

```
Ser Arg Asn Leu Lys Tyr Pro Val Leu Pro Leu Leu Pro Asp Phe Glu
                485                 490                 495

Ser Lys Leu His Ser Pro Glu Arg Ser Pro Lys Thr Tyr Arg Phe Ser
            500                 505                 510

Glu Ser Ser Glu Arg Leu Phe Asn Gly His His Leu Gln Asp Ile Ser
        515                 520                 525

Phe Ser Thr Pro Lys Gly Glu Gly Gln Asn Ser Gly Asn Val Arg Ser
    530                 535                 540

Pro Ala Ser Pro Asn Glu Phe Ala Phe Gly Ser Tyr Val Pro Ser Phe
545                 550                 555                 560

Ala Lys Thr Ser Glu Arg Ser Asn Pro Phe Ser Gln Lys Ser Ser Phe
                565                 570                 575

Leu Asp Phe Gln Arg Asn Ser Met Glu Lys Leu Ser Lys Asp Gly Val
            580                 585                 590

Asp Leu Ile Thr Arg Lys Glu Lys Lys Ala Asn Leu Met Glu Gln Leu
        595                 600                 605

Phe Gly Ala Ser Gly Ser Ser Thr Ile Ser Ser Lys Ser Ser Asp Pro
    610                 615                 620

Asn Ser Val Ala Ser Ser Lys Gly Asp Ile Asp Pro Leu Asn Phe Leu
625                 630                 635                 640

Pro Gly Asn Lys Gly Ser Arg Asp Gln Glu His Asp Glu Asp Glu Gly
                645                 650                 655

Phe Phe Leu Ser Glu Gly Arg Ser Phe Asn Pro Asn Arg His Arg Leu
            660                 665                 670

Lys His Ala Asp Asp Lys Pro Ala Val Lys Ala Ala Asp Ser Val Glu
        675                 680                 685

Asp Glu Ile Glu Glu Val Ala Leu Arg
    690                 695
```

<210> SEQ ID NO 50
<211> LENGTH: 3771
<212> TYPE: DNA
<213> ORGANISM: Artificial Sequence
<220> FEATURE:
<223> OTHER INFORMATION: pR2.1 from ATG to L-opsin gene

<400> SEQUENCE: 50

```
ccagggtgag attatgaggc tgagctgaga atatcaagac tgtaccgagt agggggcctt     60

ggcaagtgtg gagagcccgg cagctggggc agagggcgga gtacggtgtg cgtttacgga    120

cctcttcaaa cgaggtagga aggtcagaag tcaaaaaggg aacaaatgat gtttaaccac    180

acaaaaatga aaatccaatg gttggatatc cattccaaat acacaaaggc aacggataag    240

tgatccgggc caggcacaga aggccatgca cccgtaggat tgcactcaga gctcccaaat    300

gcataggaat agaagggtgg gtgcaggagg ctgaggggtg gggaaagggc atgggtgttt    360

catgaggaca gagcttccgt ttcatgcaat gaaaagagtt tggagacgga tggtggtgac    420

tggactatac acttacacac ggtagcgatg gtacactttg tattatgtat attttaccac    480

gatcttttta aagtgtcaaa ggcaaatggc caaatggttc cttgtcctat agctgtagca    540

gccatcggct gttagtgaca aagcccctga gtcaagatga cagcagcccc cataactcct    600

aatcggctct cccgcgtgga gtcatttagg agtagtcgca ttagagacaa gtccaacatc    660

taatcttcca ccctggccag ggccccagct ggcagcgagg gtgggagact ccgggcagag    720

cagagggcgc tgacattggg gcccggcctg gcttgggtcc ctctggcctt tccccagggg    780
```

-continued

```
ccctctttcc ttggggcttt cttgggccgc cactgctccc gctcctctcc ccccatccca    840
ccccctcacc ccctcgttct tcatatcctt ctctagtgct ccctccactt tcatccaccc    900
ttctgcaaga gtgtgggacc acaaatgagt tttcacctgg cctggggaca cacgtgcccc    960
cacaggtgct gagtgacttt ctaggacagt aatctgcttt aggctaaaat gggacttgat   1020
cttctgttag ccctaatcat caattagcag agccggtgaa ggtgcagaac ctaccgcctt   1080
tccaggcctc ctcccacctc tgccacctcc actctccttc ctgggatgtg gggctggca    1140
cacgtgtggc ccagggcatt ggtgggattg cactgagctg ggtcattagc gtaatcctgg   1200
acaagggcag acagggcgag cggagggcca gctccggggc tcaggcaagg ctgggggctt   1260
cccccagaca ccccactcct cctctgctgg acccccactt catagggcac ttcgtgttct   1320
caaagggctt ccaaatagca tggtggcctt ggatgcccag ggaagcctca gagttgctta   1380
tctccctcta gacagaaggg gaatctcggt caagagggag aggtcgccct gttcaaggcc   1440
acccagccag ctcatggcgg taatgggaca aggctggcca gccatcccac cctcagaagg   1500
gacccggtgg ggcaggtgat ctcagaggag gctcacttct gggtctcaca ttcttggatc   1560
cggttccagg cctcggccct aaatagtctc cctgggcttt caagagaacc acatgagaaa   1620
ggaggattcg ggctctgagc agtttcacca cccacccccc agtctgcaaa tcctgacccg   1680
tgggtccacc tgccccaaag gcggacgcag gacagtagaa gggaacagag aacacataaa   1740
cacagagagg gccacagcgg ctcccacagt caccgccacc ttcctggcgg ggatgggtgg   1800
ggcgtctgag tttggttccc agcaaatccc tctgagccgc ccttgcgggc tcgcctcagg   1860
agcaggggag caagaggtgg gaggaggagg tctaagtccc aggcccaatt aagagatcag   1920
gtagtgtagg gtttgggagc ttttaaggtg aagaggcccg ggctgatccc acaggccagt   1980
ataaagcgcc gtgaccctca ggtgatgcgc cagggccggc tgccgtcggg gacagggctt   2040
tccatagcca tgctagagga tccggtactc gaggaactga aaaaccagaa agttaactgg   2100
taagtttagt ctttttgtct tttatttcag gtcccggatc cggtggtggt gcaaatcaaa   2160
gaactgctcc tcagtggatg ttgcctttac ttctaggcct gtacggaagt gttacttctg   2220
ctctaaaagc tgcggaattg tacccgcggc cgcgggacag ggctttccat agccatggcc   2280
cagcagtgga gcctccaaag gctcgcaggc cgccatccgc aggacagcta tgaggacagc   2340
acccagtcca gcatcttcac ctacaccaac agcaactcca ccagaggccc cttcgaaggc   2400
ccgaattacc acatcgctcc cagatgggtg taccacctca ccagtgtctg gatgatcttt   2460
gtggtcactg catccgtctt cacaaatggg cttgtgctgg cggccaccat gaagttcaag   2520
aagctgcgcc acccgctgaa ctggatcctg gtgaacctgg cggtcgctga cctagcagag   2580
accgtcatcg ccagcactat cagcattgtg aaccaggtct ctggctactt cgtgctgggc   2640
caccctatgt gtgtcctgga gggctacacc gtctccctgt gtgggatcac aggtctctgg   2700
tctctggcca tcatttcctg ggagagatgg atggtggtct gcaagccctt tggcaatgtg   2760
agatttgatg ccaagctggc catcgtgggc attgccttct cctggatctg gtctgctgtg   2820
tggacagccc cgcccatctt tggttggagc aggtactggc cccacggcct gaagacttca   2880
tgcggcccag acgtgttcag cggcagctcg taccccgggg tgcagtctta catgattgtc   2940
ctcatggtca cctgctgcat catcccactc gctatcatca tgctctgcta cctccaagtg   3000
tggctggcca tccgagcggt ggcaaagcag cagaaagagt ctgaatccac ccagaaggca   3060
gagaaggaag tgacgcgcat ggtggtggtg atgatctttg cgtactgcgt ctgctgggga   3120
ccctacacct tcttcgcatg ctttgctgct gccaaccctg gttacgcctt ccaccctttg   3180
```

atggctgccc tgccggccta ctttgccaaa agtgccacta tctacaaccc cgttatctat 3240
gtctttatga accggcagtt tcgaaactgc atcttgcagc ttttcgggaa gaaggttgac 3300
gatggctctg aactctccag cgcctccaaa acggaggtct caactgtgtc ctcgacccag 3360
gtagggccta actgaggtct gcctcctacc catcccgccc accggggctt tggccacctc 3420
tcctttcccc ctccttctcc atccctgtaa aataaatgta atttatcttt gccaaaacca 3480
aaaaaaacgg aattcgtaat catgtcatag ctgtttcctg tgtgaaattg ttatccgctc 3540
acaattccac acaacatacg aggcggccgc gcggatccag acatgataag atacattgat 3600
gagtttggac aaaccacaac tagaatgcag tgaaaaaaat gctttatttg tgaaatttgt 3660
gatgctattg ctttatttgt aaccattata agctgcaata aacaagttaa caacaacaat 3720
tgcattcatt ttatgtttca ggttcagggg gaggtgtggg aggtttttta g 3771

<210> SEQ ID NO 51
<211> LENGTH: 36
<212> TYPE: DNA
<213> ORGANISM: Homo sapiens

<400> SEQUENCE: 51
gacttgatct tctgttagcc ctaatcatca attagc 36

<210> SEQ ID NO 52
<211> LENGTH: 1565
<212> TYPE: DNA
<213> ORGANISM: Homo sapiens

<400> SEQUENCE: 52
cctacagcag ccagggtgag attatgaggc tgagctgaga atatcaagac tgtaccgagt 60
agggggcctt ggcaagtgtg gagagcccgg cagctggggc agagggcgga gtacggtgtg 120
cgtttacgga cctcttcaaa cgaggtagga aggtcagaag tcaaaaaggg aacaaatgat 180
gtttaaccac acaaaaatga aaatccaatg gttggatatc cattccaaat acacaaaggc 240
aacggataag tgatccgggc caggcacaga aggccatgca cccgtaggat tgcactcaga 300
gctcccaaat gcataggaat agaagggtgg gtgcaggagg ctgaggggtg gggaaagggc 360
atgggtgttt catgaggaca gagcttccgt ttcatgcaat gaaaagagtt tggagacgga 420
tggtggtgac tggactatac acttacacac ggtagcgatg gtacactttg tattatgtat 480
attttaccac gatcttttta aagtgtcaaa ggcaaatggc caaatggttc cttgtcctat 540
agctgtagca gccatcggct gttagtgaca aagcccctga gtcaagatga cagcagcccc 600
cataactcct aatcggctct cccgcgtgga gtcatttagg agtagtcgca ttagagacaa 660
gtccaacatc taatcttcca ccctggccag ggccccagct ggcagcgagg gtgggagact 720
ccgggcagag cagagggcgc tgacattggg gcccggcctg gcttgggtcc ctctggcctt 780
tccccagggg ccctctttcc ttggggcttt cttgggccgc cactgctccc gctcctctcc 840
ccccatccca ccccctcacc ccctcgttct tcatatcctt ctctagtgct ccctccactt 900
tcatccaccc ttctgcaaga gtgtgggacc acaaatgagt tttcacctgg cctggggaca 960
cacgtgcccc cacaggtgct gagtgacttt ctaggacagt aatctgcttt aggctaaaat 1020
gggacttgat cttctgttag ccctaatcat caattagcag agccggtgaa ggtgcagaac 1080
ctaccgcctt tccaggcctc ctcccacctc tgccacctcc actctccttc ctgggatgtg 1140
ggggctggca cacgtgtggc ccagggcatt ggtgggattg cactgagctg ggtcattagc 1200

```
gtaatcctgg acaagggcag acagggcgag cggagggcca gctccggggc tcaggcaagg   1260

ctgggggctt cccccagaca ccccactcct cctctgctgg acccccactt catagggcac   1320

ttcgtgttct caaagggctt ccaaatagca tggtggcctt ggatgcccag ggaagcctca   1380

gagttgctta tctccctcta gacagaaggg gaatctcggt caagagggag aggtcgccct   1440

gttcaaggcc acccagccag ctcatggcgg taatgggaca aggctggcca gccatcccac   1500

cctcagaagg gacccggtgg ggcaggtgat ctcagaggag gctcacttct gggtctcaca   1560

ttctt                                                               1565


<210> SEQ ID NO 53
<211> LENGTH: 491
<212> TYPE: DNA
<213> ORGANISM: Homo sapiens

<400> SEQUENCE: 53

ggttccaggc ctcggcccta aatagtctcc ctgggctttc aagagaacca catgagaaag     60

gaggattcgg gctctgagca gtttcaccac ccaccccca gtctgcaaat cctgacccgt    120

gggtccacct gccccaaagg cggacgcagg acagtagaag ggaacagaga acacataaac   180

acagagaggg ccacagcggc tcccacagtc accgccacct tcctggcggg gatgggtggg   240

gcgtctgagt ttggttccca gcaaatccct ctgagccgcc cttgcgggct cgcctcagga   300

gcaggggagc aagaggtggg aggaggaggt ctaagtccca ggcccaatta agagatcagg   360

tagtgtaggg tttgggagct tttaaggtga agaggcccgg gctgatccca caggccagta   420

taaagcgccg tgaccctcag gtgatgcgcc agggccggct gccgtcgggg acagggcttt   480

ccatagccat g                                                        491


<210> SEQ ID NO 54
<211> LENGTH: 491
<212> TYPE: DNA
<213> ORGANISM: Homo sapiens

<400> SEQUENCE: 54

agtagaaacg gggtttcacc atgttagtca ggctggtcgg gaactcctga cctcaggaga     60

tctacccgcc ttggcctccc aaagtgctgg gattacaggc gtgtgccact gtgcccagcc   120

actttttttt agacagagtc ttggtctgtt gcccaggcta gagttcagtg gcgccatctc   180

agctcactgc aacctccgcc tcccagattc aagcgattct cctgcctcga cctcccagta   240

gctgggatta caggtttcca gcaaatccct ctgagccgcc cccgggggct cgcctcagga   300

gcaaggaagc aaggggtggg aggaggaggt ctaagtccca ggcccaatta agagatcaga   360

tggtgtagga tttgggagct tttaaggtga agaggcccgg gctgatccca ctggccggta   420

taaagcaccg tgaccctcag gtgacgcacc agggccggct gccgtcgggg acagggcttt   480

ccatagccat g                                                        491


<210> SEQ ID NO 55
<211> LENGTH: 239
<212> TYPE: DNA
<213> ORGANISM: Homo sapiens

<400> SEQUENCE: 55

ggtttccagc aaatccctct gagccgcccc cgggggctcg cctcaggagc aaggaagcaa     60

ggggtgggag gaggaggtct aagtcccagg cccaattaag agatcagatg gtgtaggatt   120

tgggagcttt taaggtgaag aggcccgggc tgatcccact ggccggtata aagcaccgtg   180
```

-continued accctcaggt gacgcaccag ggccggctgc cgtcggggac agggctttcc atagccatg 239

<210> SEQ ID NO 56
<211> LENGTH: 169
<212> TYPE: RNA
<213> ORGANISM: Artificial Sequence
<220> FEATURE:
<223> OTHER INFORMATION: Synthesized 5'UTR

<400> SEQUENCE: 56
gccagggccg gcugccgucg gggacagggc uuuccauagc caugcuagag gauccgguac 60
ucgaggaacu gaaaaaccag aaaguuaacu ggccuguacg gaaguguuac uucugcucua 120
aaagcugcgg aauuguaccc gcggccgcgg gacagggcuu uccauagcc 169

<210> SEQ ID NO 57
<211> LENGTH: 77
<212> TYPE: RNA
<213> ORGANISM: Artificial Sequence
<220> FEATURE:
<223> OTHER INFORMATION: Synthesized 5'UTR

<400> SEQUENCE: 57
gcaccagggc cggcugccgu cggggacagg gcuuuccaua gcccaggccu cuagagagga 60
guaucagugc cgccacc 77

<210> SEQ ID NO 58
<211> LENGTH: 213
<212> TYPE: DNA
<213> ORGANISM: Homo sapiens

<400> SEQUENCE: 58
aacggctagc ctgaggagct gctgcgacag tccactacct ttttcgagag tgactcccgt 60
tgtcccaagg cttcccagag cgaacctgtg cggctgcagg caccggcgcg tcgagtttcc 120
ggcgtccgga aggaccgagc tcttctcgcg gatccagtgt tccgtttcca gcccccaatc 180
tcagagccga gccgacagag agcagggaac cgc 213

<210> SEQ ID NO 59
<211> LENGTH: 97
<212> TYPE: DNA
<213> ORGANISM: Artificial Sequence
<220> FEATURE:
<223> OTHER INFORMATION: pR2.1 intron sequence

<400> SEQUENCE: 59
gtaagtttag tctttttgtc ttttatttca ggtcccggat ccggtggtgg tgcaaatcaa 60
agaactgctc ctcagtggat gttgccttta cttctag 97

<210> SEQ ID NO 60
<211> LENGTH: 133
<212> TYPE: DNA
<213> ORGANISM: Artificial Sequence
<220> FEATURE:
<223> OTHER INFORMATION: MNTC intron sequence

<400> SEQUENCE: 60
gtaagtatca aggttacaag acaggtttaa ggagaccaat agaaactggg cttgtcgaga 60
cagagaagac tcttgcgttt ctgataggca cctattggtc ttactgacat ccactttgcc 120
tttctctcca cag 133

<210> SEQ ID NO 61
<211> LENGTH: 1095
<212> TYPE: DNA
<213> ORGANISM: Homo sapiens

<400> SEQUENCE: 61
atggcccagc agtggagcct ccaaaggctc gcaggccgcc atccgcagga cagctatgag 60
gacagcaccc agtccagcat cttcacctac accaacagca actccaccag aggccccttc 120
gaaggcccga attaccacat cgctcccaga tgggtgtacc acctcaccag tgtctggatg 180
atctttgtgg tcactgcatc cgtcttcaca aatgggcttg tgctggcggc caccatgaag 240
ttcaagaagc tgcgccaccc gctgaactgg atcctggtga acctggcggt cgctgaccta 300
gcagagaccg tcatcgccag cactatcagc attgtgaacc aggtctctgg ctacttcgtg 360
ctgggccacc ctatgtgtgt cctggagggc tacaccgtct ccctgtgtgg gatcacaggt 420
ctctggtctc tggccatcat ttcctgggag aggtggctgg tggtgtgcaa gccctttggc 480
aatgtgagat ttgatgccaa gctggccatc gtgggcattg ccttctcctg gatctggtct 540
gctgtgtgga cagccccgcc catctttggt tggagcaggt actggcccca cggcctgaag 600
acttcatgcg gcccagacgt gttcagcggc agctcgtacc ccggggtgca gtcttacatg 660
attgtcctca tggtcacctg ctgcatcatc ccactcgcta tcatcatgct ctgctacctc 720
caagtgtggc tggccatccg agcggtggca aagcagcaga aagagtctga atccacccag 780
aaggcagaga aggaagtgac gcgcatggtg gtggtgatga tctttgcgta ctgcgtctgc 840
tggggaccct acaccttctt cgcatgcttt gctgctgcca accctggtta cgccttccac 900
cctttgatgg ctgccctgcc ggcctacttt gccaaaagtg ccactatcta caaccccgtt 960
atctatgtct ttatgaaccg gcagtttcga aactgcatct tgcagctttt cgggaagaag 1020
gttgacgatg gctctgaact ctccagcgcc tccaaaacgg aggtctcatc tgtgtcctcg 1080
gtatcgcctg catga 1095

<210> SEQ ID NO 62
<211> LENGTH: 1095
<212> TYPE: DNA
<213> ORGANISM: Homo sapiens

<400> SEQUENCE: 62
atggcccagc agtggagcct ccaaaggctc gcaggccgcc atccgcagga cagctatgag 60
gacagcaccc agtccagcat cttcacctac accaacagca actccaccag aggccccttc 120
gaaggcccga attaccacat cgctcccaga tgggtgtacc acctcaccag tgtctggatg 180
atctttgtgg tcattgcatc cgtcttcaca aatgggcttg tgctggcggc caccatgaag 240
ttcaagaagc tgcgccaccc gctgaactgg atcctggtga acctggcggt cgctgacctg 300
gcagagaccg tcatcgccag cactatcagc gttgtgaacc aggtctatgg ctacttcgtg 360
ctgggccacc ctatgtgtgt cctggagggc tacaccgtct ccctgtgtgg gatcacaggt 420
ctctggtctc tggccatcat ttcctgggag agatggatgg tggtctgcaa gccctttggc 480
aatgtgagat ttgatgccaa gctggccatc gtgggcattg ccttctcctg gatctgggct 540
gctgtgtgga cagccccgcc catctttggt tggagcaggt actggcccca cggcctgaag 600
acttcatgcg gcccagacgt gttcagcggc agctcgtacc ccggggtgca gtcttacatg 660
attgtcctca tggtcacctg ctgcatcacc ccactcagca tcatcgtgct ctgctacctc 720
caagtgtggc tggccatccg agcggtggca aagcagcaga aagagtctga atccacccag 780
aaggcagaga aggaagtgac gcgcatggtg gtggtgatgg tcctggcatt ctgcttctgc 840
tggggaccat acgccttctt cgcatgcttt gctgctgcca accctggcta ccccttccac 900
cctttgatgg ctgccctgcc ggccttcttt gccaaaagtg ccactatcta caaccccgtt 960
atctatgtct ttatgaaccg gcagtttcga aactgcatct tgcagctttt cgggaagaag 1020
gttgacgatg gctctgaact ctccagcgcc tccaaaacgg aggtctcatc tgtgtcctcg 1080
gtatcgcctg catga 1095

<210> SEQ ID NO 63
<211> LENGTH: 1092
<212> TYPE: DNA
<213> ORGANISM: Homo sapiens

<400> SEQUENCE: 63
atggcccagc agtggagcct ccaaaggctc gcaggccgcc atccgcagga cagctatgag 60
gacagcaccc agtccagcat cttcacctac accaacagca actccaccag aggccccttc 120
gaaggcccga attaccacat cgctcccaga tgggtgtacc acctcaccag tgtctggatg 180
atctttgtgg tcattgcatc cgtcttcaca aatgggcttg tgctggcggc caccatgaag 240
ttcaagaagc tgcgccaccc gctgaactgg atcctggtga acctggcggt cgctgacctg 300
gcagagaccg tcatcgccag cactatcagc gttgtgaacc aggtctatgg ctacttcgtg 360
ctgggccacc ctatgtgtgt cctggagggc tacaccgtct ccctgtgtgg gatcacaggt 420
ctctggtctc tggccatcat ttcctgggag agatggctgg tggtctgcaa gccctttggc 480
aatgtgagat ttgatgccaa gctggccatc gtgggcattg ccttctcctg gatctgggct 540
gctgtgtgga cagccccgcc catctttggt tggagcaggt actggcccta cggcctgaag 600
acttcatgcg gcccagacgt gttcagcggc agctcgtacc ccggggtgca gtcttacatg 660
attgtcctca tggtcacctg ctgcatcacc ccactcagca tcatcgtgct ctgctacctc 720
caagtgtggc tggccatccg agcggtggca aagcagcaga aagagtctga atccacccag 780
aaggcagaga aggaagtgac gcgcatggtg gtggtgatgg tcctggcatt ctgcttctgc 840
tggggaccat acgccttctt cgcatgcttt gctgctgcca accctggcta ccccttccac 900
cctttgatgg ctgccctgcc gtcctacttt gccaaaagtg ccactatcta caaccccgtt 960
atctatgtct ttatgaaccg gcagtttcga aactgcatct tgcagctttt cgggaagaag 1020
gttgacgatg gctctgaact ctccagcgcc tccaaaacgg aggtctcatc tgtgtcctcg 1080
gtatcgcctg ca 1092

<210> SEQ ID NO 64
<211> LENGTH: 1092
<212> TYPE: DNA
<213> ORGANISM: Homo sapiens

<400> SEQUENCE: 64
atggcccagc agtggagcct gcagcggctg gccggccggc acccccagga cagctacgag 60
gacagcaccc agagcagcat cttcacctac accaacagca acagcacccg gggccccttc 120
gagggcccca actaccacat cgcccccggg tgggtgtacc acctgaccag cgtgtggatg 180
atcttcgtgg tgatcgccag cgtgttcacc aacggcctgg tgctggccgc caccatgaag 240
ttcaagaagc tgcggcaccc cctgaactgg atcctggtga acctggccgt ggccgacctg 300
gccgagaccg tgatcgccag caccatcagc gtggtgaacc aggtgtacgg ctacttcgtg 360
ctgggccacc ccatgtgcgt gctggagggc tacaccgtga gcctgtgcgg catcaccggc 420
ctgtggagcc tggccatcat cagctgggag cggtggctgg tggtgtgcaa gcccttcggc 480
aacgtgcggt tcgacgccaa gctggccatc gtgggcatcg ccttcagctg gatctgggcc 540
gccgtgtgga ccgccccccc catcttcggc tggagccggt actggcccta cggcctgaag 600
accagctgcg gccccgacgt gttcagcggc agcagctacc ccggcgtgca gagctacatg 660
atcgtgctga tggtgacctg ctgcatcacc cccctgagca tcatcgtgct gtgctacctg 720
caggtgtggc tggccatccg ggccgtggcc aagcagcaga aggagagcga gagcacccag 780
aaggccgaga aggaggtgac ccggatggtg gtggtgatgg tgctggcctt ctgcttctgc 840
tggggcccct acgccttctt cgcctgcttc gccgccgcca accccggcta ccccttccac 900
cccctgatgg ccgccctgcc cagctacttc gccaagagcg ccaccatcta caaccccgtg 960
atctacgtgt tcatgaaccg gcagttccgg aactgcatcc tgcagctgtt cggcaagaag 1020
gtggacgacg gcagcgagct gagcagcgcc agcaagaccg aggtgagcag cgtgagcagc 1080
gtgagccccg cc 1092

<210> SEQ ID NO 65
<211> LENGTH: 1092
<212> TYPE: DNA
<213> ORGANISM: Homo sapiens

<400> SEQUENCE: 65
atggcccagc agtggagcct gcagcggctg gccggccggc acccccagga cagctacgag 60
gacagcaccc agagcagcat cttcacctac accaacagca acagcacccg gggccccttc 120
gagggcccca actaccacat cgcccccggg tgggtgtacc acctgaccag cgtgtggatg 180
atcttcgtgg tgatcgccag cgtgttcacc aacggcctgg tgctggccgc cacaatgaag 240
ttcaagaagc tgcggcaccc cctgaactgg atcctggtga acctggccgt ggccgacctg 300
gccgagaccg tgatcgccag cacaatcagc gtggtgaacc aggtgtacgg ctacttcgtg 360
ctgggccacc ccatgtgcgt gctggagggc tacaccgtga gcctgtgcgg catcaccggc 420
ctgtggagcc tggccatcat cagctgggag cggtggctgg tggtgtgcaa gcccttcggc 480
aacgtgcggt tcgacgccaa gctggctatc gtgggaatcg ccttcagctg gatctgggcc 540
gccgtgtgga ccgccccccc tatcttcggc tggagccggt actggcccta cggcctgaag 600
accagctgcg gccccgacgt gttcagcggc agcagctacc ccggcgtgca gagctacatg 660
atcgtgctga tggtgacctg ctgcatcacc cccctgagca tcatcgtgct gtgctacctg 720
caggtgtggc tggccatccg ggccgtggcc aagcagcaga aggagagcga gagcacccag 780
aaggccgaga aggaggtgac ccggatggtg gtggtgatgg tgctggcctt ctgcttctgc 840
tggggcccct acgccttctt cgcctgcttc gccgccgcca accccggcta ccccttccac 900
cccctgatgg ccgccctgcc cagctacttc gccaagagcg ccaccatcta caaccccgtg 960
atctacgtgt tcatgaaccg gcagttccgg aactgcatcc tgcagctgtt cggcaagaag 1020
gtggacgacg gcagcgagct gagcagcgcc agcaagaccg aggtgtcaag cgtgagcagc 1080
gtgagccccg cc 1092

<210> SEQ ID NO 66
<211> LENGTH: 1047
<212> TYPE: DNA
<213> ORGANISM: Homo sapiens

<400> SEQUENCE: 66

```
atgagaaaaa tgtcggagga agagttttat ctgttcaaaa atatctcttc agtggggccg      60

tgggatgggc ctcagtacca cattgcccct gtctgggcct tctacctcca ggcagctttc     120

atgggcactg tcttccttat agggttccca ctcaatgcca tggtgctggt ggccacactg     180

cgctacaaaa agttgcggca gcccctcaac tacattctgg tcaacgtgtc cttcggaggc     240

ttcctcctct gcatcttctc tgtcttccct gtcttcgtcg ccagctgtaa cggatacttc     300

gtcttcggtc gccatgtttg tgctttggag ggcttcctgg gcactgtagc aggtctggtt     360

acaggatggt cactggcctt cctggccttt gagcgctaca ttgtcatctg taagcccttc     420

ggcaacttcc gcttcagctc caagcatgca ctgacggtgg tcctggctac ctggaccatt     480

ggtattggcg tctccatccc acccttcttt ggctggagcc ggttcatccc tgagggcctg     540

cagtgttcct gtggccctga ctggtacacc gtgggcacca aataccgcag cgagtcctat     600

acgtggttcc tcttcatctt ctgcttcatt gtgcctctct ccctcatctg cttctcctac     660

actcagctgc tgagggccct gaaagctgtt gcagctcagc agcaggagtc agctacgacc     720

cagaaggctg aacgggaggt gagccgcatg gtggttgtga tggtaggatc cttctgtgtc     780

tgctacgtgc cctacgcggc cttcgccatg tacatggtca acaaccgtaa ccatgggctg     840

gacttacggc ttgtcaccat tccttcattc ttctccaaga gtgcttgcat ctacaatccc     900

atcatctact gcttcatgaa taagcagttc caagcttgca tcatgaagat ggtgtgtggg     960

aaggccatga cagatgaatc cgacacatgc agctcccaga aaacagaagt ttctactgtc    1020

tcgtctaccc aagttggccc caactga                                       1047
```

<210> SEQ ID NO 67
<211> LENGTH: 1064
<212> TYPE: DNA
<213> ORGANISM: Homo sapiens

<400> SEQUENCE: 67

```
acccagtcga gcatcttcac ctataccaac agcaacagta ccagaggtcc ctttgaaggc      60

cccaattatc acattgctcc caggtgggtg taccacctca ccagcgcctg gatgatcttt     120

gtggtcattg catcagtctt cactaatggg cttgtgctgg cagccaccat acggttcaag     180

aagctgcgcc atcctctgaa ttggattctg gtgaacttgg caattgctga cctaatagag     240

accatcattg ctggcactat cagtgttgtg aaccaaatct atggctactt cgtactaggc     300

caccctctgt gcgtcgtgga aggctacatt gtcgccctgt gtggcatcac aggcctctgg     360

tccctggccg ttatttcctg ggagaggtgg ctggtggtct gcaagccctt tggcaatatg     420

agatttgatg ctaagctggc cactgtggga atcatctttt cttgggtctg ggctgctgtg     480

tggacagccc caccaatctt tggttggagc aggtactggc cttatggcct gaagacatcc     540

tgtggtccag acgtgttcag cggcacttcg tatcctgggg ttcagtctta tatgatggtt     600

ctcatggtca cgtgctgcat cttcccactt agcatcatcg tgctctgcta cctccaagtg     660

tggctggcca tccgagcagt agcaaagcaa caaaaagaat ctgagtctac ccagaaggct     720

gagaaggagg tgacacgcat ggtgcttgtg atgatcttcg catactgcat ctgctggggc     780

ccctacgctg tctttgcatg ctttgctact gcccaccctg gctatgcatt ccacccactt     840

gtggcctccc taccatctta ctttgcgaaa agtgccacta tctacaaccc cattatctat     900

gtctttatga accgacagtt tcaaaactgc atcttacagc tctttggaaa gaaggttgat     960

gatagctctg aacttgccag tacctccaaa acagaaacct catctgaagc cgaattccag    1020
```

cacactggcg gccgtactag tgatccgagt cgtagcctgg accc 1064

<210> SEQ ID NO 68
<211> LENGTH: 1041
<212> TYPE: DNA
<213> ORGANISM: Homo sapiens

<400> SEQUENCE: 68
atgtcaggag aggatgactt ttacctgttt cagaatatct cttcggtggg gccctgggat 60
gggcctcagt accaccttgc tcctgtctgg gccttccgcc tccaggcagc cttcatggga 120
tttgtcttct ttgtggggac ccccactcaat gccatagtgc tggtggccac actgcattac 180
aaaaagttgc gacagcccct caactatatt ctggtcaatg tatccctcgg gggcttcctc 240
ttctgcatct tctctgtctt cacagtcttc atcgccagct gtcacggata cttcctcttt 300
ggtcgccatg tttgtgctct ggaggccttc ttgggctctg tagcaggtct agtgacagga 360
tggtcattgg ctttcctggc ttttgaacgc tacgttgtca tctgtaaacc cttcggcagc 420
atccgcttca actccaagca tgcactgatg gtggtcctgg ctacttggat tattggtatc 480
ggggtgtcca tcccaccctt ttttggctgg agcaggttca tccctgaggg cctgcagtgc 540
tcctgtggcc cagactggta cactgtgggc accaagtatc gaagcgagta ctacacctgg 600
ttcctcttca tcttctgttt catcattcct ctttccctca tctgcttctc ctactcccag 660
ttgctgagga ctctcagagc tgtggcagct cagcagcaag agtctgctac gacacaaaag 720
gctgaacggg aggtgagtca tatggtggtg gtgatggtgg gatccttctg tctctgctac 780
gtgccctatg ctgccctggc catgtacatg gtcaacaatc ggaaccacgg gctggactta 840
cggcttgtca ccatccccgc cttcttttcc aagagctcct gtgtctacaa ccccatcatc 900
tactgcttca tgaataagca gttccgggct tgcattctgg agatggtgtg caggaagccc 960
atggcagacg aatctgacgt gtctggctct cagaaaacag aagtttctac tgtctcttct 1020
agcaaagttg gccctcactg a 1041

<210> SEQ ID NO 69
<211> LENGTH: 930
<212> TYPE: DNA
<213> ORGANISM: Artificial Sequence
<220> FEATURE:
<223> OTHER INFORMATION: Synthetic construct channel rhodopsin

<400> SEQUENCE: 69
atggactatg gcggcgcttt gtctgccgtc ggacgcgaac ttttgttcgt tactaatcct 60
gtggtggtga acgggtccgt cctggtccct gaggatcaat gttactgtgc cggatggatt 120
gaatctcgcg gcacgaacgg cgctcagacc gcgtcaaatg tcctgcagtg gcttgcagca 180
ggattcagca ttttgctgct gatgttctat gcctaccaaa cctggaaatc tacatgcggc 240
tgggaggaga tctatgtgtg cgccattgaa atggttaagg tgattctcga gttctttttt 300
gagtttaaga atccctctat gctctacctt gccacaggac accgggtgca gtggctgcgc 360
tatgcagagt ggctgctcac ttgtcctgtc atccttatcc acctgagcaa cctcaccggc 420
ctgagcaacg actacagcag gagaaccatg ggactccttg tctcagacat cgggactatc 480
gtgtgggggg ctaccagcgc catggcaacc ggctatgtta aagtcatctt cttttgtctt 540
ggattgtgct atggcgcgaa cacatttttt cacgccgcca aagcatatat cgagggttat 600
catactgtgc caaagggtcg gtgccgccag gtcgtgaccg gcatggcatg gctgtttttc 660
gtgagctggg gtatgttccc aattctcttc attttggggc ccgaaggttt tggcgtcctg 720
agcgtctatg gctccaccgt aggtcacacg attattgatc tgatgagtaa aaattgttgg 780
gggttgttgg gacactacct gcgcgtcctg atccacgagc acatattgat tcacggagat 840
atccgcaaaa ccaccaaact gaacatcggc ggaacggaga tcgaggtcga gactctcgtc 900
gaagacgaag ccgaggccgg agccgtgcca 930

<210> SEQ ID NO 70
<211> LENGTH: 924
<212> TYPE: DNA
<213> ORGANISM: Artificial Sequence
<220> FEATURE:
<223> OTHER INFORMATION: Synthetic construct halorodopsin

<400> SEQUENCE: 70
atgaggggta cgcccctgct cctcgtcgtc tctctgttct ctctgcttca ggacacagag 60
accctgcctc ccgtgaccga gagtgccgtg gcccttcaag ccgaggttac ccaaagggag 120
ttgttcgagt tcgtgctgaa cgaccctttg cttgcaagca gtctctatat caacatcgca 180
cttgcaggac tgagtatact gctgttcgtt tttatgaccc gaggactcga tgatccacgg 240
gcaaaactta ttgctgtgtc aaccatcctt gtgcctgtcg tcagcattgc ctcctacact 300
ggattggcga gcggcctgac aatttccgtt cttgaaatgc cagcgggcca ttttgcagaa 360
ggcagctcag tgatgctggg aggagaagag gtagatggtg tagtcaccat gtggggacgg 420
tatctcacct gggcactttc cacgcccatg attctcctcg ctctgggtct cctggccgga 480
agcaatgcta caaagctctt cacagctatc actttcgata tcgctatgtg cgtgactggc 540
cttgccgcgg ccctgactac ctcctcccac ctcatgagat ggttctggta cgctatcagt 600
tgtgcatgct ttctggtggt cttgtatatc ctgctggtgg agtgggcaca ggacgccaaa 660
gccgcgggaa ccgctgacat gttcaatacc ctgaagctgt tgacagtagt gatgtggctg 720
gggtatccaa ttgtgtgggc tcttggagtc gagggtatcg cggtgttgcc cgttggggtg 780
acgagctggg gatattcttt cctggatatc gtggcaaagt acattttcgc attcttgctc 840
ctgaactatc tgacgtcaaa cgaatctgtc gtgtccggca gcattttgga tgttccatct 900
gcttctggga ccccggctga tgat 924

<210> SEQ ID NO 71
<211> LENGTH: 717
<212> TYPE: DNA
<213> ORGANISM: Artificial Sequence
<220> FEATURE:
<223> OTHER INFORMATION: Synthetic construct enhanced green fluorecent
protein

<400> SEQUENCE: 71
atggtgagca agggcgagga gctgttcacc ggggtggtgc ccatcctggt cgagctggac 60
ggcgacgtaa acggccacaa gttcagcgtg tccggcgagg gcgagggcga tgccacctac 120
ggcaagctga ccctgaagtt catctgcacc accggcaagc tgcccgtgcc ctggcccacc 180
ctcgtgacca ccctgaccta cggcgtgcag tgcttcagcc gctaccccga ccacatgaag 240
cagcacgact tcttcaagtc cgccatgccc gaaggctacg tccaggagcg caccatcttc 300
ttcaaggacg acggcaacta caagacccgc gccgaggtga agttcgaggg cgacaccctg 360
gtgaaccgca tcgagctgaa gggcatcgac ttcaaggagg acggcaacat cctggggcac 420
aagctggagt acaactacaa cagccacaac gtctatatca tggccgacaa gcagaagaac 480
ggcatcaagg tgaacttcaa gatccgccac aacatcgagg acggcagcgt gcagctcgcc 540
gaccactacc agcagaacac ccccatcggc gacggccccg tgctgctgcc cgacaaccac 600
tacctgagca cccagtccgc cctgagcaaa gaccccaacg agaagcgcga tcacatggtc 660
ctgctggagt tcgtgaccgc cgccgggatc actctcggca tggacgagct gtacaag 717

<210> SEQ ID NO 72
<211> LENGTH: 7
<212> TYPE: DNA
<213> ORGANISM: Artificial Sequence
<220> FEATURE:
<223> OTHER INFORMATION: Translation initiation sequence

<400> SEQUENCE: 72 accatgg 7

<210> SEQ ID NO 73
<211> LENGTH: 13
<212> TYPE: DNA
<213> ORGANISM: Artificial Sequence
<220> FEATURE:
<223> OTHER INFORMATION: Translation initiation sequence
<220> FEATURE:
<221> NAME/KEY: misc_feature
<222> LOCATION: (7)..(7)
<223> OTHER INFORMATION: n is A or G

<400> SEQUENCE: 73
gccgccncca tgg 13

<210> SEQ ID NO 74
<211> LENGTH: 221
<212> TYPE: DNA
<213> ORGANISM: Artificial Sequence
<220> FEATURE:
<223> OTHER INFORMATION: Synthetic construct pR2.1 poly A

<400> SEQUENCE: 74
agacatgata agatacattg atgagtttgg acaaaccaca actagaatgc agtgaaaaaa 60
atgctttatt tgtgaaattt gtgatgctat tgctttattt gtaaccatta taagctgcaa 120
taaacaagtt aacaacaaca attgcattca ttttatgttt caggttcagg gggagatgtg 180
ggaggttttt taaagcaagt aaaacctcta caaatgtggt a 221

<210> SEQ ID NO 75
<211> LENGTH: 85
<212> TYPE: DNA
<213> ORGANISM: Homo sapiens

<400> SEQUENCE: 75
tgaggtctgc ctcctaccca tcccgcccac cggggctttg gccacctctc ctttccccct 60
ccttctccat ccctgtaaaa taaat 85

<210> SEQ ID NO 76
<211> LENGTH: 103
<212> TYPE: DNA
<213> ORGANISM: Homo sapiens

<400> SEQUENCE: 76
cccgggtggc atccctgtga cccctcccca gtgcctctcc tggccttgga agttgccact 60
ccagtgccca ccagccttgt cctaataaaa ttaagttgca tca 103

<210> SEQ ID NO 77

<211> LENGTH: 225
<212> TYPE: DNA
<213> ORGANISM: Artificial Sequence
<220> FEATURE:
<223> OTHER INFORMATION: Synthetic construct poly A region

<400> SEQUENCE: 77
tgtgccttct agttgccagc catctgttgt ttgcccctcc cccgtgcctt ccttgaccct 60
ggaaggtgcc actcccactg tcctttccta ataaaatgag gaaattgcat cgcattgtct 120
gagtaggtgt cattctattc tggggggtgg ggtggggcag gacagcaagg gggaggattg 180
ggaagacaat agcaggcatg ctggggatgc ggtgggctct atggc 225

<210> SEQ ID NO 78
<211> LENGTH: 502
<212> TYPE: DNA
<213> ORGANISM: Artificial Sequence
<220> FEATURE:
<223> OTHER INFORMATION: Synthetic construct poly A region

<400> SEQUENCE: 78
gtgcaggctg cctatcagaa ggtggtggct ggtgtggcca atgccctggc tcacaaatac 60
cactgagatc tttttccctc tgccaaaaat tatggggaca tcatgaagcc ccttgagcat 120
ctgacttctg gctaataaag gaaatttatt ttcattgcaa tagtgtgttg gaattttttg 180
tgtctctcac tcggaaggac atatgggagg gcaaatcatt taaaacatca gaatgagtat 240
ttggtttaga gtttggcaac atatgccata tgctggctgc catgaacaaa ggtggctata 300
aagaggtcat cagtatatga aacagccccc tgctgtccat tccttattcc atagaaaagc 360
cttgacttga ggttagattt tttttatatt ttgttttgtg ttattttttt ctttaacatc 420
cctaaaattt tccttacatg ttttactagc cagatttttc ctcctctcct gactactccc 480
agtcatagct gtccctcttc tc 502

<210> SEQ ID NO 79
<211> LENGTH: 496
<212> TYPE: DNA
<213> ORGANISM: Homo sapiens

<400> SEQUENCE: 79
ggatccggtt ccaggcctcg gccctaaata gtctccctgg gctttcaaga gaaccacatg 60
agaaaggagg attcgggctc tgagcagttt caccacccac cccccagtct gcaaatcctg 120
acccgtgggt ccacctgccc caaaggcgga cgcaggacag tagaagggaa cagagaacac 180
ataaacacag agagggccac agcggctccc acagtcaccg ccaccttcct ggcggggatg 240
ggtggggcgt ctgagtttgg ttcccagcaa atccctctga gccgcccttg cgggctcgcc 300
tcaggagcag gggagcaaga ggtgggagga ggaggtctaa gtcccaggcc caattaagag 360
atcaggtagt gtagggtttg ggagctttta aggtgaagag gcccgggctg atcccacagg 420
ccagtataaa gcgccgtgac cctcaggtga tgccagggcc ggctgccgtc ggggacaggg 480
ctttccatag ccatgg 496

<210> SEQ ID NO 80
<211> LENGTH: 149
<212> TYPE: DNA
<213> ORGANISM: Homo sapiens

<400> SEQUENCE: 80
ccagcaaatc cctctgagcc gcccccgggg gctcgcctca ggagcaagga agcaaggggt 60
gggaggagga ggtctaagtc ccaggcccaa ttaagagatc agatggtgta ggatttggga 120
gcttttaagg tgaagaggcc cgggctgat 149

<210> SEQ ID NO 81
<211> LENGTH: 434
<212> TYPE: DNA
<213> ORGANISM: Homo sapiens

<400> SEQUENCE: 81
ggatccggtt ccaggcctcg gccctaaata gtctccctgg gctttcaaga gaaccacatg 60
agaaaggagg attcgggctc tgagcagttt caccacccac cccccagtct gcaaatcctg 120
acccgtgggt ccacctgccc caaaggcgga cgcaggacag tagaagggaa cagagaacac 180
ataaacacag agagggccac agcggctccc acagtcaccg ccaccttcct ggcggggatg 240
ggtggggcgt ctgagtttgg ttcccagcaa atccctctga gccgcccttg cgggctcgcc 300
tcaggagcag gggagcaaga ggtgggagga ggaggtctaa gtcccaggcc caattaagag 360
atcaggtagt gtagggtttg ggagctttta aggtgaagag gcccgggctg atcccacagg 420
ccagtataaa gcgc 434

<210> SEQ ID NO 82
<211> LENGTH: 263
<212> TYPE: DNA
<213> ORGANISM: Homo sapiens

<400> SEQUENCE: 82
ggatccggtt ccaggcctcg gccctaaata gtctccctgg gctttcaaga gaaccacatg 60
agaaaggagg attcgggctc tgagcagttt caccacccac cccccagtct gcaaatcctg 120
acccgtgggt ccacctgccc caaaggcgga cgcaggacag tagaagggaa cagagaacac 180
ataaacacag agagggccac agcggctccc acagtcaccg ccaccttcct ggcggggatg 240
ggtggggcgt ctgagtttgg ttc 263

<210> SEQ ID NO 83
<211> LENGTH: 171
<212> TYPE: DNA
<213> ORGANISM: Homo sapiens

<400> SEQUENCE: 83
ccagcaaatc cctctgagcc gcccttgcgg gctcgcctca ggagcagggg agcaagaggt 60
gggaggagga ggtctaagtc ccaggcccaa ttaagagatc aggtagtgta gggtttggga 120
gcttttaagg tgaagaggcc cgggctgatc ccacaggcca gtataaagcg c 171

<210> SEQ ID NO 84
<211> LENGTH: 102
<212> TYPE: DNA
<213> ORGANISM: Artificial Sequence
<220> FEATURE:
<223> OTHER INFORMATION: Synthesized 5'UTR

<400> SEQUENCE: 84
cccactggcc ggtataaagc accgtgaccc tcaggtgacg caccagggcc ggctgccgtc 60
ggggacaggg ctttccatag cccaggccca gagaggagac ag 102

<210> SEQ ID NO 85
<211> LENGTH: 85
<212> TYPE: DNA

<213> ORGANISM: Artificial Sequence
<220> FEATURE:
<223> OTHER INFORMATION: Synthesized 5'UTR

<400> SEQUENCE: 85
cccactggcc ggtataaagc accgtgaccc tcaggtgacg caccagggcc ggctgccgtc 60
ggggacaggg ctttccatag cccag 85

<210> SEQ ID NO 86
<211> LENGTH: 17
<212> TYPE: DNA
<213> ORGANISM: Artificial Sequence
<220> FEATURE:
<223> OTHER INFORMATION: Synthesized 5'UTR

<400> SEQUENCE: 86
gcccagagag gagacag 17

<210> SEQ ID NO 87
<211> LENGTH: 185
<212> TYPE: DNA
<213> ORGANISM: Artificial Sequence
<220> FEATURE:
<223> OTHER INFORMATION: Synthesized 5'UTR construct

<400> SEQUENCE: 87
cgtgaccctc aggtgatgcg ccagggccgg ctgccgtcgg ggacagggct ttccatagcc 60
atgctagagg atccggtact cgaggaactg aaaaaccaga aagttaactg gcctgtacgg 120
aagtgttact tctgctctaa aagctgcgga attgtacccg cggccgcggg acagggcttt 180
ccata 185

<210> SEQ ID NO 88
<211> LENGTH: 110
<212> TYPE: DNA
<213> ORGANISM: Artificial Sequence
<220> FEATURE:
<223> OTHER INFORMATION: Synthesized 5'UTR construct

<400> SEQUENCE: 88
cgtgaccctc aggtgatgcg ccagggccgg ctgccgtcgg ggacagggct ttccatagcc 60
atgctagagg atccggtact cgaggaactg aaaaaccaga aagttaactg 110

<210> SEQ ID NO 89
<211> LENGTH: 75
<212> TYPE: DNA
<213> ORGANISM: Artificial Sequence
<220> FEATURE:
<223> OTHER INFORMATION: Synthesized 5'UTR construct

<400> SEQUENCE: 89
gcctgtacgg aagtgttact tctgctctaa aagctgcgga attgtacccg cggccgcggg 60
acagggcttt ccata 75

<210> SEQ ID NO 90
<211> LENGTH: 235
<212> TYPE: DNA
<213> ORGANISM: Artificial Sequence
<220> FEATURE:
<223> OTHER INFORMATION: Synthetic construct poly A region

<400> SEQUENCE: 90
ggccgcgggg atccagacat gataagatac attgatgagt ttggacaaac cacaactaga 60
atgcagtgaa aaaaatgctt tatttgtgaa atttgtgatg ctattgcttt atttgtaacc 120
attataagct gcaataaaca agttaacaac aacaattgca ttcattttat gtttcaggtt 180
cagggggaga tgtgggaggt tttttaaagc aagtaaaacc tctacaaatg tggta 235

<210> SEQ ID NO 91
<211> LENGTH: 152
<212> TYPE: DNA
<213> ORGANISM: Artificial Sequence
<220> FEATURE:
<223> OTHER INFORMATION: Synthetic construct poly A region

<400> SEQUENCE: 91
ggccgcgggg atccagacat gataagatac attgatgagt ttggacaaac cacaactaga 60
atgcagtgaa aaaaatgctt tatttgtgaa atttgtgatg ctattgcttt atttgtaacc 120
attataagct gcaataaaca agttaacaac aa 152

<210> SEQ ID NO 92
<211> LENGTH: 1714
<212> TYPE: DNA
<213> ORGANISM: Homo sapiens

<400> SEQUENCE: 92
cctacagcag ccagggtgag attatgaggc tgagctgaga atatcaagac tgtaccgagt 60
agggggcctt ggcaagtgtg gagagcccgg cagctggggc agagggcgga gtacggtgtg 120
cgtttacgga cctcttcaaa cgaggtagga aggtcagaag tcaaaaaggg aacaaatgat 180
gtttaaccac acaaaaatga aaatccaatg gttggatatc cattccaaat acacaaaggc 240
aacggataag tgatccgggc caggcacaga aggccatgca cccgtaggat tgcactcaga 300
gctcccaaat gcataggaat agaagggtgg gtgcaggagg ctgaggggtg gggaaagggc 360
atgggtgttt catgaggaca gagcttccgt ttcatgcaat gaaaagagtt tggagacgga 420
tggtggtgac tggactatac acttacacac ggtagcgatg gtacactttg tattatgtat 480
attttaccac gatcttttta aagtgtcaaa ggcaaatggc caaatggttc cttgtcctat 540
agctgtagca gccatcggct gttagtgaca aagcccctga gtcaagatga cagcagcccc 600
cataactcct aatcggctct cccgcgtgga gtcatttagg agtagtcgca ttagagacaa 660
gtccaacatc taatcttcca ccctggccag ggccccagct ggcagcgagg gtgggagact 720
ccgggcagag cagagggcgc tgacattggg gcccggcctg gcttgggtcc ctctggcctt 780
tccccagggg ccctctttcc ttggggcttt cttgggccgc cactgctccc gctcctctcc 840
ccccatccca ccccctcacc ccctcgttct tcatatcctt ctctagtgct ccctccactt 900
tcatccaccc ttctgcaaga gtgtgggacc acaaatgagt tttcacctgg cctggggaca 960
cacgtgcccc cacaggtgct gagtgacttt ctaggacagt aatctgcttt aggctaaaat 1020
gggacttgat cttctgttag ccctaatcat caattagcag agccggtgaa ggtgcagaac 1080
ctaccgcctt tccaggcctc ctcccacctc tgccacctcc actctccttc ctgggatgtg 1140
ggggctggca cacgtgtggc ccagggcatt ggtgggattg cactgagctg ggtcattagc 1200
gtaatcctgg acaagggcag acagggcgag cggagggcca gctccggggc tcaggcaagg 1260
ctgggggctt cccccagaca ccccactcct cctctgctgg acccccactt catagggcac 1320
ttcgtgttct caaagggctt ccaaatagca tggtggcctt ggatgcccag ggaagcctca 1380
gagttgctta tctccctcta gacagaaggg gaatctcggt caagagggag aggtcgccct 1440
gttcaaggcc acccagccag ctcatggcgg taatgggaca aggctggcca gccatcccac 1500
cctcagaagg gacccggtgg ggcaggtgat ctcagaggag gctcacttct gggtctcaca 1560
ttcttccagc aaatccctct gagccgcccc cgggggctcg cctcaggagc aaggaagcaa 1620
ggggtgggag gaggaggtct aagtcccagg cccaattaag agatcagatg gtgtaggatt 1680
tgggagcttt taaggtgaag aggcccgggc tgat 1714

<210> SEQ ID NO 93
<211> LENGTH: 234
<212> TYPE: DNA
<213> ORGANISM: Artificial Sequence
<220> FEATURE:
<223> OTHER INFORMATION: Optimized promoter sequence

<400> SEQUENCE: 93
ccagcaaatc cctctgagcc gcccccgggg gctcgcctca ggagcaagga agcaaggggt 60
gggaggagga ggtctaagtc ccaggcccaa ttaagagatc agatggtgta ggatttggga 120
gcttttaagg tgaagaggcc cgggctgatc ccactggccg gtataaagca ccgtgaccct 180
caggtgacgc accagggccg gctgccgtcg ggacagggc tttccatagc ccag 234

<210> SEQ ID NO 94
<211> LENGTH: 235
<212> TYPE: DNA
<213> ORGANISM: Artificial Sequence
<220> FEATURE:
<223> OTHER INFORMATION: Optimized intron sequence

<400> SEQUENCE: 94
cccactggcc ggtataaagc accgtgaccc tcaggtgacg caccagggcc ggctgccgtc 60
ggggacaggg ctttccatag cccaggtaag tatcaaggtt acaagacagg tttaaggaga 120
ccaatagaaa ctgggcttgt cgagacagag aagactcttg cgtttctgat aggcacctat 180
tggtcttact gacatccact ttgcctttct ctccacaggc ccagagagga gacag 235

<210> SEQ ID NO 95
<211> LENGTH: 1958
<212> TYPE: DNA
<213> ORGANISM: Artificial Sequence
<220> FEATURE:
<223> OTHER INFORMATION: Cassette comprising optimized enhance,
optimized promoter, optimized 5'UTR, optimized intron, optimized
kozak and optimized polyA region

<400> SEQUENCE: 95
cctacagcag ccagggtgag attatgaggc tgagctgaga atatcaagac tgtaccgagt 60
agggggcctt ggcaagtgtg gagagcccgg cagctggggc agagggcgga gtacggtgtg 120
cgtttacgga cctcttcaaa cgaggtagga aggtcagaag tcaaaaaggg aacaaatgat 180
gtttaaccac acaaaaatga aaatccaatg gttggatatc cattccaaat acacaaaggc 240
aacggataag tgatccgggc caggcacaga aggccatgca cccgtaggat tgcactcaga 300
gctcccaaat gcataggaat agaagggtgg gtgcaggagg ctgaggggtg gggaaagggc 360
atgggtgttt catgaggaca gagcttccgt ttcatgcaat gaaaagagtt tggagacgga 420
tggtggtgac tggactatac acttacacac ggtagcgatg gtacactttg tattatgtat 480
attttaccac gatcttttta aagtgtcaaa ggcaaatggc caaatggttc cttgtcctat 540
agctgtagca gccatcggct gttagtgaca aagcccctga gtcaagatga cagcagcccc 600
cataactcct aatcggctct cccgcgtgga gtcatttagg agtagtcgca ttagagacaa 660
gtccaacatc taatcttcca ccctggccag ggccccagct ggcagcgagg gtgggagact 720
ccgggcagag cagagggcgc tgacattggg gcccggcctg gcttgggtcc ctctggcctt 780
tccccagggg ccctctttcc ttggggcttt cttgggccgc cactgctccc gctcctctcc 840
ccccatccca ccccctcacc ccctcgttct tcatatcctt ctctagtgct ccctccactt 900
tcatccaccc ttctgcaaga gtgtgggacc acaaatgagt tttcacctgg cctggggaca 960
cacgtgcccc cacaggtgct gagtgacttt ctaggacagt aatctgcttt aggctaaaat 1020
gggacttgat cttctgttag ccctaatcat caattagcag agccggtgaa ggtgcagaac 1080
ctaccgcctt tccaggcctc ctcccacctc tgccacctcc actctccttc ctgggatgtg 1140
ggggctggca cacgtgtggc ccagggcatt ggtgggattg cactgagctg ggtcattagc 1200
gtaatcctgg acaagggcag acagggcgag cggagggcca gctccggggc tcaggcaagg 1260
ctgggggctt cccccagaca ccccactcct cctctgctgg acccccactt catagggcac 1320
ttcgtgttct caaagggctt ccaaatagca tggtggcctt ggatgcccag ggaagcctca 1380
gagttgctta tctccctcta gacagaaggg gaatctcggt caagagggag aggtcgccct 1440
gttcaaggcc acccagccag ctcatggcgg taatgggaca aggctggcca gccatcccac 1500
cctcagaagg gacccggtgg ggcaggtgat ctcagaggag gctcacttct gggtctcaca 1560
ttcttccagc aaatccctct gagccgcccc cgggggctcg cctcaggagc aaggaagcaa 1620
ggggtgggag gaggaggtct aagtcccagg cccaattaag agatcagatg gtgtaggatt 1680
tgggagcttt taaggtgaag aggcccgggc tgatcccact ggccggtata aagcaccgtg 1740
accctcaggt gacgcaccag ggccggctgc cgtcggggac agggctttcc atagcccagg 1800
taagtatcaa ggttacaaga caggtttaag gagaccaata gaaactgggc ttgtcgagac 1860
agagaagact cttgcgtttc tgataggcac ctattggtct tactgacatc cactttgcct 1920
ttctctccac aggcccagag aggagacagg ccgccacc 1958

<210> SEQ ID NO 96
<211> LENGTH: 7
<212> TYPE: PRT
<213> ORGANISM: Artificial Sequence
<220> FEATURE:
<223> OTHER INFORMATION: Synthetic peptide insertion in the AAV GH loop

<400> SEQUENCE: 96

Leu Gly Glu Thr Thr Arg Pro
1               5

<210> SEQ ID NO 97
<211> LENGTH: 7
<212> TYPE: PRT
<213> ORGANISM: Artificial Sequence
<220> FEATURE:
<223> OTHER INFORMATION: Synthetic peptide insertion in the AAV GH loop

<400> SEQUENCE: 97

Asn Glu Thr Ile Thr Arg Pro
1               5

<210> SEQ ID NO 98
<211> LENGTH: 7
<212> TYPE: PRT
<213> ORGANISM: Artificial Sequence
<220> FEATURE:
<223> OTHER INFORMATION: Synthetic peptide insertion in the AAV GH loop

<400> SEQUENCE: 98

Lys Ala Gly Gln Ala Asn Asn
1 5

<210> SEQ ID NO 99
<211> LENGTH: 7
<212> TYPE: PRT
<213> ORGANISM: Artificial Sequence
<220> FEATURE:
<223> OTHER INFORMATION: Synthetic peptide insertion in the AAV GH loop

<400> SEQUENCE: 99

Lys Asp Pro Lys Thr Thr Asn
1 5

<210> SEQ ID NO 100
<211> LENGTH: 7
<212> TYPE: PRT
<213> ORGANISM: Artificial Sequence
<220> FEATURE:
<223> OTHER INFORMATION: Synthetic peptide insertion in the AAV GH loop

<400> SEQUENCE: 100

Lys Asp Thr Asp Thr Thr Arg
1 5

<210> SEQ ID NO 101
<211> LENGTH: 7
<212> TYPE: PRT
<213> ORGANISM: Artificial Sequence
<220> FEATURE:
<223> OTHER INFORMATION: Synthetic peptide insertion in the AAV GH loop

<400> SEQUENCE: 101

Arg Ala Gly Gly Ser Val Gly
1 5

<210> SEQ ID NO 102
<211> LENGTH: 7
<212> TYPE: PRT
<213> ORGANISM: Artificial Sequence
<220> FEATURE:
<223> OTHER INFORMATION: Synthetic peptide insertion in the AAV GH loop

<400> SEQUENCE: 102

Ala Val Asp Thr Thr Lys Phe
1 5

<210> SEQ ID NO 103
<211> LENGTH: 7
<212> TYPE: PRT
<213> ORGANISM: Artificial Sequence
<220> FEATURE:
<223> OTHER INFORMATION: Synthetic peptide insertion in the AAV GH loop

<400> SEQUENCE: 103

Ser Thr Gly Lys Val Pro Asn
1 5

COMPOSITIONS AND METHODS FOR ENHANCED GENE EXPRESSION IN CONE CELLS

CROSS REFERENCE TO RELATED APPLICATIONS

Pursuant to 35 U.S.C. § 119 (e), this application claims priority to U.S. patent application Ser. No. 15/984,085 filed May 18, 2018, which is a Continuation of U.S. patent application Ser. No. 14/660,657 filed Mar. 17, 2015 (now U.S. Pat. No. 10,000,741 issued Jun. 19, 2018), which claims the benefit of U.S. Provisional Patent Application Ser. No. 61/954,330, filed Mar. 17, 2014 and U.S. Provisional Patent Application Ser. No. 62/127,185, filed Mar. 2, 2015, the full disclosures of which are herein incorporated by reference.

STATEMENT REGARDING SEQUENCE LISTING

The Sequence Listing associated with this application is provided in text format in lieu of a paper copy, and is hereby incorporated by reference into the specification. The name of the text file containing the Sequence Listing is AVBI_005_05US_ST25.txt. The text file is about 308 KB, was created on Dec. 20, 2021, and is being submitted electronically via EFS-Web.

FIELD OF THE INVENTION

This invention pertains to gene therapy of retinal disorders.

BACKGROUND OF THE INVENTION

Vision disorders of the eye often relate to known primary defects in cone cells. These include macular dystrophies such as Stargardt's macular dystrophy, cone dystrophy, cone-rod dystrophy, Spinocerebellar ataxia type 7, and Bardet-Biedl syndrome-1, as well as color vision disorders, including achromotopsia, blue cone monochromacy, and protan, deutan, and tritan defects.

In addition to those disorders where the known cause is intrinsic to cone photoreceptors, there are vision disorders of the central macula (within primates) that may be treated by targeting cone cells. These include age-related macular degeneration, macular telangiectasia, retinitis pigmentosa, diabetic retinopathy, retinal vein occlusions, glaucoma, Sorsby's fundus dystrophy, adult vitelliform macular dystrophy, Best's disease, and X-linked retinoschisis.

A promising approach to treating and preventing ophthalmic disease that addresses the limitations of existing treatment is delivery of therapeutic agents to the eye with a gene therapy vector such as an adeno-associated virus (AAV). AAV is a 4.7 kb, single stranded DNA virus. Recombinant vectors based on AAV are associated with excellent clinical safety, since wild-type AAV is nonpathogenic and has no etiologic association with any known diseases. In addition, AAV offers the capability for highly efficient gene delivery and sustained transgene expression in numerous tissues, including eye, muscle, lung, and brain. Furthermore, AAV has shown promise in human clinical trials. One example is Leber's congenital amaurosis in which patients treated with a therapeutic delivered by a single subretinal administration of an rAAV vector have experienced sustained clinical benefit from expression of the therapeutic agent for more than four years from the initial date of treatment.

A number of challenges remain with regard to designing polynucleotide cassettes and expression vectors for use in gene therapy to treat eye disease generally and cone cells specifically. One significant challenge is obtaining sufficient expression of the transgene in target cells, especially in cone cells of the retina. A longstanding unmet need in the art has been sufficiently robust expression of transgenes following gene transfer. In some cases, more efficient expression is required for the efficacy of certain vectors, for example plasmid DNA vectors. In other cases, more efficient gene expression cassettes are desirable to allow for a lower therapeutic dose that has a more favorable safety profile or a less invasive route of administration (e.g., intravitreal vs. subretinal). In some settings, efficient expression has been achieved using a strong, ubiquitous promoter, but it is often desirable to have high transgene expression using a nucleic acid expression cassette that is only expressed in target cell types.

Previous efforts to express transgenes in cone cells, for example as disclosed in US patent application US 2012/0172419, showed some promise, but often the expression levels were lower than optimal or not cell specific. Given that a number of vision disorders result from primary defects in cone cells, specific expression of transgenes in cone cells, with high expression levels, would represent a meaningful advance in the art. Therefore, there remains a need for improved methods and optimized nucleic acid cassettes and vectors for expressing genes in cone cells.

SUMMARY OF THE INVENTION

The present disclosure provides polynucleotide cassettes, expression vectors and methods for the expression of a gene in cone cells.

In some aspects of the invention, polynucleotide cassettes are provided for the expression of a transgene in cone cells of a mammalian retina. In some embodiments, the expression of the transgene is enhanced expression. In certain embodiments, the expression of the coding sequence is greater than expression of the transgene operably linked to SEQ ID NO:1. In some embodiments, the expression of the transgene is cone-specific.

In some embodiments, the polynucleotide cassette comprises a promoter region, wherein the promoter region promotes the expression of a gene in retinal cone cells; and a polyadenylation site. In some embodiments, the expression is specifically in cone cells. In some such embodiments, the promoter region comprises a polynucleotide sequence having a sequence identity of 85% or more to a sequence selected from the group consisting of SEQ ID NO:1, SEQ ID NO:2, SEQ ID NO:3, SEQ ID NO:53, SEQ ID NO:54, SEQ ID NO:55, SEQ ID NO:79, SEQ ID NO:80, SEQ ID NO:81. SEQ ID NO:82, and SEQ ID NO:83, or a functional fragment thereof. In some embodiments, the promoter region is less than 492 nucleotides in length. In some embodiments, the promoter region consists essentially of a polynucleotide sequence having a sequence identity of 85% or more to the full length of SEQ ID NO:55 or a functional fragment thereof.

In some embodiments, the polynucleotide cassette comprises a polynucleotide sequence encoding an untranslated region 5' for a coding sequence, referred to herein as a 5'UTR. In some such embodiments, the 5'UTR comprises a sequence having a sequence identity of 85% or more to a sequence selected from the group consisting of SEQ ID NO:56, SEQ ID NO:57, SEQ ID NO:58, SEQ ID NO:84, SEQ ID NO:85, SEQ ID NO:86, SEQ ID NO:87, SEQ ID NO:88, and SEQ ID NO:89, or a fragment thereof. In some embodiments, some or all of the 5'UTR sequence is comprised by a promoter region as disclosed in, for example, SEQ ID NO:1, SEQ ID NO:2, SEQ ID NO:3, SEQ ID NO:53, SEQ ID NO:54, SEQ ID NO:55, or SEQ ID NO:79. In some embodiments, the 5'UTR sequence is heterologous to the promoter sequence. In some embodiments, the 5'UTR consists essentially of a sequence having a sequence identity of 85% or more to the full length of SEQ ID NO:85 or SEQ ID NO:86, or a fragment thereof. In some embodiments, the 5'UTR does not comprise a polynucleotide ATG.

In some embodiments, the polynucleotide cassette comprises an intron. In some such embodiments, the intron comprises a sequence having a sequence identity of 85% or more to a sequence selected from the group consisting of SEQ ID NO:5, SEQ ID NO:59, and SEQ ID NO:60. In certain embodiments, the intron is located within the polynucleotide sequence encoding a 5'UTR.

In some embodiments, the polynucleotide cassette comprises a translation initiation sequence. In some such embodiments, the translation initiation sequence comprises a polynucleotide sequence consisting essentially of SEQ ID NO:72 or SEQ ID NO:73.

In some embodiments, the polynucleotide cassette comprises an enhancer sequence. In some such embodiments, the enhancer sequence comprises a polynucleotide sequence having a sequence identity of 85% or more to SEQ ID NO:52 or a functional fragment thereof. In certain embodiments, the enhancer sequence consists essentially of a sequence having a sequence identity of 85% or more to the full length of SEQ ID NO:51.

In some embodiments, the polynucleotide cassette comprises a coding sequence operably linked to the promoter. In some embodiments, the coding sequence is heterologous to the promoter region and/or the 5'UTR sequence. In some embodiments, the coding sequence encodes a polypeptide having a sequence identity of at least 85%, 90%, or 95% to SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, and a polymorph of SEQ ID NO:11 selected from the group consisting of: (i) Thr65Ile (ii) Ile111Val (iii) Ser116Tyr (iv) Leu153Met (v) Ile171Val (vi) Ala174Val (vii) Ile178Val (viii) Ser180Ala (ix) Ile230Thr (x) Ala233Ser (xi) Val236Met (xii) Ile274Val (xiii) Phe275Leu (xiv) Tyr277Phe (xv) Val279Phe (xvi) Thr285Ala (xvii) Pro298Ala; and (xviii) Tyr309Phe. In some embodiments, the coding sequence has a sequence identity of at least 85%, 90%, or 95% to SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, or SEQ ID NO:71. In some embodiments, the sequence between the transcription initiation site and the end of coding sequence does not contain an open reading frame, other than the transgene open reading frame, that is more than 500 nucleotides in length. In some embodiments, the sequence between the transcription initiation site and the end of coding sequence does not contain an open reading frame, other than the transgene open reading frame, that is more than 273 nucleotides in length. In some embodiments, the sequence between the transcription initiation site and the end of coding sequence does not contain an open reading frame, other than the transgene open reading frame, that is more than 250 nucleotides in length. In some embodiments, at least one open reading frame of the coding sequence has been removed.

In some embodiments, the polynucleotide comprises a promoter region, wherein the promoter region promotes the expression of a gene in retinal cone cells; a 5' untranslated region; an intron; a translation initiation sequence; a coding sequence operatively linked to the promoter region; and a polyadenylation site. In some embodiments, the polynucleotide comprises a promoter region, wherein the promoter region promotes the expression of a gene specifically in retinal cone cells; a 5' untranslated region; an intron; a translation initiation sequence; a coding sequence operatively linked to the promoter region; and a polyadenylation site.

In some aspects of the invention, gene delivery vectors are provided comprising a polynucleotide cassette of the present invention. In some embodiments, the gene delivery vector is a recombinant adeno-associated virus, wherein the recombinant adeno-associated virus comprises an AAV capsid protein. In some embodiments, the AAV capsid protein is a wild type AAV capsid protein. In other embodiments, the AAV capsid protein is a variant AAV capsid protein. In certain embodiments, the variant AAV capsid protein comprises a peptide insertion in the AAV GH loop selected from the group consisting of LGETTRP (SEQ ID NO:96), NETITRP (SEQ ID NO:97), KAGQANN (SEQ ID NO:98), KDPKTTN (SEQ ID NO:99), KDTDTTR (SEQ ID NO:100), RAGGSVG (SEQ ID NO:101), AVDTTKF (SEQ ID NO:102), and STGKVPN (SEQ ID NO:103).

In some aspects of the invention, pharmaceutical compositions are provided comprising a polynucleotide cassette of the invention and a pharmaceutical excipient. In some embodiments, the pharmaceutical composition comprises a gene delivery vector of the invention and a pharmaceutical excipient.

In some aspects of the invention, methods are provided for expressing a transgene in cone cells. In some embodiments, the method comprises contacting one or more cone cells with an effective amount of a polynucleotide cassette of the invention or a gene delivery vector of the invention, wherein the transgene is expressed at detectable levels in the one or more cone cells. In some embodiments, the method is in vitro. In other embodiments, the method is in vivo. In certain such embodiments, the contacting comprises injection of the polynucleotide cassette or gene delivery vector into the vitreous of a mammal eye. In other such embodiments, the method comprises injection of the polynucleotide cassette or gene delivery vector into the subretinal space of a mammal eye. In some embodiments, the method further comprises detecting the expression of the transgene in cone cells, wherein expression is detected in 80% or more of the cone cells. In some embodiments, the expression is specific for cone cells.

In some aspects of the invention, methods are provided for the treatment or prophylaxis of a cone cell disorder in a mammal in need of treatment or prophylaxis for a cone cell disorder. In some embodiments, the method comprises administering to the eye of the mammal an effective amount of a pharmaceutical composition of the invention, wherein the coding sequence encodes a therapeutic gene product. In some embodiments, the administering comprises injecting the pharmaceutical composition into the vitreous of the mammal eye. In other such embodiments, the method comprises injecting the pharmaceutical composition into the subretinal space of a mammal eye.

In some embodiments, the cone cell disorder is a color vision disorder. In certain embodiments, the color vision disorder is selected from the group consisting of achromotopsia, blue cone monochromacy, a protan defect, a deutan defect, and a tritan defect. In some such embodiments, the method further comprises detecting a change in the disease symptoms, wherein the change comprises an increase in the ability of the mammal to perceive a color. In some embodiments, the cone cell disorder is a macular dystrophy. In certain embodiments, the macular dystrophy is selected from the group consisting of Stargardt's macular dystrophy, cone dystrophy, cone-rod dystrophy, Spinocerebellar ataxia type 7, and Bardet-Biedl syndrome-1. In some embodiments, the cone cell disorder is a vision disorder of the central macula. In certain embodiments, vision disorder of the central macula is selected from the group consisting of age-related macular degeneration, macular telangiectasia, retinitis pigmentosa, diabetic retinopathy, retinal vein occlusions, glaucoma, Sorsby's fundus dystrophy, adult vitelliform macular dystrophy, Best's disease, rod-cone dystrophy, Leber's congenital amaurosis, and X-linked retinoschisis. In some such embodiments, the method further comprises detecting a change in the disease symptoms. In some such embodiments, the change comprises a stabilization in the health of the cone cells and/or a reduction in the rate of visual acuity loss of the mammal. In certain such embodiments, the change comprises an improvement in the health of the cone cells and/or an improvement in the visual acuity of the mammal.

BRIEF DESCRIPTION OF THE DRAWINGS

The novel features of the disclosure are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 6A-6B shows results when AAV2-7m8.MNTC.GFP was injected into the central vitreous of a baboon and expression was observed (FIG. 6A) 5 weeks and (FIG. 6B) 8 weeks later by fundus fluorescence. FIGS. 6C-6D show natural GFP fluorescence within a 15 micron section of the fovea at approximately 6 months after injection with AAV2-7m8.MNTC.GFP at low magnification (FIG. 6C) and high magnification (FIG. 6D).

FIGS. 7A-7B show examples of GFP fluorescence 11 weeks after mice received intravitreal injections of $5.04\times10^{10}$ vector genomes via intravitreal injection. FIGS. 7C-7E show retinas that were harvested for histology 14 weeks after injection and cone outersegments were labeled with an antibody to L/M opsin (red). In FIG. 7C, the red channel is turned off so only the native GFP is visible; FIG. 7D is the same image with the red channel on to allow visualization of cone outersegments. Comparison of FIG. 7C and FIG. 7D shows that most if not all cones were transduced by the virus. FIG. 7E provides an image from the same retina as in FIG. 7C and FIG. 7D from a different angle showing profiles of cone photoreceptors.

FIG. 8A shows expression of GFP directed by AAV2-7m8.CMV.GFP and AAV2-7m8.MNTC.GFP, visualized 4 weeks after intravitreal administration. Gerbils 12-10, 12-11, and 12-12 were injected with AAV2-7m8.CMV.GFP, while gerbils 12-13, 12-14, and 12-15 were injected with AAV2-7m8.MNTC.GFP. OD, oculus dexter (right eye). OS, oculus sinister (left eye). FIG. 8B shows expression of GFP directed by AAV2-7m8.pR2.1.GFP and AAV2-7m8.MNTC.GFP, 4 and 8 weeks later as detected by fundus fluorescence imaging.

FIG. 10A shows the pMNTC and pR2.1 expression cassettes. FIG. 10B shows the experimental expression cassettes, in which each element in pMNTC is replaced one-by-one by the corresponding element in pR2.1. FIGS. 10C-10D show expression of the luciferase transgene in the retinas of gerbils intravitreally injected with each of the test articles (n=6-8 eyes per construct) as detected (FIG. 10C) 4 weeks and (FIG. 10D) 8 weeks after injection by IVIS imaging. "7m8.CMV" served as the positive control.

DEFINITIONS

Figure 1A:
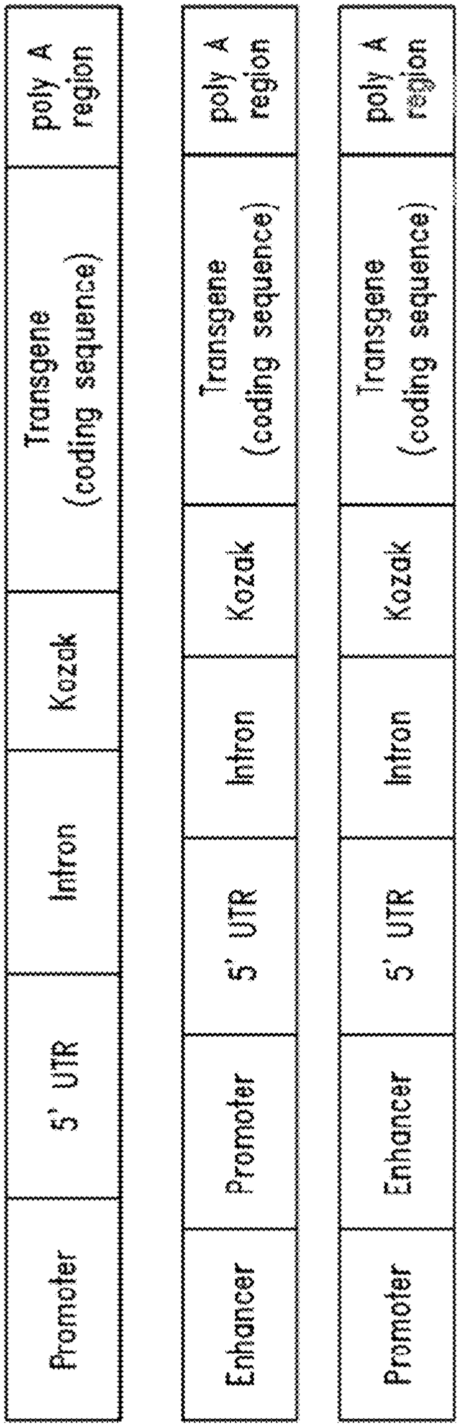
FIG. 1A depicts the schematic overview of polynucleotide cassettes for enhanced expression of a transgene in cone cells.
Figure 1B:
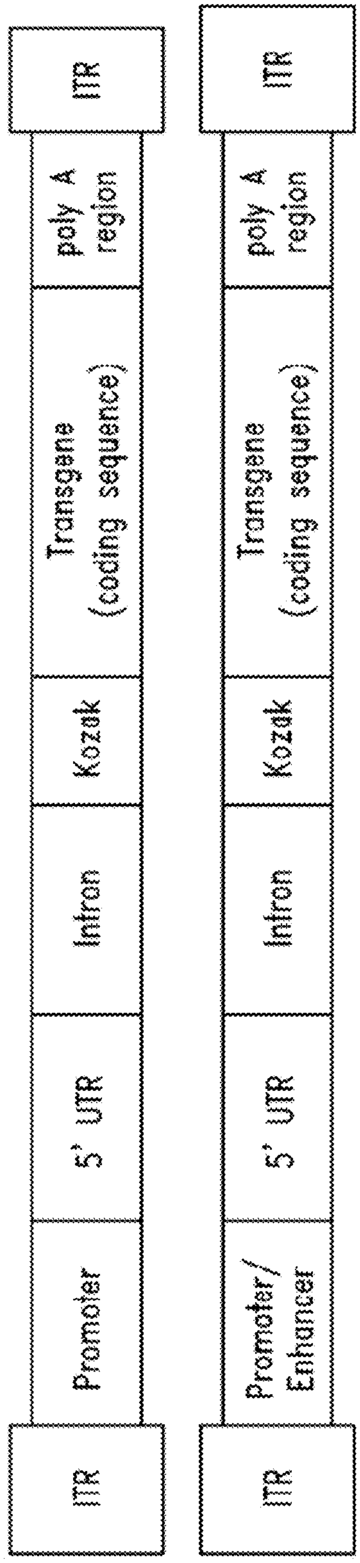
FIG. 1B depicts a schematic overview of viral vectors comprising polynucleotide cassettes for enhanced expression of a transgene in cone cells.
Figure 2:
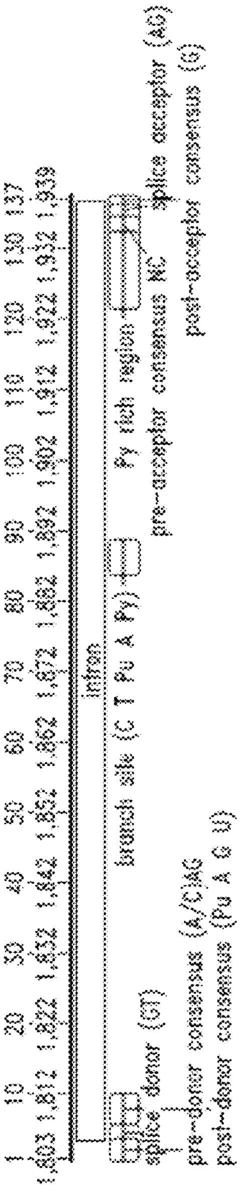
FIG. 2 depicts an example intron containing canonical features, including consensus sequences for the splice donor (A/C) A G G T Pu A G U; branch site C T Pu A Py; Py-rich region; and acceptor N C A G G.

A "vector" as used herein refers to a macromolecule or association of macromolecules that comprises or associates with a polynucleotide and which can be used to mediate delivery of the polynucleotide to a cell. Illustrative vectors include, for example, plasmids, viral vectors, liposomes, and other gene delivery vehicles.

The term "AAV" is an abbreviation for adeno-associated virus, and may be used to refer to the virus itself or derivatives thereof. The term covers all subtypes and both naturally occurring and recombinant forms, except where required otherwise. The term "AAV" includes AAV type 1 (AAV-1), AAV type 2 (AAV-2), AAV type 3 (AAV-3), AAV type 4 (AAV-4), AAV type 5 (AAV-5), AAV type 6 (AAV-6), AAV type 7 (AAV-7), AAV type 8 (AAV-8), avian AAV, bovine AAV, canine AAV, equine AAV, primate AAV, non-primate AAV, and ovine AAV. "Primate AAV" refers to AAV that infect primates, "non-primate AAV" refers to AAV that infect non-primate mammals, "bovine AAV" refers to AAV that infect bovine mammals, etc.

An "AAV virus" or "AAV viral particle" or "rAAV vector particle" refers to a viral particle composed of at least one AAV capsid protein (typically by all of the capsid proteins of a wild-type AAV) and an encapsidated polynucleotide rAAV vector. If the particle comprises a heterologous polynucleotide (i.e. a polynucleotide other than a wild-type AAV genome such as a transgene to be delivered to a mammalian cell), it is typically referred to as a "rAAV vector particle" or simply a "rAAV vector". Thus, production of rAAV particle necessarily includes production of rAAV vector, as such a vector is contained within a rAAV particle.

The term "replication defective" as used herein relative to an AAV viral vector of the invention means the AAV vector cannot independently replicate and package its genome. For example, when a cell of a subject is infected with rAAV virions, the heterologous gene is expressed in the infected cells, however, due to the fact that the infected cells lack AAV rep and cap genes and accessory function genes, the rAAV is not able to replicate further.

An "AAV variant" or "AAV mutant" as used herein refers to a viral particle composed of: a) a variant AAV capsid protein, where the variant AAV capsid protein comprises at least one amino acid difference (e.g., amino acid substitution, amino acid insertion, amino acid deletion) relative to a corresponding parental AAV capsid protein, and where the variant capsid protein confers increased infectivity of a retinal cell compared to the infectivity of the retinal cell by an AAV virion comprising the corresponding parental AAV capsid protein, where the AAV capsid protein does not comprise an amino acid sequence present in a naturally occurring AAV capsid protein; and b) a heterologous nucleic acid comprising a nucleotide sequence encoding a heterologous gene product.

The abbreviation "rAAV" refers to recombinant adeno-associated virus, also referred to as a recombinant AAV vector (or "rAAV vector"). A "rAAV vector" as used herein refers to an AAV vector comprising a polynucleotide sequence not of AAV origin (i.e., a polynucleotide heterologous to AAV), typically a sequence of interest for the genetic transformation of a cell. In general, the heterologous polynucleotide is flanked by at least one, and generally by two AAV inverted terminal repeat sequences (ITRs). The term rAAV vector encompasses both rAAV vector particles and rAAV vector plasmids.

As used herein, the term "gene" or "coding sequence" refers to a nucleotide sequence in vitro or in vivo that encodes a gene product. In some instances, the gene consists or consists essentially of coding sequence, that is, sequence that encodes the gene product. In other instances, the gene comprises additional, non-coding, sequence. For example, the gene may or may not include regions preceding and following the coding region, e.g. 5' untranslated (5' UTR) or "leader" sequences and 3' UTR or "trailer" sequences, as well as intervening sequences (introns) between individual coding segments (exons).

As used herein, a "therapeutic gene" refers to a gene that, when expressed, confers a beneficial effect on the cell or tissue in which it is present, or on a mammal in which the gene is expressed. Examples of beneficial effects include amelioration of a sign or symptom of a condition or disease, prevention or inhibition of a condition or disease, or conferral of a desired characteristic. Therapeutic genes include genes that correct a genetic deficiency in a cell or mammal.

As used herein, a transgene is a gene that is delivered to a cell by a vector.

As used herein, the term "gene product" refers to the desired expression product of a polynucleotide sequence such as a polypeptide, peptide, protein or interfering RNA including short interfering RNA (siRNA), miRNA or small hairpin RNA (shRNA).

As used herein, the terms "polypeptide," "peptide," and "protein" refer to polymers of amino acids of any length. The terms also encompass an amino acid polymer that has been modified; for example, disulfide bond formation, glycosylation, lipidation, phosphorylation, or conjugation with a labeling component.

By "comprising" it is meant that the recited elements are required in, for example, the composition, method, kit, etc., but other elements may be included to form the, for example, composition, method, kit etc. within the scope of the claim. For example, an expression cassette "comprising" a gene encoding a therapeutic polypeptide operably linked to a promoter is an expression cassette that may include other elements in addition to the gene and promoter, e.g. polyadenylation sequence, enhancer elements, other genes, linker domains, etc.

By "consisting essentially of", it is meant a limitation of the scope of the, for example, composition, method, kit, etc., described to the specified materials or steps that do not materially affect the basic and novel characteristic(s) of the, for example, composition, method, kit, etc. For example, an expression cassette "consisting essentially of" a gene encoding a therapeutic polypeptide operably linked to a promoter and a polyadenylation sequence may include additional sequences, e.g. linker sequences, so long as they do not materially affect the transcription or translation of the gene. As another example, a variant, or mutant, polypeptide fragment "consisting essentially of" a recited sequence has the amino acid sequence of the recited sequence plus or minus about 10 amino acid residues at the boundaries of the sequence based upon the full length naïve polypeptide from which it was derived, e.g. 10, 9, 8, 7, 6, 5, 4, 3, 2 or 1 residue less than the recited bounding amino acid residue, or 1, 2, 3, 4, 5, 6, 7, 8, 9, or 10 residues more than the recited bounding amino acid residue.

By "consisting of", it is meant the exclusion from the composition, method, or kit of any element, step, or ingredient not specified in the claim. For example, an expression cassette "consisting of" a gene encoding a therapeutic polypeptide operably linked to a promoter, and a polyadenylation sequence consists only of the promoter, polynucleotide sequence encoding the therapeutic polypeptide, and polyadenylation sequence. As another example, a polypeptide "consisting of" a recited sequence contains only the recited sequence.

As used herein, the terms "sequence identity," e.g. "% sequence identity," refers to the degree of identity between two or more polynucleotides when aligned using a nucleotide sequence alignment program; or between two or more polypeptide sequences when aligned using an amino acid sequence alignment program. Similarly, the term "identical" or percent "identity" when used herein in the context of two or more nucleotide or amino acid sequences refers to two sequences that are the same or have a specified percentage of amino acid residues or nucleotides when compared and aligned for maximum correspondence, for example as measured using a sequence comparison algorithm, e.g. the Smith-Waterman algorithm, etc., or by visual inspection. For example, the percent identity between two amino acid sequences may be determined using the Needleman and Wunsch, (1970, J. Mol. Biol. 48: 444-453) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. As another example, the percent identity between two nucleotide sequences may be determined using the GAP program in the GCG software package, using a NWSgapdna.CMP matrix and a gap weight of 40, 50, 60, 70, or 80 and a length weight of 1, 2, 3, 4, 5, or 6. A particularly preferred set of parameters (and the one that should be used unless otherwise specified) are a Blossum 62 scoring matrix with a gap penalty of 12, a gap extend penalty of 4, and a frameshift gap penalty of 5. The percent identity between two amino acid or nucleotide sequences can also be determined using the algorithm of E. Meyers and W. Miller (1989, Cabios, 4: 11-17) which has been incorporated into the ALIGN program (version 2.0), using a PAM120 weight residue table, a gap length penalty of 12 and a gap penalty of 4. The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al., (1990, J. Mol. Biol, 215: 403-10). BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (1997, Nucleic Acids Res, 25: 3389-3402). When utilizing BLAST and Gapped BLAST programs, the default parameters of the respective programs (e.g., XBLAST and NBLAST) can be used.

The term "% homology" is used interchangeably herein with the term "% identity" herein and refers to the level of nucleic acid or amino acid sequence identity between two or more aligned sequences, when aligned using a sequence alignment program. For example, as used herein, 80% homology means the same thing as 80% sequence identity determined by a defined algorithm, and accordingly a homologue of a given sequence has greater than 80% sequence identity over a length of the given sequence.

As used herein, the terms "complement" and "complementary" refer to two antiparallel nucleotide sequences capable of pairing with one another upon formation of hydrogen bonds between the complementary base residues in the antiparallel nucleotide sequences. For example, an shRNA might be complementary, i.e. 100% complementary, or substantially complementary, e.g. 80% complementary, 85% complementary, 90% complementary, 95% complementary, 98% complementary, or more to a target sequence. The term "expression" as used herein encompasses the transcription and/or translation of an endogenous gene, a transgene or a coding sequence in a cell.

An "expression vector" as used herein encompasses a vector, e.g. plasmid, minicircle, viral vector, liposome, and the like as discussed above or as known in the art, comprising a polynucleotide which encodes a gene product of interest, and is used for effecting the expression of a gene product in an intended target cell. An expression vector also comprises control elements operatively linked to the encoding region to facilitate expression of the gene product in the target. The combination of control elements, e.g. promoters, enhancers, UTRs, miRNA targeting sequences, etc., and a gene or genes to which they are operably linked for expression is sometimes referred to as an "expression cassette." Many such control elements are known and available in the art or can be readily constructed from components that are available in the art.

A "promoter" as used herein encompasses a DNA sequence that directs the binding of RNA polymerase and thereby promotes RNA synthesis, i.e., a minimal sequence sufficient to direct transcription. Promoters and corresponding protein or polypeptide expression may be ubiquitous, meaning strongly active in a wide range of cells, tissues and species or cell-type specific, tissue-specific, or species specific. Promoters may "constitutive," meaning continually active, or "inducible," meaning the promoter can be activated or deactivated by the presence or absence of biotic or abiotic factors. Also included in the nucleic acid constructs or vectors of the invention are enhancer sequences that may or may not be contiguous with the promoter sequence.

Enhancer sequences influence promoter-dependent gene expression and may be located in the 5' or 3' regions of the native gene.

An"enhancer" as used herein encompasses a cis-acting element that stimulates or inhibits transcription of adjacent genes. An enhancer that inhibits transcription also is termed a "silencer". Enhancers can function (i.e., can be associated with a coding sequence) in either orientation, over distances of up to several kilobase pairs (kb) from the coding sequence and from a position downstream of a transcribed region.

A "termination signal sequence" as used herein encompasses any genetic element that causes RNA polymerase to terminate transcription, such as for example a polyadenylation signal sequence.

A "polyadenylation signal sequence" as used herein encompasses a recognition region necessary for endonuclease cleavage of an RNA transcript that is followed by the polyadenylation consensus sequence AATAAA. A polyadenylation signal sequence provides a "polyA site", i.e. a site on a RNA transcript to which adenine residues will be added by post-transcriptional polyadenylation.

As used herein, the terms "operatively linked" or "operably linked" refers to a juxtaposition of genetic elements, e.g. promoter, enhancer, termination signal sequence, polyadenylation sequence, etc., wherein the elements are in a relationship permitting them to operate in the expected manner. For instance, a promoter is operatively linked to a coding region if the promoter helps initiate transcription of the coding sequence. There may be intervening residues between the promoter and coding region so long as this functional relationship is maintained. As used herein, the term "heterologous" means derived from a genotypically distinct entity from that of the rest of the entity to which it is being compared. For example, a polynucleotide introduced by genetic engineering techniques into a plasmid or vector derived from a different species is a heterologous polynucleotide. As another example, a promoter removed from its native coding sequence and operatively linked to a coding sequence with which it is not naturally found linked is a heterologous promoter. Thus, for example, an rAAV that includes a heterologous nucleic acid encoding a heterologous gene product is an rAAV that includes a nucleic acid not normally included in a naturally-occurring, wild-type AAV, and the encoded heterologous gene product is a gene product not normally encoded by a naturally-occurring, wild-type AAV.

The term "endogenous" as used herein with reference to a nucleotide molecule or gene product refers to a nucleic acid sequence, e.g. gene or genetic element, or gene product, e.g. RNA, protein, that is naturally occurring in or associated with a host virus or cell.

The term "native" as used herein refers to a nucleotide sequence, e.g. gene, or gene product, e.g. RNA, protein, that is present in a wildtype virus or cell. The term "variant" as used herein refers to a mutant of a reference polynucleotide or polypeptide sequence, for example a native polynucleotide or polypeptide sequence, i.e. having less than 100% sequence identity with the reference polynucleotide or polypeptide sequence. Put another way, a variant comprises at least one amino acid difference (e.g., amino acid substitution, amino acid insertion, amino acid deletion) relative to a reference polynucleotide sequence, e.g. a native polynucleotide or polypeptide sequence. For example, a variant may be a polynucleotide having a sequence identity of 70% or more with a full length native polynucleotide sequence, e.g. an identity of 75% or 80% or more, such as 85%, 90%, or 95% or more, for example, 98% or 99% identity with the full length native polynucleotide sequence. As another example, a variant may be a polypeptide having a sequence identity of 70% or more with a full length native polypeptide sequence, e.g. an identity of 75% or 80% or more, such as 85%, 90%, or 95% or more, for example, 98% or 99% identity with the full length native polypeptide sequence. Variants may also include variant fragments of a reference, e.g. native, sequence sharing a sequence identity of 70% or more with a fragment of the reference, e.g. native, sequence, e.g. an identity of 75% or 80% or more, such as 85%, 90%, or 95% or more, for example, 98% or 99% identity with the native sequence.

As used herein, the terms "biological activity" and "biologically active" refer to the activity attributed to a particular biological element in a cell. For example, the "biological activity" of an "immunoglobulin", "antibody" or fragment or variant thereof refers to the ability to bind an antigenic determinant and thereby facilitate immunological function. As another example, the biological activity of a polypeptide or functional fragment or variant thereof refers to the ability of the polypeptide or functional fragment or variant thereof to carry out its native functions of, e.g., binding, enzymatic activity, etc. As a third example, the biological activity of a gene regulatory element, e.g. promoter, enhancer, kozak sequence, and the like, refers to the ability of the regulatory element or functional fragment or variant thereof to regulate, i.e. promote, enhance, or activate the translation of, respectively, the expression of the gene to which it is operably linked.

The terms "administering" or "introducing", as used herein refer to delivery of a vector for recombinant protein expression to a cell, to cells and/or organs of a subject, or to a subject. Such administering or introducing may take place in vivo, in vitro or ex vivo. A vector for expression of a gene product may be introduced into a cell by transfection, which typically means insertion of heterologous DNA into a cell by physical means (e.g., calcium phosphate transfection, electroporation, microinjection or lipofection); infection, which typically refers to introduction by way of an infectious agent, i.e. a virus; or transduction, which typically means stable infection of a cell with a virus or the transfer of genetic material from one microorganism to another by way of a viral agent (e.g., a bacteriophage).

"Transformation" is typically used to refer to bacteria comprising heterologous DNA or cells which express an oncogene and have therefore been converted into a continuous growth mode such as tumor cells. A vector used to "transform" a cell may be a plasmid, virus or other vehicle.

Typically, a cell is referred to as "transduced", "infected"; "transfected" or "transformed" dependent on the means used for administration, introduction or insertion of heterologous DNA (i.e., the vector) into the cell. The terms "transduced", "transfected" and "transformed" may be used interchangeably herein regardless of the method of introduction of heterologous DNA.

The term "host cell", as used herein refers to a cell which has been transduced, infected, transfected or transformed with a vector. The vector may be a plasmid, a viral particle, a phage, etc. The culture conditions, such as temperature, pH and the like, are those previously used with the host cell selected for expression, and will be apparent to those skilled in the art. It will be appreciated that the term "host cell" refers to the original transduced, infected, transfected or transformed cell and progeny thereof.

The terms "treatment", "treating" and the like are used herein to generally mean obtaining a desired pharmacologic and/or physiologic effect. The effect may be prophylactic in terms of completely or partially preventing a disease or symptom thereof, e.g. reducing the likelihood that the disease or symptom thereof occurs in the subject, and/or may be therapeutic in terms of a partial or complete cure for a disease and/or adverse effect attributable to the disease. "Treatment" as used herein covers any treatment of a disease in a mammal, and includes: (a) preventing the disease from occurring in a subject which may be predisposed to the disease but has not yet been diagnosed as having it; (b) inhibiting the disease, i.e., arresting its development; or (c) relieving the disease, i.e., causing regression of the disease. The therapeutic agent may be administered before, during or after the onset of disease or injury. The treatment of ongoing disease, where the treatment stabilizes or reduces the undesirable clinical symptoms of the patient, is of particular interest. Such treatment is desirably performed prior to complete loss of function in the affected tissues. The subject therapy will desirably be administered during the symptomatic stage of the disease, and in some cases after the symptomatic stage of the disease.

The terms "individual," "host," "subject," and "patient" are used interchangeably herein, and refer to a mammal, including, but not limited to, human and non-human primates, including simians and humans; mammalian sport animals (e.g., horses); mammalian farm animals (e.g., sheep, goats, etc.); mammalian pets (dogs, cats, etc.); and rodents (e.g., mice, rats, etc.).

The various compositions and methods of the invention are described below. Although particular compositions and methods are exemplified herein, it is understood that any of a number of alternative compositions and methods are applicable and suitable for use in practicing the invention. It will also be understood that an evaluation of the expression constructs and methods of the invention may be carried out using procedures standard in the art.

The practice of the present invention will employ, unless otherwise indicated, conventional techniques of cell biology, molecular biology (including recombinant techniques), microbiology, biochemistry and immunology, which are within the scope of those of skill in the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology" (D. M. Weir & C. C. Blackwell, eds.); "Gene Transfer Vectors for Mammalian Cells" (J. M. Miller & M. P. Calos, eds., 1987); "Current Protocols in Molecular Biology" (F. M. Ausubel et al., eds., 1987); "PCR: The Polymerase Chain Reaction", (Mullis et al., eds., 1994); and "Current Protocols in Immunology" (J. E. Coligan et al., eds., 1991), each of which is expressly incorporated by reference herein.

Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. The present invention is not limited by the illustrated ordering of acts or events, as some acts may occur in different orders and/or concurrently with other acts or events. Furthermore, not all illustrated acts or events are required to implement a methodology in accordance with the present invention.

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising".

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

All publications mentioned herein are incorporated herein by reference to disclose and describe the methods and/or materials in connection with which the publications are cited. It is understood that the present disclosure supersedes any disclosure of an incorporated publication to the extent there is a contradiction.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

The publications discussed herein are provided solely for their disclosure prior to the filing date of the present application. Nothing-herein is to be construed as an admission that the present invention is not entitled to antedate such publication by virtue of prior invention. Further, the dates of publication provided may be different from the actual publication dates which may need to be independently confirmed.

Unless otherwise indicated, all terms used herein have the same meaning as they would to one skilled in the art and the practice of the present invention will employ, conventional techniques of microbiology and recombinant DNA technology, which are within the knowledge of those of skill of the art.

DETAILED DESCRIPTION OF THE INVENTION

The present disclosure provides polynucleotide cassettes and expression vectors for the expression of a gene in cone cells. Also provided are methods for the use of these compositions in promoting the expression of a gene in cone cells, for example, in an individual, e.g. for the treatment or prophylaxis of a cone cell disorder. These and other objects, advantages, and features of the invention will become apparent to those persons skilled in the art upon reading the details of the compositions and methods as more fully described below.

Compositions

In some aspects of the disclosure, compositions are provided for the expression of a transgene in cone cells. By a "cone cell", also referred to herein as a "cone photoreceptor" or "cone", it is meant the subtype of photoreceptor cells in the retina of the eye that function best in relatively bright light. Cones are sensitive to specific wavelengths of light and hence support the perception of color. In addition, cones respond faster to stimuli than rod photoreceptors, perceiving finer detail and more rapid changes in images than rods, and hence, support high acuity vision for activities where visual detail is of primary importance such as reading and driving. Cones are readily identifiable in cross-sections of the retina by the cone-like shape of their outer segments. They are also readily identifiable by their location in the retina, the highest density of cones existing at the 1.5 mm depression located in the center of the macula of the retina, called the "fovea centralis" or "foveal pit".

In some embodiments of the disclosure, the composition that provides for the expression of a transgene in cone cells is a polynucleotide cassette. By a "polynucleotide cassette" it is meant a polynucleotide sequence comprising two or more polynucleotide sequences, e.g. regulatory elements, translation initiation sequences, coding sequences, termination sequences, etc., typically in operably linkage to one another. Likewise, by a "polynucleotide cassette for the expression of a transgene in a cone cell," it is meant a combination of two or more polynucleotide sequences, e.g. promoter, enhancer, 5'UTR, translation initiation sequence, coding sequence, termination sequences, etc. that promotes the expression of the transgene in a cone cell.

For example, in some embodiments, the polynucleotide cassette comprises:

(a) a promoter region, wherein the promoter region promotes the expression of a coding sequence in cone cells; and
(b) a coding sequence operatively linked to the promoter region.

As another example, in some embodiments, the polynucleotide cassette comprises:

(a) a promoter region, wherein the promoter region promotes the expression of a coding sequence in retinal cone cells;
(b) a translation initiation sequence; and
(c) a coding sequence operatively linked to the promoter region.

As a third example, in some embodiments, the polynucleotide cassette comprises:

(a) a promoter region, wherein the promoter region promotes the expression of a coding sequence in retinal cone cells;
(b) a 5' untranslated region;
(c) a translation initiation sequence; and
(d) a coding sequence operatively linked to the promoter region.

As a fourth example, in some embodiments, the polynucleotide cassette comprises:

(a) a promoter region, wherein the promoter region promotes the expression of a coding sequence in retinal cone cells;
(b) a 5' untranslated region;
(c) an intron;
(d) a translation initiation sequence; and
(e) a coding sequence operatively linked to the promoter region.

As a fifth example, in some embodiments, the polynucleotide cassette comprises:

(a) a promoter region, wherein the promoter region promotes the expression of a coding sequence in retinal cone cells;
(b) a 5' untranslated region;
(c) an intron;
(d) a translation initiation sequence; and
(e) a polyadenylation sequence.

In some embodiments, the polynucleotide cassettes of the present disclosure provide for enhanced expression of a transgene in cone cells. As demonstrated by the working examples of the present disclosure, the present inventors have discovered a number of polynucleotide elements, i.e. improved elements as compared to those known in the art, which individually and synergistically provide for the enhanced expression of transgenes in cone cells. By "enhanced" it is meant that expression of the transgene is increased, augmented, or stronger, in cone cells carrying the polynucleotide cassettes of the present disclosure relative to in cone cells carrying the transgene operably linked to comparable regulatory elements, e.g. as known in the art. Put another way, expression of the transgene is increased, augmented, or stronger, from the polynucleotide cassettes of the present disclosure relative to expression from a polynucleotide cassette not comprising the one or more optimized elements of the present disclosure, i.e. a reference control. For example, expression of the transgene is enhanced, or augmented, or stronger, in cone cells comprising a polynucleotide cassette comprising a promoter disclosed herein than in cone cells that carry the transgene operably linked to a different promoter, e.g. as known in the art. As another example, expression of the transgene is enhanced, or increased, augmented, or stronger, in cone cells comprising a polynucleotide cassette comprising an enhancer sequence disclosed herein than in cone cells that carry the transgene operably linked to a different enhancer sequence. As another example, expression of the transgene is enhanced, or increased, augmented, or stronger, in cone cells comprising a polynucleotide cassette encoding a 5'UTR disclosed herein than in cone cells that carry the transgene operably linked to a different 5'UTR coding sequence. As another example, expression of the transgene is enhanced, or increased, augmented, or stronger, in cone cells comprising a polynucleotide cassette comprising an intron as disclosed herein than in cone cells that carry the transgene operably linked to a different intronic sequence as known in the art. Exemplary sequences comprising elements (e.g., promoters, enhancer sequences, 5'UTRs, and intons) that may be used as references for comparison include sequences encompassed by the native L-opsin promoter (SEQ ID NO:1) and variants thereof, sequences encompassed by the synthetic promoter pR2.1 (SEQ ID NO:50) and variants thereof (e.g. pR1.7, pR1.5, pR1.1) as disclosed in, e.g. US Application No. 2013/0317091, and sequences encompassed by the IRBP/GNAT2 promoter (US Application No. 2014/0275231).

Without wishing to be bound by theory, enhanced expression of a transgene in cells is believed to be due to a faster build-up of gene product in the cells or a more stable gene product in the cells. Thus, enhanced expression of a transgene by the polynucleotide cassettes of the subject disclosure may be observed in a number of ways. For example, enhanced expression may be observed by detecting the expression of the transgene following contact of the polynucleotide cassette to the cone cells sooner, e.g. 7 days sooner, 2 weeks sooner, 3 weeks sooner, 4 weeks sooner, 8 weeks sooner, 12 weeks sooner, or more, than expression would be detected if the transgene were operably linked to comparable regulatory elements, e.g. as known in the art. Enhanced expression may also be observed as an increase in the amount of gene product per cell. For example, there may be a 2-fold increase or more, e.g. a 3-fold increase or more, a 4-fold increase or more, a 5-fold increase or more, or a 10-fold increase or more in the amount of gene product per cone cell. Enhanced expression may also be observed as an increase in the number of cone cells that express detectable levels of the transgene carried by the polynucleotide cassette. For example, there may be a 2-fold increase or more, e.g. a 3-fold increase or more, a 4-fold increase or more, a 5-fold increase or more, or a 10-fold increase or more in the number of cone cells that express detectable levels of the transgene. As another example, the polynucleotide of the present invention may promote detectable levels of the transgene in a greater percentage of cells as compared to a conventional polynucleotide cassette; for example, where a conventional cassette may promote detectable levels of transgene expression in, for example, less than 5% of the cone cells in a certain region, the polynucleotide of the present invention promotes detectable levels of expression in 5% or more of the cone cells in that region; e.g. 10% or more, 15% or more, 20% or more, 25% or more, 30% or more, 35% or more, 40% or more, or 45% or more, in some instances 50% or more, 55% or more; 60% or more, 65% or more, 70% or more, or 75% or more, for example 80% or more, 85% or more, 90% or more, or 95% or more of the cone cells that are contacted, will express detectable levels of gene product. Enhanced expression may also be observed as an alteration in the viability and/or function of the cone cells, e.g. as measured using assessment tools such as fundus photography, OCT, adaptive optics, cERG, color vision tests, visual acuity tests, and the like, as known in the art and as described herein.

The polynucleotide cassettes of the present disclosure typically comprise a promoter region. Any suitable promoter region or promoter sequence therein can be used in the subject polynucleotide cassettes, so long as the promoter region promotes expression of a coding sequence in retinal cone cells. In some embodiments, the promoter specifically promotes expression of the gene in mammalian retinal cone cell; more preferably primate retinal cone cells; more preferably in Catarrhini retinal cone cells; even more preferably in human retinal cone cells. By "specifically" it is meant that the promoter predominately promotes expression of the gene in the target cells as compared to other cell types. Thus, for example, when a promoter region that specifically promotes expression in cone cells is employed, more than 50% of the expression, for example, at least any of 60%, 65%, 70% or 75% or more of the expression, e.g. at least any of 80%, 85%, 90%, 91%, 92%, 93%, 94%, 95%, 96%, 97%, 97%, 98%, 99%, 99.5%, or more of expression of the gene after delivery of the subject polynucleotide cassette to the eye will be in cone cells.

Exemplary suitable promoter regions include the promoter region for any cone-specific gene, such as a 492 L-opsin promoter region (SEQ ID NO:1), a 491 L-opsin promoter region (SEQ ID NO:53), a 496 L-opsin promoter region (SEQ ID NO:79), an M-opsin promoter region (SEQ ID NO:2, SEQ ID NO:54), a minimal M-opsin promoter region (SEQ ID NO:55, SEQ ID NO:93), a core M-opsin promoter sequence as disclosed for the first time herein (SEQ ID NO:80), an S-opsin promoter region (SEQ ID NO:3), an hRK promoter region, and a cone arrestin promoter region; or portions or variants thereof which retain activity promoting the expression of a gene in cone cells. Nonlimiting examples of portions, or fragments, of promoter regions that find use in the subject polynucleotide cassettes include promoter sequence immediately upstream of the 5'UTR, and canonical binding sequences for transcription factors as known in the art. Such portions, or fragments, may be readily determined using any convenient method as known in the art or described herein. For example, the promoter sequence immediately upstream of the 5'UTR in SEQ ID NO:54 and SEQ ID NO:55 may readily determined by in silico evaluation of the sequence as consisting essentially of nucleotides 1-406 of SEQ ID NO:54 or nucleotides 1-154 of SEQ ID NO:55 using publicly available tools such as, e.g. the UCSC genome BLAT browser; or by empirical testing through operable linkage with a reporter gene and introduction into cone cells, e.g. as described in the working examples herein. Shorter promoter sequences are, in some embodiments, preferable to longer promoter sequences, as they provide for more space in the vector for other nucleotide elements. In some embodiments, the promoter region is less than 492 base pairs in length. For example, in some embodiments, the functional fragment does not comprise nucleotides 1-10 or more of SEQ ID NO:1, for example, the functional fragment does not comprise nucleotides 1-20 or more, nucleotides 1-30 or more, nucleotides 1-40 or more, nucleotides 1-50 or more of SEQ ID NO:1, e.g. nucleotides 1-60 or more, nucleotides 1-70 or more, nucleotides 1-80 or more, nucleotides 1-90 or more, nucleotides 1-100 or more of SEQ ID NO:1, in some instances nucleotides 1-120 or more, nucleotides 1-140 or more, nucleotides 1-160 or more, nucleotides 1-180 or more, nucleotides 1-200 or more, nucleotides 1-220 or more, nucleotides 1-240 or more, or about nucleotides 1-260 of SEQ ID NO:1. Any suitable method for identifying a promoter region capable of driving expression in mammalian or primate cone cells can be used to identify promoter regions and promoter sequences therein that find use in the polynucleotide cassettes of the present disclosure.

In some embodiments, the promoter region of the subject polynucleotide cassette comprises one of the promoter regions disclosed herein, e.g. a 492 L-opsin promoter region (SEQ ID NO:1), a 491 L-opsin promoter region (SEQ ID NO:53), a 496 L-opsin promoter region (SEQ ID NO:79), an M opsin promoter region (SEQ ID NO:2, SEQ ID NO:54), a minimal M opsin promoter region (SEQ ID NO:55, SEQ ID NO:93), the core M-opsin promoter sequence disclosed herein (SEQ ID NO:80), or the S opsin promoter region (SEQ ID NO:3), or a functional fragment or variant thereof, e.g. a sequence having an identity of 75% or more, e.g. 80% or more, 85% or more, 90% or more, or 95% or more, (e.g., 80%, 85%, 90% Or 95%), to an aforementioned sequence or functional fragment thereof. In some embodiments, the promoter sequence of the subject polynucleotide cassette consists essentially of one of the promoter regions disclosed herein, i.e. SEQ ID NO:1, SEQ ID NO:53, SEQ ID NO:79, SEQ ID NO:2, SEQ ID NO:54, SEQ ID NO:55, SEQ ID NO:93, SEQ ID NO:80, or SEQ ID NO:3, or a functional fragment or variant thereof, e.g. a sequence having an identity of 75% or more, e.g. 80%, or more 85% or more, 90% or more, or 95% or more, (e.g., 80%, 85%, 90% Or 95%), to the full length of an aforementioned sequence plus or minus 1, 2, 3, 4, 5, 6, 7, 8, 9, or 10 nucleotides, or functional fragment thereof. In some embodiments, the promoter region of the subject polynucleotide cassette consists of one of the promoter regions disclosed herein, i.e. SEQ ID NO:1, SEQ ID NO:53, SEQ ID NO:79, SEQ ID NO:2, SEQ ID NO:54, SEQ ID NO:55, SEQ ID NO:93, SEQ ID NO:80, or SEQ ID NO:3, or a functional fragment or variant thereof, e.g. a sequence having an identity of 75% or more, e.g. 80%, 85%, 90%, 95% or more, to the full length of an aforementioned sequence or functional fragment thereof. In certain embodiments, the promoter region consists essentially of SEQ ID NO:74. In some such embodiments, the promoter sequence consists essentially of SEQ ID NO:80. In some embodiments, the promoter results in enhanced expression in cone cells compared to other promoters known in the art, e.g., the synthetic promoters pR2.1, pR1.7, pR1.1, and IRBP/GNAT2.

In some embodiments, the polynucleotide cassette further comprises an enhancer element. Enhancers are nucleic acid elements known in the art to enhance transcription, and can be located anywhere in association with the gene they regulate, e.g. upstream, downstream, within an intron, etc. Any enhancer element can be used in the polynucleotide cassettes and gene therapy vectors of the present disclosure, so long as it enhances expression of the gene when used in combination with the promoter. In a preferred embodiment, the enhancer element is specific for retinal cone cells; more preferably, it is specific for primate retinal cone cells; more preferably in Catarrhini retinal cone cells; even more preferably in human retinal cone cells. By "specifically" it is meant that the enhancer predominately enhances expression of the gene in the target cells compared to other cell types. Thus, for example, when an enhancer that specifically enhances expression in cone cells is employed, more than 50% of the expression, for example, at least any of 60%, 65%, 70%, 75% or more of the expression, e.g., at least 80%, and preferably 85%, 90%, 91%, 92%, 93%, 94%, 95%, 96%, 97%, 97%, 98%, 99%, 99.5%, or more of expression of the gene after delivery of the vector to the eye will be in cone cells.

Exemplary enhancer regions that find use in the polynucleotide cassettes of the present disclosure include those that comprise, consist essentially of, or consist of the enhancer region for any cone-specific gene or fragments or variants thereof which retain enhancer activity. For example, the L/M minimal opsin enhancer, referred to as the Locus Control Region (LCR) (Wang et al., 1992. Neuron 9: 429-440) (SEQ ID NO:52) can be used to enhance gene expression in cone cells; its absence results in blue cone monochromacy (Nathans et al., 1989; Science, 245: 831-838). The LCR has been shown to be useful in gene therapy, for example with AAV vectors (Li et al., Vision Research 48(2008): 332-338). Furthermore, a functional fragment consisting essentially of a 36 bp "core" LCR sequence has been identified that is necessary and sufficient for expression from the opsin promoter in cone cells (Komaromy et al. Targeting gene expression to cones with human cone opsin promoters in recombinant AAV. Gene Ther. 2008; 15(14): 1049-55) (SEQ ID NO:51). In some embodiments, the enhancer of the polynucleotide cassette comprises SEQ ID NO:51 or SEQ ID NO:52. In certain embodiments, the enhancer of the polynucleotide cassette consists essentially of SEQ ID NO:51 or SEQ ID NO:52.

L/M enhancer elements of 100, 200, 300, 400, 500, 600, 700, 800, 900, 1000, 1100, 1200, 1300, 1400, 1500, 1600, 1700, 1800, 1900, 2000, or more nucleotides that comprise one or more copies of the L/M minimal opsin enhancer, and the full L/M opsin enhancer, or other portions or variants thereof which retain activity enhancing expression of genes in a cone-specific manner find use in the present compositions. Any suitable method for identifying enhancer sequences capable of driving expression in primate cone cells can be used to identify such enhancers, as will be understood by those of skill in the art based on the teachings herein.

The length of the promoter and enhancer regions can be of any suitable length for their intended purpose, and the spacing between the promoter and enhancer regions can be any suitable spacing to promote cone-specific expression of the gene product. In various preferred embodiments, the enhancer is located 0-1500; 0-1250; 0-1000; 0-750; 0-600; 0-500; 0-400; 0-300; 0-200; 0-100; 0-90; 0-80; 0-70; 0-60; 0-50; 0-40; 0-30; 0-20; or 0-10 nucleotides upstream of the promoter. The promoter can be any suitable distance upstream of the encoded gene.

In some embodiments, the subject polynucleotide cassette comprises a sequence encoding a 5' untranslated region, i.e. polynucleotide sequence encoding an untranslated region 5' to the coding sequence, also called the 5'UTR. In an expression cassette, the 5'UTR is known in the art as the sequence between the transcription initiation site and the Kozak sequence where protein translation begins. Secondary mRNA structure of the 5'UTR is known to affect transcription levels. Specifically, for enhanced gene expression, the sequence of the 5'UTR region in the present invention is selected to minimize or avoid secondary structures and upstream AUG (uAUG) codons which are known to decrease translation efficiency due to inefficient ribosome scanning and false translational starts (Kozak, 1995. PNAS 92:2662). See Davuluri et al., Genome Research, 2000: 10 (11); 1807-1816. For example, the 5'UTR sequence from the human gene HSP70 (SEQ ID NO:58) has been identified for its unusual ability to enhance mRNA translation, possibly due to an IRES mechanism (Rubtsova et al., 2003. PNAS 278(25): 22350-22356; Vivinus et al, 2001. Eur J Biochem. 268: 1908-1917). Any 5' UTR can be used, but ideally the sequence of the 5'UTR has minimal secondary mRNA structure and upstream AUG sequences. Put another way, in some embodiments, the sequence between the transcription initiation site and the translation initiation site of the polynucleotide cassette does not contain the polynucleotide ATG. In some embodiments, the 5' UTR comprises, consists essentially, or consists of SEQ ID NO:56, SEQ ID NO:57, SEQ ID NO:58, SEQ ID NO:84, SEQ ID NO:85, SEQ ID NO:86, SEQ ID NO:87, SEQ ID NO:88, or SEQ ID NO:89; or a functional fragment or variant thereof, for example, a polynucleotide sequence having a sequence identity of 85% or more to a sequence selected from the group consisting of SEQ ID NO:56, SEQ ID NO:57, SEQ ID NO:58, SEQ ID NO:84, SEQ ID NO:85, SEQ ID NO:86, SEQ ID NO:87, SEQ ID NO:88, and SEQ ID NO:89, or a fragment thereof. In some embodiments, some or all of the 5'UTR sequence is comprised by a promoter region as disclosed in, for example, SEQ ID NO:1, SEQ ID NO:2, SEQ ID NO:3, SEQ ID NO:53, SEQ ID NO:54, SEQ ID NO:55, or SEQ ID NO:79. In other embodiments, the 5'UTR is not comprised by the promoter region; see, e.g. the core promoter sequence SEQ ID NO:84, which does not encode for 5' UTR sequence. In some embodiments, the 5'UTR sequence is heterologous to the promoter sequence. In various preferred embodiments, the 3' end of the UTR is 0-20; 0-15; 0-10; 0-9; 0-8; 0-7; 0-6; or 0-5 nucleotides upstream of the coding sequence, and its 5' end is 0-20; 0-15; 0-10; 0-9; 0-8; 0-7; 0-6; or 0-5 nucleotides downstream of the proximal promoter region. In some embodiments, the 5'UTR element results in enhanced expression in cone cells compared to other 5'UTRs known in the art, e.g., the 5'UTRs comprised by the synthetic promoters pR2.1, pR1.7, pR1.1, and IRBP/GNAT2.

In some embodiments, the subject polynucleotide cassette further comprises an intron comprising a splice donor/acceptor region. In some embodiments, the intron is located downstream of the promoter region and is located upstream of the translation initiation sequence of the gene, i.e. the intron is located within the 5'UTR. In other embodiments, the intron is located downstream of the translation initiation sequence of the gene, i.e. the intron is located within the coding sequence. As is generally known in the art, introns are DNA polynucleotides that are transcribed into RNA and removed during mRNA processing through intron splicing. Polynucleotide cassettes containing introns generally have higher expression than those without introns. Introns can stimulate expression between 2- and 500-fold (Buchman and Berg, 1988. *Mol Cel Bio,* 8(10): 4395). Efficiently spliced introns contain a pre-splice donor, branchpoint, and Py rich region (Senapathy et al, 1990; Meth. Enzymol. 183, 252-78; Wu and Krainer, 1999; Mol Cell Biol 19(5):3225-36). 5' introns are generally more efficient compared to introns at the 3' end (Huang and Gorman, 1990; Mol Cell Bio, 10:1805). Although introns are known generally to increase the level of gene expression, the specific increase (if any) of a given cDNA is empirical and must be tested; for example the chimeric intron in the pSI vector increases CAT expression by 21-fold, but luciferase expression by only 3-fold.

Any intron can be used in the subject polynucleotide cassettes, so long as it comprises a splice donor/acceptor region recognized in mammalian or in primate cone cells, so that the intron can be spliced out of the resulting mRNA product. In one embodiment, the intron comprises, consists essentially of, or consists of an SV40 intron according to SEQ ID NO:5. In another embodiment, the intron comprises, consists essentially of, or consists of the chimeric intron from pSI (SEQ ID NO:60) or a variant thereof. In another embodiment, the intron comprises, consists essentially of, or consists of the CMV intron A or a variant thereof. In yet another embodiment, the intron comprises, consists essentially of, or consists of the pR2.1 intron (SEQ ID NO:59) or a variant thereof, or alternatively, the rabbit or human beta globin intron (Xu et al, 2001, Gene 272:149; Xu et al. 2002; J Control Rel 81:155) or a variant thereof. In some such embodiments, the intron comprises a sequence having a sequence identity of 85% or more to a sequence selected from the group consisting of SEQ ID NO:5, SEQ ID NO:59, and SEQ ID NO:60. Typically, the intron is heterologous to the promoter region and/or the 5'UTR.

In some embodiments, the intron resides within a 5'UTR. In other words, the DNA sequence encoding the 5'UTR is interrupted by intronic DNA sequence. For example, the coding sequence for the 5'UTR that is SEQ ID NO:84 may be encoded in two parts, e.g. SEQ ID NO:85 and SEQ ID NO:86, with an intronic sequence between them. As another example, the coding sequences for the 5'UTR that is SEQ ID NO:88 may be encoded in two parts, e.g. SEQ ID NO:89 and SEQ ID NO:73, with an intronic sequence between them. In various embodiments, the 3' end of the intron is 0-20; 0-15; 0-10; 0-9; 0-8; 0-7; 0-6; or 0-5 nucleotides upstream of the gene, and its 5' end is 0-20; 0-15; 0-10; 0-9; 0-8; 0-7; 0-6; or 0-5 nucleotides downstream of the proximal promoter region. In other embodiments, the intron resides within the coding sequence of the gene.

In some embodiments, the polynucleotides cassettes of the present disclosure comprise a translation initiation sequence, also know as a “Kozak sequence” or “Kozak translation initiation sequence. This is the nucleic acid sequence where the ribosome attaches and translation begins. Examples include ACCATGG (Kozak, 1986. Cell, 44:283-292) and (GCC)GCC(A/G)CCATGG (Kozak, 1987. Nucl Acid Res; 15(20): 8125) (SEQ ID NO:73). Any suitable Kozak sequence can be used in the polynucleotide cassette, preferably selected to increase expression of the coding sequence in retinal cone cells. In one embodiment, the translation initiation sequence comprises SEQ ID NO:72. In an alternative embodiment, the translation initiation sequence comprises SEQ ID NO:73. In some embodiments, the Kozak element results in enhanced expression in cone cells compared to other Kozak sequences known in the art, e.g., the Kozak sequences comprised by the synthetic promoters pR2.1, pR1.7, pR1.1, and IRBP/GNAT2.

In some aspects of the present invention, the subject polynucleotide cassettes are used to deliver a gene to cone cells of an animal, e.g. to determine the effect that the gene has on cell viability and/or function, to treat a cone cell disorder, etc. Accordingly, in some embodiments, the polynucleotide cassettes of the present disclosure further comprise a gene to be delivered as a transgene to cone cells of an animal in vitro or in vivo. The gene coding sequence is typically operatively linked to the promoter region of the subject polynucleotide cassette, and in instances in which an enhancer element is present, to the enhancer element of the subject polynucleotide cassette, such that the promoter and optionally enhancer elements promote the expression of the coding sequence or cDNA in cone cells of the subject.

The coding sequence to be expressed in the cone cells can be any polynucleotide sequence, e.g. gene or cDNA that encodes a gene product, e.g. polypeptide or RNA-based therapeutic (siRNA, antisense, ribozyme, shRNA, etc.). The coding sequence may be heterologous to the promoter sequence and/or 5'UTR sequence to which it is operably linked, i.e. not naturally operably associated with it. Alternatively, the coding sequence may be endogenous to the promoter sequence and/or 5'UTR sequence to which it is operably linked, i.e. is associated in nature with that promoter or 5'UTR. The gene product may act intrinsically in the cone cell, or it may act extrinsically, e.g. it may be secreted. For example, when the transgene is a therapeutic gene, the coding sequence may be any gene that encodes a desired gene product or functional fragment or variant thereof that can be used as a therapeutic for treating a cone cell disease or disorder, or as a means to otherwise enhance vision, including but not limited to promoting tetrachromatic color vision. In various preferred embodiments, the transgene encodes a therapeutic protein or functional fragment or variant thereof selected from the group consisting of:

(a) SEQ ID NO:7 (SEQ ID NO:6) Homo sapiens opsin 1 (cone pigments), short-wave-sensitive (OPN1SW), mRNA NCBI Reference Sequence: NM_001708.2;
(b) SEQ ID NO:9 (SEQ ID NO:8) Homo sapiens opsin 1 (cone pigments), medium-wave-sensitive (OPN1MW), mRNA NCBI Reference Sequence: NM_000513.2;
(c) SEQ ID NO:11 (SEQ ID NO:10) Homo sapiens opsin 1 (cone pigments), long-wave-sensitive (OPN1LW), mRNA NCBI Reference Sequence: NM_020061.4;
(d) SEQ ID NO:13 (SEQ ID NO:12) ATP binding cassette retina gene (ABCR) gene (NM_000350);
(e) SEQ ID NO:15 (SEQ ID NO:14) retinal pigmented epithelium-specific 65 kD protein gene (RPE65) (NM_000329);
(f) SEQ ID NO:17 (SEQ ID NO:16) retinal binding protein 1 gene (RLBP1) (NM_000326);
(g) SEQ ID NO:19 (SEQ ID NO:18) peripherin/retinal degeneration slow gene, (NM_000322);
(h) SEQ ID NO:21 (SEQ ID NO:20) arrestin (SAG) (NM_000541);
(i) SEQ ID NO:23 (SEQ ID NO:22) alpha-transducin (GNAT1) (NM_000172);

(j) SEQ ID NO:24 guanylate cyclase activator 1A (GUCA1A) (NP_000400.2);
(k) SEQ ID NO:25 retina specific guanylate cyclase (GUCY2D), (NP_000171.1);
(l) SEQ ID NO:26 & 27 alpha subunit of the cone cyclic nucleotide gated cation channel (CNGA3) (NP_001073347.1 or NP_001289.1);
(m) SEQ ID NO:28 Human cone transducin alpha subunit (incomplete achromotopsia);
(n) SEQ ID NO:29 cone cGMP-specific 3',5'-cyclic phosphodiesterase subunit alpha', protein (cone dystrophy type 4);
(o) SEQ ID NO:30 retinal cone rhodopsin-sensitive cGMP 3',5'-cyclic phosphodiesterase subunit gamma, protein (retinal cone dystrophy type 3A);
(p) SEQ ID NO:31 cone rod homeobox, protein (Cone-rod dystrophy);
(q) SEQ ID NO:32 cone photoreceptor cyclic nucleotide-gated channel beta subunit, protein (achromatopsia);
(r) SEQ ID NO:33 cone photoreceptor cGMP-gated cation channel beta-subunit, protein (total color blindness, for example, among Pingelapese Islanders);
(s) SEQ ID NO:35 (SEQ ID NO:34) retinitis pigmentosa 1 (autosomal dominant) (RP 1);
(t) SEQ ID NO:37 (SEQ ID NO:36) retinitis pigmentosa GTPase regulator interacting protein 1 (RPGRIP 1);
(u) SEQ ID NO:39 (SEQ ID NO:38) PRP8;
(v) SEQ ID NO:41 (SEQ ID NO:40) centrosomal protein 290 kDa (CEP290);
(w) SEQ ID NO:43 (SEQ ID NO:42) IMP (inosine 5'-monophosphate) dehydrogenase 1 (IMPDH1), transcript variant 1;
(x) SEQ ID NO:45 (SEQ ID NO:44) aryl hydrocarbon receptor interacting protein-like 1 (AIPL1), transcript variant 1;
(y) SEQ ID NO:47 (SEQ ID NO:46) retinol dehydrogenase 12 (all-trans/9-cis/11-cis) (RDH12);
(z) SEQ ID NO:49 (SEQ ID NO:48) Leber congenital amaurosis 5 (LCA5), transcript variant 1; and
(aa) exemplary OPN1LW/OPN1MW2 polymorphs (compared to OPN1LW (L opsin) polypeptide sequence; the amino acid to the left of the number is the residue present in the L opsin sequence; the number is the reside number in L opsin, and the reside to the right of the number is the variation from L opsin. Polymorphs according to these embodiments may comprise one or more of the amino acid substitutions selected from Thr65Ile; Ile111Val; Ser116Tyr; Leu153Met; Ile171Val; Ala174Val; Ile178Val; Ser180Ala; Ile230Thr; Ala233Ser; Val236Met; Ile274Val; Phe275Leu; Tyr277Phe; Val279Phe; Thr285Ala; Pro298Ala; Tyr309Phe;
(ab) Additional Opsin Sequence Variation 1 (SEQ ID NO:61);
(ac) Additional Opsin Sequence Variation 2 (SEQ ID NO:62);
(ad) Additional Opsin Sequence Variation 3 (SEQ ID NO:63);
(ae) Additional Opsin Sequence Variation 4 (SEQ ID NO:64);
(af) Additional Opsin Sequence Variation 5 (SEQ ID NO:65);
(ag) Additional Opsin Sequence Variation 6 (SEQ ID NO:65);
(ah) Additional Opsin Sequence Variation 7 (SEQ ID NO:66);
(ai) Additional Opsin Sequence Variation 8 (SEQ ID NO:67);
(aj) Additional Opsin Sequence Variation 9 (SEQ ID NO:68);
(ak) hCHR2 (channel rhodopsin) (SEQ ID NO:69);
(al) NpHR (halorhodopsin) (SEQ ID NO:70); and
(am) eGFP (SEQ ID NO:71).

In some embodiments, the coding sequence encoded by the transgene encodes a polypeptide having at least 85% sequence identity to a polypeptide encoded by a sequence disclosed above or herein, for example at least 90% sequence identity, e.g. at least 95% sequence identity, at least 98% sequence identity, or at least 99% sequence identity. Thus, for example, the coding sequence encodes a cone opsin having at least 85%, at least 90%, at least 95% identity, at least 98% sequence identity, or at least 99% sequence identity, to the polypeptide encoded by OPN1LW, OPN1MW, or OPN1SW. In some embodiments, the coding sequence has a sequence identity of at least 85%, 90%, 95%, 98% or at least 99% to SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, or SEQ ID NO:71.

The proteins recited in (a)-(c) and (aa-aj) are all involved in color vision. The exemplary polymorphs include ones at positions 65, 116, 180, 230, 233, 277, 285, and 309 that affect the spectra of the pigments in cone cells expressing them. Positions 274, 275, 277, 279, 285, 298 and 309 together distinguish L opsin from M opsin.

The proteins recited (d)-(z) are exemplary eye disease-associated genes such as in retinitis pigmentosa (polypeptides "e"-"l", "s"-"y"), incomplete achromatopsia (polypeptide "m"), Stargardt's (polypeptide "d"); Leber congenital amaurosis (polypeptide "z"); cone dystrophy, such as cone dystrophy type 4 (polypeptide "n"); retinal cone dystrophy; for example, retinal cone dystrophy type 3A (polypeptide "o"); Cone-rod dystrophy (polypeptide "p"); achromatopsia (polypeptide "q"); and total color blindness, for example, among Pingelapese Islanders (polypeptide "r").

In one embodiment of the invention, the transgene coding sequence is modified, or "codon optimized" to enhance expression by replacing infrequently represented codons with more frequently represented codons. The coding sequence is the portion of the mRNA sequence that encodes the amino acids for translation. During translation, each of 61 trinucleotide codons are translated to one of 20 amino acids, leading to a degeneracy, or redundancy, in the genetic code. However, different cell types, and different animal species, utilize tRNAs (each bearing an anticodon) coding for the same amino acids at different frequencies. When a gene sequence contains codons that are infrequently represented by the corresponding tRNA, the ribosome translation machinery may slow, impeding efficient translation. Expression can be improved via "codon optimization" for a particular species, where the coding sequence is altered to encode the same protein sequence, but utilizing codons that are highly represented, and/or utilized by highly expressed human proteins (Cid-Arregui et al., 2003; J. Virol. 77: 4928). In one aspect of the present invention, the coding sequence of the transgene is modified to replace codons infrequently expressed in mammal or in primates with codons frequently expressed in primates. For example, in some embodiments, the coding sequence encoded by the transgene encodes a polypeptide having at least 85% sequence identity to a polypeptide encoded by a sequence disclosed above or herein, for example at least 90% sequence identity, e.g. at least 95% sequence identity, at least 98% identity, at least 99% identity, wherein at least one codon of the coding sequence has a higher tRNA frequency in humans than the corresponding codon in the sequence disclosed above or herein.

Figure 3A:
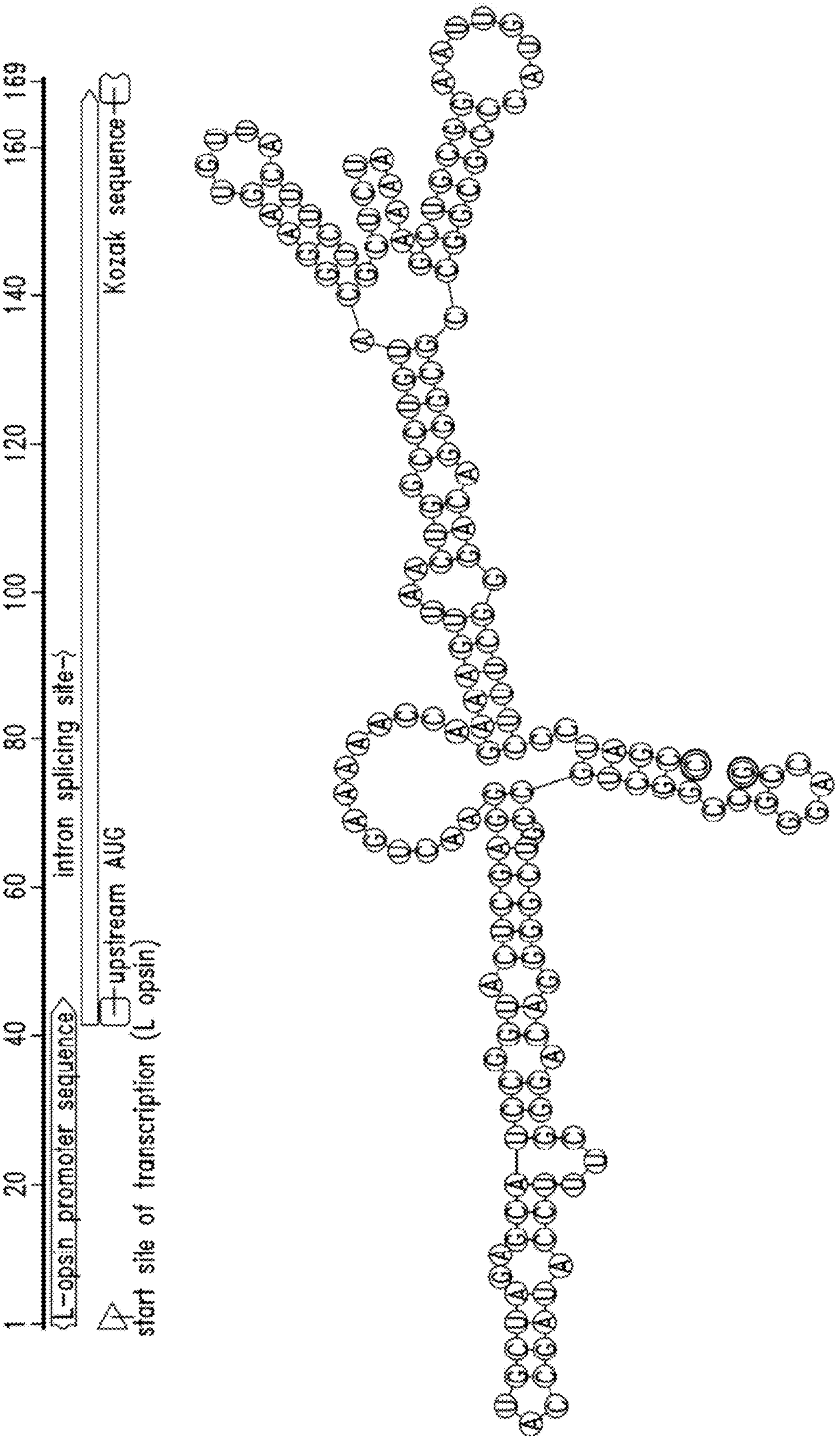
FIG. 3A depicts an example 5'UTR mRNA structure (SEQ ID NO:56), the 5'UTR mRNA structure from pR2.1 (Mancuso et al.). This 5' UTR has two upstream AUGs and open reading frames (ORF), a high level of base pairing and hairpin structure, and a shorter Kozak sequence.
Figure 3B:
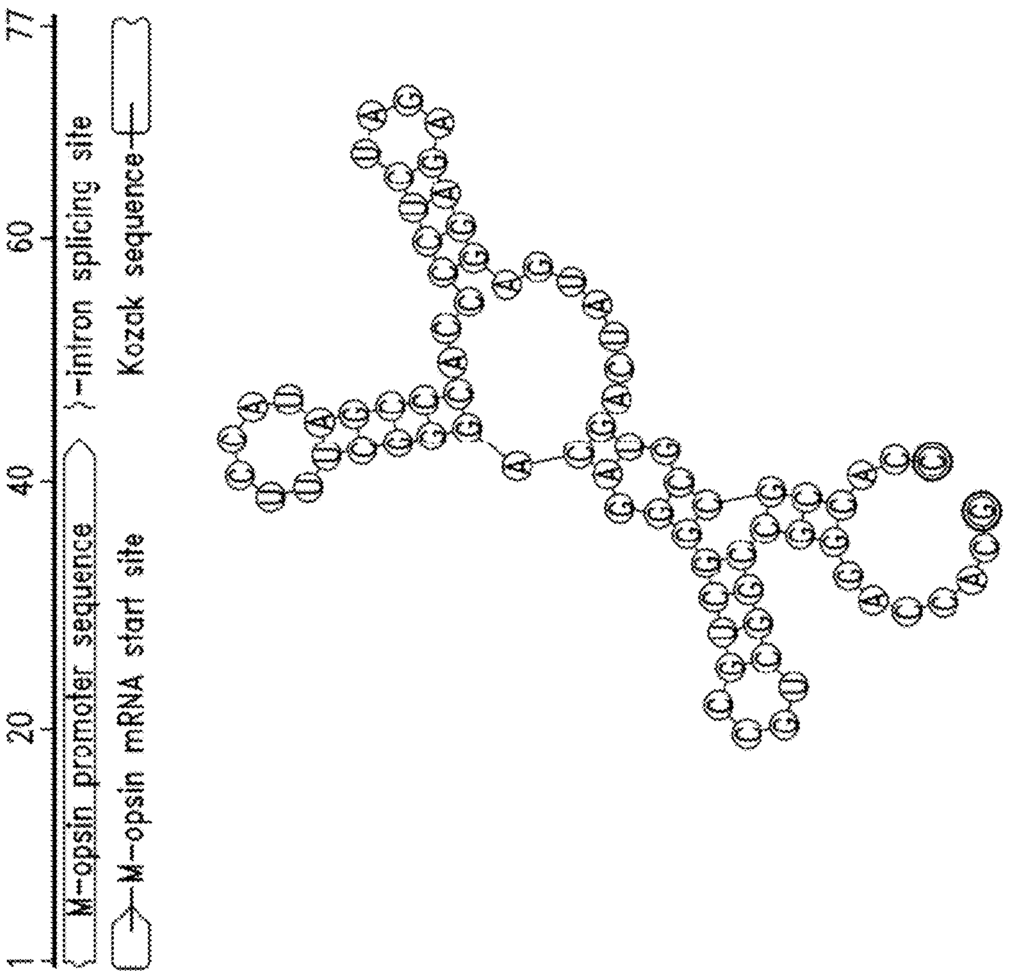
FIG. 3B depicts an example 5'UTR mRNA and structure (SEQ ID NO:57) from an optimized cassette of the present disclosure. The 5' UTR comprises no upstream AUG and no ORFs. In addition, as compared to the 5' UTR of FIG. 3A, the 5' UTR of FIG. 3B is shorter, with less base pairing; and the Kozak sequence is longer.
Figure 4A:
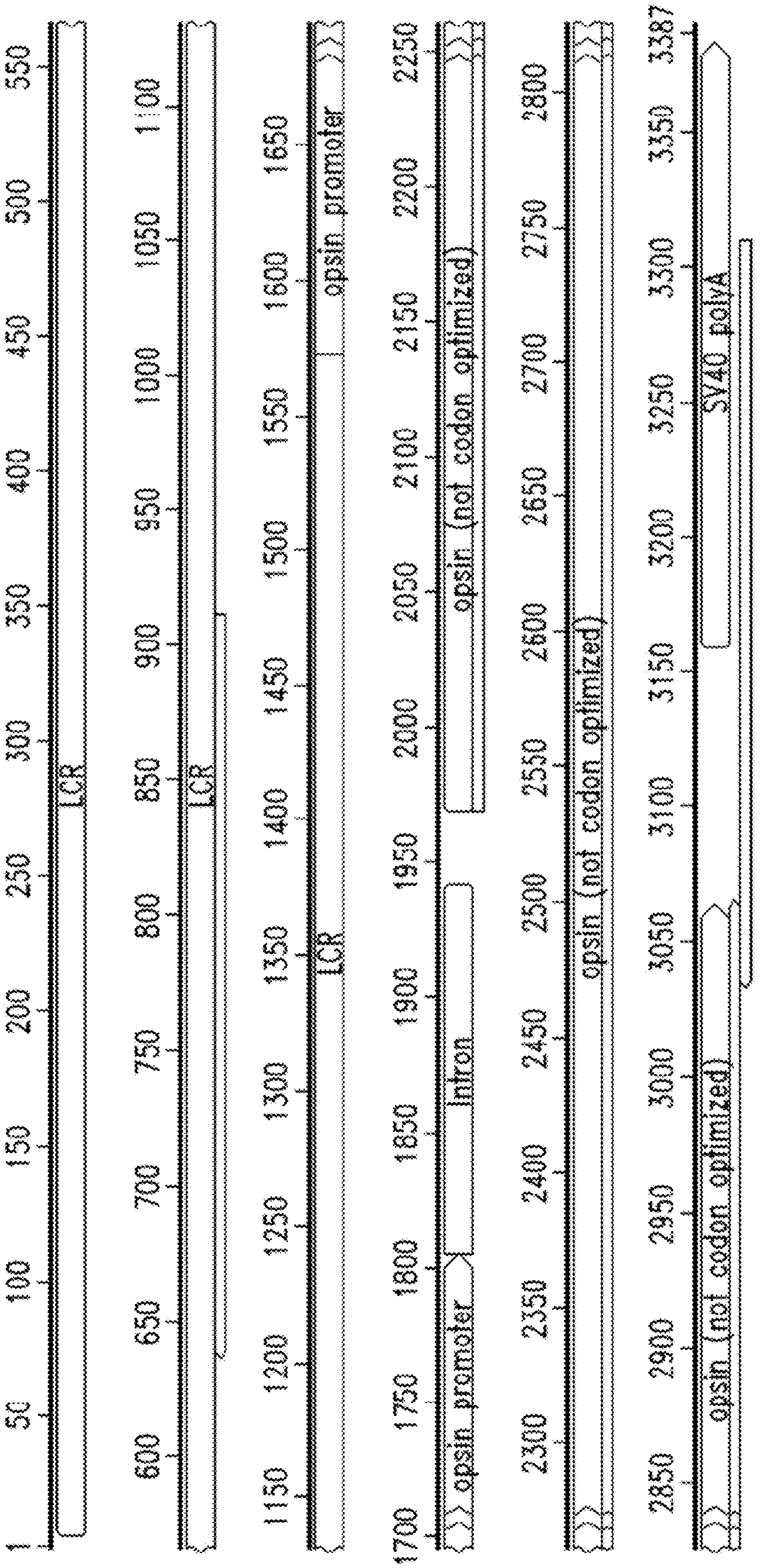
FIG. 4A depicts a polynucleotide cassette before codon optimization. Open reading frames (ORFs) greater than 250 nucleotides in length are shown in gray below the sequence.
Figure 4B:
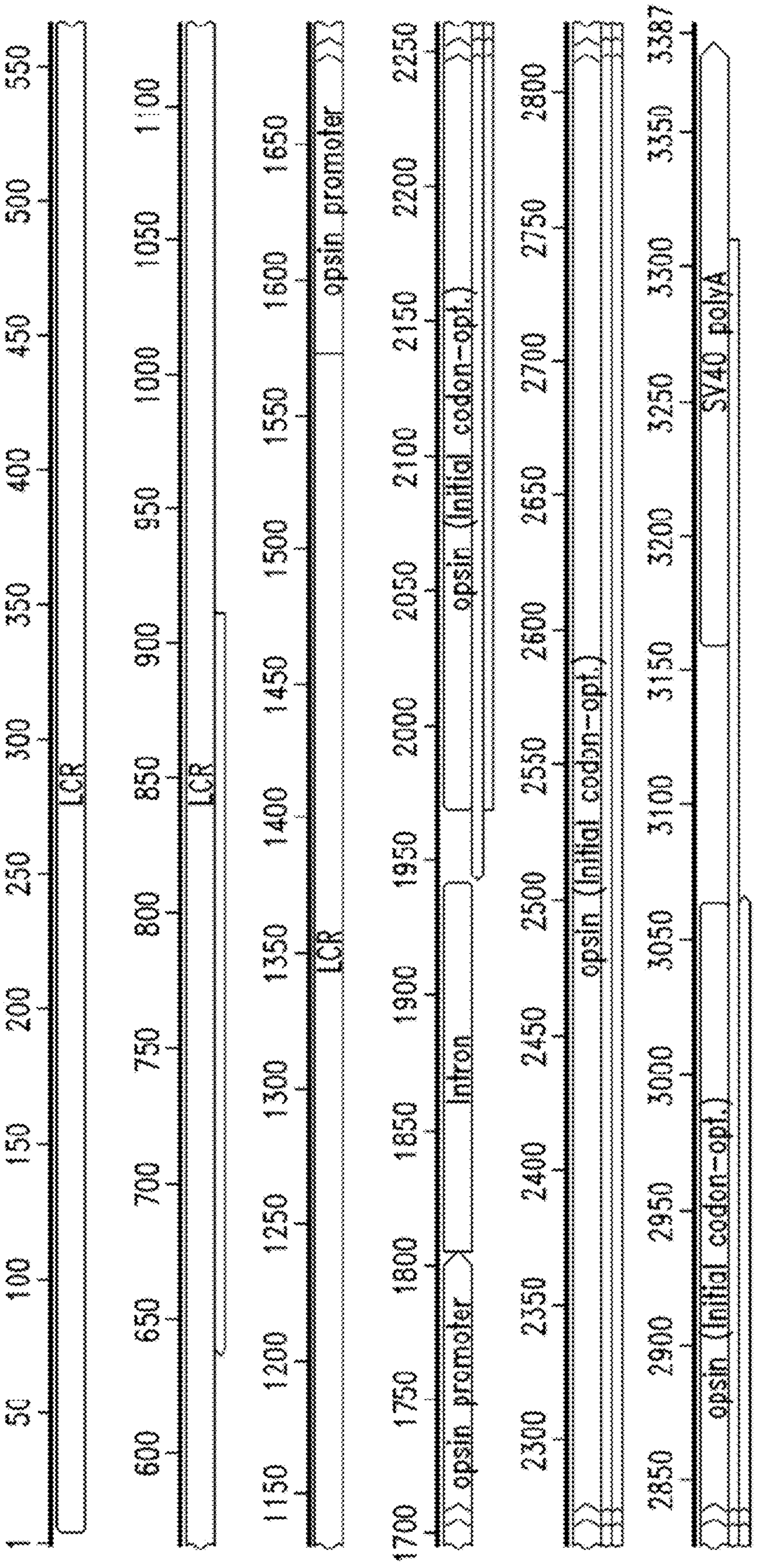
FIG. 4B depicts a polynucleotide cassette after codon optimization, but before removal of non-transgene ORFs. ORFs greater than 250 nucleotides are shown in gray below sequence diagram. Note the introduction of a new ORF in reverse orientation beginning from SV40 polyA and extending 1,365 bases.
Figure 4C:
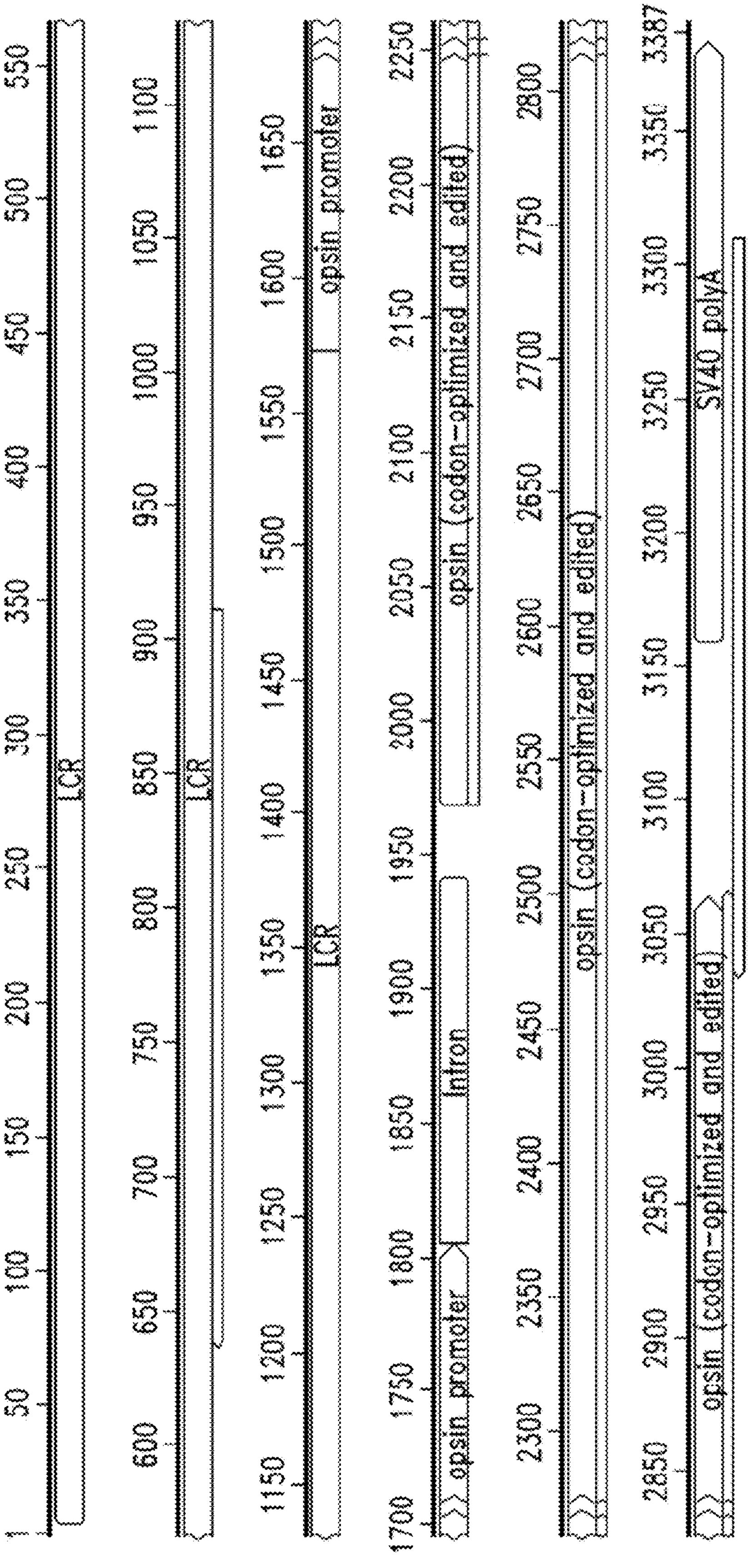
FIG. 4C depicts a polynucleotide cassette after codon optimization and removal of ORFs. ORFs greater than 250 nucleotides are shown in gray below the sequence diagram. Note that the sequence has been optimized so that newly introduced ORFs are shortened or removed.

In an additional embodiment of the invention, the transgene coding sequence is modified to enhance expression by termination or removal of open reading frames (ORFs) that do not encode the desired transgene. An open reading frame (ORF) is the nucleic acid sequence that follows a start codon and does not contains a stop codons. ORFs may be in the forward or reverse orientation, and may be "in frame" or "out of frame" compared with the gene of interest. Such open reading frames have the potential to be expressed in an expression cassette alongside the gene of interest, and could lead to undesired adverse effects. In one aspect of the present invention, the coding sequence of the transgene has been modified to remove open reading frames by further altering codon usage. This was done by eliminating start codons (ATG) and introducing stop codons (TAG, TAA, or TGA) in reverse orientation or out-of-frame ORFs, while preserving the amino acid sequence and maintaining highly utilized codons in the gene of interest (i.e., avoiding codons with frequency <20%). In the present invention, the transgene coding sequence may be optimized by either of codon optimization and removal of non-transgene ORFs or using both techniques. As will be apparent to one of ordinary skill in the art, it is preferable to remove or minimize non-transgene ORFs after codon optimization in order to remove ORFs introduced during codon optimization. Examples of codon optimization and removal of ORFs are shown in FIGS. 3A-3B.

In some embodiments, the polynucleotide cassette of the present invention further comprises a polyadenylation region. As is understood in the art, RNA polymerase II transcripts are terminated by cleavage and additional of a polyadenylation region, also known as a poly A signal, poly A region or poly A tail. The poly A region contains multiple consecutive adenosine monophosphates, often with repeats of the motif AAUAAA. Several efficient polyadenylation sites have been identified, including those from SV40, bovine growth hormone, human growth hormone and rabbit beta globin (Xu et al, 2001; Gene 272: 149; Xu et al., 2002; J Control Rel. 81:155). The most efficient polyA signal for expression of a transgene in cone cells may depend on the cell type and species of interest and the particular vector used. In some embodiments of the invention, the polynucleotide cassette comprises, consists essentially of, or consists of the polyA region selected from the group consisting of SEQ ID NO:74, SEQ ID NO:75, SEQ ID NO:76, SEQ ID NO:77, SEQ ID NO:78, SEQ ID NO:90 or SEQ ID NO:91 or functional fragment or variant thereof of any of the preceding sequences. In certain embodiments, the polyA region comprises SEQ ID NO:90 or a variant thereof. In some such embodiments, the polyA region consists essentially of SEQ ID NO:90 or a variant thereof.

As will be appreciated by the ordinarily skilled artisan, two or more of the aforementioned polynucleotide elements may be combined to create the polynucleotide cassettes of the present disclosure. Thus, for example, the subject polynucleotide cassette may comprise a promoter region comprising an improved promoter sequence in operable linkage with an improved 5'UTR sequence, for example SEQ ID NO:80 in operable combination with SEQ ID NO:84 or SEQ ID NO:85, see, e.g. SEQ ID NO:2, SEQ ID NO:54, SEQ ID NO:55, SEQ ID NO:93, SEQ ID NO:94, or SEQ ID NO:95. As another example, the subject polynucleotide cassette may comprise an improved enhancer sequence or region in operable linkage with an improved promoter sequence or region, for example SEQ ID NO:51 or SEQ ID NO:52 in operable combination with SEQ ID NO:80, SEQ ID NO:2, SEQ ID NO:54, SEQ ID NO:55, or SEQ ID NO:93; see, e.g. SEQ ID NO:92 or SEQ ID NO:95. As another example, the subject polynucleotide cassette may comprise an improved 5'UTR sequence in operable linkage with an improved intron sequence, for example SEQ ID NO:84 or SEQ ID NO:86 in operable combination with SEQ ID NO:60; see, e.g. SEQ ID NO:94 or SEQ ID NO:95. As another example, the subject polynucleotide cassette may comprise an improved 5'UTR sequence in operable linkage with an improved intron sequence and an improved Kozak sequence, for example, SEQ ID NO:84 or SEQ ID NO:86 in operable combination with SEQ ID NO:60 and with SEQ ID NO:73; see, e.g. SEQ ID NO:95. As another example, the subject polynucleotide cassette may comprise an improved enhancer, improved promoter, improved 5'UTR, improved intron, improved kozak and improved polyA region in operable linkage; see, e.g. SEQ ID NO:95. Other combinations of elements both as disclosed herein or as known in the art will be readily appreciated by the ordinarily skilled artisan.

Additionally, as will be recognized by one of ordinary skill in the art, the polynucleotide cassettes may optionally contain other elements including, but not limited to restriction sites to facilitate cloning and regulatory elements for a particular gene expression vector. Examples of regulatory sequence include ITRs for AAV vectors, bacterial sequences for plasmid vectors, attP or attB sites for phage integrase vectors, and transposable elements for transposons.

Gene Therapy Vectors

As alluded to above, in some aspects of the present invention, the subject polynucleotide cassettes are used to deliver a gene to cone cells of an animal, e.g. to determine the effect that the gene has on cell viability and/or function, to treat a cone cell disorder, etc. Accordingly, in some aspects of the invention, the composition that provides for the expression of a transgene in cone cells is a gene delivery vector, wherein the gene delivery vector comprises the polynucleotide cassettes of the present disclosure.

Any convenient gene therapy vector that finds use delivering polynucleotide sequences to cone cells is encompassed by the gene delivery vectors of the present disclosure. For example, the vector may comprise single or double stranded nucleic acid, e.g. single stranded or double stranded DNA. For example, the gene delivery vector may be a naked DNA, e.g. a plasmid, a minicircle, etc. As another example, the gene delivery vector may be a virus, e.g. an adenovirus, an adeno-associated virus, or a retrovirus, e.g. Moloney murine leukemia virus (M-MuLV), Moloney murine sarcoma virus (MoMSV), Harvey murine sarcoma virus (HaMuSV), murine mammary tumor virus (MuMTV), gibbon ape leukemia virus (GaLV), feline leukemia virus (FLV), spumavirus, Friend murine leukemia virus, Murine Stem Cell Virus (MSCV) and Rous Sarcoma Virus (RSV)) or lentivirus. While embodiments encompassing the use of adeno-associated virus are described in greater detail below, it is expected that the ordinarily skilled artisan will appreciate that similar knowledge and skill in the art can be brought to bear on non-AAV gene therapy vectors as well. See, for example, the discussion of retroviral vectors in, e.g., U.S.

Pat. Nos. 7,585,676 and 8,900,858, and the discussion of adenoviral vectors in, e.g. U.S. Pat. No. 7,858,367, the full disclosures of which are incorporated herein by reference.

In some embodiments, the gene delivery vector is a recombinant adeno-associated virus (rAAV). In such embodiments, the subject polynucleotide cassette is flanked on the 5' and 3' ends by functional AAV inverted terminal repeat (ITR) sequences. By "functional AAV ITR sequences" is meant that the ITR sequences function as intended for the rescue, replication and packaging of the AAV virion. Hence, AAV ITRs for use in the gene delivery vectors of the invention need not have a wild-type nucleotide sequence, and may be altered by the insertion, deletion or substitution of nucleotides or the AAV ITRs may be derived from any of several AAV serotypes, e.g. AAV1, AAV2, AAV3, AAV4, AAV5, AAV6, AAV7, AAV8, AAV9, AAV10. Preferred AAV vectors have the wild type REP and CAP genes deleted in whole or part, but retain functional flanking ITR sequences.

In such embodiments, the subject polynucleotide cassette is encapsidated within an AAV capsid, which may be derived from any adeno-associated virus serotype, including without limitation, AAV1, AAV2, AAV3, AAV4, AAV5, AAV6, AAV7, AAV8, AAV9, AAV10, etc. For example, the AAV capsid may be a wild type, or native, capsid. Wild type AAV capsids of particular interest include AAV2, AAV5, and AAV9. However, as with the ITRs, the capsid need not have a wild-type nucleotide sequence, but rather may be altered by the insertion, deletion or substitution of nucleotides in the VP1, VP2 or VP3 sequence, so long as the capsid is able to transduce cone cells. Put another way, the AAV capsid may be a variant AAV capsid. Variant AAV capsids of particular interest include those comprising a peptide insertion within residues 580-600 of AAV2 or the corresponding residues in another AAV, e.g. LGETTRP, NETITRP, KAGQANN, KDPKTTN, KDTDTTR, RAGGSVG, AVDTTKF, or STGKVPN, as disclosed in US Application No. US 2014/0294771, the full disclosure of which is incorporated by reference herein. In some embodiments, the AAV vector is a "pseudotyped" AAV created by using the capsid (cap) gene of one AAV and the rep gene and ITRs from a different AAV, e.g. a pseudotyped AAV2 created by using rep from AAV2 and cap from AAV1, AAV3, AAV4, AAV5, AAV6, AAV7, AAV8, or AAV9 together with a plasmid containing a vector based on AAV2. For example, the AAV vector may be rAAV2/1, rAAV2/3, rAAV2/4, rAAV2/5, rAAV2/6, rAAV2/7, rAAV2/8, rAAV2/9, etc. Preferably, the rAAV is replication defective, in that the AAV vector cannot independently further replicate and package its genome. For example, when cone cells are transduced with rAAV virions, the gene is expressed in the transduced cone cells, however, due to the fact that the transduced cone cells lack AAV rep and cap genes and accessory function genes, the rAAV is not able to replicate.

Gene therapy vectors, e.g. rAAV) virions encapsulating the polynucleotide cassettes of the present disclosure, may be produced using standard methodology. For example, in the case of rAAV virions, an AAV expression vector according to the invention may be introduced into a producer cell, followed by introduction of an AAV helper construct, where the helper construct includes AAV coding regions capable of being expressed in the producer cell and which complement AAV helper functions absent in the AAV vector. This is followed by introduction of helper virus and/or additional vectors into the producer cell, wherein the helper virus and/or additional vectors provide accessory functions capable of supporting efficient rAAV virus production. The producer cells are then cultured to produce rAAV. These steps are carried out using standard methodology. Replication-defective AAV virions encapsulating the recombinant AAV vectors of the instant invention are made by standard techniques known in the art using AAV packaging cells and packaging technology. Examples of these methods may be found, for example, in U.S. Pat. Nos. 5,436,146; 5,753,500, 6,040,183, 6,093,570 and 6,548,286, expressly incorporated by reference herein in their entirety. Further compositions and methods for packaging are described in Wang et al. (US 2002/0168342), also incorporated by reference herein in its entirety.

Any suitable method for producing viral particles for delivery of the subject polynucleotide cassettes can be used, including but not limited to those described in the examples that follow. Any concentration of viral particles suitable to effectively transducer cone cells can be prepared for contacting cone cells in vitro or in vivo. For example, the viral particles may be formulated at a concentration of $10^8$ vector genomes per ml or more, for example, $5\times10^8$ vector genomes per mL; $10^9$ vector genomes per mL; $5\times10^9$ vector genomes per mL, $10^{10}$ vector genomes per mL, $5\times10^{10}$ vector genomes per mL; $10^{11}$vector genomes per mL; $5\times10^{11}$vector genomes per mL; $10^{12}$ vector genomes per mL; $5\times10^{12}$ vector genomes per mL; $10^{13}$ vector genomes per mL; $1.5\times10^{13}$ vector genomes per mL; $3\times10^{13}$ vector genomes per mL; $5\times10^{13}$ vector genomes per mL; $7.5\times10^{13}$ vector genomes per mL; $9\times10^{13}$ vector genomes per mL; $1\times10^{14}$ vector genomes per mL, $5\times10^{14}$ vector genomes per mL or more, but typically not more than $1\times10^{15}$ vector genomes per mL. Similarly, any total number of viral particles suitable to provide appropriate transduction of retinal cone cells to confer the desired effect or treat the disease can be administered to the mammal or to the primate's eye. In various preferred embodiments, at least $10^8$; $5\times10^8$; $10^9$; $5\times10^9$, $10^{10}$, $5\times10^{10}$; $10^{11}$; $5\times10^{11}$; $10^{12}$; $5\times10^{12}$; $10^{13}$; $1.5\times10^{13}$; $3\times10^{13}$; $5\times10^{13}$; $7.5\times10^{13}$; $9\times10^{13}$, $1\times10^{14}$ viral particles, or $5\times10^{14}$ viral particles or more, but typically not more than $1\times10^{15}$ viral particles are injected per eye. Any suitable number of administrations of the vector to the mammal or the primate eye can be made. In one embodiment, the methods comprise a single administration; in other embodiments, multiple administrations are made over time as deemed appropriate by an attending clinician.

The subject viral vector may be formulated into any suitable unit dosage, including, without limitation, $1\times10^8$ vector genomes or more, for example, $1\times10^9$, $1\times10^{10}$, $1\times10^{11}$, $1\times10^{12}$, or $1\times10^{13}$ vector genomes or more, in certain instances, $1\times10^{14}$ vector genomes, but usually no more than $4\times10^{15}$ vector genomes. In some cases, the unit dosage is at most about $5\times10^{15}$ vector genomes, e.g. $1\times10^{14}$ vector genomes or less, for example $1\times10^{13}$, $1\times10^{12}$, $1\times10^{11}$, $1\times10^{10}$, or $1\times10^9$ vector genomes or less, in certain instances $1\times10^8$vector genomes or less, and typically no less than $1\times10^8$ vector genomes. In some cases, the unit dosage is $1\times10^{10}$ to $1\times10^{11}$ vector genomes. In some cases, the unit dosage is $1\times10^{10}$ to $3\times10^{12}$ vector genomes. In some cases, the unit dosage is $1\times10^9$ to $3\times10^{13}$ vector genomes. In some cases, the unit dosage is $1\times10^8$ to $3\times10^{14}$ vector genomes.

In some cases, the unit dosage of pharmaceutical composition may be measured using multiplicity of infection (MOI). By MOI it is meant the ratio, or multiple, of vector or viral genomes to the cells to which the nucleic acid may be delivered. In some cases, the MOI may be $1\times10^6$. In some cases, the MOI may be $1\times10^5$-$1\times10^7$. In some cases, the MOI may be $1\times10^4$-$1\times10^8$. In some cases, recombinant viruses of the disclosure are at least about $1\times10^1$, $1\times10^2$, $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, $1\times10^{15}$, $1\times10^{16}$, $1\times10^{17}$, and $1\times10^{18}$ MOI. In some cases, recombinant viruses of this disclosure are $1\times10^8$ to $3\times10^{14}$ MOI. In some cases, recombinant viruses of the disclosure are at most about $1\times10^1$, $1\times10^2$, $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, $1\times10^{15}$, $1\times10^{16}$, $1\times10^{17}$, and $1\times10^{18}$ MOI.

In some aspects, the amount of pharmaceutical composition comprises about $1\times10^8$ to about $1\times10^{15}$ recombinant viruses, about $1\times10^9$ to about $1\times10^{14}$ recombinant viruses, about $1\times10^{10}$ to about $1\times10^{13}$ recombinant viruses, or about $1\times10^{11}$ to about $3\times10^{12}$ recombinant viruses.

In preparing the subject rAAV compositions, any host cells for producing rAAV virions may be employed, including, for example, mammalian cells (e.g. 293 cells), insect cells (e.g. SF9 cells), microorganisms and yeast. Host cells can also be packaging cells in which the AAV rep and cap genes are stably maintained in the host cell or producer cells in which the AAV vector genome is stably maintained and packaged. Exemplary packaging and producer cells are derived from SF-9, 293, A549 or HeLa cells. AAV vectors are purified and formulated using standard techniques known in the art.

For instances in which cone cells are to be contacted in vivo, the subject polynucleotide cassettes or gene delivery vectors comprising the subject polynucleotide cassette can be treated as appropriate for delivery to the eye. In particular, the present invention include pharmaceutical compositions comprising a polynucleotide cassette or gene delivery vector described herein and a pharmaceutically-acceptable carrier, diluent or excipient. The subject polynucleotide cassettes or gene delivery vector can be combined with pharmaceutically-acceptable carriers, diluents and reagents useful in preparing a formulation that is generally safe, non-toxic, and desirable, and includes excipients that are acceptable for primate use. Such excipients can be solid, liquid, semisolid, or, in the case of an aerosol composition, gaseous. Examples of such carriers or diluents include, but are not limited to, water, saline, Ringer's solutions, dextrose solution, and 5% human serum albumin. Supplementary active compounds can also be incorporated into the formulations. Solutions or suspensions used for the formulations can include a sterile diluent such as water for injection, saline solution, fixed oils, polyethylene glycols, glycerine, propylene glycol or other synthetic solvents; antibacterial compounds such as benzyl alcohol or methyl parabens; antioxidants such as ascorbic acid or sodium bisulfate; chelating compounds such as ethylenediaminetetraacetic acid (EDTA); buffers such as acetates, citrates or phosphates; detergents such as Tween 20 to prevent aggregation; and compounds for the adjustment of tonicity such as sodium chloride or dextrose. The pH can be adjusted with acids or bases, such as hydrochloric acid or sodium hydroxide.

Pharmaceutical compositions suitable for internal use in the present invention further include sterile aqueous solutions or dispersions and sterile powders for the extemporaneous preparation of sterile injectable solutions or dispersion. For intravenous administration, suitable carriers include physiological saline, bacteriostatic water, or phosphate buffered saline (PBS). In some cases, the composition is sterile and should be fluid to the extent that easy syringability exists. In certain embodiments, it is stable under the conditions of manufacture and storage and is preserved against the contaminating action of microorganisms such as bacteria and fungi. The carrier can be, e.g., a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the internal compositions can be brought about by including in the composition an agent which delays absorption, for example, aluminum monostearate and gelatin.

Sterile solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

In one embodiment, active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser, e.g. syringe, e.g. a prefilled syringe, together with instructions for administration.

The pharmaceutical compositions of the invention encompass any pharmaceutically acceptable salts, esters, or salts of such esters, or any other compound which, upon administration to an animal comprising a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bio-equivalents.

The term "prodrug" indicates a therapeutic agent that is prepared in an inactive form that is converted to an active form (i.e., drug) within the body or cells thereof by the action of endogenous enzymes or other chemicals and/or conditions.

The term "pharmaceutically acceptable salt" refers to physiologically and pharmaceutically acceptable salts of the compounds of the invention: i.e., salts that retain the desired biological activity of the parent compound and do not impart undesired toxicological effects thereto. A variety of pharmaceutically acceptable salts are known in the art and described, e.g., in in "Remington's Pharmaceutical Sciences", 17th edition, Alfonso R. Gennaro (Ed.), Mark Publishing Company, Easton, PA, USA, 1985 (and more recent editions thereof), in the "Encyclopaedia of Pharmaceutical Technology", 3rd edition, James Swarbrick (Ed.), Informa Healthcare USA (Inc.), NY, USA, 2007, and in J. Pharm. Sci. 66: 2 (1977). Also, for a review on suitable salts, see Handbook of Pharmaceutical Salts: Properties, Selection, and Use by Stahl and Wermuth (Wiley-VCH, 2002).

Pharmaceutically acceptable base addition salts are formed with metals or amines, such as alkali and alkaline earth metals or organic amines. Metals used as cations comprise sodium, potassium, magnesium, calcium, and the like. Amines comprise N—N'-dibenzylethylenediamine, chloroprocaine, choline, diethanolamine, dicyclohexylamine, ethylenediamine, N-methylglucamine, and procaine (see, for example, Berge et al., "Pharmaceutical Salts," J. Pharma Sci., 1977, 66, 119). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention.

The subject polynucleotide cassette or gene delivery vector, e.g. recombinant virus (virions), can be incorporated into pharmaceutical compositions for administration to mammalian patients, particularly primates and more particularly humans. The subject polynucleotide cassette or gene delivery vector, e.g. virions can be formulated in nontoxic, inert, pharmaceutically acceptable aqueous carriers, preferably at a pH ranging from 3 to 8, more preferably ranging from 6 to 8. Such sterile compositions will comprise the vector or virion containing the nucleic acid encoding the therapeutic molecule dissolved in an aqueous buffer having an acceptable pH upon reconstitution.

In some embodiments, the pharmaceutical composition provided herein comprise a therapeutically effective amount of a vector or virion in admixture with a pharmaceutically acceptable carrier and/or excipient, for example saline, phosphate buffered saline, phosphate and amino acids, polymers, polyols, sugar, buffers, preservatives and other proteins. Exemplary amino acids, polymers and sugars and the like are octylphenoxy polyethoxy ethanol compounds, polyethylene glycol monostearate compounds, polyoxyethylene sorbitan fatty acid esters, sucrose, fructose, dextrose, maltose, glucose, mannitol, dextran, sorbitol, inositol, galactitol, xylitol, lactose, trehalose, bovine or human serum albumin, citrate, acetate, Ringer's and Hank's solutions, cysteine, arginine, carnitine, alanine, glycine, lysine, valine, leucine, polyvinylpyrrolidone, polyethylene and glycol. Preferably, this formulation is stable for at least six months at 4° C.

In some embodiments, the pharmaceutical composition provided herein comprises a buffer, such as phosphate buffered saline (PBS) or sodium phosphate/sodium sulfate, tris buffer, glycine buffer, sterile water and other buffers known to the ordinarily skilled artisan such as those described by Good et al. (1966) Biochemistry 5:467. The pH of the buffer in which the pharmaceutical composition comprising the tumor suppressor gene contained in the adenoviral vector delivery system, may be in the range of 6.5 to 7.75, preferably 7 to 7.5, and most preferably 7.2 to 7.4.

Methods

As alluded to above, the subject polynucleotide cassettes and gene delivery vectors, referred to collectively herein as the "subject compositions", find use in expressing a transgene in cone cells of an animal. For example, the subject compositions may be used in research, e.g. to determine the effect that the gene has on cone cell viability and/or function. As another example, the subject compositions may be used in medicine, e.g. to treat a cone cell disorder. Thus, in some aspects of the invention, methods are provided for the expression of a gene in cone cells, the method comprising contacting cone cells with a composition of the present disclosure. In some embodiments, contacting occurs in vitro. In some embodiments, contacting occurs in vivo, i.e., the subject composition is administered to a subject.

For instances in which cone cells are to be contacted in vitro with a subject polynucleotide cassette or gene delivery vector comprising a subject polynucleotide cassette, the cells may be from any mammalian species, e.g. rodent (e.g. mice, rats, gerbils, squirrels), rabbit, feline, canine, goat, ovine, pig, equine, bovine, primate, human. Cells may be from established cell lines, e.g. WERI cells, 661W cells, or they may be primary cells, where "primary cells", "primary cell lines", and "primary cultures" are used interchangeably herein to refer to cells and cells cultures that have been derived from a subject and allowed to grow in vitro for a limited number of passages, i.e. splittings, of the culture. For example, primary cultures are cultures that may have been passaged 0 times, 1 time, 2 times, 4 times, 5 times, 10 times, or 15 times, but not enough times go through the crisis stage. Typically, the primary cell lines of the present invention are maintained for fewer than 10 passages in vitro.

If the cells are primary cells, they may be harvested from a mammal by any convenient method, e.g. whole explant, biopsy, etc. An appropriate solution may be used for dispersion or suspension of the harvested cells. Such solution will generally be a balanced salt solution, e.g. normal saline, PBS, Hank's balanced salt solution, etc., conveniently supplemented with fetal calf serum or other naturally occurring factors, in conjunction with an acceptable buffer at low concentration, generally from 5-25 mM. Convenient buffers include HEPES, phosphate buffers, lactate buffers, etc. The cells may be used immediately, or they may be stored, frozen, for long periods of time, being thawed and capable of being reused. In such cases, the cells will usually be frozen in 10% DMSO, 50% serum, 40% buffered medium, or some other such solution as is commonly used in the art to preserve cells at such freezing temperatures, and thawed in a manner as commonly known in the art for thawing frozen cultured cells.

To promote expression of the transgene, the subject polynucleotide cassette or gene delivery vector comprising a subject polynucleotide cassette will be contacted with the cells for about 30 minutes to 24 hours or more, e.g., 1 hour, 1.5 hours, 2 hours, 2.5 hours, 3 hours, 3.5 hours 4 hours, 5 hours, 6 hours, 7 hours, 8 hours, 12 hours, 16 hours, 18 hours, 20 hours, 24 hours, etc. The subject polynucleotide cassette or gene delivery vector comprising a subject polynucleotide cassette may be provided to the subject cells one or more times, e.g. one time, twice, three times, or more than three times, and the cells allowed to incubate with the agent(s) for some amount of time following each contacting event e.g. 16-24 hours, after which time the media is replaced with fresh media and the cells are cultured further. Contacting the cells may occur in any culture media and under any culture conditions that promote the survival of the cells. For example, cells may be suspended in any appropriate nutrient medium that is convenient, such as Iscove's modified DMEM or RPMI 1640, supplemented with fetal calf serum or heat inactivated goat serum (about 5-10%), L-glutamine, a thiol, particularly 2-mercaptoethanol, and antibiotics, e.g. penicillin and streptomycin. The culture may contain growth factors to which the cells are responsive. Growth factors, as defined herein, are molecules capable of promoting survival, growth and/or differentiation of cells, either in culture or in the intact tissue, through specific effects on a transmembrane receptor. Growth factors include polypeptides and non-polypeptide factors.

Typically, an effective amount of subject polynucleotide cassette or gene delivery vector comprising a subject polynucleotide cassette is provided to produce the expression of the transgene in cells. As discussed elsewhere herein, the effective amount may be readily determined empirically, e.g. by detecting the presence or levels of transgene gene product, by detecting an effect on the viability or function of the cone cells, etc. Typically, an effect amount of subject polynucleotide cassette or gene delivery vector comprising a subject polynucleotide cassette will promote greater expression of the transgene in cone cells than the same amount of a polynucleotide cassette as known in the art, e.g. a pR2.1 (nucleotides 1-2274 of SEQ ID NO:50), pR1.7, pR1.5, pR1.1, or IRBP/GNAT2 cassette. Typically, expression will be enhanced 2-fold or more relative to the expression from a reference, or control, polynucleotide cassette e.g. as known in the art, for example 3-fold, 4-fold, or 5-fold or more, in some instances 10-fold, 20-fold or 50-fold or more, e.g. 100-fold.

In some embodiments, as when the transgene is a selectable marker, the population of cells may be enriched for those comprising the subject polynucleotide cassette by separating the modified cells from the remaining population. Separation may be by any convenient separation technique appropriate for the selectable marker used. For example, if the transgene is a fluorescent marker, cells may be separated by fluorescence activated cell sorting, whereas if the transgene is a cell surface marker, cells may be separated from the heterogeneous population by affinity separation techniques, e.g. magnetic separation, affinity chromatography, "panning" with an affinity reagent attached to a solid matrix, or other convenient technique. Techniques providing accurate separation include fluorescence activated cell sorters, which can have varying degrees of sophistication, such as multiple color channels, low angle and obtuse light scattering detecting channels, impedance channels, etc. The cells may be selected against dead cells by employing dyes associated with dead cells (e.g. propidium iodide). Any technique may be employed which is not unduly detrimental to the viability of the cells. Cell compositions that are highly enriched for cells comprising the subject polynucleotides are achieved in this manner. By "highly enriched", it is meant that the genetically modified cells will be 70% or more, 75% or more, 80% or more, 85% or more, 90% or more of the cell composition, for example, about 95% or more, or 98% or more of the cell composition. In other words, the composition may be a substantially pure composition of genetically modified cells.

For instances in which cone cells are to be contacted in vivo with a subject polynucleotide cassette or gene delivery vector comprising a subject polynucleotide cassette, the subject may be any mammal, e.g. rodent (e.g. mice, rats, gerbils), rabbit, feline, canine, goat, ovine, pig, equine, bovine, or primate. In certain embodiments, the subject is a primate of the Parvorder Catarrhini. As is known in the art, Catarrhini is one of the two subdivisions of the higher primates (the other being the New World monkeys), and includes Old World monkeys and the apes, which in turn are further divided into the lesser apes or gibbons and the great apes, consisting of the orangutans, gorillas, chimpanzees, bonobos, and humans. In a further preferred embodiment, the primate is a human.

The subject composition may be administered to the retina of the subject by any suitable method. For example, the subject composition may be administered intraocularly via intravitreal injection or subretinal injection. The general methods for delivering a vector via intravitreal injection or via subretinal injection may be illustrated by the following brief outlines. These examples are merely meant to illustrate certain features of the methods, and are in no way meant to be limiting.

For subretinal administration, the vector can be delivered in the form of a suspension injected subretinally under direct observation using an operating microscope. Typically, a volume of 1 to 200 uL, e.g. 50 uL, 100 uL, 150 ul, or 200 uL, but usually no more than 200 uL, of the subject composition will be administered by such methods. This procedure may involve vitrectomy followed by injection of vector suspension using a fine cannula through one or more small retinotomies into the subretinal space. Briefly, an infusion cannula can be sutured in place to maintain a normal globe volume by infusion (of e.g. saline) throughout the operation. A vitrectomy is performed using a cannula of appropriate bore size (for example 20 to 27 gauge), wherein the volume of vitreous gel that is removed is replaced by infusion of saline or other isotonic solution from the infusion cannula. The vitrectomy is advantageously performed because (1) the removal of its cortex (the posterior hyaloid membrane) facilitates penetration of the retina by the cannula; (2) its removal and replacement with fluid (e.g. saline) creates space to accommodate the intraocular injection of vector, and (3) its controlled removal reduces the possibility of retinal tears and unplanned retinal detachment.

For intravitreal administration, the vector can be delivered in the form of a suspension. Initially, topical anesthetic is applied to the surface of the eye followed by a topical antiseptic solution. The eye is held open, with or without instrumentation, and the vector is injected through the sclera with a short, narrow, for example a 30 gauge needle, into the vitreous cavity of the eye of a subject under direct observation. Typically, a volume of 1 to 100 uL, e.g. 25 uL, 50 uL, or 100 uL, and usually no more than 100 uL, of the subject composition may be delivered to the eye by intravitreal injection without removing the vitreous. Alternatively, a vitrectomy may be performed, and the entire volume of vitreous gel is replaced by an infusion of the subject composition. In such cases, up to about 4 mL of the subject composition may be delivered, e.g. to a human eye. Intravitreal administration is generally well tolerated. At the conclusion of the procedure, there is sometimes mild redness at the injection site. There is occasional tenderness, but most patients do not report any pain. No eye patch or eye shield is necessary after this procedure, and activities are not restricted. Sometimes, an antibiotic eye drop is prescribed for several days to help prevent infection.

The methods and compositions of the present disclosure find use in the treatment of any condition that can be addressed, at least in part, by gene therapy of cone photoreceptor cells. Thus, the compositions and methods of the present disclosure find use in the treatment of individuals in need of a cone cell therapy. By a person in need of a cone cell therapy, it is meant an individual having or at risk of developing a cone cell disorder. By a "cone cell disorder" it is meant any disorder impacting retinal cone cells, including but not limited to vision disorders of the eye that are associated with a defect within cone cells, i.e. a cone-intrinsic defect, e.g. macular dystrophies such as Stargardt's macular dystrophy, cone dystrophy, cone-rod dystrophy, Spinocerebellar ataxia type 7, and Bardet-Biedl syndrome-1; as well as color vision disorders, including achromatopsia, incomplete achromatopsia, blue cone monochromacy, and protan, deutan, and tritan defects; as well as vision disorders of the central macula (within primates) that may be treated by targeting cone cells, e.g. age-related macular degeneration, macular telangiectasia, retinitis pigmentosa, diabetic retinopathy, retinal vein occlusions, glaucoma, Sorsby's fundus dystrophy, adult vitelliform macular dystrophy, Best's disease, rod-cone dystrophy, Leber's congenital amaurosis, and X-linked retinoschisis.

Stargardt's macular dystrophy. Stargardt's macular dystrophy, also known as Stargardt Disease and fundus flavimaculatus, is an inherited form of juvenile macular degeneration that causes progressive vision loss usually to the point of legal blindness. The onset of symptoms usually appears between the ages of six and thirty years old (average of about 16-18 years). Mutations in several genes, including ABCA4, CNGB3, ELOVL4, PROM1, are associated with the disorder. Symptoms typically develop by twenty years of age, and include wavy vision, blind spots, blurriness, impaired color vision, and difficulty adapting to dim lighting. The main symptom of Stargardt disease is loss of visual acuity, which ranges from 20/50 to 20/200. In addition, those with Stargardt disease are sensitive to glare; overcast days offer some relief. Vision is most noticeably impaired when the macula is damaged, which can be observed by fundus exam.

Cone dystrophy. Cone dystrophy (COD) is an inherited ocular disorder characterized by the loss of cone cells. The most common symptoms of cone dystrophy are vision loss (age of onset ranging from the late teens to the sixties), sensitivity to bright lights, and poor color vision. Visual acuity usually deteriorates gradually, but it can deteriorate rapidly to 20/200; later, in more severe cases, it drops to "counting fingers" vision. Color vision testing using color test plates (HRR series) reveals many errors on both red-green and blue-yellow plates. It is believed that the dystrophy is primary, since subjective and objective abnormalities of cone function are found before ophthalmoscopic changes can be seen. However, the retinal pigment epithelium (RPE) rapidly becomes involved, leading to a retinal dystrophy primarily involving the macula. The fundus exam via ophthalmoscope is essentially normal early on in cone dystrophy, and definite macular changes usually occur well after visual loss. The most common type of macular lesion seen during ophthalmoscopic examination has a bull's-eye appearance and consists of a doughnut-like zone of atrophic pigment epithelium surrounding a central darker area. In another, less frequent form of cone dystrophy there is rather diffuse atrophy of the posterior pole with spotty pigment clumping in the macular area. Rarely, atrophy of the choriocapillaris and larger choroidal vessels is seen in patients at an early stage. Fluorescein angiography (FA) is a useful adjunct in the workup of someone suspected to have cone dystrophy, as it may detect early changes in the retina that are too subtle to be seen by ophthalmoscope. Because of the wide spectrum of fundus changes and the difficulty in making the diagnosis in the early stages, electroretinography (ERG) remains the best test for making the diagnosis. Abnormal cone function on the ERG is indicated by a reduced single-flash and flicker response when the test is carried out in a well-lit room (photopic ERG). Mutations in several genes, including GUCA1A, PDE6C, PDE6H, and RPGR, are associated with the disorder.

Cone-rod dystrophy. Cone-rod dystrophy (CRD, or CORD) is an inherited retinal dystrophy that belongs to the group of pigmentary retinopathies. CRD is characterized by retinal pigment deposits visible on fundus examination, predominantly localized to the macular region and the loss of both cone and rod cells. In contrast to rod-cone dystrophy (RCD) resulting from the primary loss in rod photoreceptors and later followed by the secondary loss in cone photoreceptors, CRD reflects the opposite sequence of events: primary cone involvement, or, sometimes, by concomitant loss of both cones and rods. Symptoms include decreased visual acuity, color vision defects, photoaversion and decreased sensitivity in the central visual field, later followed by progressive loss in peripheral vision and night blindness. Mutations in several genes, including ADAMS, PCDH21, CRX, GUCY2D, PITPNM3, PROM1, PRPH2, RAX2, RIMS1, RPGR, and RPGRIP1, are associated with the disorder.

Spinocerebellar ataxia type 7. Spinocerebellar ataxia is a progressive, degenerative, inherited disease characterized by slowly progressive incoordination of gait and is often associated with poor coordination of hands, speech, and eye movements. There are multiple types of SCA, with Spinocerebellar ataxia type 7 (SCA-7) differing from most other SCAs in that visual problems can occur in addition to poor coordination. SCA-7 is associated with autosomal dominant mutations in the ATXN7/SCA7 gene. When the disease manifests itself before age 40, visual problems rather than poor coordination are typically the earliest signs of disease. Early symptoms include difficulty distinguishing colors and decreased central vison. In addition, symptoms of ataxia (incoordination, slow eye movements, and mild changes in sensation or reflexes) may be detectable. Loss of motor control, unclear speech, and difficulty swallowing become prominent as the disease progresses.

Bardet-Biedl syndrome-1. Bardet-Biedl syndrome-1 (BBS-1) is a pleiotropic disorder with variable expressivity and a wide range of clinical variability observed both within and between families. The main clinical features are rod-cone dystrophy, with childhood-onset visual loss preceded by night blindness; postaxial polydactyly; truncal obesity that manifests during infancy and remains problematic throughout adulthood; specific learning difficulties in some but not all individuals; male hypogenitalism and complex female genitourinary malformations; and renal dysfunction, a major cause of morbidity and mortality. Vision loss is one of the major features of Bardet-Biedl syndrome. Problems with night vision become apparent by mid-childhood, followed by blind spots that develop in the peripheral vision. Over time, these blind spots enlarge and merge to produce tunnel vision. Most people with Bardet-Biedl syndrome also develop blurred central vision (poor visual acuity) and become legally blind by adolescence or early adulthood. Bardet-Biedl syndrome can result from mutations in at least 14 different genes (often called BBS genes) known or suspected to play critical roles in cilia function, with mutations in BBS1 and BBS10 being the most common.

Achromatopsia. Achromatopsia, or Rod monochromatism, is a disorder in which subjects experience a complete lack of the perception of color, such that the subject sees only in black, white, and shades of grey. Other symptoms include reduced visual acuity, photophobia, nystagmus, small central scotoma, and eccentric fixation. The disorder is frequently noticed first in children around six months of age by their photophobic activity and/or their nystagmus. Visual acuity and stability of the eye motions generally improve during the first 6-7 years of life (but remain near 20/200). Mutations in CNGB3, CNGA3, GNAT2, PDE6C, and PDE6HI have been associated with the disorder.

Incomplete achromatopsia. Incomplete achromatopsia is similar to Achromatopsia but with less penetrance. In incomplete achromatopsia, the symptoms are similar to those of complete achromatopsia except in a diminished form. Individuals with incomplete achromatopsia have reduced visual acuity with or without nystagmus or photophobia. Furthermore, these individuals show only partial impairment of cone cell function but again have retained rod cell function.

Blue cone monochromacy. Blue cone (S cone) monochromatism (BCM) is a rare X-linked congenital stationary cone dysfunction syndrome, affecting approximately 1 in 100,000 individuals. Affected males with BCM have no functional long wavelength sensitive (L) or medium wavelength sensitive (M) cones in the retina, due to mutations at the genetic locus for the L and M-opsin genes. Color discrimination is severely impaired from birth, and vision is derived from the remaining preserved S cones and rod photoreceptors. BCM typically presents with reduced visual acuity (6/24 to 6/60), pendular nystagmus, photophobia, and patients often have myopia. The rod-specific and maximal electroretinogram (ERG) usually show no definite abnormality, whereas the 30 Hz cone ERG cannot be detected. Single flash photopic ERG is often recordable, albeit small and late, and the S cone ERG is well preserved.

Color vision deficiency. Color vision deficiency (CVD), or color blindness, is the inability or decreased ability to see color, or perceive color differences, under normal lighting conditions. Individuals suffering from color blindness may be identified as such using any of a number of color vision tests, e.g., color ERG (cERG), pseudoisochromatic plates (Ishihara plates, Hardy-Rand-Ritter polychromatic plates), the Farnsworth-Munsell 100 hue test, the Farnsworth's panel D-15, the City University test, Kollner's rule, etc. Examples of color vision deficiencies include protan defects, deutan defects, and tritan defects. Protan defects include protanopia (an insensitivity to red light) and protanomaly (a reduced sensitivity to red light), and are associated with mutations in the L-Opsin gene (OPN1LW). Deutan defects include deuteranopia (an insensitivity to green light) and deutanomaly (a reduced sensitivity to green light), and are associated with mutations in the M-Opsin gene (OPN1MW). Tritan defects include tritanopia (an insensitivity to blue light) and tritanomaly (a reduced sensitivity to blue light), and are associated with mutations in the S-Opsin gene (OPN1SW).

Age-related macular degeneration. Age-related macular degeneration (AMD) is one of the leading causes of vision loss in people over the age of 50 years. AMD mainly affects central vision, which is needed for detailed tasks such as reading, driving, and recognizing faces. The vision loss in this condition results from a gradual deterioration of photoreceptors in the macula. Side (peripheral) vision and night vision are generally not affected.

Researchers have described two major types of age-related macular degeneration, known as the dry, or "non-exudative" form, and the wet, or "exudative" or "neovascular", form, both of which may be treated by delivering transgenes in the context of the subject polynucleotide cassettes.

Dry AMD is characterized by a buildup of yellow deposits called drusen between the retinal pigment epithelium and the underlying choroid of the macula, which may be observed by Fundus photography. This results in a slowly progressive loss of vision. The condition typically affects vision in both eyes, although vision loss often occurs in one eye before the other. Other changes may include pigment changes and RPE atrophy. For example, in certain cases called central geographic atrophy, or "GA", atrophy of the retinal pigment epithelial and subsequent loss of photoreceptors in the central part of the eye is observed. Dry AMD has been associated with mutations in CD59 and genes in the complement cascade.

Wet AMD is a progressed state of dry AMD, and occurs in abut 10% of dry AMD patients. Pathological changes include retinal pigment epithelial cells (RPE) dysfunction, fluid collecting under the RPE, and choroidal neovascularization (CNV) in the macular area. Fluid leakage, RPE or neural retinal detachment and bleeding from ruptured blood vessels can occur in severe cases. Symptoms of wet AMD may include visual distortions, such as straight lines appearing wavy or crooked, a doorway or street sign looking lopsided, or objects appearing smaller or farther away than they really are; decreased central vision; decreased intensity or brightness of colors; and well-defined blurry spot or blind spot in the field of vision. Onset may be abrupt and worsen rapidly. Diagnosis may include the use of an Amsler grid to test for defects in the subject's central vision (macular degeneration may cause the straight lines in the grid to appear faded, broken or distorted), fluorescein angiogram to observe blood vessel or retinal abnormalities, and optical coherence tomography to detect retina swelling or leaking blood vessels. A number of cellular factors have been implicated in the generation of CNV, among which are vascular endothelial growth factor (VEGF), platelet-derived growth factor (PDGF), pigment epithelium-derived factor (PEDF), hypoxia inducible factor (HIF), angiopoietin (Ang), and other cytokines, mitogen-activated protein kinases (MAPK) and others.

Macular telangiectasia. Macular telangiectasia (MacTel) is a form of pathologically dilated blood vessels (telangiectasia) in the parafoveal region of the macula. The tissue deteriorates and the retinal structure becomes scarred due to the development of liquid-filled cysts, which impairs nutrition of the photoreceptor cells and destroys vision permanently. There are two types of MacTel, type 1 and type 2. Macular telangiectasia type 2 is a bilateral disease, whose prevalence has recently been shown to be as high as 0.1% in persons 40 years and older. Biomicroscopy may show reduced retinal transparency, crystalline deposits, mildly ectatic capillaries, blunted venules, retinal pigment plaques, foveal atrophy, and neovascular complexes. Fluorescein angiography shows telangiectatic capillaries predominantly temporal to the foveola in the early phase and a diffuse hyperfluorescence in the late phase. High-resolution optical coherence tomography (OCT) may reveal disruption of the photoreceptor inner segment-outer segment border, hyporeflective cavities at the level of the inner or outer retina, and atrophy of the retina in later stages. In Type 1 macular telangiectasia, the disease almost always occurs in one eye, which differentiates it from Type 2. While MacTel does not usually cause total blindness, it commonly causes loss of the central vision, which is required for reading and driving vision, over a period of 10-20 years.

Retinitis pigmentosa. Retinitis Pigmentosa (RP) is a group of inherited disorders characterized by progressive peripheral vision loss and night vision difficulties (nyctalopia) that can lead to central vision loss. Presenting signs and symptoms of RP vary, but the classic ones include nyctalopia (night blindness, most commonly the earliest symptom in RP); visual loss (usually peripheral, but in advanced cases, central visual loss); and photopsia (seeing flashes of light). Because RP is a collection of many inherited diseases, significant variability exists in the physical findings. Ocular examination involves assessment of visual acuity and pupillary reaction, as well as anterior segment, retinal, and funduscopic evaluation. In some instances, the RP is one aspect of a syndrome, e.g. syndromes that are also associated with hearing loss (Usher syndrome, Waardenburg syndrome, Alport syndrome, Refsum disease); Kearns-Sayre syndrome (external ophthalmoplegia, lid ptosis, heart block, and pigmentary retinopathy); Abetalipoproteinemia (Fat malabsorption, fat-soluble vitamin deficiencies, spinocerebellar degeneration, and pigmentary retinal degeneration); mucopolysaccharidoses (eg, Hurler syndrome, Scheie syndrome, Sanfilippo syndrome); Bardet-Biedl syndrome (Polydactyly, truncal obesity, kidney dysfunction, short stature, and pigmentary retinopathy); and neuronal ceroid lipofuscinosis (Dementia, seizures, and pigmentary retinopathy; infantile form is known as Jansky-Bielschowsky disease, juvenile form is Vogt-Spielmeyer-Batten disease, and adult form is Kufs syndrome). Retinitis pigmentosa is most commonly associated with mutations in the RHO, RP2, RPGR, RPGRIP1, PDE6A, PDE6B, MERTK, PRPH2, CNGB1, USH2A, ABCA4, BBS genes.

Diabetic retinopathy. Diabetic retinopathy (DR) is damage to the retina caused by complications of diabetes, which can eventually lead to blindness. Without wishing to be bound by theory, it is believed that hyperglycemia-induced intramural pericyte death and thickening of the basement membrane lead to incompetence of the vascular walls. These damages change the formation of the blood-retinal barrier and also make the retinal blood vessels become more permeable.

There are two stages of diabetic retinopathy: non-proliferative diabetic retinopathy (NPDR), and proliferative diabetic retinopathy (PDR). Nonproliferative diabetic retinopathy is the first stage of diabetic retinopathy, and is diagnosed by fundoscopic exam and coexistent diabetes. In cases of reduced vision, fluorescein angiography may be done to visualize the vessels in the back of the eye to and any retinal ischemia that may be present. All people with diabetes are at risk for developing NPDR, and as such, would be candidates for prophylactic treatment with the subject vectors. Proliferative diabetic retinopathy is the second stage of diabetic retinopathy, characterized by neovascularization of the retina, vitreous hemorrhage, and blurred vision. In some instances, fibrovascular proliferation causes tractional retinal detachment. In some instances, the vessels can also grow into the angle of the anterior chamber of the eye and cause neovascular glaucoma. Individuals with NPDR are at increased risk for developing PDR, and as such, would be candidates for prophylactic treatment with the subject vectors.

Diabetic macular edema. Diabetic macular edema (DME) is an advanced, vision-limiting complication of diabetic retinopathy that affects nearly 30% of patients who have had diabetes for at least 20 years, and is responsible for much of the vision loss due to DR. It results from retinal microvascular changes that compromise the blood-retinal barrier, causing leakage of plasma constituents into the surrounding retina and, consequently, retinal edema. Without wishing to be bound by theory, it is believed that hyperglycemia, sustained alterations in cell signaling pathways, and chronic microvascular inflammation with leukocyte-mediated injury leads to chronic retinal microvascular damage, which triggers an increase in intraocular levels of VEGF, which in turn increases the permeability of the vasculature.

Patients at risk for developing DME include those who have had diabetes for an extended amount of time and who experience one or more of severe hypertension (high blood pressure), fluid retention, hypoalbuminemia, or hyperlipidemia. Common symptoms of DME are blurry vision, floaters, double vision, and eventually blindness if the condition is allowed to progress untreated. DME is diagnosed by funduscopic examination as retinal thickening within 2 disc diameters of the center of the macula. Other methods that may be employed include Optical coherence tomography (OCT) to detect retinal swelling, cystoid edema, and serous retinal detachment; fluorescein angiography, which distinguishes and localizes areas of focal versus diffuse leakage, thereby guiding the placement of laser photocoagulation if laser photocoagulation is to be used to treat the edema; and color stereo fundus photographs, which can be used to evaluate long-term changes in the retina. Visual acuity may also be measured, especially to follow the progression of macular edema and observe its treatment following administration of the subject pharmaceutical compositions.

Retinal vein occlusions. A retinal vein occlusion (RVO) is a blockage of the portion of the circulation that drains the retina of blood. The blockage can cause back-up pressure in the capillaries, which can lead to hemorrhages and also to leakage of fluid and other constituents of blood.

Glaucoma. Glaucoma is a term describing a group of ocular (eye) disorders that result in optic nerve damage, often associated with increased fluid pressure in the eye (intraocular pressure)(IOP). The disorders can be roughly divided into two main categories, "open-angle" and "closed-angle" (or "angle closure") glaucoma. Open-angle glaucoma accounts for 90% of glaucoma cases in the United States. It is painless and does not have acute attacks. The only signs are gradually progressive visual field loss, and optic nerve changes (increased cup-to-disc ratio on fundoscopic examination). Closed-angle glaucoma accounts for less than 10% of glaucoma cases in the United States, but as many as half of glaucoma cases in other nations (particularly Asian countries). About 10% of patients with closed angles present with acute angle closure crises characterized by sudden ocular pain, seeing halos around lights, red eye, very high intraocular pressure (>30 mmHg), nausea and vomiting, suddenly decreased vision, and a fixed, mid-dilated pupil. It is also associated with an oval pupil in some cases. Modulating the activity of proteins encoded by DLK, NMDA, INOS, CASP-3, Bcl-2, or Bcl-xl may treat the condition.

Sorsby's fundus dystrophy. Sorsby's fundus dystrophy is an autosomal dominant, retinal disease associated with mutations in the TIMP3 gene. Clinically, early, mid-peripheral, drusen and colour vision deficits are found. Some patients complain of night blindness. Most commonly, the presenting symptom is sudden acuity loss, manifest in the third to fourth decades of life, due to untreatable submacular neovascularisation. Histologically, there is accumulation of a confluent lipid containing material 30 μm thick at the level of Bruch's membrane.

Vitelliform macular dystrophy. Vitelliform macular dystrophy is a genetic eye disorder that can cause progressive vision loss. Vitelliform macular dystrophy is associated with the buildup of fatty yellow pigment (lipofuscin) in cells underlying the macula. Over time, the abnormal accumulation of this substance can damage cells that are critical for clear central vision. As a result, people with this disorder often lose their central vision, and their eyesight may become blurry or distorted. Vitelliform macular dystrophy typically does not affect side (peripheral) vision or the ability to see at night.

Researchers have described two forms of vitelliform macular dystrophy with similar features. The early-onset form (known as Best disease) usually appears in childhood; the onset of symptoms and the severity of vision loss vary widely. It is associated with mutations in the VMD2/BEST1 gene. The adult-onset form (Adult vitelliform macular dystrophy) begins later, usually in mid-adulthood, and tends to cause vision loss that worsens slowly over time. It has been associated with mutations in the PRPH2 gene. The two forms of vitelliform macular dystrophy each have characteristic changes in the macula that can be detected during an eye examination.

Rod-cone dystrophy. Rod-cone dystrophies are a family of progressive diseases in which rod dysfunction, which leads to night blindness and loss of peripheral visual field expanses, is either the prevailing problem or occurring at least as severely as cone dysfunction. A scallop-bordered lacunar atrophy may be seen in the midperiphery of the retina. The macula is only mildly involved by clinical examination although central retinal thinning is seen in all cases. Dyschromatopsia is mild early and usually becomes more severe. The visual fields are moderately to severely constricted although in younger individuals a typical ring scotoma is present. The peripheral retina contains 'white dots' and often resembles the retinal changes seen in retinitis punctate albescens. Retinitis pigmentosa is the main group of diseases included under this definition and, as a whole, is estimated to affect approximately one in every 3,500 people. Depending on the classification criteria used, about 60-80% of all retinitis pigmentosa patients have a clear-cut rod-cone dystrophy pattern of retinal disease and once other syndromic forms are taken into account, about 50-60% of all retinitis pigmentosas fall in the rod-cone dystrophy nonsyndromic category.

Leber's congenital amaurosis. Leber's congenital amaurosis (LCA) is a severe dystrophy of the retina that typically becomes evident in the first year of life. Visual function is usually poor and often accompanied by nystagmus, sluggish or near-absent pupillary responses, photophobia, high hyperopia, and keratoconus. Visual acuity is rarely better than 20/400. A characteristic finding is Franceschetti's oculo-digital sign, comprising eye poking, pressing, and rubbing. The appearance of the fundus is extremely variable. While the retina may initially appear normal, a pigmentary retinopathy reminiscent of retinitis pigmentosa is frequently observed later in childhood. The electroretinogram (ERG) is characteristically "nondetectable" or severely subnormal. Mutations in 17 genes are known to cause LCA: GUCY2D (locus name: LCA1), RPE65 (LCA2), SPATA7 (LCA3), AIPL1 (LCA4), LCAS (LCAS), RPGRIP1 (LCA6), CRX (LCAT), CRB1 (LCA8), NMNAT1 (LCA9), CEP290 (LCA10), IMPDH1 (LCA11), RD3 (LCA12), RDH12 (LCA13), LRAT (LCA14), TULP1 (LCA15), KCNJ13 (LCA16), and IQCB1. Together, mutations in these genes are estimated to account for over half of all LCA diagnoses. At least one other disease locus for LCA has been reported, but the gene is not known.

X-linked retinoschisis. X-linked retinoschisis (XLRS) is characterized by symmetric bilateral macular involvement with onset in the first decade of life, in some cases as early as age three months. Fundus examination shows areas of schisis (splitting of the nerve fiber layer of the retina) in the macula, sometimes giving the impression of a spoke wheel pattern. Schisis of the peripheral retina, predominantly inferotemporally, occurs in approximately 50% of individuals. Affected males typically have vision of 20/60 to 20/120. Visual acuity often deteriorates during the first and second decades of life but then remains relatively stable until the fifth or sixth decade. The diagnosis of X-linked juvenile retinoschisis is based on fundus findings, results of electrophysiologic testing, and molecular genetic testing. RS1 is the only gene known to be associated with X-linked juvenile retinoschisis.

An individual affected by a cone cell disorder or at risk for developing a cone cell disorder can be readily identified using techniques to detect the symptoms of the disorder as known in the art, including, without limitation, fundus photography; Optical coherence tomography (OCT); adaptive optics (AO); electroretinography, e.g. ERG, color ERG (cERG); color vision tests such as pseudoisochromatic plates (Ishihara plates, Hardy-Rand-Ritter polychromatic plates), the Farnsworth-Munsell 100 hue test, the Farnsworth's panel D-15, the City university test, Kollner's rule, and the like; and visual acuity tests such as the ETDRS letters test, Snellen visual acuity test, visual field test, contrast sensitivity test, and the like; as will be known by the ordinarily skilled artisan. Additionally or alternatively, the individual affected by a cone cell disorder or at risk for developing a cone cell disorder can be readily identified using techniques to detect gene mutations that are associated with the cone cell disorder as known in the art, including, without limitation, PCR, DNA sequence analysis, restriction digestion, Southern blot hybridization, mass spectrometry, etc. In some embodiments, the method comprises the step of identifying the individual in need of a cone cell therapy. In such instances, any convenient method for determining if the individual has the symptom(s) of a cone cell disorder or is at risk for developing a cone cell disorder, for example by detecting the symptoms described herein or known in the art, by detecting a mutation in a gene as herein or as known in the art, etc. may be utilized to identify the individual in need of a cone cell therapy.

In practicing the subject methods, the subject composition is typically delivered to the retina of the subject in an amount that is effective to result in the expression of the transgene in the cone cells. In some embodiments, the method comprises the step of detecting the expression of the transgene in the cone cells.

There are a number of ways to detect the expression of a transgene, any of which may be used in the subject embodiments. For example, expression may be detected directly, i.e. by measuring the amount of gene product, for example, at the RNA level, e.g. by RT-PCR, Northern blot, RNAse protection; or at the protein level, e.g. by Western blot, ELISA, immunohistochemistry, and the like. As another example, expression may be detected indirectly, i.e. by detecting the impact of the gene product on the viability or function of the cone photoreceptor in the subject. For example, if the gene product encoded by the transgene improves the viability of the cone cell, the expression of the transgene may be detected by detecting an improvement in viability of the cone cell, e.g. by fundus photography, Optical coherence tomography (OCT), Adaptive Optics (AO), and the like. If the gene product encoded by the transgene alters the activity of the cone cell, the expression of the transgene may be detected by detecting a change in the activity of the cone cell, e.g. by electroretinogram (ERG) and color ERG (cERG); functional adaptive optics; color vision tests such as pseudoisochromatic plates (Ishihara plates, Hardy-Rand-Ritter polychromatic plates), the Farnsworth-Munsell 100 hue test, the Farnsworth's panel D-15, the City university test, Kollner's rule, and the like; and visual acuity tests such as the ETDRS letters test, Snellen visual acuity test, visual field test, contrast sensitivity test, and the like, as a way of detecting the presence of the delivered polynucleotide. In some instances, both an improvement in viability and a modification in cone cell function may be detected.

In some embodiments, the subject method results in a therapeutic benefit, e.g. preventing the development of a disorder, halting the progression of a disorder, reversing the progression of a disorder, etc. In some embodiments, the subject method comprises the step of detecting that a therapeutic benefit has been achieved. The ordinarily skilled artisan will appreciate that such measures of therapeutic efficacy will be applicable to the particular disease being modified, and will recognize the appropriate detection methods to use to measure therapeutic efficacy. For example, therapeutic efficacy in treating macular degeneration may be observed as a reduction in the rate of macular degeneration or a cessation of the progression of macular degeneration, effects which may be observed by, e.g., fundus photography, OCT, or AO, by comparing test results after administration of the subject composition to test results before administration of the subject composition. As another example, therapeutic efficacy in treating a progressive cone dysfunction may be observed as a reduction in the rate of progression of cone dysfunction, as a cessation in the progression of cone dysfunction, or as an improvement in cone function, effects which may be observed by, e.g., ERG and/or cERG; color vision tests; functional adaptive optics; and/or visual acuity tests, for example, by comparing test results after administration of the subject composition to test results before administration of the subject composition and detecting a change in cone viability and/or function. As a third example, therapeutic efficacy in treating a color vision deficiency may be observed as an alteration in the individual's perception of color, e.g. in the perception of red wavelengths, in the perception of green wavelengths, in the perception of blue wavelengths, effects which may be observed by, e.g., cERG and color vision tests, for example, by comparing test results after administration of the subject composition to test results before administration of the subject composition and detecting a change in cone viability and/or function.

Expression of the transgene using the subject transgene is expected to be robust. Accordingly, in some instances, the expression of the transgene, e.g. as detected by measuring levels of gene product, by measuring therapeutic efficacy, etc., may be observed two months or less after administration, e.g. 4, 3 or 2 weeks or less after administration, for example, 1 week after administration of the subject composition. Expression of the transgene is also expected to persist over time. Accordingly, in some instances, the expression of the transgene, e.g. as detected by measuring levels of gene product, by measuring therapeutic efficacy, etc., may be observed 2 months or more after administration of the subject composition, e.g., 4, 6, 8, or 10 months or more, in some instances 1 year or more, for example 2, 3, 4, or 5 years, in certain instances, more than 5 years.

In certain embodiments, the method comprises the step of detecting expression of the transgene in the cone cells, wherein expression is enhanced relative to expression from a polynucleotide cassette not comprising the one or more improved elements of the present disclosure, i.e. a reference control, e.g. the pR2.1 promoter or variants thereof (e.g. pR1.7, pR1.5, pR1.1, etc.) as disclosed in, e.g., US Application No. 2013/0317091, or the synthetic IRBP/GNAT2 promoter as disclosed in US Application No. 2014/0275231; the full disclosures of which are incorporated herein by reference. Typically, expression will be enhanced 2-fold or more relative to the expression from a reference, i.e. a control polynucleotide cassette, e.g. as known in the art, for example 3-fold, 4-fold, or 5-fold or more, in some instances 10-fold, 20-fold or 50-fold or more, e.g. 100-fold, as evidenced by, e.g. earlier detection, higher levels of gene product, a stronger functional impact on the cells, etc.

Typically, if the subject composition is an rAAV comprising the subject a polynucleotide cassette of the present disclosure, an effective amount to achieve a change in will be about $1\times10^8$ vector genomes or more, in some cases $1\times10^9$, $1\times10^{10}$, $1\times10^{11}$, $1\times10^{12}$, or $1\times10^{13}$ vector genomes or more, in certain instances, $1\times10^{14}$ vector genomes or more, and usually no more than $1\times10^{15}$ vector genomes. In some cases, the amount of vector genomes that is delivered is at most about $1\times10^{15}$ vector genomes, e.g. $1\times10^{14}$ vector genomes or less, for example $1\times10^{13}$, $1\times10^{12}$, $1\times10^{11}$, $1\times10^{10}$, or $1\times10^9$ vector genomes or less, in certain instances $1\times10^8$ vector genomes, and typically no less than $1\times10^8$ vector genomes. In some cases, the amount of vector genomes that is delivered is $1\times10^{10}$ to $1\times10^{11}$ vector genomes. In some cases, the amount of vector genomes that is delivered is $1\times10^{10}$ to $3\times10^{12}$ vector genomes. In some cases, the amount of vector genomes that is delivered is $1\times10^9$ to $3\times10^{13}$ vector genomes. In some cases, the amount of vector genomes that is delivered is $1\times10^8$ to $3\times10^{14}$ vector genomes.

In some cases, the amount of pharmaceutical composition to be administered may be measured using multiplicity of infection (MOI). In some cases, MOI may refer to the ratio, or multiple of vector or viral genomes to the cells to which the nucleic may be delivered. In some cases, the MOI may be $1\times10^6$. In some cases, the MOI may be $1\times10^5$-$1\times10^7$. In some cases, the MOI may be $1\times10^4$-$1\times10^8$. In some cases, recombinant viruses of the disclosure are at least about $1\times10^1$, $1\times10^2$, $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, $1\times10^{15}$, $1\times10^{16}$, $1\times10^{17}$, and $1\times10^{18}$ MOI. In some cases, recombinant viruses of this disclosure are $1\times10^8$ to $3\times10^{14}$ MOI. In some cases, recombinant viruses of the disclosure are at most about $1\times10^1$, $1\times10^2$, $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, $1\times10^{15}$, $1\times10^{16}$, $1\times10^{17}$, and $1\times10^{18}$ MOI.

In some aspects, the amount of pharmaceutical composition comprises about $1\times10^8$ to about $1\times10^{15}$ particles of recombinant viruses, about $1\times10^9$ to about $1\times10^{14}$ particles of recombinant viruses, about $1\times10^{10}$ to about $1\times10^{13}$ particles of recombinant viruses, or about $1\times10^{11}$ to about $3\times10^{12}$ particles of recombinant viruses.

Individual doses are typically not less than an amount required to produce a measurable effect on the subject, and may be determined based on the pharmacokinetics and pharmacology for absorption, distribution, metabolism, and excretion ("ADME") of the subject composition or its by-products, and thus based on the disposition of the composition within the subject. This includes consideration of the route of administration as well as dosage amount, which can be adjusted for subretinal (applied directly to where action is desired for mainly a local effect), intravitreal (applied to the vitreous for a pan-retinal effect), or parenteral (applied by systemic routes, e.g. intravenous, intramuscular, etc.) applications. Effective amounts of dose and/or dose regimen can readily be determined empirically from pre-clinical assays, from safety and escalation and dose range trials, individual clinician-patient relationships, as well as in vitro and in vivo assays such as those described herein and illustrated in the Experimental section, below.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

Examples

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

General methods in molecular and cellular biochemistry can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference. Reagents, cloning vectors, and kits for genetic manipulation referred to in this disclosure are available from commercial vendors such as BioRad, Stratagene, Invitrogen, Sigma-Aldrich, and ClonTech.

Background

New therapies are needed for the treatment of many cone photoreceptor associated disorders, including macular dystrophies such as cone-rod dystrophy, cone dystrophy, Stargardt macular dystrophy, and achromatopsia; color vision disorders such as protan, deutan, and tritan defects; and vision disorders of the central macula such as age-related macular degeneration, macular telangiectasia, retinitis pigmentosa, diabetic retinopathy, retinal vein occlusions, glaucoma, Sorsby's fundus dystrophy, adult vitelliform macular dystrophy, Best's disease, and X-linked retinoschisis. As these vision disorders are associated with a loss of function and/or viability of the cone photoreceptors, it is hypothesized that these disorders may be treatable by delivering a therapeutic gene to cone photoreceptors to rescue cone viability and function.

Figure 10A:
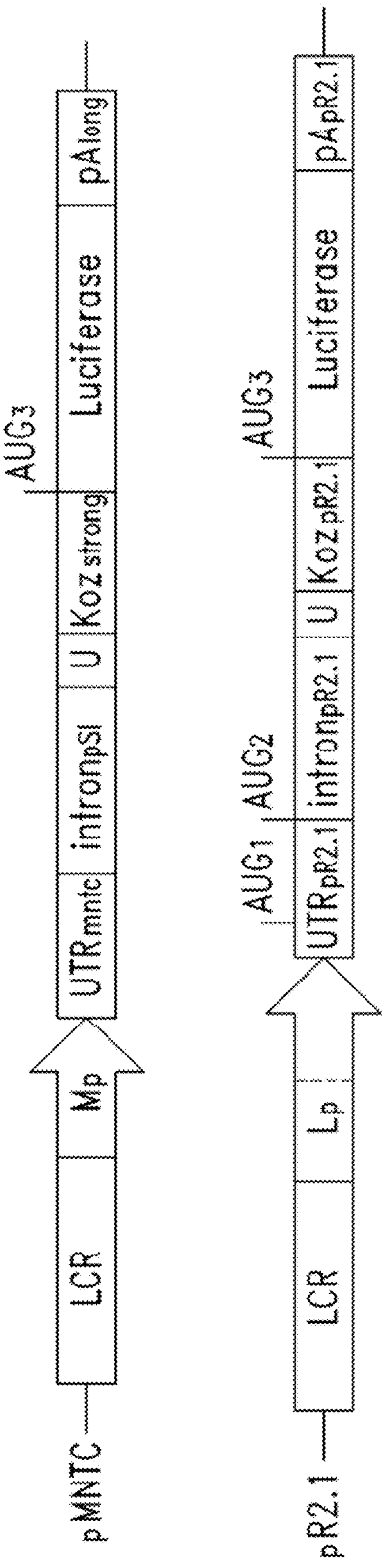
FIGS. 10A-10D demonstrate the contribution of each of the optimized pMNTC elements to the more robust expression observed.
Figure 10B:
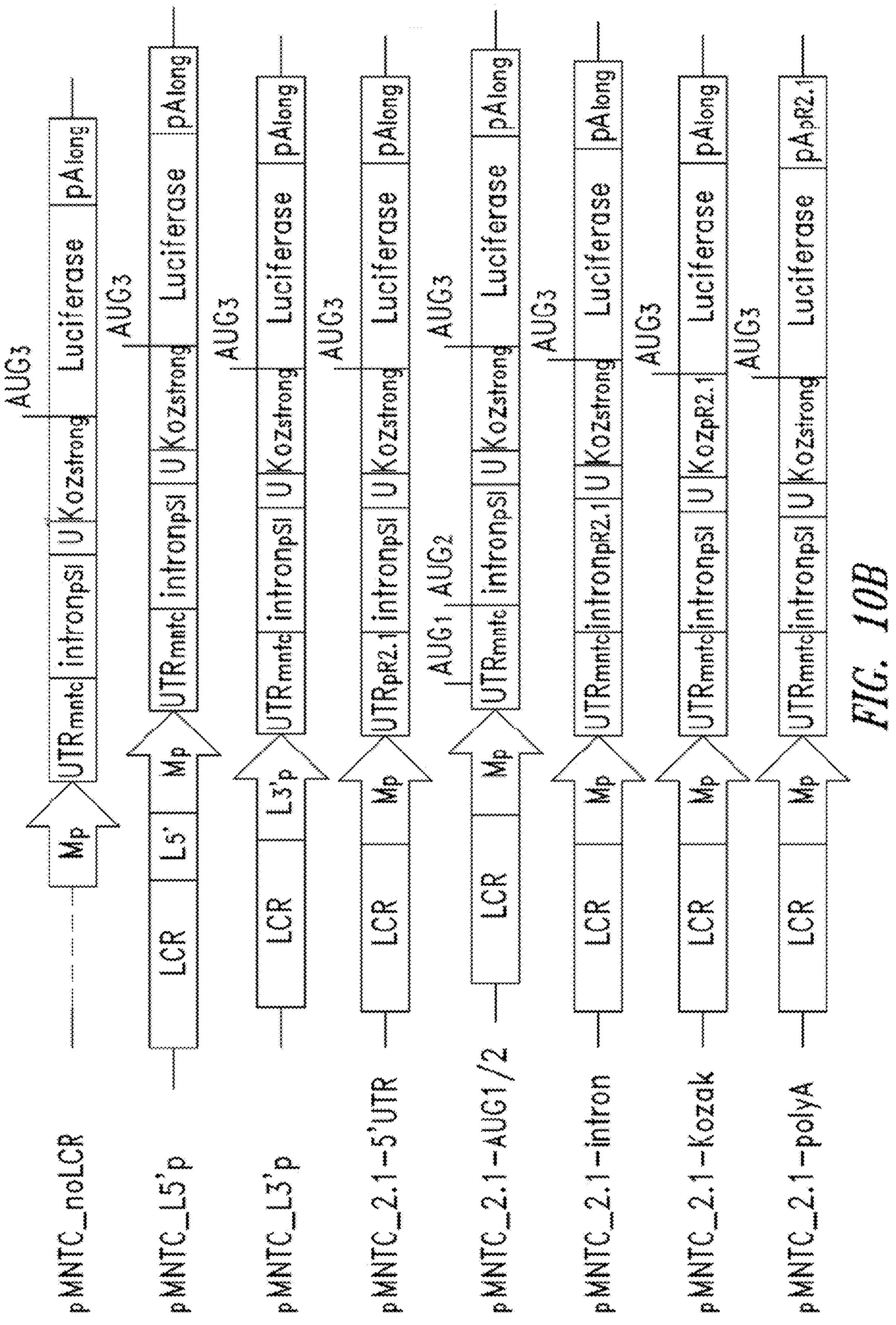
Figure 10C:
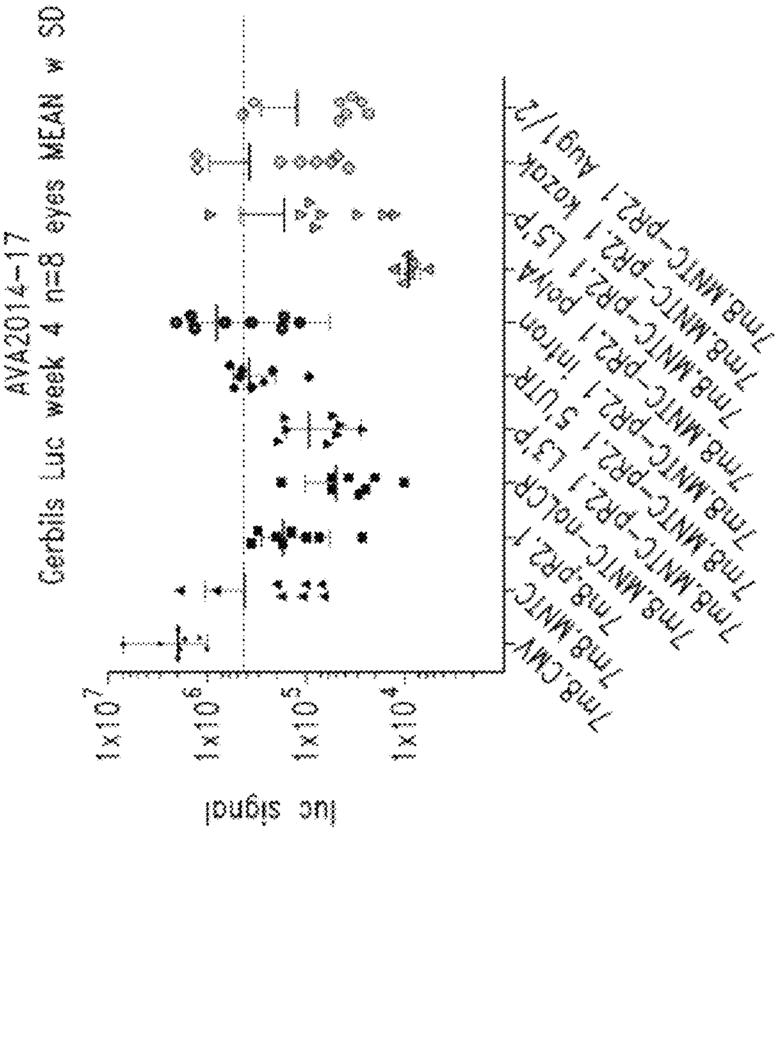
Figure 10D:
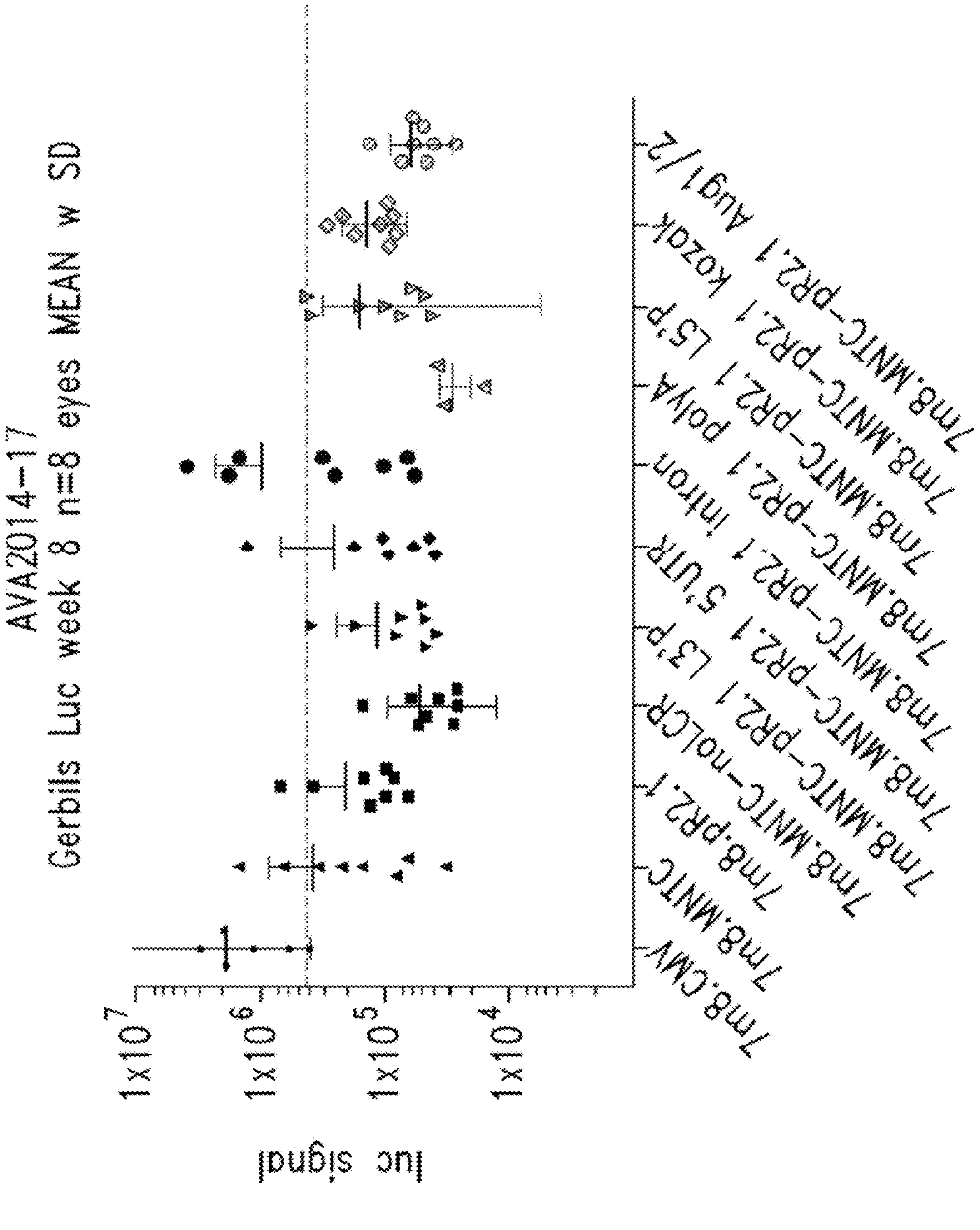

To that end, the polynucleotide cassette "pMNTC" was designed in which enhancer, promoter, 5'UTR, intron, Kozak, and polyadenylation sequences were designed for cone-specific expression (FIG. 10*a*). The cassette included an LCR enhancer sequence from the L- and M-opsin genomic locus and a truncated promoter sequence from the M-Opsin gene, comprising about 140 nucleotides upstream of the transcriptional start site. In addition, the cassette included a 5' untranslated region (5' UTR) based on the M-opsin 5'UTR but modified to have minimal secondary structure (see FIGS. 3A-3B) and to include additional sequence at its 3' end into which an intron was inserted. The intronic sequence used was a pSI chimeric intron having the 5'-donor site from the first intron of the human β-globin gene and the branch and 3'-acceptor site from the intron that lies between the leader and the body of an immunoglobulin gene heavy chain variable region (Bothwell, A. L. et al. (1981) Heavy chain variable region contribution to the NPb family of antibodies: Somatic mutation evident in a gamma 2a variable region. Cell 24, 625-37). The sequences of the donor and acceptor sites, along with the branchpoint site, were changed to match the consensus sequences for splicing (Senapathy, P., Shapiro, M. B. and Harris, N. L. (1990) Meth. Enzymol. 183, 252-78). Also included in the pMNTC polynucleotide cassette was a strong Kozak sequence and an SV40 polyadenylation sequence.

Experiments were also performed to identify the best AAV with which to deliver transgenes to cone cells. Successful delivery of polynucleotides to cells of the retina for the purposes of gene therapy has been achieved using viral vectors such as AAV and lentivirus. However, these viruses must be injected subretinally to reach the cells of the non-human primate (NHP) retina, a procedure that carries with it the risk of retinal damage. A less disruptive approach is administration by intravitreal injection. However, efficient transduction of cone photoreceptors following intravitreal delivery of AAV or lentivirus has never been demonstrated: while reports exist of AAVs with the ability to transduce retinal cone cells with high efficiency (Merigan et al. IOVS 2008, 49 E-abstract 4514), later reports have questioned the efficacy of these vectors (Yin et al. IOVS 2011, 52(5):2775-2783).

Results

Figure 5:
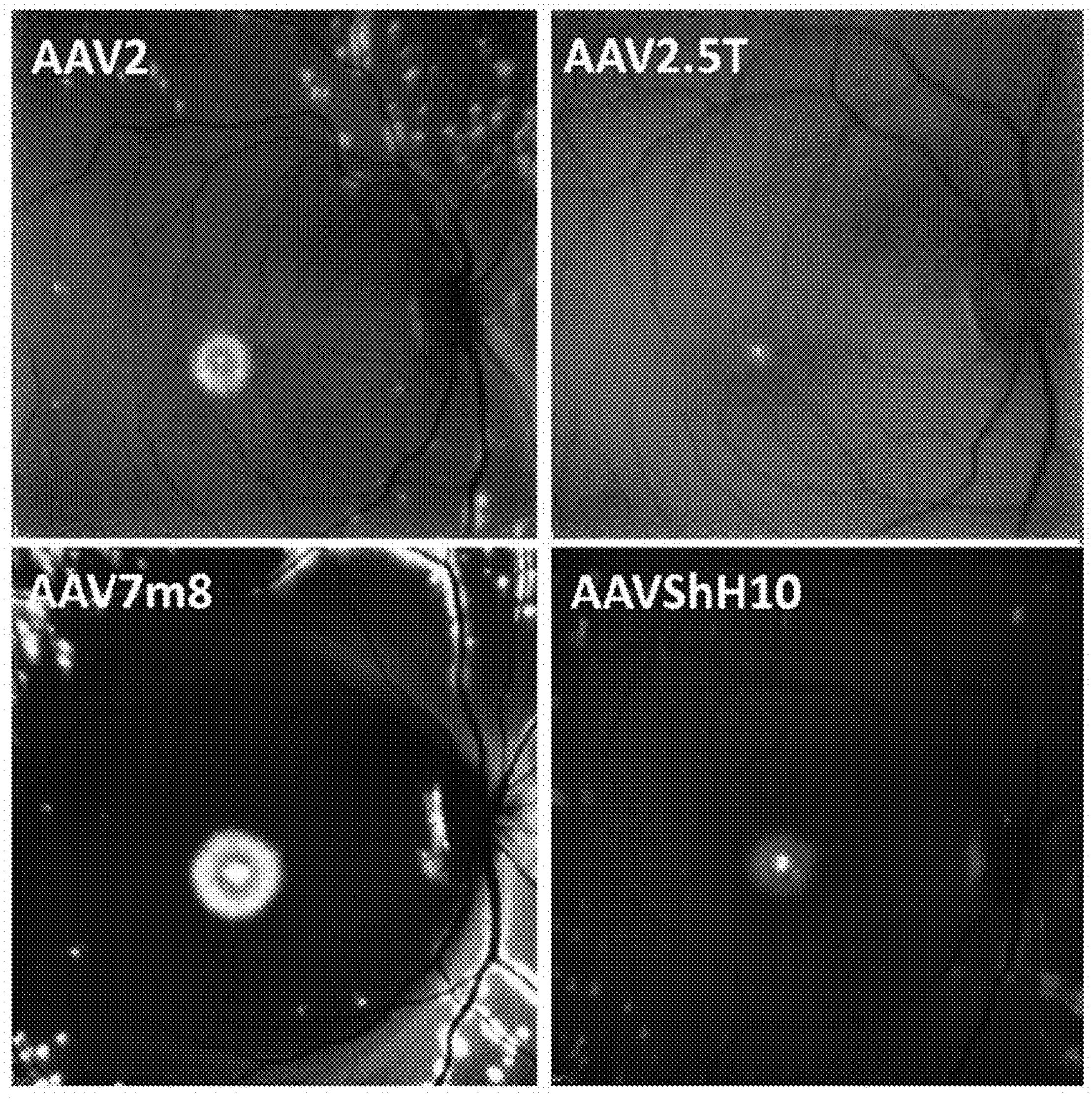
FIG. 5 illustrates how intravitreally-delivered AAV2 variant AAV2-7m8 transduces retinal cells in the fovea centralis and parafovea of primates more efficiently than intravitreally-delivered AAV2. $5\times10^{11}$ vector genomes of AAV2.CMV.GFP (upper left); AAV-2.5T.CMV.GFP (upper right) (Excoffon K. J., et al. 2009. Proc. Natl. Acad. Sci. U.S.A. 106:3865-3870); (lower left) AAV2-7.8.CMV.GFP (Dalkara D, et al. Sci Transl Med. 2013 Jun. 12; 5(189): 189ra76); or AAV-ShH10.CMV.GFP (lower right) (Klimczak R R et al. PLoS One. 2009 Oct. 14; 4(10):e7467) was injected into the vitreous of an African green monkey in a volume of 50 uL, and GFP expression was observed 8 weeks later by OCT fluorescence imaging in vivo.
Figure 6A:
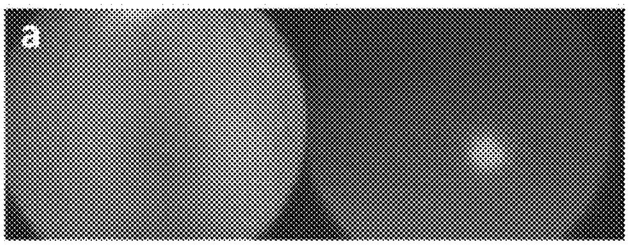
FIGS. 6A-6D illustrate how robustly the pMNTC regulatory cassette promotes gene expression in foveal cones of primates.
Figure 6B:
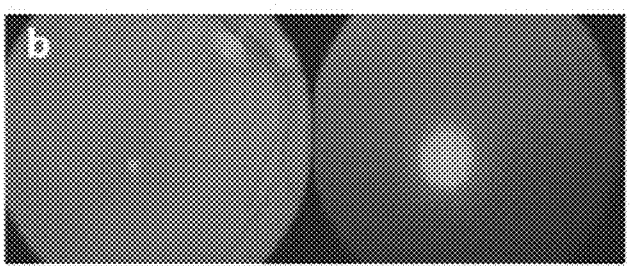
Figure 6C:
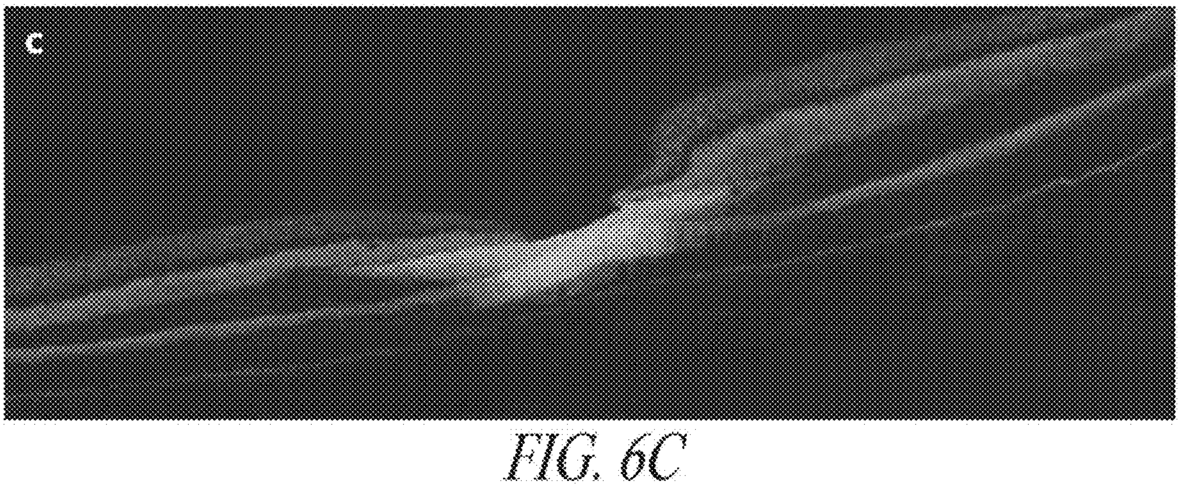
Figure 6D:
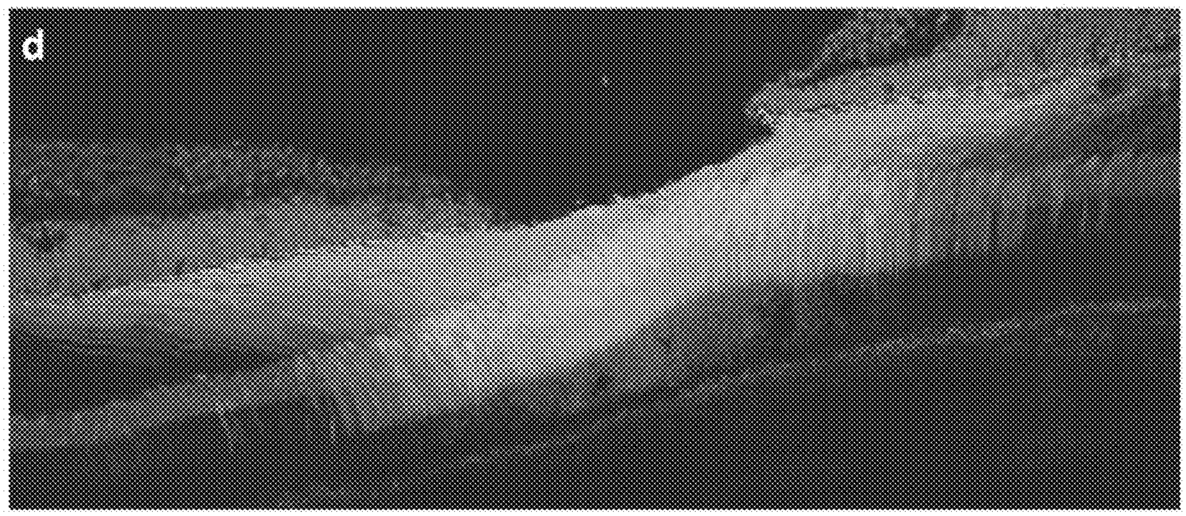
Figure 7A:
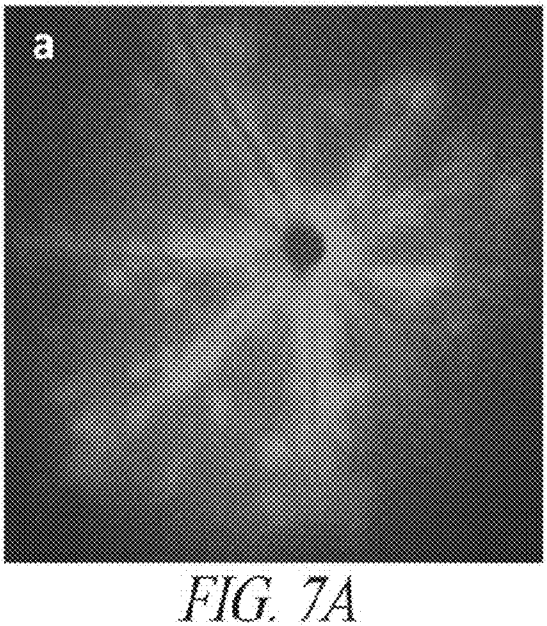
FIGS. 7A-7E illustrate robust and cone-specific gene expression in the cones of a mouse retina following intravitreal injection of AAV-delivery MNTC.GFP.
Figure 7B:
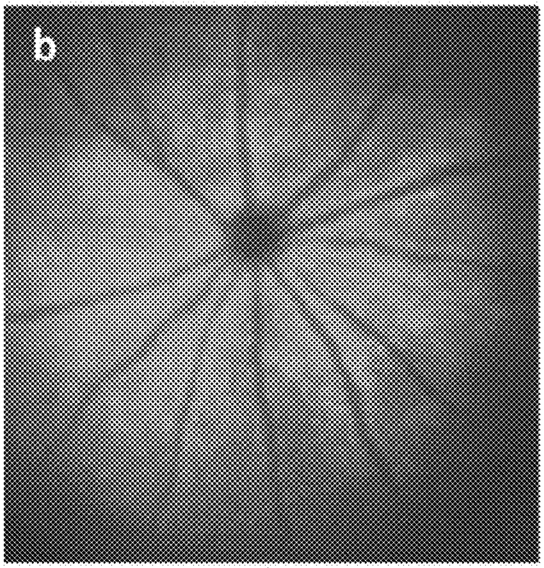
Figure 7C:
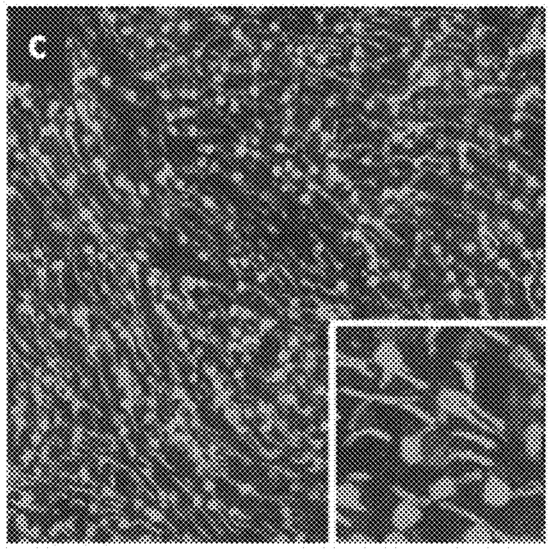
Figure 7D:
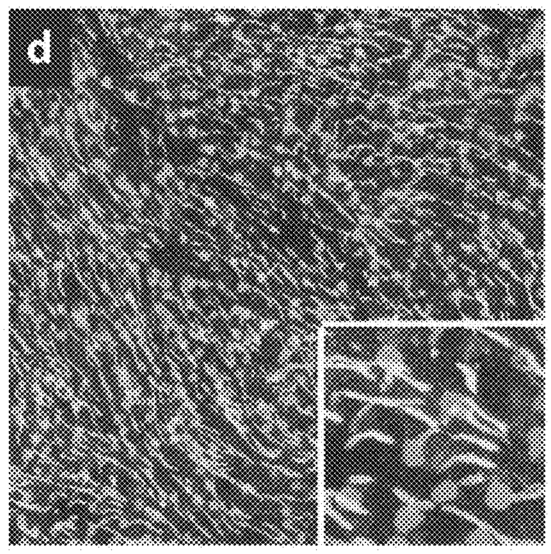
Figure 7E:
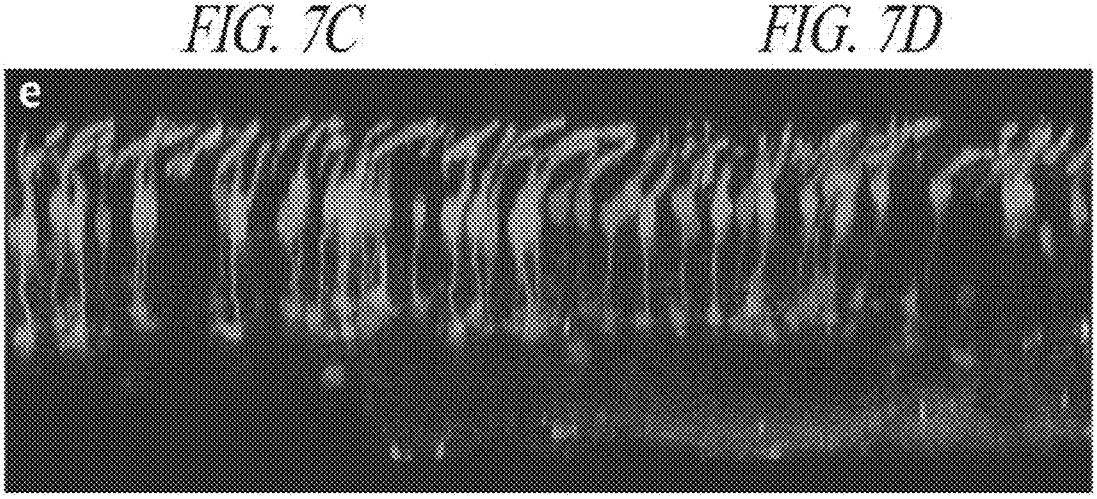

Directed evolution of AAV2 has led to the identification of the viral variant "7m8" that is able to transduce photoreceptors better than wild type AAV2 (Dalkara et al. Sci Transl Med 2013). However, the retina contains two types of photoreceptors—rods and cones—and no reports exist demonstrated whether AAV2-7m8 can transduce cone photoreceptors, per se, and more particularly, cone photoreceptors in the highly cone-enriched area of the fovea. To test this possibility, we delivered AAV2-7m8 carrying an expression cassette of the ubiquitous promoter CMV operably linked to GFP to the retina of African Green monkey by intravitreal injection. Intravitreally delivered AAV2-7m8.CMV.GFP appeared to transduce retinal cells in the fovea centralis (the 0.35 mm diameter rod-free region of retina at the center of the foveal pit) and parafovea (the lip of the depression) of primates more efficiently than intravitreally-delivered AAV2 or other AAV variants previously shown in the art to transduce retinal cells. Neither AAV2-7m8 nor the other AAVs tested appeared to be able to transduce the cones of the primate fovea, the 1.5 mm-diameter cone-enriched region of retina that surrounds the foveola and forms the slopes of the pit (FIG. 5).

Figure 8A:
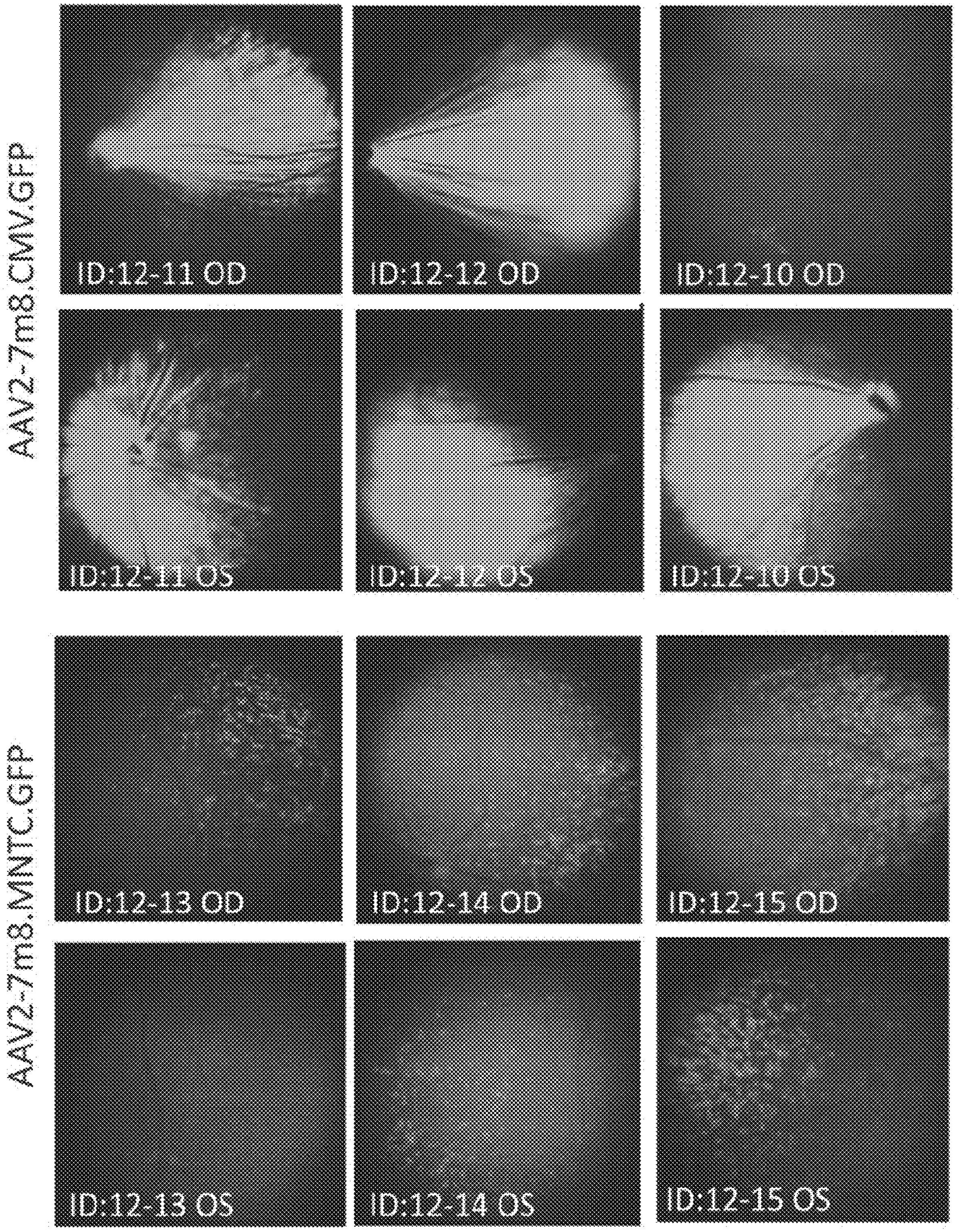
FIGS. 8A-8B illustrate gene expression directed by the pMNTC regulatory cassette in the cones of the Mongolian gerbil retina. $1\times10^{10}$-$2\times10^{10}$ vector genomes of virus carrying GFP under the control of the CMV, pR2.1, or MNTC promoter were injected in a volume of 5 uL into the vitreous of a Mongolian gerbil, and GFP expression visualized at the designated time points by fundus fluorescence imaging.

We next packaged a genome comprising pMNTC operably linked to GFP within the AAV2-7m8 capsid, and assessed the ability of this vector composition to express the GFP transgene in cone cells in vivo when injected intravitreally. Expression was evaluated in a number of species with varying numbers of retinal cones cells among total photoreceptors, including mouse (3% cones), rat (1% cones), gerbil (13% cones), and nonhuman primate (5% cones). Contrary to our results in FIG. 5, strong gene expression could be detected throughout the nonhuman primate fovea (FIGS. 6A-6D). These data indicate that intravitreally delivered AAV2-7m8 can, in fact, transduce retinal cones, and that pMNTC acts as a robust expression cassette in cone cells. Robust reporter gene expression was also seen in the intravitreally injected retina of the rat (data not shown) and gerbil (FIG. 8A), with expression levels and anatomic location correlating with cone abundance and location in all species.

To determine the cell-specificity of pMNTC-directed expression, whole mounts of transduced mouse retina were analyzed by immunohistochemistry using an antibody that is specific for cone L and M opsins. The expression of L/M opsin, which labels the outer segments of cone photoreceptors only, was observed in virtually all of the cones of the mouse retina that expressed GFP from the AAV2-7m8.MNTC.GFP vector (FIGS. 7A-7E), indicating that MNTC-directed expression of transgenes is highly cone-specific. Moreover 80% or more of the cone outer segments that were labelled by the L/M opsin-specific antibody also expressed the GFP transgene, indicating that AAV2-7m8 transduces cones highly efficiently (FIGS. 7A-7E).

We next compared the ability of pMNTC to promote expression in cone cells to that of pR2.1. pR2.1 comprises the human L/M opsin enhancer ("LCR") and the promoter region from the human L-Opsin gene. In addition, pR2.1 comprises the L-Opsin 5'UTR fused to additional 5'UTR sequence at its 3' end, into which modified SV40 late 16s intronic sequence has been inserted. This is followed by the L-Opsin Kozak sequence, which is then typically linked in-frame to a transgene. At the end of the cassette is an SV40 polyA tail.

Figure 8B:
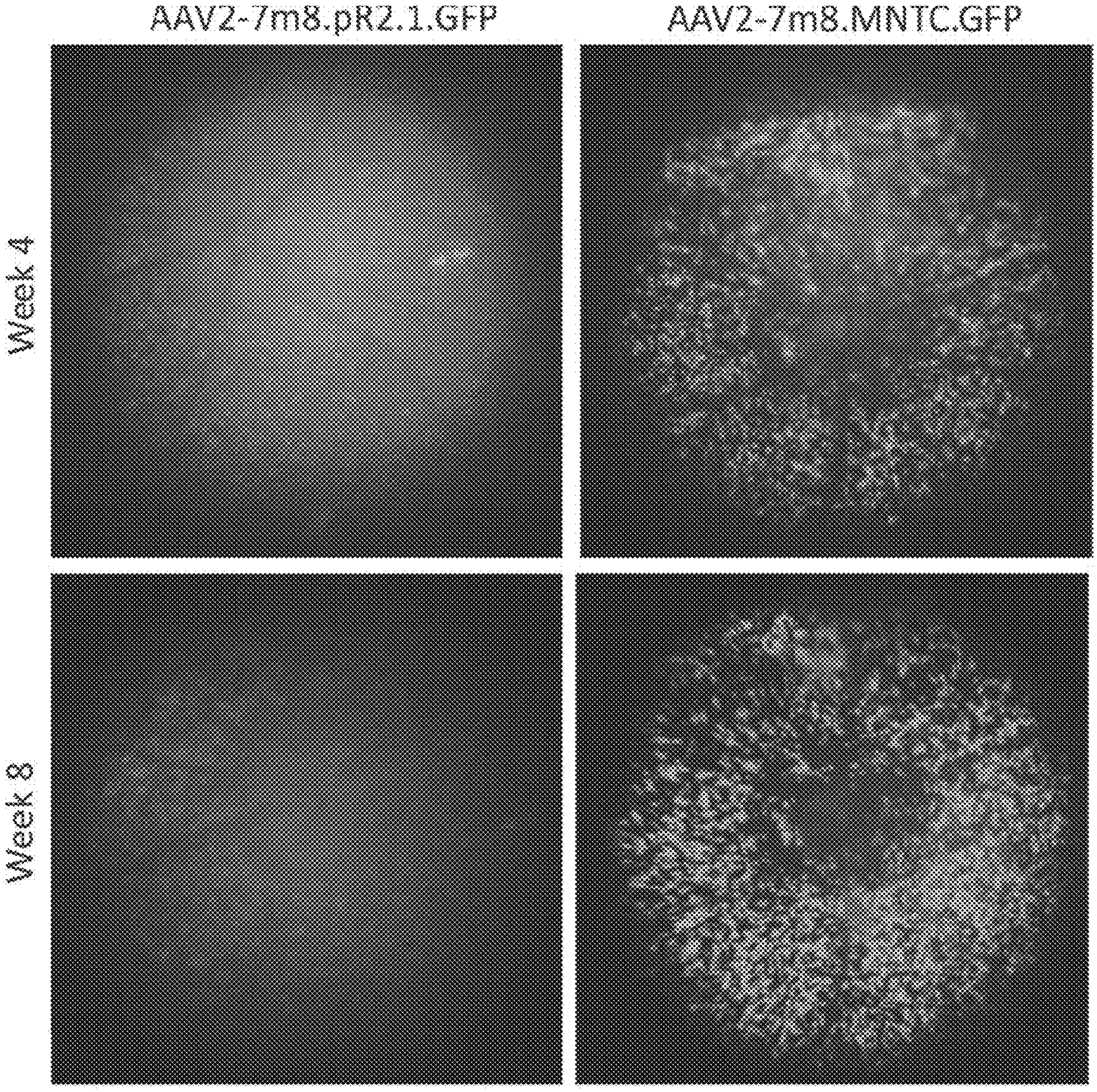
Figure 9A:
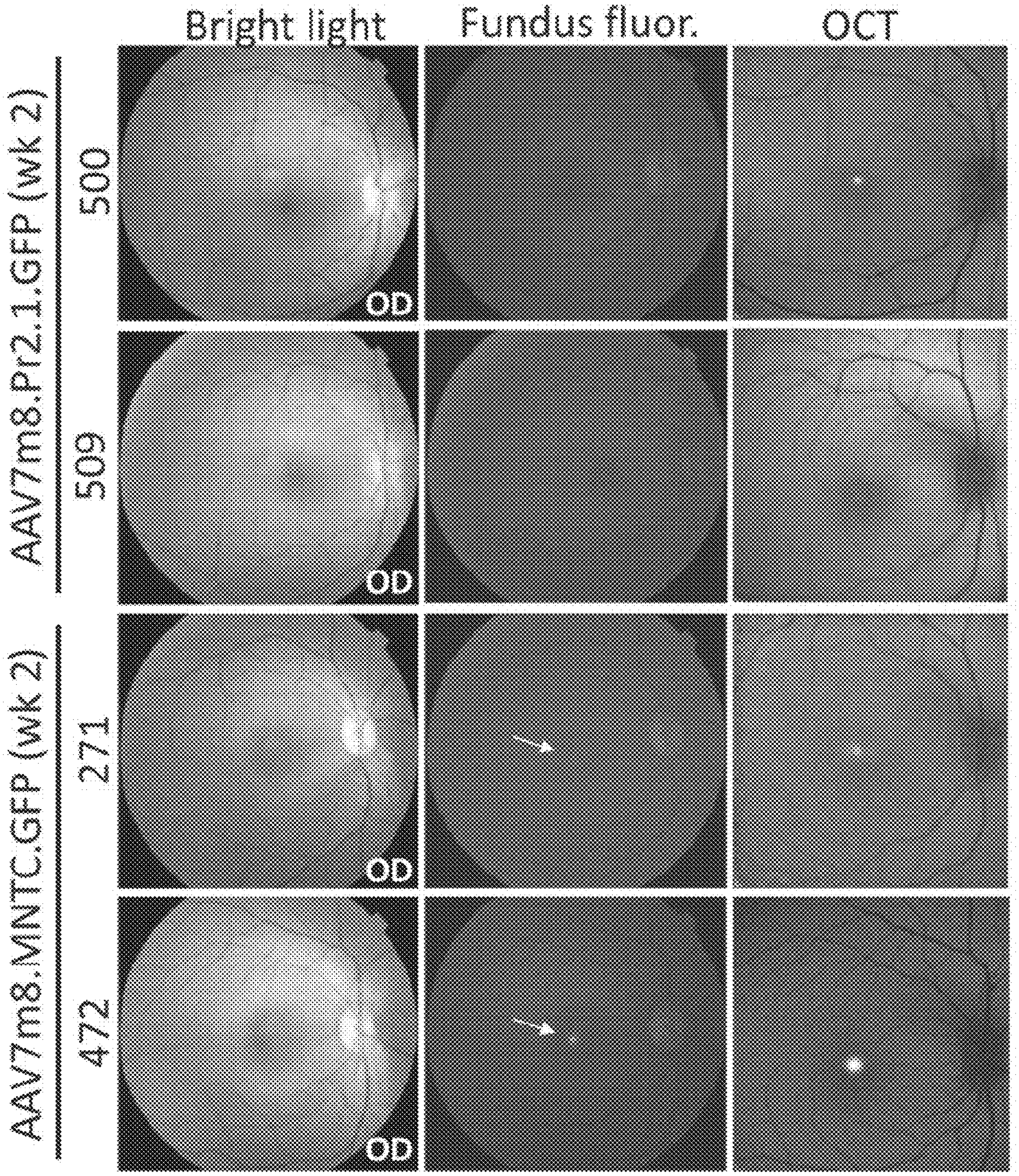
FIGS. 9A-9D demonstrate that the pMNTC regulatory cassette provides for more robust gene expression in foveal cones of primates than the cone promoter pR2.1. $5\times10^{11}$ vector genomes of AAV2-7m8.MNTC.GFP or AAV2-7m8.pR2.1.GFP were injected in a volume of 50 uL into the vitreous of African Green Monkeys as indicated (AAV2-7m8.MNTC.GFP into animals 271 and 472; AAV2-7m8.pR2.1.GFP into animals 500 and 509). Retinas were visualized in vivo at (FIG. 9A) 2 weeks, (FIG. 9B) 4 weeks, (FIG. 9C) 8 weeks, and (FIG. 9D) 12 weeks for GFP using a fundus fluorescence camera (FIGS. A-D) or autofluorescence on Heidelberg Spectralis OCT (FIGS. 9A-9B; data not shown for weeks 8 and 12). OD, oculus dexter (right eye). OS, oculus sinister (left eye).
Figure 9B:
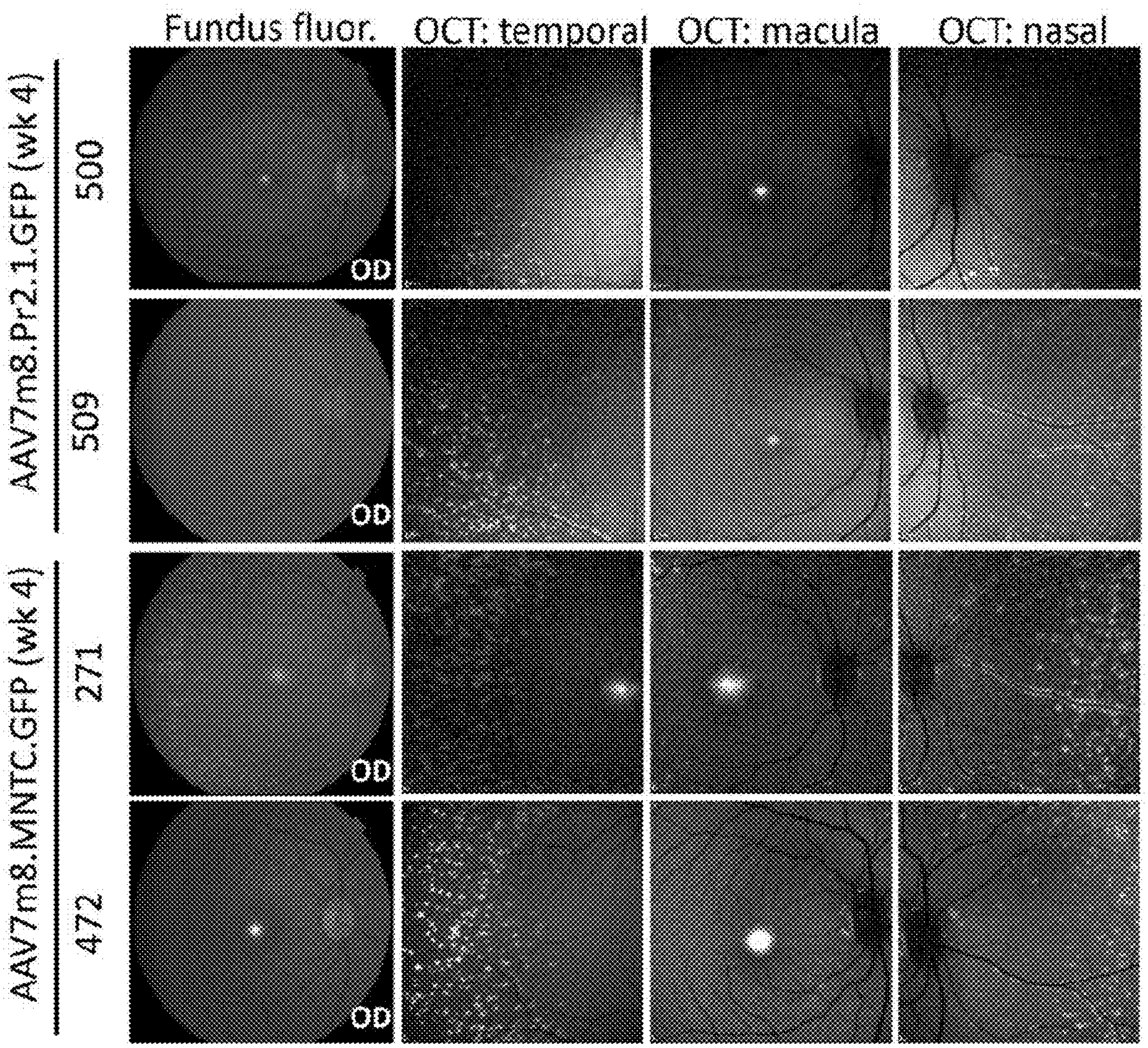
Figure 9C:
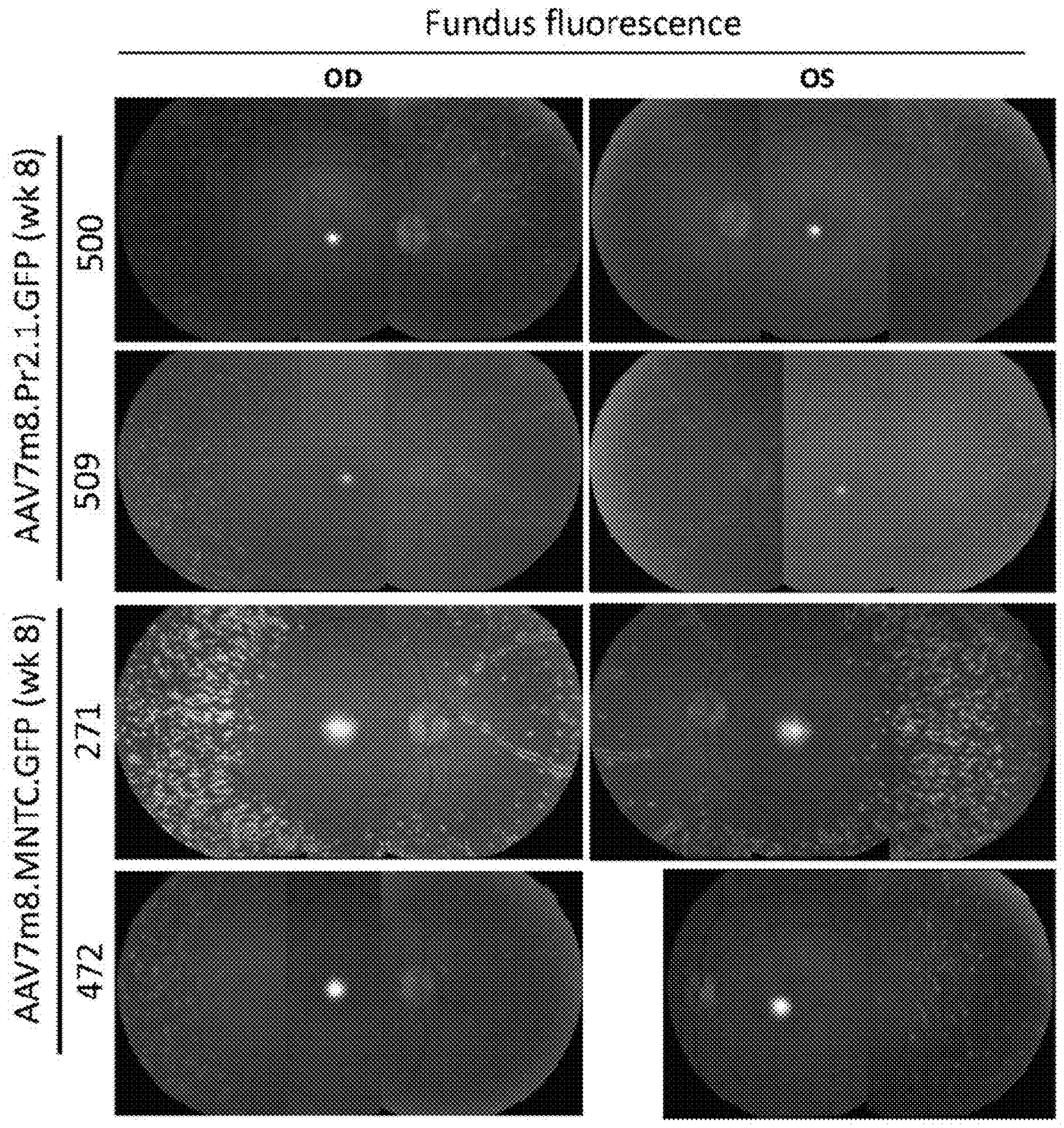
Figure 9D:
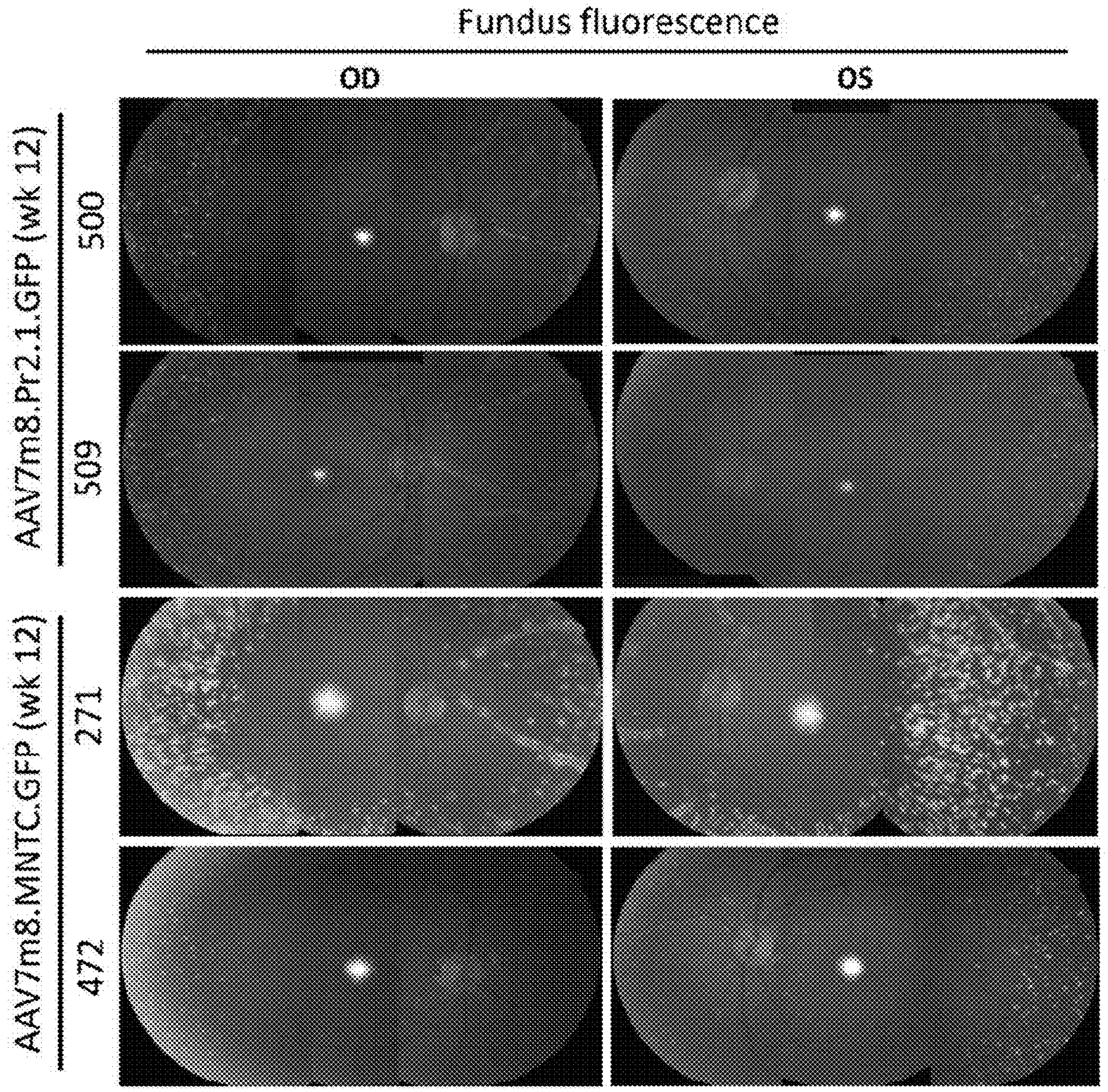

Viral preparations of AAV2-7m8.MNTC.GFP and AAV2-7m8.pR2.1.GFP were delivered intravitreally to the retinas of gerbils and nonhuman primates in vivo, and the retinas imaged in vivo 2 weeks, 4 weeks, 8 weeks, and 12 weeks later by fundus autofluorescence and OCT. GFP reporter expression was detected sooner, more strongly, and in more cones in gerbil retina transduced with rAAV carrying the pMNTC.GFP expression cassette than in gerbil retinas carrying the pR2.1.GFP expression cassette (FIG. 8B). Likewise, GFP reporter expression was detected sooner and in more cones in nonhuman primate retinas transduced with rAAV carrying the pMNTC.GFP expression cassette as compared to NHP retinas transduced with the pR2.1 expression cassette (FIGS. 9A-9D, n=4 eyes). In both gerbils and NHP, GFP was consistently observed to be stronger from pMNTC than from pR2.1 throughout the duration of the study.

To determine the contribution of each of the elements in the pMNTC expression cassette to the overall improvement in expression, a series of expression constructs were cloned in which each of the elements in pMNTC was substituted one-by-one with the corresponding element from the pR2.1 expression cassette. These constructs were then packaged into AAV2-7m8 and delivered by intravitreal injection to the gerbil retina. Gerbil retinas were assessed 4 and 8 weeks later in vivo by in vivo bioluminescence (IVIS imaging system, PerkinElmer), which provides a quantitative readout of reporter expression across the entire eye.

As expected, expression of the luciferase reporter under the control of pMNTC was higher than expression of the luciferase reporter under the control of pR2.1. Replacement of the pMNTC promoter sequence with the pR2.1 promoter sequence having the most sequence homology to it (SEQ ID NO:83) reduced expression (construct pMNTC_pR2.1 L3'P), as did the inclusion of pR2.1 promoter sequence that lies more distal to the 5'UTR of pR2.1 (SEQ ID NO:82) (construct pMNTC_pR2.1-L5'P). Expression was also reduced by the introduction into the pMNTC 5'UTR of two false start sequences ("AUG1" and "AUG2") that were observed in the pR2.1 5'UTR (construct pMNTC_2.1-AUG1/2). Interestingly, expression was not reduced when the pMNTC 5'UTR was replaced with a modified pR2.1 5'UTR sequence in which these false starts had been removed (SEQ ID NO:87, nucleotide 17 changed to C, nt 61and 62 changed to CA) (pMNTC_pR2.1-5'UTR), suggesting that the pR2.1 5'UTR would promote strong expression in cone cells but for the false AUGs in the pR2.1 5'UTR element. Also interestingly, the pR2.1 intron (SEQ ID NO:59) appeared to provide more robust expression than the pSI chimeric intron of pMNTC, suggesting that inclusion of the pR2.1 intron in the polynucleotide cassettes of the present disclosure may be used to further improve expression in cone cells. Lastly, removal of the L/M enhancer (found in both pR2.1 and pMNTC) reduced expression as well. While the polyA tailed seemed at first to also have a significant impact on expression, re-sequencing of the pMNTC construct comprising this pR2.1 element revealed that the polyA tail was not operably linked to the transgene, thereby explaining why only background levels of expression were observed from this construct. Thus, the L/M opsin LCR, the inclusion of the M opsin core promoter rather than the L opsin promoter, and the exclusion of false starts in the 5'UTR all contribute to the enhancement in gene expression achieved using the pMNTC promoter.

In conclusion, we have identified an AAV variant, the AAV variant comprising a 7m8 peptide in the GH loop, which may be used for the intravitreal delivery of polynucleotides to retinal cones. Likewise, we have identified a number of polynucleotide cassette elements that may be used to promote strong expression in cone photoreceptors. Together, these discoveries represent improvements that may facilitate the development of therapeutic agents for cone-associated disorders.

Materials and Methods

Transgene expression in vitro in WERI-RB-1 cells. WERI-Rb-1 retinoblastoma cells expressing cone photoreceptor pigments cells are transfected with a polynucleotide cassette of the present disclosure according to the method described by Shaaban and Deeb, 1998; IOVS 39(6)885-896.

The polynucleotide cassettes are transfected as plasmid DNA using well established techniques of molecular biology, such as cloning (Maniatis et al.) or via de novo DNA synthesis. All regulatory elements are placed in the cassette and used to drive the enhanced GFP protein. Plasmid DNA is then introduced into cells using established techniques for non-viral transfection, for example using a lipid-based transfection reagent (Altogen Biosystems, NV) or Lipofectamine LTX (Life Technologies). Cells are then cultured for 72 hours and eGFP expression is measured using flow cytometry and fluorescence microscopy. Transgene expression in cells transfected with the polynucleotide cassette of the present invention (i.e., constructs designed for cone photoreceptor expression) is compared to the un-optimized counterparts (i.e., those based on pR2.1) and is found to be stronger from cassettes carrying improved elements In vitro expression is also evaluated using other mammalian cell lines that express cone opsins, such as 661W cells (Tan et al., IOVS 2004; 45(3) 764-768).

Similarly, in vitro expression is evaluated using non-photoreceptor cell lines that have been engineered to express cone photoreceptor-specific proteins. Such a system has been described with HEK293 cells that have been genetically engineered to express CRX/Sp1 (Khani et al., IOVS 2007; 48: 3954). Marker genes are also used (eGFP, dsRed, mCherry, luciferase) as well as physiologic genes (opsin, ACHR genes). Physiologic genes are tested by examining mRNA levels (e.g., by RT-PCR) or protein levels (e.g., by ELISA or Western blot).

Animal care. All experiments conformed to the principles regarding the care and use of animals adopted by the American Physiological Society and the Society for Neuroscience, and were approved by the Institutional Animal Care and Use Committee (IACUC).

Small animal studies. The expression of the gene product encoded by the coding sequence of the expression cassettes are evaluated in vivo in mice, rats, and gerbils. This is accomplished by intravitreal injection in vivo of an rAAV preparation comprising the expression cassette (Li et al., 2008; Mol Vis 48: 332-338). Note that electroporation of plasmid DNA may be performed instead (Matsuda/Cepko).

Mouse studies. Mice used in this study were C57BL/6. Animals were anesthetized with ketamine/xylazine (110 mg/kg intraperitoneal). A beveled 34 gauge disposable needle loaded with test article was inserted into the vitreous of the eye, and $5.04\times10^{10}$ vector genomes of rAAV in a volume of 1.5 μl was injected into the vitreous.

Gerbil and rat studies. Mongolian gerbils (*Meriones unguiculatus*) and brown Norway rats were used in this study. Pupils were dilated with 10% phenylephrine and 0.5% tropicamide. Animals were anesthetized with an intraperitoneal or intramuscular injection of 0.1-0.2 mL of a ketamine/xylazine solution (70 mg/mL ketamine and 10 mg/mL xylazine for rats; 25 mg/mL ketamine and 0.3 mg/mL xylazine for gerbils). A beveled 34 gauge disposable needle loaded with test article in a 100 μL Hamilton syringe was inserted into the vitreous of the eye through the sclera at an optimized superior-temporal point about 1 mm from Limbus. $1\times10^{10}$-$2\times10^{10}$ vector genomes of test article ($2\times10^{10}$ vg of rAAV.GFP, or $1.15\times10^{10}$ vg of rAAV.luciferase) in a 5 uL volume was injected slowly with a microinjection pump into the vitreous, after which the needle tip was held in the injected eye at the injected position for 10 seconds so as to ensure adequate test article dispensing. The needle was then withdrawn.

Non-human primate (NHP) studies. The polynucleotide cassettes and expression vectors are also tested in large animals. This is done by using AAV, for example using the techniques of Mancuso et al. Briefly, an AAV cassette is made, the AAV encapsidating the expression cassette is manufactured, and the viral prep is injected intravitreally (up to 170 uL in the vitreous) or subretinally (up to 3, 100 uL injections at different locations; vitrectomy may be performed prior to injection) in nonhuman primates. Expression is evaluated by reporter (GFP), color ERG, and/or behavioral testing using the Cambridge Color Test or on animals trained to make a saccade (eye movement) when a target enters the field of view. The saccades are monitored using an eye tracker. Prior to treatment animals are trained to perform a color vision test or to make a saccade when it sees a colored target. An ERG is performed to estimate the spectral sensitivity of the cones present. Data from the color vision test performance and the ERG provide evidence that the animal is dichromatic (colorblind). For animals that receive a vector carrying the GFP gene, expression is monitored using fundus imaging with RetCam II or similar device under light that produces excitation of the GFP. For animals receiving a photopigment gene that differs in spectral sensitivity compared to the animal's endogenous pigments, expression is monitored using the multifocal color ERG to measure spectral sensitivity at up to 106 different retinal locations, and by behavioral testing.

Baboons were sedated with 10-15 mg/kg ketamine following by sevofluorane. African Green monkeys were sedated with an intramuscular injection of 5:1 ketamine: xylazine mix (0.2 ml/kg of 100 mg/ml ketamine and 20 mg/ml xylazine). Mydriasis was achieved with topical 10% phenylephrine. An eye speculum was placed in the eye to facilitate injections. A drop of proparacaine hydrochloride 0.5% and then 5% betadine solution was applied, followed by a rinse with sterile saline. Baboons (FIGS. 6A-6D) received 60 μl of a $3.4\times10^{13}$ vg preparation of rAAV by intravitreal (ITV) injection to yield a final dose of $2.02\times10^{12}$ vg per eye. African Green monkeys received 50 uL of a $1\times10^{13}$ preparation of rAAV vector by ITV injection to yield a final dose of $5\times10^{11}$ vg per eye. ITV injections to the central vitreous were administered using a 31-gauge 0.375 inch needle (Terumo) inserted inferotemporally at the level of the or a serrata ~2.5 mm poster to the limbus under a surgical magnification to allow full visualization of extraocular and intraocular needle placement. Central vitreous placement was confirmed by direct observation of the needle tip at the time of the injection. Following ITV injections a topical triple antibiotic ointment was administered.

Slit-lamp biomicroscopy. The anterior segment of each monkey eye was examined by slit-lamp biomicroscopy during baseline screening and at week 4 (day 28), week 8 (day 56) and week 12 (day 84) post-injection to monitor inflammation. No abnormalities were observed.

Fundus examination and photography. Eye examination and fundus photography of rat and gerbil retinas was performed using a Phoenix Micron IV fundus microscope. All animals received a baseline screening/photographing to confirm ocular health, and then photographed at the designated timepoints to monitor the expression of the GFP transgene. Any change to the optic nerves and retina or appearance of gross lesions were recorded by a color fundus photography and expression of GFP was visualized using fluorescence fundus imaging with a fluorescein filter.

Retinal examination, fundus color and fluorescence photography, and autofluorescence OCT of NHP were performed by using a Topcon TRC-50EX retinal camera with Canon 6D digital imaging hardware and New Vision Fundus Image Analysis System software and Spectralis OCT Plus. All animals received a baseline imaging. GFP expression was also documented at week 2, 4, 8, and 12 post-intravitreal vector injection.

IVIS Imaging System. Expression of luciferase in the retina following delivery of rAAV.luciferase was quantified in vivo 2, 4 and 8 weeks post-intravitreal injection using an IVIS Imaging System. Gerbils were injected subcutaneously with 150 mg/kg luciferin (PerkinElmer) (15 mg/ml luciferin at a dose of 15 ml/kg). Approximately 22 minutes later, animals were sedated by inhalation of 4% isoflurane for 3-5 minutes. Immediately thereafter, animals were placed on the imaging platform in pairs, and the luminescence of the one eye of each animal quantified followed immediately by imaging of the contralateral eye. A naïve gerbil was used as a negative standard, with background levels of luminescence typically registering a luminescence of $1\times10^4$ photons/second. Bioluminescence verification using a phantom mouse (XPM-2 Perkin Elmer phantom mouse for bioluminescence imaging) was performed prior to imaging to ensure calibration of the imaging system.

Immunohistochemistry. Mice were euthanized with a lethal dose of sodium pentobarbital and tissues fixed via cardiac perfusion first with 0.13M phosphate buffered saline (PBS) pH 7.2-7.4 containing 2 units of heparin per mL, followed by 4% paraformaldehyde (PFA) in PBS, followed by 4% paraformaldehyde plus 1% glutaraldehyde in PBS. Glutaraldehyde served to keep the neural retina attached to the RPE so that the cone outer segments would remain intact. Each solution was warmed to ~37° C. just prior to administration and ~35-40 mL of perfusate was delivered at each stage. Once the perfusion was stopped, the mouse was wrapped in a moist paper towel and left to further fix for 2-3 hours before enucleation and dissection.

Permanent ink was used to mark the orientation of the eye, the anterior segment was removed, and the eye-cup was fixed in 4% PFA overnight at 4° C. and then stored in PBS at 4° C. Retinal whole-mounts were made by flattening the dissected retina between tissues soaked in 4% PFA for two hours and then transferring them to a culture plate for 6 more hours of fixation. Afterward, the PFA was replaced with PBS containing 0.03% sodium azide (Sigma).

Antibody labeling was carried out on a rotating table shaker. To block non-specific labeling, whole mounts were incubated overnight at 4° C. with a solution containing 5% donkey serum (Jackson ImmunoResearch, Cat #004-000-120), 1 mg/ml BSA (Jackson ImmunoResearch, Cat #001-000-161), and 0.03% Triton X-100 in PBS (pH 7.4). The primary antibody used in this study was rabbit anti red-green (L/M) opsin diluted 1:200 (Millipore, Cat #AB5405. Specimens were washed in PBS 3 times for 30 minutes each, then incubated at 4° C. overnight with DAPI (4',6-diamidino-2-phenylindole, dihydrochloride 1:10,000; Invitrogen, Cat #D-21490) plus secondary antibodies. The secondary antibody for the L/M-opsin antibody was Alexa Fluor 488 labeled donkey anti-rabbit IgG(H+L) diluted 1:200 in antibody dilution buffer (Invitrogen, Cat #A21206). The incubation with secondary antibody was followed by three 30 minute PBS washes, 30 minutes of post-fixation with 4% paraformaldehyde, and three more 30 minute PBS washes. Finally, the retinal slices were placed on slides with 2% DABCO in glycerol and covered with cover slips.

Microscopy. Widefield images of mouse retina whole mounts were acquired using a Nikon Eclipse E1000 with a 20× (open-air) objective and camera set with a 1.5× optical zoom. For each specimen, 50 optical sections were taken 0.5 μm apart and the M-opsin Z-stack was reconstructed in ImageJ. The Z-stack was oriented so that the lengths of the outer segments were in plane, and the distance between where antibody staining began and ended was measured as an estimate of the length of the outer segments. Further, a 3D projection of the Z-stack was generated and the number of cones with visible M-opsin in the outer segment could be quantified.

Confocal image slices were acquired using an Olympus FluoView™ FV1000. Sections were imaged using a 20× oil immersion lens (40 images taken 0.5 μm apart) and the Z-stacks were reconstructed in ImageJ. Channel exposure levels were balanced within and across images using Adobe Photoshop. For the retinal whole mounts, images were taken using a 10× open-air lens and mosaics were constructed with Adobe Photoshop's native mosaic construction software.

Experiments testing the tissue specificity of the polynucleotide cassettes. In this instance, a construct encoding GFP is injected via one or more routes of administration, such as intravitreal, subretinal, or intravenously. The animal is then sacrificed and tissues are analyzed by qPCR—to detect DNA sequences indicating presence of the construct—and GFP expression—to detect areas where the construct is actively expressed. Whereas absence of DNA sequence indicates lack of biodistribution to a given tissue, the presence of DNA sequence together with the lack of transgene expression (mRNA or protein level) indicates presence of vector but lack of expression in that tissue. In this way, the level of specificity for cone photoreceptors can be established, and used to determine the utility of this invention in terms of restricting expression to target cone photoreceptor cells without expression in non-targeted tissues such as optic nerve, liver, spleen, or brain tissue. Intravitreal AAV is known to biodistribute to the brain (Provost et al) so highly expressed, improved constructs for targeting cone photoreceptors would be useful to limit expression to target cells of the retina and limit potential adverse events associated with off-target transgene expression.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims.

What is claimed is:

1. A polynucleotide cassette for enhanced expression of a transgene in cone cells of a mammalian retina, comprising:

(a) a promoter region consisting of a truncated opsin promoter having a sequence selected from the group consisting of (i) 95% or more sequence identity to SEQ ID NO: 55 or functional fragment thereof comprising SEQ ID NO:80, (ii) SEQ ID NO: 82, and (iii) SEQ ID NO: 83;

(b) a coding sequence operatively linked to the promoter region; and (c) a polyadenylation site operatively linked to the coding sequence.

2. The polynucleotide cassette of claim 1, further comprising a 5' untranslated region (5'UTR) consisting essentially of a sequence having a sequence identity of 95% or more to a sequence selected from the group consisting of SEQ ID NO: 56, SEQ ID NO:57, SEQ ID NO:58, SEQ ID NO: 84, SEQ ID NO: 85, SEQ ID NO: 86, SEQ ID NO: 87, SEQ ID NO:88, and SEQ ID NO:89.

3. The polynucleotide cassette of claim 2, wherein the 5' UTR does not comprise a polynucleotide ATG.

4. The polynucleotide cassette of claim 2, wherein the 5' UTR consists essentially of a sequence having a sequence identity of 95% or more to the full length of SEQ ID NO:85 or SEQ ID NO:86.

5. The polynucleotide cassette of claim 2, further comprising an intron.

6. The polynucleotide cassette of claim 5, wherein the intron comprises a sequence having a sequence identity of 95% or more to a sequence selected from the group consisting of SEQ ID NO:5, SEQ ID NO:59, and SEQ ID NO:60.

7. The polynucleotide cassette of claim 6, wherein the intron is located within the polynucleotide sequence comprising the 5' UTR.

8. The polynucleotide cassette of claim 1, further comprising a translation initiation sequence.

9. The polynucleotide cassette of claim 8, wherein the translation initiation sequence comprises a polynucleotide sequence consisting essentially of SEQ ID NO:72 or SEQ ID NO:73.

10. The polynucleotide cassette of claim 1, further comprising an enhancer sequence having a sequence identity of 95% or more to SEQ ID NO:52 or a functional fragment thereof.

11. The polynucleotide cassette of claim 10, wherein the enhancer sequence consists essentially of a sequence having a sequence identity of 95% or more to the full length of SEQ ID NO:51.

12. The polynucleotide cassette of claim 1, wherein expression of the coding sequence is greater than expression of the coding sequence when the promoter region is replaced with the promoter region of SEQ ID NO: 1 when introduced into a mammalian cone cell.

13. A recombinant adeno-associated virus (rAAV) comprising:

(a) an AAV capsid protein, and (b) the polynucleotide cassette of claim 1 flanked by AAV ITRs.

14. A pharmaceutical composition comprising an rAAV comprising (a) an AAV capsid protein and (b) a polynucleotide cassette for enhanced expression of a transgene in cone cells of a mammalian retina, comprising:

(a) a promoter region consisting of a truncated opsin promoter having a sequence selected from the group consisting of (i) 95% or more sequence identity to SEQ ID NO: 55 or functional fragment thereof comprising SEQ ID NO:80, (ii) SEQ ID NO: 82, and (iii) SEQ ID NO: 83;

(b) a coding sequence operatively linked to the promoter region; and (c) a polyadenylation site operatively linked to the coding sequence; wherein the polynucleotide cassette is flanked by AAV ITRs and a pharmaceutical excipient.

15. A method for expressing a transgene in cone cells, comprising:

contacting one or more cone cells with an effective amount of a recombinant adeno-associated virus comprising (a) an AAV capsid protein and (b) a polynucleotide cassette for enhanced expression of a transgene in cone cells of a mammalian retina, comprising:

(a) a promoter region consisting of a truncated opsin promoter having a sequence selected from the group consisting of (i) 95% or more sequence identity to SEQ ID NO: 55 or functional fragment thereof comprising SEQ ID NO:80, (ii) SEQ ID NO: 82, and (iii) SEQ ID NO: 83;

(b) a coding sequence operatively linked to the promoter region; and (c) a polyadenylation site operatively linked to the coding sequence; wherein the polynucleotide cassette is flanked by AAV ITRs, wherein the transgene is expressed at detectable levels in the one or more cone cells.

16. The method according to claim 15, comprising detecting the expression in the cone cells, wherein expression is detected in 60% or more of the cone cells.

* * * * *